US008454974B2

(12) United States Patent
Scheel et al.

(10) Patent No.: US 8,454,974 B2
(45) Date of Patent: Jun. 4, 2013

(54) ADAPTIVE MUTATIONS ALLOW ESTABLISHMENT OF JFH1-BASED CELL CULTURE SYSTEMS FOR HEPATITIS C VIRUS GENOTYPE 4A

(75) Inventors: Troels Kasper Høyer Scheel, Copenhagen Nv (DK); Judith M. Gottwein, Frederiksberg C (DK); Jesper Eugen-Olsen, Hellerup (DK); Jens Bukh, Præstø (DK)

(73) Assignee: Hvidovre Hospital, Hvidovre (DK)

( * ) Notice: Subject to any disclaimer, the term of this patent is extended or adjusted under 35 U.S.C. 154(b) by 701 days.

(21) Appl. No.: 12/595,825

(22) PCT Filed: Apr. 11, 2008

(86) PCT No.: PCT/DK2008/050085
§ 371 (c)(1),
(2), (4) Date: Feb. 3, 2010

(87) PCT Pub. No.: WO2008/125119
PCT Pub. Date: Oct. 23, 2008

(65) Prior Publication Data
US 2010/0158948 A1 Jun. 24, 2010

(30) Foreign Application Priority Data

Apr. 13, 2007 (DK) .................................. 2007 00545
Dec. 20, 2007 (DK) .................................. 2007 01841

(51) Int. Cl.
| *A61K 39/29* | (2006.01) |
| *C12N 7/02* | (2006.01) |
| *C12N 15/06* | (2006.01) |
| *C12Q 1/02* | (2006.01) |
| *C07H 21/00* | (2006.01) |

(52) U.S. Cl.
USPC .................. 424/228.1; 424/192.1; 424/199.1; 435/235.1; 435/239; 435/320.1; 435/455; 435/5; 514/44 R; 536/23.72

(58) Field of Classification Search
None
See application file for complete search history.

(56) References Cited

U.S. PATENT DOCUMENTS

| 5,428,145 A | 6/1995 | Okamoto et al. |
| 6,638,714 B1 | 10/2003 | Linnen et al. |
| 2007/0073039 A1 | 3/2007 | Chisari |

FOREIGN PATENT DOCUMENTS

| EP | 1 801 209 A1 | 6/2007 |
| EP | 1 930 416 A1 | 6/2008 |
| WO | WO 99/04008 A2 | 1/1999 |
| WO | WO 01/21807 A1 | 3/2001 |
| WO | WO 02/052015 A2 | 7/2002 |
| WO | WO 02/059321 A2 | 8/2002 |
| WO | WO 2005/047463 A2 | 5/2005 |
| WO | WO 2005/053516 A2 | 6/2005 |
| WO | WO 2006/096459 A2 | 9/2006 |
| WO | WO 2007/037429 A1 | 4/2007 |
| WO | WO 2007/041487 A2 | 4/2007 |
| WO | WO 2007/073039 A1 | 6/2007 |
| WO | WO 2008/125117 A1 | 10/2008 |
| WO | WO 2008/125119 A1 | 10/2008 |
| WO | WO 2008/141651 A1 | 11/2008 |
| WO | WO 2009/080052 A1 | 7/2009 |
| WO | WO 2009/080053 A1 | 7/2009 |

OTHER PUBLICATIONS

Pietschmann T, Kaul A, Koutsoudakis G, Shavinskaya A, Kallis S, Steinmann E, Abid K, Negro F, Dreux M, Cosset FL, Bartenschlager R. Construction and characterization of infectious intragenotypic and intergenotypic hepatitis C virus chimeras. Proc Natl Acad Sci U S A. May 9, 2006;103(19):7408-13.*
Krieger N, Lohmann V, Bartenschlager R. Enhancement of hepatitis C virus RNA replication by cell culture-adaptive mutations. J Virol. May 2001;75(10):4614-24.*
Chamberlain RW, Adams N, Saeed AA, Simmonds P, Elliott RM. Complete nucleotide sequence of a type 4 hepatitis C virus variant, the predominant genotype in the Middle East.J Gen Virol. Jun. 1997;78 ( Pt 6):1341-7.*
Thomas Pietschmann et al. Construction and characterization of infectious intragenotypic and intergenotypic hepatitis C virus chimeras. Proc Natl Acad Sci U S A. May 9, 2006; 103(19): 7408-7413.*
Timm J et al. Characterization of full-length hepatitis C virus genotype 4 sequences. J Viral Hepat. May 2007;14(5):330-7.*

(Continued)

*Primary Examiner* — Mary E Mosher
*Assistant Examiner* — Nick Zou
(74) *Attorney, Agent, or Firm* — Thompson Coburn LLP; Charles P. Romano

(57) ABSTRACT

The present inventors developed three 4a/2a intergenotypic recombinants in which the JFH1 structural genes (Core, E1 and E2), p7 and all of or part of NS2 were replaced by the corresponding genes of the genotype 4a reference strain ED43. The 4a/2a junction in NS2 was placed after the first transmembrane domain (α), in the cytoplasmic part (β) or at the NS2/NS3 cleavage site (y). Following transfection of Huh7.5 cells with RNA transcripts, infectious viruses were produced in the ED43/JFH1-β and -y cultures only. Compared to the 2a control virus, production of infectious viruses was significantly delayed. However, in subsequent passages efficient spread of infection and high HCV RNA titers were obtained. Infectivity titers were approximately 10-fold lower than for the 2a control virus. Sequence analysis of recovered 4a/2a recombinants from 3 serial passages and subsequent reverse genetic studies revealed a vital dependence on a mutation in the NS2 4a part. ED43/JFH1-γ further depended on a second NS2 mutation. Infectivity of the 4a/2a viruses was CD81 dependent. Conclusion: The developed 4a/2a viruses provide a robust in vitro tool for research in HCV genotype 4, including vaccine studies and functional analyses of an increasingly important genotype in the Middle East and Europe.

25 Claims, 9 Drawing Sheets

OTHER PUBLICATIONS

Figure 1:
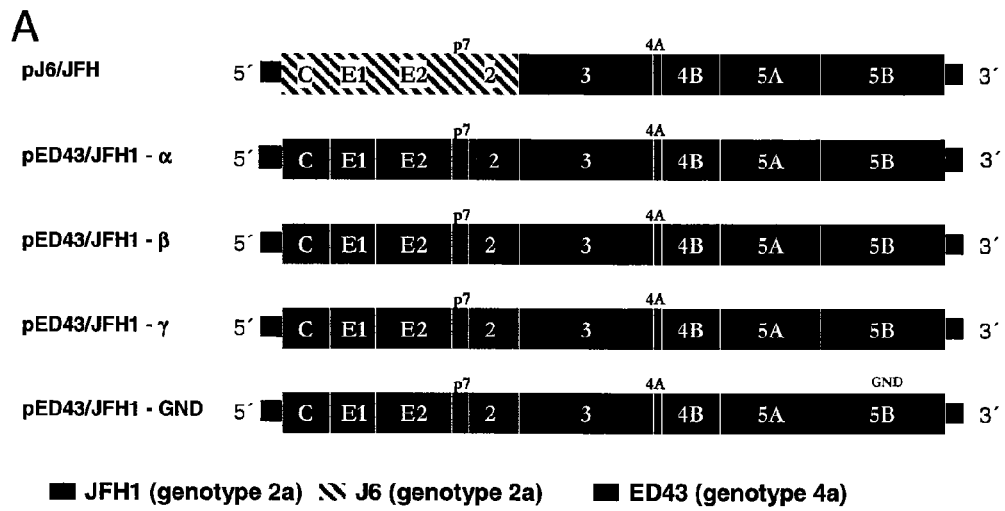
Figure 1:
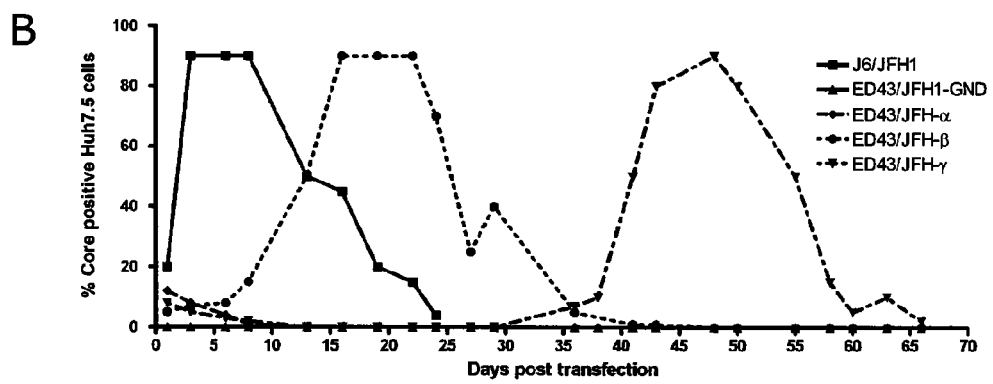
Figure 1:
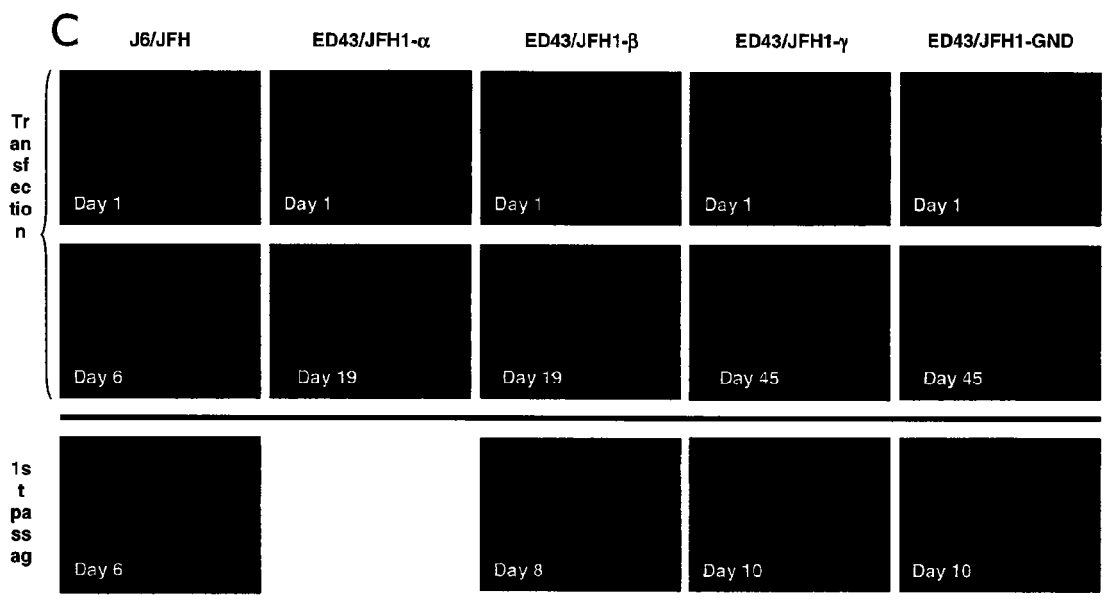

Kukolj G et al. Binding site characterization and resistance to a class of non-nucleoside inhibitors of the hepatitis C virus NS5B polymerase. Biol Chem. Nov. 25, 2005;280(47):39260-7. Epub Sep. 27, 2005.*

Appel, Nicole et al., "Mutational Analysis of Hepatitis C Virus Nonstructural Protein 5A: Potential Role of Differential Phosphorylation in RNA Replication and Identification of a Genetically Flexible Domain" Journal of Virology, Mar. 2005, pp. 3187-3194, vol. 79, No. 5.

Appel, Nicole et al., "Essential Role of Domain III of Nonstructural Protein 5A for Hepatitis C Virus Infectious Particle Assembly" PLOS Pathogens, Mar. 2008, pp. 1-14, vol. 4, Issue 3.

Bukh, Jens et al., "Mutations that permit efficient replication of hepatitis C virus RNA in Huh-7 cells prevent productive replication in chimpanzees" Proc. Natl. Acad. Sci., Oct. 29, 2002, pp. 14416-14421, vol. 99, No. 22.

Chamberlain, Richard W. et al., "Complete nucleotide sequence of a type 4 hepatitis C virus variant, the predominant genotype in the Middle East" Journal of General Virology, 1997, pp. 1341-1347, vol. 78.

Forns, Xavier et al., "Hepatitis C virus lacking the hypervariable region 1 of the second envelope protein is infectious and causes acute resolving or persistent infection in chimpanzees" Proceedings of the National Academy of Sciences of the United States of America, Nov. 21, 2000, pp. 13318-13323, vol. 97, No. 24.

Gottwein, Judith M. et al., "Robust Hepatitis C Genotype 3a Cell Culture Releasing Adapted Intergenotypic 3a/2a (S52/JFH1) Viruses" Gastroenterology, 2007, pp. 1614-1626, vol. 133.

Gottwein, Judith M. et al., "Development and Characterization of Hepatitis C Virus Genotype 1-7 Cell Culture Systems: Role of CD81 and Scavenger Receptor Class B Type I and Effect of Antiviral Drugs" Hepatology, Oct. 9, 2008, pp. 364-377, vol. 49, No. 2.

Gottwein, Judith M. et al., "Monocistronic Hepatitis C Reporter Virus Recombinants of All Major Genotypes Expressing Enhanced Green Fluorescent Protein Tagged NS5A Protein" Journal of Hepatology, Apr. 2009, p. S33, vol. 50, No. sup1.

Gottwein, Judith M. et al., "Novel Chimeric Cell Culture Systems for Hepatitis C Genotypes 1A, 1B, 3A and 4A" J. Hepatology, Apr. 2007, p. S30, vol. 46.

Graham, Donald J. et al., "A genotype 2b NS5B polymerase with novel substitutions supports replication of a chimeric HCV 1b:2b replicon containing a genotype 1b NS3-5A background" Antiviral Research, 2006, pp. 24-30, vol. 69.

Hou, Wei et al., "A recombinant replication-competent hepatitis C virus expressing Azami-Green, a bright green-emitting fluorescent protein, suitable for visualization of infected cells" Biochemical and Biophysical Research Communications, Sep. 9, 2008, pp. 7-11, vol. 377, No. 1.

Jensen, Tanja Bertelsen "Efficient cell culture system for Hepatitis C Virus genotype 5a" Department of Infectious Diseases and Clinical Research Unit, Copenhagen University Hospital, Master Thesis, Mar. 2007, pp. 1-60.

Jensen, Tanja B. et al., "Highly Efficient JFH1-Based Cell-Culture System for Hepatitis C Virus Genotype 5a: Failure of Homologous Neutralizing-Antibody Treatment to Control Infection" Journal of Infectious Diseases, Dec. 15, 2008, pp. 1756-1765, vol. 198.

Kato, Takanobu et al., "Sequence Analysis of Hepatitis C Virus Isolated From a Fulminant Hepatitis Patient" Journal of Medical Virology, 2001, pp. 334-339, vol. 64.

Kato, Takanobu et al., "Efficient Replication of the Genotype 2a Hepatitis C Virus Subgenomic Replicon" Gastroenterology, 2003, pp. 1808-1817, vol. 125.

Kaul, Artur et al., "Cell Culture Adaptation of Hepatitis C Virus and In Vivo Viability of an Adapted Variant" Journal of Virology, Dec. 2007, pp. 13168-13179, vol. 81, No. 23.

Kim, Chon Saeng et al., "Monitoring the Antiviral Effect of Alpha Interferon on Individual Cells" Journal of Virology, Aug. 2007, pp. 8814-8820, vol. 81, No. 16.

Krieger, Nicole et al., "Enhancement of Hepatitis C Virus RNA Replication by Cell Culture-Adaptive Mutations" Journal of Virology, May 2001, pp. 4614-4624, vol. 75, No. 10.

Lindenbach, Brett D. et al., "Complete Replication of Hepatitis C Virus in Cell Culture" Science, Jul. 22, 2005, pp. 623-626, vol. 309.

Lohmann, Volker et al., "Mutations in Hepatitis C Virus RNAs Conferring Cell Culture Adaptation" Journal of Virology, Feb. 2001, pp. 1437-1449, vol. 75, No. 3.

Moradpour, Darius et al., "Insertion of Green Fluorescent Protein into Nonstructural Protein 5A Allows Direct Visualization of Functional Hepatitis C Virus Replication Complexes" Journal of Virology, Jul. 2004, pp. 7400-7409, vol. 78, No. 14.

Murphy, D. "Hepatitis C virus isolate QC69 polyprotein gene, complete cds" Database EMBL E.B.I. Hinxton U.K., Nov. 7, 2007.

Murphy, Donald et al., "A New Genotype of Hepatitis C Virus Originating From Central Africa" Hepatology, Oct. 2007, p. 623A, vol. 64, No. 4.

Pietschmann, Thomas et al., "Construction and characterization of infectious intragenotypic and intergenotypic hepatitis C virus chimeras" Proc. Natl. Acad. Sci., May 9, 2006, pp. 7408-7413, vol. 103, No. 19.

Prentoe, Jannick C. et al., "HCV entry related studies" Booklet, 4th Smögen Summer Symposium on Virology, Aug. 2008, p. 23.

Schaller, Torsten et al., "Analysis of Hepatitis C Virus Superinfection Exclusion by Using Novel Fluorochrome Gene-Tagged Viral Genomes" Journal of Virology, May 2007, pp. 4591-4603, vol. 81, No. 9.

Scheel, Troels K. H. et al., "Development of JFH1-based cell culture systems for hepatitis C virus genotype 4a and evidence for cross-genotype neutralization" Proceedings of the National Academy of Sciences, Jan. 22, 2008, pp. 997-1002, vol. 105, No. 3.

Simmonds, Peter et al., "Consensus Proposals for a Unified System of Nomenclature of Hepatitis C Virus Genotypes" Hepatology, Oct. 2005, pp. 962-973, vol. 42, No. 4.

Suzuki, T. et al., "Novel Chimeric hepatitis C virus genome comprising nucleic acid encoding epitope tag peptide at hypervariable region 1 of E2 protein, useful as vaccine for preventing or treating hepatitis-c viral infection" Database WPI Week 200914, Thomson Scientific, AN 2009-E03534, Jan. 22, 2009.

Wakita, Takaji et al., "Production of infectious hepatitis C Virus in tissue culture from a cloned viral genome" Nature Medicine, Jul. 2005, pp. 791-796, vol. 11, No. 7.

Yanagi, Masayuki et al., "Transcripts of a Chimeric cDNA Clone of Hepatitis C Virus Genotype 1b Are Infectious in Vivo" Virology, 1998, pp. 161-172, vol. 244.

Yi, Minkyung et al., "Compensatory Mutations in E1, p7, NS2, and NS3 Enhance Yields of Cell Culture-Infectious Intergenotypic Chimeric Hepatitis C Virus" Journal of Virology, Jan. 2007, pp. 629-638, vol. 81, No. 2.

Blight, et al., "Efficient Replication of Hepatitis C Virus Genotype 1a RNAs in Cell Culture", Journal of Virology, Mar. 2003, p. 3181-3190, vol. 77, No. 5.

Gottwein et al., "Cutting the Gordian Knot—Development and Biological Relevance of Hepatitis C Virus Cell Culture Systems", Advances in Virus Research, 2008 p. 51-133, vol. 71.

Kalinina et al., "A Natural Intergenotypic Recombinant of Hepatitis C Virus Identified in St. Petersburg" Journal of Virology, Apr. 2002, p. 4034-4043, vol. 76, No. 8.

Scheel et al., "Efficient Culture Adaptation of Hepatitis C Virus Recombinants with Genotype-Specific Core-NS2 by Using Previously Identified Mutations", Journal of Virology, Mar. 2011, p. 2891-2906, vol. 85, No. 6.

Scheel et al., "Development of JFH1-based Cell Culture Systems for Hepatitis C Virus Genotype 4a and Evidence for Cross-Genotype Neutralization", PNAS, Jan. 22, 2008, p. 997-1002, vol. 105, No. 3.

* cited by examiner

US 8,454,974 B2

ADAPTIVE MUTATIONS ALLOW ESTABLISHMENT OF JFH1-BASED CELL CULTURE SYSTEMS FOR HEPATITIS C VIRUS GENOTYPE 4A

Cross Reference to Related Applications

This application claims the benefit of priority to and is a U.S. National Phase Application of PCT International Application Number PCT/DK2008/050085, filed on Apr. 11, 2008, designating the United States of America and published in the English language, which is an International Application of and claims the benefit of priority to Danish Patent Application No. PA 2007 00545, filed on Apr. 13, 2007, and Danish Patent Application No. PA 2007 01841, filed on Dec. 20, 2007. The disclosures of the above-referenced applications are hereby expressly incorporated by reference in their entireties.

FIELD OF THE INVENTION

This invention provides infectious recombinant hepatitis C genotype 4 viruses (HCV), and vectors, cells and animals comprising the same. The present invention provides methods of producing the infectious recombinant HCV genotype 4, and their use in identifying anti-HCV therapeutic and including for use in vaccines and diagnostics and, as well as sequences of HCV associated with HCV pathogenesis.

BACKGROUND

Hepatitis C virus, is one of the most widespread infectious diseases in the world. About 170 million people are infected with hepatitis C virus (HCV) worldwide with a yearly incidence of 3-4 million. While the acute phase of infection is mostly asymptomatic, the majority of acutely infected individuals develops chronic hepatitis and is at increased risk of developing liver cirrhosis and hepatocellular carcinoma. Thus, HCV infection is a major contributor to end-stage liver disease and in developed countries to liver transplantation.

HCV is a small, enveloped virus classified as a member of the Flaviviridae family. Its genome consists of a 9.6 kb single stranded RNA of positive polarity composed of 5' and 3' untranslated regions (UTR) and one long open reading frame (ORF) encoding a polyprotein, which is co- and posttranslationally cleaved and thus yields the structural (Core, E1, E2), p7 and nonstructural (NS2, NS3, NS4A, NS4B, NS5A, NS5B) proteins.

HCV isolates from around the world exhibit significant genetic heterogeneity. At least 6 major HCV genotypes (genotypes 1-6) have been identified, which differ in nucleotide and amino acid sequence composition by 31-35% (Bukh et al. 1993). In addition, there are numerous subtypes (a, b, c, etc.). In the Middle East, particularly in Egypt, up to 15% of the population are infected with HCV. From this geographic region HCV genotype 4 constitute about 90% of the cases diagnosed. The high prevalence of HCV genotype 4 and in particular HCV genotype 4a in Egypt is believed to be caused by unintended transmission to the population through parenteral intervention against schistosomiasis. The prevalence HCV genotype 4 in Western countries has traditionally been low, but in certain European regions this genotype has been shown to be significant mainly among intravenous dug users. At present the incidences continues to increase.

The only approved therapy for HCV comprises a combination therapy with interferon and ribavirin. Such therapy is expensive and associated with severe side-effects and contraindications. Sustained viral response can be achieved in only about 55% of treated patients in general, in 85-90% of patients infected with genotypes 2 and 3 and only in 40-50% of patients infected with genotype 1 and 4. There is no vaccine against HCV.

Since its discovery in 1989, research on HCV has been hampered by the lack of appropriate cell culture systems allowing for research on the complete viral life cycle as well as new therapeutics and vaccines. Full-length consensus cDNA clones of HCV strain H77 (genotype 1a) and J6 (genotype 2a) shown to be infectious in the chimpanzee model, were apparently not infectious in vitro. Replicon systems permitted the study of HCV RNA replication in cell culture using the human liver hepatoma cell line Huh7 but were dependent on adaptive mutations, that were deleterious for infectivity in vivo.

In 2001, a genotype 2a isolate (JFH1) was described (Kato et al., 2001), which yielded high RNA titers in the replicon system without adaptive mutations (Kato et al., 2003).

A major breakthrough occurred in 2005, when formation of infectious viral particles was reported after transfection of RNA transcripts from the JFH1 full-length consensus cDNA clone into Huh7 cells (Wakita et al., 2005) (Zhong et al., 2005)

At the same time, Lindenbach et al. demonstrated that the intragenotypic 2a/2a recombinant genome (J6/JFH1), in which the structural genes (C, E1, E2), p7 and NS2 of JFH1 were replaced by the respective genes of pJ6CF, produced infectious viral particles in Huh7.5 cells (a cell line derived from bulk Huh7 cells) with an accelerated kinetic (Lindenbach et al., 2005). Cell culture derived J6/JFH viruses were apparently fully viable in vivo.

Despite the importance of the described cell culture systems they represent only a single subtype (genotype 2a) of HCV. It is important to develop cell culture systems for representative strains of other HCV genotypes, since neutralizing antibodies are not expected to cross-neutralize all genotypes and new specific antiviral compounds might have differential efficiencies against different genotypes. For the genotype specific study of the function of the structural proteins, p7 and NS2 as well as related therapeutics such as neutralizing antibodies, fusion inhibitors, ion-channel blockers and protease inhibitors, it would be sufficient to construct intergenotypic recombinant viruses in analogy to J6/JFH.

Pietschmann et al. 2006 disclose construction and characterization of infectious intragenotypic and intergenotypic hepatitis C virus recombinants. The authors created a series of recombinant genomes allowing production of infectious genotype 1a, 1b, 2a and 3a particles by constructing hybrid genomes between the JFH1 isolate and the HCV isolates: H77 (genotype 1a), Con1 (genotype 1b), J6 (genotype 2a) and 452 (genotype 3a) respectively. Thus, disclosing both genotypes completely different from the genotype disclosed in the present application and relating to completely different strains of origin.

The infectious titers of the 1a, 1b and 3a genotypes disclosed in Pietschmann et al. 2006 are not at a level sufficiently high for practical utilization in functional analysis, drug and vaccine development or other applications. For such applications, including screening of potential drugs and development of potential vaccine candidates, the skilled person will know that infectivity titers below $10^3$ TCID50/mL contain insufficient amounts of infectious virus.

Accordingly, the study does not attempt cell culture adaptation of the genotype recombinants, e.g. by serial passage of cell culture derived viruses to naïve cells and it is not investigated whether adaptive mutations develop after transfection in cell culture. In fact, Pietschmann et al does not even provide any sequence data of the virus produced in the cell culture.

SUMMARY OF THE INVENTION

In the present study, the inventors used the ED43 reference isolate (genotype 4a) to construct a viable, JFH1-based genome. The present inventors serially passaged ED43/JFH1 virus in cell culture, obtained relatively high HCV RNA titers and infectivity titers, and identified adaptive mutations required for efficient growth.

The present inventors have developed a robust cell culture system for HCV genotype 4a. This is an important advance for the study of HCV, since genotype 4a is highly prevalent especially in the Middle East, and since it permits detailed molecular studies of HCV and enhances the potential for developing broadly reactive reagents against HCV, including but not limited to small molecule drugs, antibodies and vaccines. Accordingly, the present invention may be used for individualised treatment of patients infected with one of the six major genotypes.

In one aspect the present invention relates to a replicating RNA comprising the structural genes (Core, E1, E2), p7 and the non-structural gene NS2 of genotype 4a and the non-structural genes NS3, NS4A, NS4B, NS5A and NS5B and part of NS2 from the JFH1 strain.

In another aspect the present invention pertains to an isolated nucleic acid molecule which encodes human hepatitis C virus of genotype 4a/JFH1, wherein said molecule is capable of expressing said virus when transfected into cells.

In yet another aspect the present invention pertains to a composition comprising a nucleic acid molecule according to the present invention, a cassette vector for cloning viral genomes, methods for producing a cell which replicates HCV 4a/JFH1 RNA and cells obtainable there from.

In another aspect the present invention pertains to methods for producing a hepatitis C virus particle, methods for in vitro producing a hepatitis C virus-infected cell.

In a further aspect the present invention pertains to methods for screening an anti-hepatitis C virus substance, hepatitis C vaccines comprising a hepatitis C virus particle, methods for producing a hepatitis C virus vaccine and antibodies against hepatitis C virus.

DETAILED DESCRIPTION

The present invention advantageously provides hepatitis C virus (HCV) nucleotide sequences capable of replication, expression of functional HCV proteins, and infection in vivo and in vitro for development of antiviral therapeutics and diagnostics.

The present inventors have established the first cell culture system for studying HCV genotype 4. Except for the HCV retroviral pseudo particle system (HCVpp) incorporating E1 and E2 of genotype 4a isolates, this is the first functional in vitro model system for studying genotype 4, which is an increasingly important genotype dominating the Middle East, regions of Africa and currently spreading to Europe. This is a significant step in extending the current HCV cell culture systems to all six major genotypes.

Nucleic Acid Molecules (cDNA Clones and RNA Transcripts)

In a broad aspect, the present invention is directed to a genetically engineered hepatitis C virus (HCV) encoded by nucleic acid sequences such as a complementary DNA (cDNA) sequence and replicating RNA (ED43/JFH1-α or -β) comprising the structural genes (core, E1, E2), p7 and part of the non-structural gene NS2 of genotype 4a (e.g. strain ED43, genbank accession number Y11604) and the non-structural genes NS3, NS4A, NS4B, NS5A and NS5B and part of NS2 from the JFH1 strain (genbank accession number AB047639) as well as a replicating RNA (ED43/JFH1-γ) comprising the structural genes (core, E1, E2), p7 and non-structural gene NS2 of genotype 4a (e.g. strain ED43) and the non-structural genes NS3, NS4A, NS4B, NS5A and NS5B from the JFH1 strain.

Thus in one embodiment, the present invention relates to a replicating RNA comprising the structural genes (Core, E1, E2), p7 and the non-structural gene NS2 of genotype 4a and the non-structural genes NS3, NS4A, NS4B, NS5A and NS5B from the JFH1 strain.

In another embodiment part of the non-structural gene NS2 is of genotype 4a and part is of the JFH1 strain.

In another embodiment the genotype 4a is of the strain ED43.

In yet another embodiment the strains are ED43/JFH1-α, ED43/JFH1-β or ED43/JFH 1-γ.

The invention provides an isolated nucleic acid molecule encoding an infectious recombinant HCV genome, which nucleic acid comprises an intergenotypic HCV genome. In one embodiment, the intergenotypic HCV genome comprises sequences encoding structural genes (Core, E1, E2), p7 and nonstructural genes (NS2) or parts hereof from a first HCV strain, and sequences encoding the 5' untranlated region (UTR), nonstructural genes (NS2) NS3, NS4A, NS4B, NS5A, NS5B, and the 3' UTR from a second HCV strain.

In one embodiment, the first HCV strain and the second HCV strain are from different genotypes.

In one embodiment, the first HCV strain is strain ED43, and in another embodiment, the second HCV strain is strain JFH1.

The present inventors constructed three ED43/JFH1 viruses (α, β and γ) with different C-terminal genotype junctions. As expected, since replication depend on JFH1 non-structural sequences, all JFH1-based recombinants replicated in Huh7.5 cell culture after transfection. For ED43/JFH1-α, the junction was placed after the first TM domain of NS2.

Interestingly, in difference to a study on JFH1-based inter- and intra-genotypic recombinants by Pietschmann et al. suggesting using the α-junction in obtaining the most efficient phenotype, no infectious ED43/JFH1-α viruses were produced. Thus, our results suggest that the conclusion, that the α-junction in general is favourable for construction of JFH1-based recombinants, is strongly dependent on the considered isolate. ED43/JFH1-β and -γ virus production was significantly delayed compared to the control 2a virus following initial transfection but not in subsequent passages. Four cell-free passages with immediate spread of ED43/JFH1-β and -γ, confirmed the robust genotype 4a in vitro infection.

We mimicked a natural 2k/1b isolate in the construction of ED43/JFH1-β, placing the junction in the cytoplasmic protease domain and hereby generated an in vitro infectious virus. Some controversy has been whether the NS2 C-terminal part is located cytoplasmic preceded by three TM domains or luminal, preceded by four TM domains. Anyhow, our selection of genotype junction shows the advantage in considering natural evolution for in vitro research. The fact that ED43/JFH-β but not -α generated infectious viruses indicates that ED43 sequences between the two junction sites are needed for interaction with upstream sequence in the Core-p7 region or the N-terminal part of NS2 during assembly and/or release. NS2 ™ regions possibly require genotype specific interactions with each other and/or TM regions of E1, E2 or p7, while the protease domain can be of a different genotype. This is in accordance with findings in a study on H77/JFH1 recombinants, that homogenous genotype in the Core-p7 region and the NS2 sequence N-terminal to the β-junction is necessary for infectivity, but in contradiction to Pietschmann et al.'s findings on similar JFH1-based constructs of genotype 1a and 1b.

The viability of ED43/JFH1-γ underlines the permissiveness of intergenotypic recombinants harbouring an NS2/NS3 junction similar to the J6/JFH virus and some natural occurring isolates. Importantly, this construct also contains the longest ED43 region tested. The production of infectious viruses from ED43/JFH1-γ supports others and our findings, that the unique ability of JFH1 to efficiently replicate HCV RNA is compatible with replacement of Core-NS2 of other genotypes In one embodiment, the HCV nucleic acid molecule of the present invention comprises the nucleic acid sequence (cDNA) of ED43/JFH1-β, SEQ ID NO 1 and of ED43/JFH1-γ, SEQ ID NO 2 and of ED43/JFH-α, SEQ ID NO 5. In another embodiment the nucleic acid molecule has at least a functional portion of a sequence as shown in SEQ ID NO: 1 and SEQ ID NO 2 and SEQ ID NO 5, which represents a specific embodiment of the present invention exemplified herein.

In yet an embodiment the nucleic acid molecule comprises the nucleic acid sequence with a sequence identity of at least 90% to that of SEQ ID NO 1 and/or SEQ ID NO 2 and/or SEQ ID NO 5.

In another embodiment, the nucleic acid comprises a sequence sharing at least 90% identity with that set forth in SEQ ID NO 1 or SEQ ID NO 2 or SEQ ID NO 5, such as 90% identity, 91% identity, 92% identity, 93% identity, 94% identity, 95% identity, 96% identity, 97% identity, 98% identity, or 99% identity.

As commonly defined "identity" is here defined as sequence identity between genes or proteins at the nucleotide or amino acid level, respectively. Thus, in the present context "sequence identity" is a measure of identity between proteins at the amino acid level and a measure of identity between nucleic acids at nucleotide level. The protein sequence identity may be determined by comparing the amino acid sequence in a given position in each sequence when the sequences are aligned. Similarly, the nucleic acid sequence identity may be determined by comparing the nucleotide sequence in a given position in each sequence when the sequences are aligned.

To determine the percent identity of two amino acid sequences or of two nucleic acids, the sequences are aligned for optimal comparison purposes (e.g., gaps may be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

One may manually align the sequences and count the number of identical amino acids. Alternatively, alignment of two sequences for the determination of percent identity may be accomplished using a mathematical algorithm. Such an algorithm is incorporated into the NBLAST and XBLAST programs of (Altschul et al. 1990). BLAST nucleotide searches may be performed with the NBLAST program, score=100, wordlength=12, to obtain nucleotide sequences homologous to a nucleic acid molecules of the invention. BLAST protein searches may be performed with the XBLAST program, score=50, wordlength=3 to obtain amino acid sequences homologous to a protein molecule of the invention. To obtain gapped alignments for comparison purposes, Gapped BLAST may be utilised. Alternatively, PSI-Blast may be used to perform an iterated search which detects distant relationships between molecules. When utilising the NBLAST, XBLAST, and Gapped BLAST programs, the default parameters of the respective programs may be used. See http://www.ncbi.nlm.nih.gov. Alternatively, sequence identity may be calculated after the sequences have been aligned e.g. by the BLAST program in the EMBL database (www.ncbi.nlm.gov/cgi-bin/BLAST). Generally, the default settings with respect to e.g. "scoring matrix" and "gap penalty" may be used for alignment. In the context of the present invention, the BLASTN and PSI BLAST default settings may be advantageous.

The percent identity between two sequences may be determined using techniques similar to those described above, with or without allowing gaps. In calculating percent identity, only exact matches are counted.

It should be noted that while SEQ ID NO 1, SEQ ID NO 2 and SEQ ID NO 5 are DNA sequences, the present invention contemplates the corresponding RNA sequence, and DNA and RNA complementary sequences as well.

In a further embodiment, a region from an HCV isolate is substituted for a corresponding region, e.g., of an HCV nucleic acid having a sequence of SEQ ID NO 1 or SEQ ID NO 2 or SEQ ID NO 5.

In another embodiment, the HCV nucleic acid is a DNA that codes on expression or after in vitro transcription for a replication-competent HCV RNA genome, or is itself a replication-competent HCV RNA genome.

In one embodiment, the HCV nucleic acid of the invention has a full-length sequence as depicted in or corresponding to SEQ ID NO:1, SEQ ID NO 2 and SEQ ID NO 5. Various modifications for example of the 5' and 3' UTR are also contemplated by the invention. In another embodiment, the nucleic acid further comprises a reporter gene, which, in one embodiment, is a gene encoding neomycin phosphotransferase, Renilla luciferase, secreted alkaline phosphatase (SEAP), Gaussia luciferase or the green fluorescent protein.

Naturally, as noted above, the HCV nucleic acid sequence of the invention is selected from the group consisting of double stranded DNA, positive-sense cDNA, or negative-sense cDNA, or positive-sense RNA or negative-sense RNA or double stranded RNA. Thus, where particular sequences of nucleic acids of the invention are set forth, both DNA and corresponding RNA are intended, including positive and negative strands thereof.

In a further embodiment, the nucleic acid sequence of SEQ ID NO 1 or SEQ ID NO 2 or SEQ ID NO 5 or the said nucleic acid sequence with any mutation described in this document is obtained by any other means than what is described above.

In another embodiment, the complementary DNA (cDNA) provided by the present invention encodes human hepatitis C virus of genotype 4a/JFH1, wherein said molecule is capable of expressing said virus when transfected into cells and further capable of infectivity in vivo and wherein said molecule encodes the amino acid sequence of ED43/JFH1-β, SEQ ID NO 3 or ED43/JFH1-γ, SEQ ID NO 4 or ED43/JFH-α, SEQ ID NO 6.

According to various aspects of the invention, HCV nucleic acid, including the polyprotein coding region, can be mutated or engineered to produce variants or derivatives with, e.g., silent mutations, conservative mutations, etc. In a further preferred aspect, silent nucleotide changes in the polyprotein coding regions (i.e., variations of the first, second or third base of a codon leading to a new codon that encodes the same amino acid) are incorporated as markers of specific HCV clones.

Thus, one aspect of the present invention relates to any of the amino acid sequences disclosed herein, such as but not limited to SEQ ID NO 3, 4, and 6.

In yet an embodiment the isolated nucleic acid molecule encodes the amino acid sequence with a sequence identity of at least 90% to that of SEQ ID NO 3 and/or SEQ ID NO 4 and/or SEQ ID NO 6.

In another embodiment, the amino acid sequences comprises a sequence sharing at least 90% identity with that set forth in SEQ ID NO 3 or SEQ ID NO 4 or SEQ ID NO 6, such as 90% identity, 91% identity, 92% identity, 93% identity, 94% identity, 95% identity, 96% identity, 97% identity, 98% identity, or 99% identity.

It should be understood that a sequence identity of at least 90%, such as 90% identity, 91% identity, 92% identity, 93% identity, 94% identity, 95% identity, 96% identity, 97% identity, 98% identity, or 99% identity applies to all sequences disclosed in the present application.

Nucleic acid molecules according to the present invention may be inserted in a plasmid vector for translation of the corresponding HCV RNA. Thus, the HCV DNA may comprise a promoter 5' of the 5'-UTR on positive-sense DNA, whereby transcription of template DNA from the promoter produces replication-competent RNA. The promoter can be selected from the group consisting of a eukaryotic promoter, yeast promoter, plant promoter, bacterial promoter, or viral promoter.

In one embodiment the present invention provides a cassette vector for cloning viral genomes, comprising, inserted therein, the nucleic acid sequence according to the invention and having an active promoter upstream thereof.

Adaptive Mutations

Adapted mutants of a HCV-cDNA construct or HCV-RNA full-length genome with improved abilities to generate infectious viral particles in cell culture compared to the original HCV-cDNA construct or the original HCV-RNA full-length genome are characterized in that they are obtainable by a method in which the type and number of mutations in a cell culture adapted HCV-RNA genome are determined through sequence analysis and sequence comparison and these mutations are introduced into a HCV-cDNA construct, particularly a HCV-cDNA construct according to the present invention, or into an (isolated) HCV-RNA full-length genome, either by site-directed mutagenesis, or by exchange of DNA fragments containing the relevant mutations.

The present inventors here reports adaptive mutations, which allow efficient formation and release of viral particles in cell culture, and thus the present invention relates to these adaptive mutations in the present use as well as use in other strains by changing equivalent positions of such genomes to the adapted nucleotide or amino acid described.

A group of preferred HCV-cDNA constructs, HCV-RNA full-length genomes with the ability to release viral particles in cell culture, which are consequently highly suitable for practical use is characterized in that it contains one, several or all of the nucleic acid exchanges listed below and/or one or several or all of the following amino acid exchanges.

ED43/JFH1-β and -γ virus production was significantly delayed compared to the control 2a virus following initial transfection but not in subsequent passages, indicating a need for adaptive mutations.

Sequencing $1^{st}$, $2^{nd}$ and $3^{rd}$ passage viruses, the present inventors observed a complete changed mutation in the first TM domain of NS2 (A2819G, amino acid T827A) in both infectious ED43/JFH1 recombinants.

ED43/JFH1-γ A3269T (amino acid T977S) further changed completely in the γ-specific ED43 cytoplasmic part of NS2.

The requirement for these adaptations was confirmed by reverse genetics. Thus, introducing these mutation only, leading to the constructs pED43/JFH1-βA2819G and pED43/JFH1-γA2819G,A3269T (SEQ ID NO 7 and 8 with resulting amino acid sequences SEQ ID NO 18 and 19), led to immediate production of infectious viral particles after transfection in cell culture. Introduction of one the two mutations found for ED43/JFH1-γ only, leading to the constructs pED43/JFH1-γA2819G and pED43/JFH1-γA3269T (SEQ ID NO 9 and 10 with resulting amino acid sequences SEQ ID NO 20 and 21), did not lead to production of infectious particles after transfection.

Adaptation was not caused by suboptimal sequences inserted during construction, since the patient ED43 sequence (Chamberlain et al 1997) and ED43 viruses passaged in a chimpanzee (cloning source in the present invention) are identical at these positions.

The E1 mutation A1325T (amino acid T329S) was dominating in $1^{st}$ viral passage, but continued only as a mixture in $2^{nd}$ and $3^{rd}$ passage, and was not at all detected in the $3^{rd}$ passage clonal analysis. Furthermore reverse genetics studies showed A1325T to cause a slightly attenuated phenotype and a need for further genomic adaptation. Hence, A1325T was probably co-selected with A2819G and A3269T and later reversed to the more fit wild-type sequence.

Figure 2:
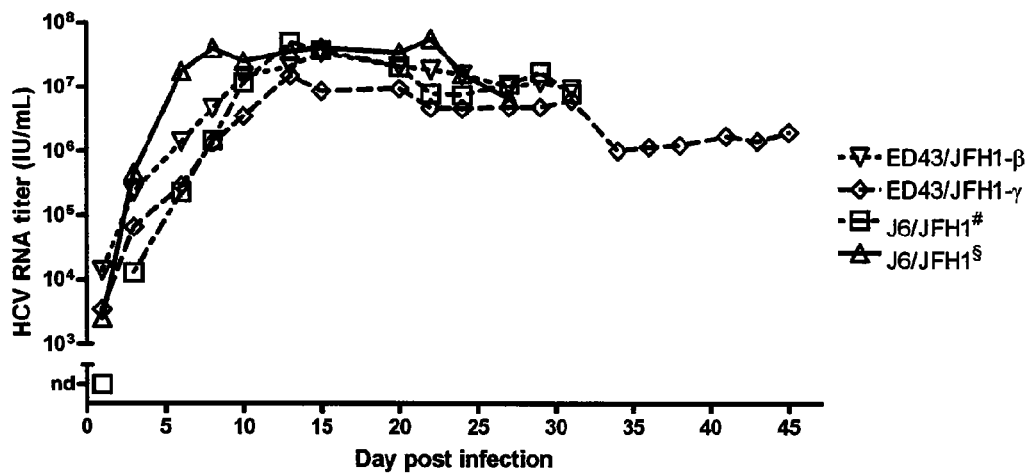
Figure 2:
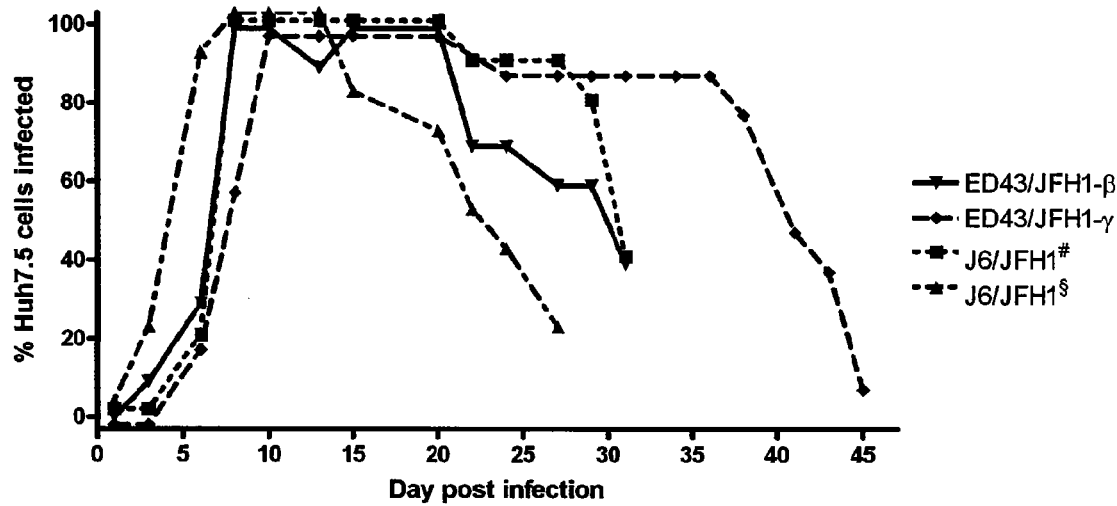
Figure 2:
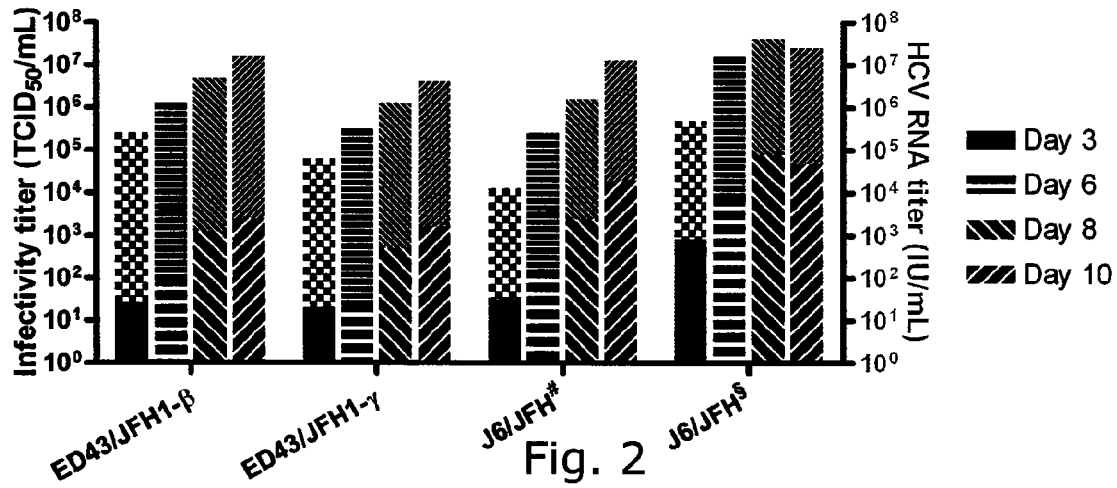

In the $3^{rd}$ and $4^{th}$ passage of ED43/JFH1-γ most cells stayed infected for up to 30 days accompanied by continuance of high RNA titers and reduced cell death compared to earlier passages and J6/JFH, which showed massive infection for approximately 10 days only, followed by proliferation of uninfected cells (FIGS. 2A and B).

Zhong et al. earlier reported on virus-host interaction patterns for JFH1 infecting Huh7 derived cells, showing that the expansion of non-infected cells could be ascribed cellular resistance mechanisms.

The prolonged infection was not observed with adapted recombinants harbouring A1325T, A2819G or A3269T. This could be indicative of a virus-host adapted phenotype introduced in $3^{rd}$ passage.

The amino acid C2270R (DNA T7148C) mutation in NS5A, not seen earlier than $3^{rd}$ passage and present in 7/10 $3^{rd}$ passage clones, could be the determinant of this virus-host optimized phenotype. For instance, NS5A is speculated to be involved in regulation of host cell defence mechanisms such as the IFN-α induced dsRNA dependent protein kinase, PKR as well as 2,5 oligoadenylate synthetase, that has been found to interact with NS5A. The PKR interaction domain has been mapped to include AA 2209-2274 of the H77 reference sequence AF009606 including C2270R. $3^{rd}$ passage ED43/JFH1-β also showed NS5A mutations in the N-terminal membrane anchor sequence (C6306T, amino acid T1989I) and in the very C-terminal region (G7646T, amino acid V2436L).

The ED43/JFH1-γ E1 mutation, G986A (amino acid A216T), was also only found in $3^{rd}$ passage. A number of known genotype 1 and 4 sequences but not ED43 have threonine at position 216 too. We did not analyse non-coding mutations in reverse genetic studies, but still succeeded in generating adapted infectious cDNA clones. Silent mutations could possibly represent co-selection, and have earlier been shown to be functional in infectious cDNA clones. However, non-coding mutations could be important for functional RNA elements e.g. in Core.

For the first time we demonstrated that HCV of genotype 4 utilizes CD81 for entry into host cells.

The infectivity titer of the ED43/JFH1 viruses was diminished by 10-100 fold compared to J6/JFH and earlier studies on J6/JFH, but significantly greater than similar constructs of H77/JFH1 (1a/2a), Con1/JFH1 (1b/2a) and 452/JFH1 (3a/2a) constructed by Pietschmann et al.

In a study using HCV pseudo particles (HCVpp) with HCV E1 and E2 glycoproteins of genotype 4a, McKeating et al. find a significantly lower incorporation of glycoproteins and infectivity in Hep3B cells compared to J6 HCVpp. This could reflect a generally lower infectivity of genotype 4a viruses. On the other hand, the chosen 4a E1 and E2 proteins deviate from ED43 at four AA positions, and large infectivity deviations are seen among different HCVpp isolates of same subtype. In another study on ED43 HCVpp with proteins identical to the ones in our constructs, infectivity was apparently not reduced compared to J6 HCVpp. It has been showed that HCV virions are produced in a spectrum of different boyant densities showing large variation in infectivity. Hence steps of assembly, where ED43 proteins such as Core, E1, E2 and NS2 have to interact with JFH1 proteins could lower production ratio of infectious to non-infectious viral particles. The new possibilities of studying HCV infection in cell culture calls for further studies on variations in infectivity among different isolates, and elucidation of the biological relevance of such will be important for future studies on genotype 4.

Thus in one embodiment, the present invention relates to nucleic acid molecules according to the present invention, wherein said molecule comprises adaptive mutations in E1 and NS2 and NS5A singly or in combination.

In the context of the present invention the term "adaptive mutation" is meant to cover mutations identified in passaged ED43/JFH1 viruses that provides the original ED43/JFH1 genome and any other HCV sequence the ability to grow efficiently in culture. Furthermore all introductions of mutations into the ED43/JFH1 sequence described, whether or not yielding better growth abilities, and the introduction of these mutations into any HCV sequence should be considered Thus the described mutations enable the HCV-RNA genome (e.g. derived from a HCV-cDNA clone) to form viral particles in and release these from suitable cell lines. In addition some of the described mutations might change the function of the concerned proteins in favourable ways, which might be exploited in other experimental systems employing these proteins. This also include other HCV genomes with adaptive mutations, all of them, combinations of them or individual mutations, that grows in culture. In this case the titers might be lower than those listed.

It should be understood that any feature and/or aspect discussed above in connection with the mutations according to the invention apply by analogy to both single mutation and any combination of the mutations.

Clonal analysis of $3^{rd}$ passage viruses showed the conversion of the input plasmid sequence into a quasispecies population of viruses, in accordance to what is seen in HCV in vivo infections. In the limited prepared clonal analysis we detected 6 subpopulations of ED43/JFH1-β and 3 of ED43/JFH1-γ, when positions mutated in at least 5/10 clones were taken into account.

The $3^{rd}$ passage dominating quasispecies containing amino acid mutations, E989K (NS2), T1989I and V2436L (both NS5A) (β) or A216T (E1) and C2270R (NS5A) (γ) in addition to the NS2 mutations T827A (β) or T827A and T977S (γ) found already in $1^{st}$ passage, did not enhance infectivity titers compared to earlier passages. Selected single $3^{rd}$ passage mutations can be of importance for vaccine development. Hence, future studies on ED43 cell culture systems should include analyses of biological function of the identified NS2 mutations as well as relevance of $3^{rd}$ passage mutations and the prolonged cell culture infection.

Furthermore a number of additional mutations were found by direct sequencing of $1^{st}$, $2^{nd}$ and $3^{rd}$ passage as well as in 10 clones of ED43/JFH1-β and ED43/JFH-γ from $3^{rd}$ passage each. Mutations found in at least two clones are likely to occur because the virus has adapted to cell culture. Mutations found in less than two clones could be due to PCR errors and are not listed.

To test various combinations of adaptive mutations, the following constructs were made, and in addition to SEQ ID NO 7 and 8 found to efficiently produce infectious viral particles in culture after transfection (see Example 4); pED43/JFH1-γA1325T,A2819G,A3269T, pED43/JFH1-βT827A,E989K, pED43/JFH1-βT827A,V2436L, pED43/JFH1-βT827A,E989K,T1989I,V2436L, pED43/JFH1-γA216T,T827A,T977S, pED43/JFH1-γT827A,T977S,C2270R and pED43/JFH1-γA216T,T827A,T977S,C2270R (SEQ ID NO 11, 12, 13, 14, 15, 16 and 17 with resulting amino acid sequences SEQ ID NO 22, 23, 24, 25, 26, 27 and 28).

This study demonstrates the possibility for development of recombinant ED43/JFH1 viruses with different genotype junctions. It further underlines the importance in choosing the junction-site for compatibility between the genotypes. As such it presents important information for further studies implementing larger regions of ED43 in the process of obtaining genotype 4 full-length cell culture systems. The developed systems are the first for studying HCV replication genotype 4 in vitro, and could be important for development of inactivated vaccine candidates, since the high-endemic Egypt, a potential region for clinical vaccine trials, mainly have genotype 4a infections. Furthermore the developed systems for the first time allow for genotype 4 specific functional studies and studies of neutralising antibodies and anti-viral drugs in a true cell culture system.

When sequencing HCV genomes from the supernatant of ED43/JFH1-β infected cell cultures, the following changes at the nucleotide level were observed at least once; G787A, C1944G, T2021C, C2206T, A2772G, A2819G, G3305A, T3392C, C4222T, T5836C, C6306T, G7147C, G7198A, A7640G, G7646T and G8150A. These mutations caused the amino acid changes T535S, F561L, D811G, T827A, E989K, Y1018H, T1989I, E2269D, T2434A, V2436L and G2604S.

Thus, one embodiment of the present invention relates to adaptive mutations, wherein said adaptive mutation is at least one of the replacements of the first said nucleotide at the said position of SEQ ID NO 1 by the following said nucleotide selected from the group consisting of G787A, C1944G, T2021C, C2206T, A2772G, A2819G, G3305A, T3392C, C4222T, T5836C, C6306T, G7147C, G7198A, A7640G, G7646T and G8150A.

One embodiment of the present invention relates to adaptive mutations, wherein said adaptive mutation is at least one of the replacements of the first said nucleotide at the said position of SEQ ID NO 1 by the following said nucleotide selected from the group consisting of G787A, C2206T, A2819G, G3305A, C4222T, C6306T and G7646T.

One embodiment of the present invention relates to adaptive mutations, wherein said adaptive mutation is at least one of the replacements of the first said nucleotide at the said position of SEQ ID NO 1 by the following said nucleotide selected from the group consisting of A2819G.

When sequencing HCV genomes from the supernatant of ED43/JFH1-γ infected cell cultures, the following changes at the nucleotide level were observed at least once; C373T, A387C, C436A, G723A, C781A, G986A, G1026A, T1150C, T1211G, A1325T, A1336G, T1369C, T2093A, A2114G, G2251A, C2480T, T2727C, T2731C, A2785G, A2819G, T2916C, T2937C, A2995G, C3001G, G3154A, G3208A, A3269T, A4152G, C4459T, T4540C, G4918A, C4944T, G5079A, A5592G, A5668G, T6184G, A6248G, G7022A, A7103G, T7125C, A7128G, T7148C, G7291A, G7534A, G7584A, T7809C, T7879C, T7985C and A8212G.

These mutations caused the amino acid changes N16T, C128Y, A216T, C229Y, F291V, T329S, C585S, T592A, L714F, L796P, T827A, V859A, V866A, D887E, M956I, T977S, T1531I, G1580E, Q1751R, I1970V, D2228N, M2255V, L2262P, E2263G, C2270R, G2415E and V2490A.

Thus, one embodiment of the present invention relates to adaptive mutations, wherein said adaptive mutation is at least one of the replacements of the first said nucleotide at the said position of SEQ ID NO 2 by the following said nucleotide selected from the group consisting of C373T, A387C, C436A, G723A, C781A, G986A, G1026A, T1150C, T1211G, A1325T, A1336G, T1369C, T2093A, A2114G, G2251A, C2480T, T2727C, T2731C, A2785G, A2819G, T2916C, T2937C, A2995G, C3001G, G3154A, G3208A, A3269T, A4152G, C4459T, T4540C, G4918A, C4944T, G5079A, A5592G, A5668G, T6184G, A6248G, G7022A, A7103G, T7125C, A7128G, T7148C, G7291A, G7534A, G7584A, T7809C, T7879C, T7985C and A8212G.

One embodiment of the present invention relates to adaptive mutations, wherein said adaptive mutation is at least one of the replacements of the first said nucleotide at the said position of SEQ ID NO 2 by the following said nucleotide selected from the group consisting of G986A, A1325T, A1336G, A2785G, A2819G, A3269T, C4459T, G4918A, G7022A, A7128G, T7148C.

One embodiment of the present invention relates to adaptive mutations, wherein said adaptive mutation is at least one of the replacements of the first said nucleotide at the said position of SEQ ID NO 2 by the following said nucleotide selected from the group consisting of A2819G and A3269T.

In another embodiment all the amino acid changes observed herein are provided by the present application. The skilled addressee can easily obtain the same amino acid change by mutating another base of the codon and hence all means of obtaining the given amino acid sequence is intended.

One embodiment of the present invention relates to adaptive mutations, wherein said adaptive mutation is at least one of the replacements of the first said amino acid at the said position of SEQ ID NO 3 by the following said amino acid selected from the group consisting of T535S, F561L, D811G, T827A, E989K, Y1018H, T1989I, E2269D, T2434A, V2436L and G2604S.

One embodiment of the present invention relates to adaptive mutations, wherein said adaptive mutation is at least one of the replacements of the first said amino acid at the said position of SEQ ID NO 3 by the following said amino acid selected from the group consisting of T827A, E989K, T1989I and V2436L.

One embodiment of the present invention relates to adaptive mutations, wherein said adaptive mutation is at least one of the replacements of the first said amino acid at the said position of SEQ ID NO 3 by the following said amino acid selected from the group consisting of T827A.

One embodiment of the present invention relates to adaptive mutations, wherein said adaptive mutation is at least one of the replacements of the first said amino acid at the said position of SEQ ID NO 4 by the following said amino acid selected from the group consisting of N16T, C128Y, A216T, C229Y, F291V, T329S, C585S, T592A, L714F, L796P, T827A, V859A, V866A, D887E, M956I, T977S, T1531I, G1580E, Q1751R, I1970V, D2228N, M2255V, L2262P, E2263G, C2270R, G2415E and V2490A.

One embodiment of the present invention relates to adaptive mutations, wherein said adaptive mutation is at least one of the replacements of the first said amino acid at the said position of SEQ ID NO 4 by the following said amino acid selected from the group consisting of A216T, T329S, T827A, T977S, D2228N, E2263G and C2270R.

One embodiment of the present invention relates to adaptive mutations, wherein said adaptive mutation is at least one of the replacements of the first said amino acid at the said position of SEQ ID NO 4 by the following said amino acid selected from the group consisting of T827A and T977S.

The crucial role of adaptive mutations for the viability of intergenotypic recombinant viruses has recently been found also by others. After transfection of Intergenotypic 1a/2a (H77/JFH1) recombinants, a lag phase was observed before infectious viruses were produced yielding infectivity titers of $10^4$-$10^5$ FFU/ml. It is difficult to evaluate the performance of the 1a/2a recombinants, since the original non-adapted JFH1 genome was used as reference system, which has been shown to perform sub-optimally in the absence of adaptive mutations.

Further the efficiency of the 1a/2a recombinants cannot be directly compared to that of the recombinants used in this study, because it has not been clarified, how different measures of infectivity (FFU versus TCID50) compare The present study also points to a low infectivity of the original ED43/JFH1 viruses. First, the present inventors found low infectivity titers shortly after transfection with pED43/JFH1 in vitro transcripts, which eventually became undeterminable. Second, the original pED43/JFH1 sequence could not be detected in clonal analysis of virus genomes derived from a 3rd viral passage.

The skilled addressee may use the present invention to determine whether the identified sets of mutations can confer viability to other JFH1 based intergenotypic genotype 4a recombinants, which would allow in vitro studies of any patient 4a isolate of interest.

Finally, it would be interesting to elucidate the mechanism of action of the identified mutations. In principle they might enable efficient intergenotypic protein interaction and/or lead to improvement of protein function independent of these intergenotypic interactions, for example by influencing interactions with host cell proteins.

Titer

To determine the efficiency of the developed system, HCV RNA titers are determined in IU/ml (international units/ml) with Taq-Man Real-Time-PCR and infectious titers are determined with a tissue culture infectious dose −50 method. This titer indicates the dilution of the examined viral stock, at which 50% of the replicate cell cultures used in the assay become infected and is given in $TCID_{50}$/ml.

One embodiment of the present invention releates to a nucleic acid molecule of the present invention, wherein said molecule is capable of generating a HCV RNA titer of $10^4$ IU/ml or above following transfection and/or subsequent viral passage, such as a titer of at least $10^5$ IU/mL, such as a titer of at least $10^6$ IU/mL, such as a titer of at least $10^7$ IU/mL, such as a titer of at least $10^8$ IU/mL, such as a titer of at least $10^9$ IU/mL, such as a titer of at least $10^{10}$ IU/mL, such as a titer of at least $10^{11}$ IU/mL, or such as a titer of at least $10^{12}$ IU/mL.

In another embodiment, the present invention relates to a nucleic acid molecule according to the invention, wherein said molecule is capable of generating a HCV infectivity titer of at least $10^2$ $TCID_{50}$/ml or above following transfection and/or subsequent viral passage, such as a titer of at least $10^3$ $TCID_{50}$/ml, such as a titer of at least $10^4$ $TCID_{50}$/ml, such as a titer of at least $10^5$ $TCID_{50}$/ml, such as a titer of at least $10^6$ $TCID_{50}$/ml, such as a titer of at least $10^7$ $TCID_{50}$/ml, such as a titer of at least $10^8$ $TCID_{50}$/ml, such as a titer of at least $10^9$ $TCID_{50}$/ml or such as a titer of at least $10^{10}$ $TCID_{50}$/ml.

It is of course evident to the skilled addressee that the titers described here is obtained using the assay described in this text. Any similar or equivalent titer determined by any method is thus evidently within the scope of the present invention.

Compositions

One embodiment of the present invention relates to a composition comprising a nucleic acid molecule according to the invention suspended in a suitable amount of a pharmaceutical acceptable diluent or excipient.

In another embodiment, this invention provides for compositions comprising an isolated nucleic acid, vector or cell of this invention, or an isolated nucleic acid obtained via the methods of this invention.

In one embodiment, the term "composition" refers to any such composition suitable for administration to a subject, and such compositions may comprise a pharmaceutically acceptable carrier or diluent, for any of the indications or modes of administration as described. The active materials in the compositions of this invention can be administered by any appropriate route, for example, orally, parenterally, intravenously, intradermally, subcutaneously, or topically, in liquid or solid form.

It is to be understood that any applicable drug delivery system may be used with the compositions and/or agents/vectors/cells/nucleic acids of this invention, for administration to a subject, and is to be considered as part of this invention.

The compositions of the invention can be administered as conventional HCV therapeutics. The compositions of the invention may include more than one active ingredient which interrupts or otherwise alters groove formation, or occupancy by RNA or other cellular host factors, in one embodiment, or replicase components, in another embodiment, or zinc incorporation, in another embodiment.

The precise formulations and modes of administration of the compositions of the invention will depend on the nature of the anti-HCV agent, the condition of the subject, and the judgment of the practitioner. Design of such administration and formulation is routine optimization generally carried out without difficulty by the practitioner.

It is to be understood that any of the methods of this invention, whereby a nucleic acid, vector or cell of this invention is used, may also employ a composition comprising the same as herein described, and is to be considered as part of this invention.

"Pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopoeia or other generally recognized pharmacopoeia for use in animals, and more particularly in humans.

The term "excipient" refers to a diluent, adjuvant, carrier, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The term "adjuvant" refers to a compound or mixture that enhances the immune response to an antigen. An adjuvant can serve as a tissue depot that slowly releases the antigen and also as a lymphoid system activator that non-specifically enhances the immune response. Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvmm*. Preferably, the adjuvant is pharmaceutically acceptable.

Cells

The nucleotides of the present invention may be used to provide a method for identifying additional cell lines that are permissive for infection with HCV, comprising contacting (e.g. transfecting) a cell line in tissue culture with an infectious amount of HCV RNA of the present invention, e.g., as produced from the plasmid clones, and detecting replication and formation and release of viral particles of HCV in cells of the cell line.

Naturally, the invention extends as well to a method for identifying an animal that is permissive for infection with HCV, comprising introducing an infectious amount of the HCV RNA, e.g., as produced by the plasmids, to the animal, and detecting replication and formation and release of viral particles of HCV in the animal. By providing infectious HCV, e.g. comprising a dominant selectable marker, the invention further provides a method for selecting for HCV with further adaptive mutations that permit higher levels of HCV replication in a permissive cell line or animal comprising contacting (e.g. transfecting) a cell line in culture, or introducing into an animal, an infectious amount of the HCV RNA, and detecting progressively increasing levels of HCV RNA and infectious HCV viral particles in the cell line or the animal.

In a specific embodiment, the adaptive mutation permits modification of HCV tropism. An immediate implication of this aspect of the invention is creation of new valid cell culture and animal models for HCV infection.

The permissive cell lines or animals that are identified using the nucleic acids of the invention are very useful, inter alia, for studying the natural history of HCV infection, isolating functional components of HCV, and for sensitive, fast diagnostic applications, in addition to producing authentic HCV virus or components thereof.

Because the HCV DNA, e.g., plasmid vectors, of the invention encode HCV components, expression of such vectors in a host cell line transfected, transformed, or transduced with the HCV DNA can be effected.

For example, a baculovirus or plant expression system can be used to express HCV virus particles or components thereof. Thus, a host cell line may be selected from the group consisting of a bacterial cell, a yeast cell, a plant cell, an insect cell, and a mammalian cell.

In one embodiment, the cell is a hepatocyte, or in another embodiment, the cell is the Huh-7 hepatoma cell line or a derived cell line such as Huh7.5, Huh7.5.1 cell line.

In one embodiment, the cell, or in another embodiment, cell systems of this invention comprise primary cultures or other, also non hepatic cell lines. "Primary cultures" refers, in one embodiment, to a culture of cells that is directly derived from cells or tissues from an individual, as well as cells derived by passage from these cells, or immortalized cells.

In one embodiment, "cell line" refers to a population of cells capable of continuous or prolonged growth and division in vitro. The term "cell lines" also includes immortalized cells. Often, cell lines are clonal populations derived from a single progenitor cell. Such cell lines are also termed "cell clones". It is further known in the art that spontaneous or induced changes can occur in karyotype during storage or transfer of such clonal populations. Therefore, cells derived from the cell clones referred to may not be precisely identical to the ancestral cells or cultures. According to the present invention, such cell clones may be capable of supporting replication of a vector, virus, viral particle, etc., of this invention, without a significant decrease in their growth properties, and are to be considered as part of this invention.

It is to be understood that any cell of any organism that is susceptible to infection by or propagation of an HCV construct, virus or viral particle of this invention is to be considered as part of this invention, and may be used in any method of this invention, such as for screening or other assays, as described herein.

Thus in one embodiment the present invention relates to a method for producing a cell which replicates HCV 4a/JFH1 RNA and produces a virus particle comprising introducing the said RNA according to the invention into a cell.

In one embodiment the 4a strain is ED43.

Also, a method for in vitro producing a hepatitis C virus-infected cell comprising culturing the cell which produces virus particles of the present invention and infecting other cells with the produced virus particle in the culture.

Naturally, the invention extends to any cell obtainable by such methods, for example any in vitro cell line infected with HCV, wherein the HCV has a genomic RNA sequence as described herein. Such as a hepatitis C virus infected cell obtainable by any of the methods described.

In one embodiment, the cell line is a hepatocyte cell line such as Huh7 or derived cell lines e.g. Huh7.5 or Huh7.5.1.

In another embodiment the cell is Huh7.5.

In another embodiment the cell is any cell expressing the genes necessary for HCV infection and replication, such as but not limited to CD81, SR-BI, Claudin-1, -4, -6 or -9 and the low-density lipid receptor.

The invention further provides various methods for producing HCV virus particles, including by isolating HCV virus particles from the HCV-infected non-human animal of invention; culturing a cell line of the invention under conditions that permit HCV replication and virus particle formation; or culturing a host expression cell line transfected with HCV DNA under conditions that permit expression of HCV particle proteins; and isolating HCV particles or particle proteins from the cell culture. The present invention extends to an HCV virus particle comprising a replication-competent HCV genome RNA, or a replication-defective HCV genome RNA, corresponding to an HCV nucleic acid of the invention as well.

Virus Particle

The production of authentic virus proteins (antigens) may be used for the development and/or evaluation of diagnostics. The cell culture system according to the invention also allows the expression of HCV antigens in cell cultures. In principle these antigens can be used as the basis for diagnostic detection methods.

The production of HCV viruses and virus-like particles, in particular for the development or production of therapeutics and vaccines as well as for diagnostic purposes is an embodiment of the present invention. Especially cell culture adapted complete HCV genomes, which could be produced by using the cell culture system according to the invention, are able to replicate and form viral particles in cell culture with high efficiency. These genomes have the complete functions of HCV and in consequence they are able to produce infectious viruses.

Thus in one embodiment the present invention relates to a method for producing a hepatitis C virus particle of the present invention or parts thereof, comprising culturing a cell or an animal to allow either to produce the virus.

In another embodiment the inventions provides a hepatitis C virus particle obtainable by the method described.

Because the invention provides, inter alia, infectious HCV RNA, the invention provides a method for infecting an animal with HCV which comprises administering an infectious dose of HCV RNA, such as the HCV RNA transcribed from the plasmids described above, to the animal. Naturally, the invention provides a non-human animal infected with HCV of the invention, which non-human animal can be prepared by the foregoing methods.

A further advantage of the present invention is that, by providing a complete functional HCV genome, authentic HCV viral particles or components thereof, which may be produced with native HCV proteins or RNA in a way that is not possible in subunit expression systems, can be prepared.

In addition, since each component of HCV of the invention is functional (thus yielding the authentic HCV), any specific HCV component is an authentic component, i.e., lacking any errors that may, at least in part, affect the clones of the prior art. Indeed, a further advantage of the invention is the ability to generate HCV virus particles or virus particle proteins that are structurally identical to or closely related to natural HCV virions or proteins. Thus, in a further embodiment, the invention provides a method for propagating HCV in vitro comprising culturing a cell line contacted with an infectious amount of HCV RNA of the invention, e.g., HCV RNA translated from the plasmids described above, under conditions that permit replication of the HCV RNA.

Further the viability of the developed viruses may be determined in vivo, either in SCID-uPA mice engrafted with human liver tissue or in chimpanzees as shown in Lindenbach et al. 2006.

In one embodiment, the method further comprises isolating infectious HCV. In another embodiment, the method further comprises freezing aliquots of said infectious HCV. According to this aspect of the invention, and in one embodiment, the HCV is infectious following thawing of said aliquots, and in another embodiment, the HCV is infectious following repeated freeze-thaw cycles of said aliquots.

Screening for anti-viral drugs and the determination of drug resistance

It can be assumed that resistance to therapy occurs due to the high mutation rate of the HCV genome. This resistance, which is very important for the clinical approval of a substance, can be detected with the cell culture system according to the invention. Cell lines, in which the HCV-RNA construct or the HCV genome or subgenome replicates and produces infectious viral particles, are incubated with increasing concentrations of the relevant substance and the replication of the viral RNA is either determined by means of an introduced reporter gene or through the qualitative or quantitative detection of the viral nucleic acids or proteins. The release of viral particles is determined by measuring HCV RNA and infectivity titers in the cell culture supernatant. Resistance is given if no or a reduced inhibition of the replication and release of viral particles can be observed with the normal concentration of the active substance. The nucleotide and amino acid replacements responsible for the therapy resistance can be determined by recloning the HCV-RNA (for example by the means of RT-PCR) and sequence analysis. By cloning the relevant replacement(s) into the original construct its causality for the resistance to therapy can be proven.

While the replicon systems facilitated testing of drugs interfering with replication such as NS3/4A protease and polymerase inhibitors, the variant genomes obtained in the present study may prove useful for different research topics. Genomes with the original ED43 Core could be applied to examine genotype 4a specific features of Core.

The systems developed in this study are ideal candidates for the genotype 4a specific testing of therapeutics targeting viral entry, assembly and release. Genomes with the original ED43 E1 and E2 are valuable for testing of neutralizing antibodies and other drugs acting on entry level, such as fusion inhibitors.

The present inventors conducted cross-genotype neutralization studies in HCV cell culture systems recapitulating the entire viral life cycle using JFH1-based viruses with envelope sequences of all 6 major genotypes, which has previously not been possible. HCV E1/E2 assembled on HCV pseudo particles (HCVpp), used in previous neutralization studies could show an unphysiological confirmation, glycosylation pattern and/or lipoprotein association due to the nature of the HCVpp as well as the non-hepatic producer cell-lines used in such experiments. In such studies the viral particles are incubated with the neutralizing substance, e.g. patient derived antibodies present in serum, prior to incubation with cells permissive and susceptible to viral infection. The neutralizing effect, i.e. the inhibitory effect on viral entry, is measured e.g. by relating the number of focus forming units (FFUs, defined as foci of adjacent infected cells) to the equivalent count in a control experiment done under same circumstances without the active inhibitor molecule.

The inventors of the present invention showed that JFH1-based viruses of genotype 1a, 4a, 5a and 6a were efficiently neutralized by chronic phase H06 genotype 1a serum derived from reference Patient H (Table 6). Neutralization of the ancestral H77C/JFH1 virus, whose sequence originates from acute phase Patient H serum, is in agreement with an extensive longitudinal study on neutralizing antibodies in Patient H carried out in the HCVpp system showing neutralization by serum samples taken later but not concurrently or earlier than the envelope sequence used for HCVpp. The results in the cell culture systems compare well to neutralization experiments using Patient H serum from year 26 (H03) carried out in HCVpp systems with envelope proteins of the same prototype isolates of all 6 HCV genotypes as used in the present application, and heterogeneity between the genotypes is thus as previously reported by Meunier et al. 2005.

In addition the present inventors found that cross-genotype neutralization extended to a chronic phase genotype 4a serum (AA), which efficiently neutralized genotype 4a, 5a and 6a and to a lesser extent 1a (Table 6). Accordingly, the JFH1-based cell culture systems which has been developed for HCV genotype 1a/1b, 2a, 3a, 4a, 5a and 6a provides a valuable tool for efficiently screening for and identifying new candidate HCV genotype 1a/1b, 2a, 3a, 4a, 5a and 6a inhibitors e.g. of entry e.g. in serum derived from infected patients. Accordingly this invention, allows identification and raise of cross-neutralizing antibodies, which is important for the development of active and passive immunization strategies. Furthermore the availability of cell culture grown HCV particles bearing envelope proteins of the six major genotypes enables the development of inactivated whole virus vaccines and comprehensive virus neutralization studies.

Figure 5:
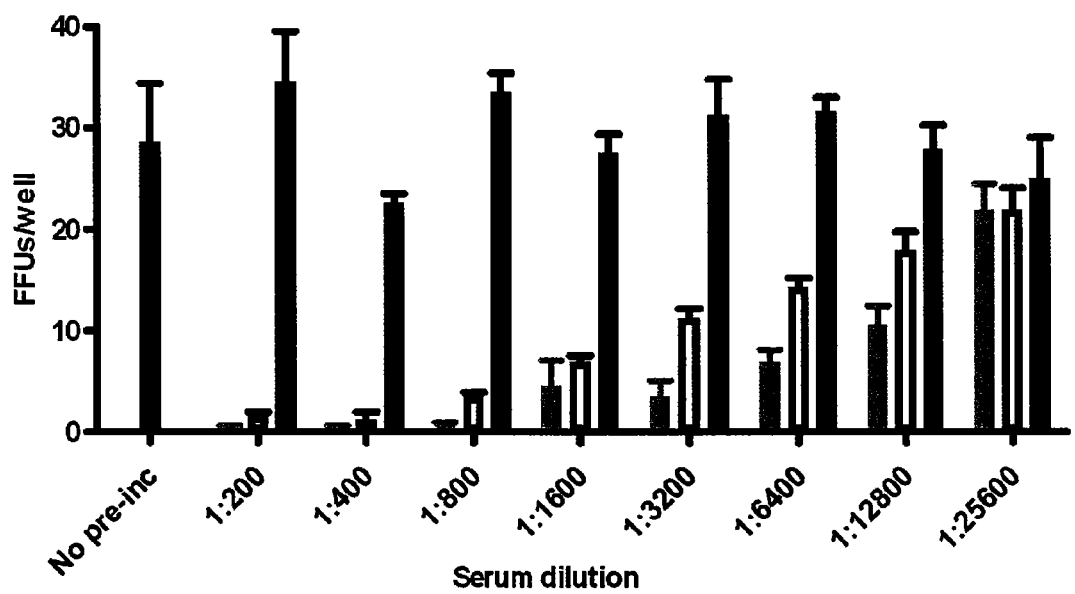

Furthermore the present inventors showed neutralization of 4a/JFH virus (ED43/JFH1-$\gamma_{T827A,T977S}$) with sera from patients infected with genotype 1a and 4a and 5a as can be seen in FIG. 5 and Table 6 and 7.

In one embodiment the present invention relates to a method for identifying neutralizing antibodies.

In another embodiment the present invention relates to a method for identifying cross-genotype neutralizing antibodies.

In one embodiment the present invention relates to a method of raising neutralizing antibodies.

In another embodiment the present invention relates to a method of raising cross neutralizing antibodies.

In one embodiment the present invention related to a method for screening new HCV genotype 1a/1b, 2a, 3a, 4a, 5a and/or 6a inhibitors or neutralizing antibodies, comprising:
a. culturing at least one selected from the group consisting of a cell according to the present invention, a hepatitis C virus infected cell according to the present invention and a hepatitis C virus particle obtainable by the present invention together with a hepatitis C virus permissive cell,
b. subjecting said virus or virus infected cell culture to a blood sample or derivatives thereof or synthetically produced equivalents from a HCV genotype 1a/1b, 2a, 3a, 4a, 5a and/or 6a infected patient, and
c. detecting the amount of replicating RNA and/or the virus particles.

The p7 peptide features two transmembrane domains (TM1 and TM2), and p7 monomers multimerize to form a putative ion channel. Additionally p7 has been shown to contain genotype specific sequences required for genotype specific interactions between p7 and other HCV proteins. Hence, new compounds targeting the putative p7 ion-channel and autoprotease inhibitors interfering with NS2, and drugs targeting cellular proteins involved in the described processes can be tested.

Figure 9:
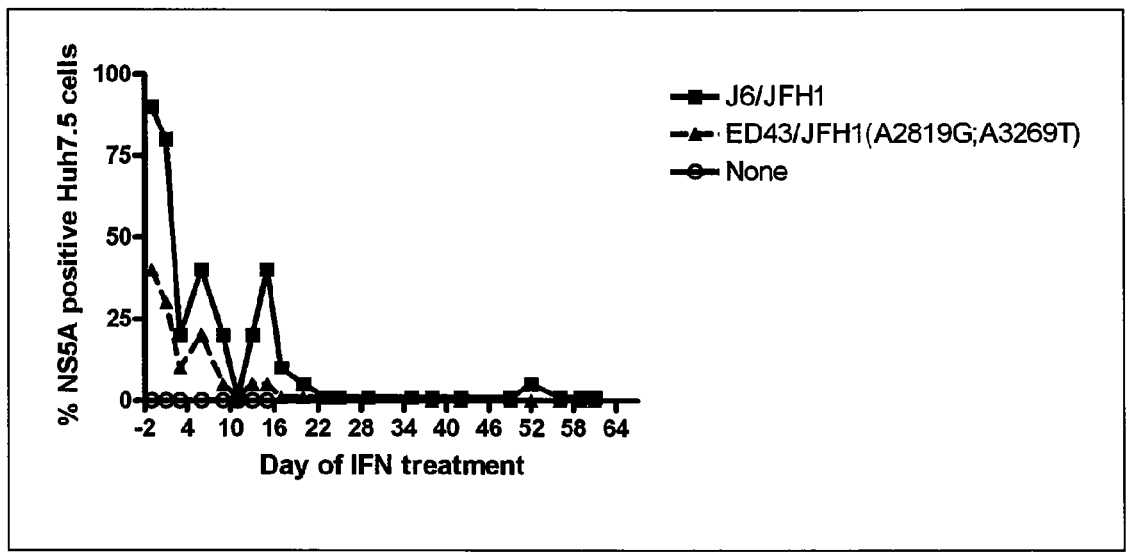

As proof of principle of using the present invention in testing of anti-hepatitis C virus substances, the effects of interferon-α, currently used in combination therapy for HCV, were tested on the infected cell culture. As shown in FIG. 9, addition of interferon-α to a 4a/JFH1 infected culture immediately and significantly reduced the percentage of infected cells. In this in vitro system, prolonged treatment of the culture with interferon-α resulted in complete absence of HCV protein expression as determined by immuno staining.

Thus, one embodiment of the present invention relates to a method for screening an anti-hepatitis C virus substance, comprising
a. culturing at least one selected from the group consisting of a cell according to the present invention, a hepatitis C virus infected cell according to the present invention and a hepatitis C virus particle obtainable by the present invention together with a hepatitis C virus permissive cell, and
b. subjecting said virus or virus infected cell culture to the anti-hepatitis C virus substance, and In another embodiment the present invention relates to a method for screening an anti-hepatitis C virus substance, comprising
 a) culturing at least one selected from the group consisting of a cell according to the present invention, a hepatitis C virus infected cell according to the present invention and a hepatitis C virus particle obtainable by the present invention together with a hepatitis C virus permissive cell,
 b) subjecting said virus or virus infected cell culture to the anti-hepatitis C virus substance, and
 c) detecting the replicating RNA and/or the virus particles in the resulting culture.

In another embodiment, the inhibition of HCV replication and/or infection and/or pathogenesis includes inhibition of downstream effects of HCV. In one embodiment, downstream effects include neoplastic disease, including, in one embodiment, the development of hepatocellular carcinoma.

In one embodiment, the invention provides a method of screening for anti-HCV therapeutics, the method comprising contacting a cell with an isolated nucleic acid molecule encoding an infectious recombinant HCV genome, comprising a chimeric HCV genome and contacting the cell with a candidate molecule, independently contacting the cell with a placebo and determining the effects of the candidate molecule on HCV infection, replication, or cell-to-cell spread, versus the effects of the placebo, wherein a decrease in the level of HCV infection, replication, or cell-to-cell spread indicates the candidate molecule is an anti-HCV therapeutic.

In one embodiment, the method may be conducted be in vitro or in vivo. In one embodiment, the cells as described may be in an animal model, or a human subject, entered in a clinical trial to evaluate the efficacy of a candidate molecule.

In one embodiment, the molecule is labelled for easier detection, including radio-labelled, antibody labelled for fluorescently labelled molecules, which may be detected by any means well known to one skilled in the art.

In one embodiment, the candidate molecule is an antibody.

In one embodiment, the term "antibody" refers to intact molecules as well as functional fragments thereof, such as Fab, F(ab')2, and Fv. In one embodiment, the term "Fab" refers to a fragment, which contains a monovalent antigen-binding fragment of an antibody molecule, and in one embodiment, can be produced by digestion of whole antibody with the enzyme papain to yield an intact light chain and a portion of one heavy chain, or in another embodiment can be obtained by treating whole antibody with pepsin, followed by reduction, to yield an intact light chain and a portion of the heavy chain. In one embodiment, the term "F(ab')2", refers to the fragment of the antibody that can be obtained by treating whole antibody with the enzyme pepsin without subsequent reduction, F(ab')2 is a dimer of two Fab' fragments held together by two disulfide bonds. In another embodiment, the term "Fv" refers to a genetically engineered fragment containing the variable region of the light chain and the variable region of the heavy chain expressed as two chains, and in another embodiment, the term "single chain antibody" or "SCA" refers to a genetically engineered molecule containing the variable region of the light chain and the variable region of the heavy chain, linked by a suitable polypeptide linker as a genetically fused single chain molecule.

Methods of producing these fragments are known in the art.

In another embodiment, the candidate molecule is a small molecule. In one embodiment, the phrase "small molecule" refers to, inter-alia, synthetic organic structures typical of pharmaceuticals, peptides, nucleic acids, peptide nucleic acids, carbohydrates, lipids, and others, as will be appreciated by one skilled in the art. In another embodiment, small molecules, may refer to chemically synthesized peptidomimetics of the 6-mer to 9-mer peptides of the invention.

In another embodiment, the candidate molecule is a nucleic acid. Numerous nucleic acid molecules can be envisioned for use in such applications, including antisense, siRNA, ribozymes, etc., as will be appreciated by one skilled in the art.

It is to be understood that the candidate molecule identified and/or evaluated by the methods of this invention, may be any compound, including, inter-alia, a crystal, protein, peptide or nucleic acid, and may comprise an HCV viral product or derivative thereof, of a cellular product or derivative thereof. The candidate molecule in other embodiments, may be isolated, generated synthetically, obtained via translation of sequences subjected to any mutagenesis technique, or obtained via protein evolution techniques, well known to those skilled in the art, each of which represents an embodiment of this invention, and may be used in the methods of this invention, as well.

In one embodiment, the compound identified in the screening methods as described, may be identified by computer modeling techniques, and others, as described herein. Verification of the activity of these compounds may be accomplished by the methods described herein, where, in one embodiment, the test compound demonstrably affects HCV infection, replication and/or pathogenesis in an assay, as described. In one embodiment, the assay is a cell-based assay, which, in one embodiment, makes use of primary isolates, or in another embodiment, cell lines, etc. In one embodiment, the cell is within a homogenate, or in another embodiment, a tissue slice, or in another embodiment, an organ culture. In one embodiment, the cell or tissue is hepatic in origin, or is a derivative thereof. In another embodiment, the cell is a commonly used mammalian cell line, which has been engineered to express key molecules known to be, or in another embodiment, thought to be involved in HCV infection, replication and/or pathogenesis.

In another embodiment, protein, or in another embodiment, peptide or in another embodiment, other inhibitors of the present invention cause inhibition of infection, replication, or pathogenesis of HCV in vitro or, in another embodiment, in vivo when introduced into a host cell containing the virus, and may exhibit, in another embodiment, an IC50 in the range of from about 0.0001 nM to 100 μM in an in vitro assay for at least one step in infection, replication, or pathogenesis of HCV, more preferably from about 0.0001 nM to 75 μM, more preferably from about 0.0001 nM to 50 μM, more preferably from about 0.0001 nM to 25 μM, more preferably from about 0.0001 nM to 10 μM, and even more preferably from about 0.0001 nM to 1 μM.

In another embodiment, the inhibitors of HCV infection, or in another embodiment, replication, or in another embodiment, pathogenesis, may be used, in another embodiment, in ex vivo scenarios, such as, for example, in routine treatment of blood products wherein a possibility of HCV infection exists, when serology indicates a lack of HCV infection.

In another embodiment, the anti-HCV therapeutic compounds identified via any of the methods of the present invention can be further characterized using secondary screens in cell cultures and/or susceptible animal models. In one embodiment, a small animal model may be used, such as, for example, a tree shrew Tupaia belangeri chinensis. In another embodiment, an animal model may make use of a chimpanzee. Test animals may be treated with the candidate compounds that produced the strongest inhibitory effects in any of the assays/methods of this invention. In another embodiment, the animal models provide a platform for pharmacokinetic and toxicology studies.

Vaccines

The construct according to the invention by itself can also be used for various purposes in all its embodiments. This includes the construction of hepatitis C viruses or HCV-like particles and their production in cell cultures as described.

These HCV or HCV-like particles can be used in particular as vaccine. Thus, one embodiment of the present invention relates to a hepatitis C vaccine comprising a hepatitis C virus particle according to the invention or a part thereof.

In another embodiment, the nucleic acids, vectors, viruses, or viral particles may be further engineered to express a heterologous protein, which, in another embodiment, is mammalian or a derivative thereof, which is useful in combating HCV infection or disease progression. Such proteins may comprise cytokines, growth factors, tumor suppressors, or in one embodiment, may following infection, be expressed predominantly or exclusively on an infected cell surface. According to this aspect of the invention, and in one embodiment, such molecules may include costimulatory molecules, which may serve to enhance immune response to infected cells, or preneoplastic cells, or neoplastic cells, which may have become preneoplastic or neoplastic as a result of HCV infection. In one embodiment, the heterologous sequence encoded in the nucleic acids, vectors, viruses, or viral particles of this invention may be involved in enhanced uptake of a nucleic acids, vectors, viruses, or viral particles, and may specifically target receptors thought to mediate HCV infection.

Further, the present invention relates to a method for producing a hepatitis C virus vaccine comprising using a hepatitis C virus particle according to the invention as an antigen, and naturally any antibody against such hepatitis C virus particle.

Uses

The genotype 4a cell culture system developed of the present invention will be a valuable tool to address different research topics. It will allow the genotype specific study of functions of the structural proteins (Core, E1, E2) as well as p7 and NS2 using reverse genetics. While the replicon systems facilitated testing of drugs interfering with replication such as NS3/4A protease and polymerase inhibitors, the system developed in this study is ideal for the genotype 4 specific testing of new drugs, such as drugs interfering with viral entry, such as fusion inhibitors, as well as assembly and release.

Accordingly the genotype 1a/1b, 2a, 3a, 4a, 5a and 6a developed cell culture systems allows individual patient targeting. This means that when a new potential therapeutic candidate is discovered it is possible to test this particular candidate or combination of candidates on each of the individual genotypes. Knowing which specific genotype(s) the candidate is functioning towards, it allows an individual treatment of each patient dependent on which specific genotype the patient is infected with. Furthermore these cell culture systems allow the development of antibodies and vaccines targeting individual patients.

In addition new therapeutics targeting the putative p7 ion-channel and protease inhibitors targeting NS2 can be tested specifically for genotype 4 thus allowing individual patient targeting.

As ED43/JFH1 viability does not seem to depend on mutations in the envelope glycoproteins, these recombinant viruseses will be well suited for screenings for broadly reactive neutralizing antibodies, thus aiding vaccine development.

The replication level of a virus can be determined, in other embodiments, using techniques known in the art, and in other embodiments, as exemplified herein. For example, the genome level can be determined using RT-PCR. To determine the level of a viral protein, one can use techniques including ELISA, immunoprecipitation, immunofluorescence, EIA, RIA, and Western blotting analysis. To determine the replication rate of a virus, one can use the method described in, e.g., Billaud et al., Virology 266 (2000) 180-188.

In one embodiment, the invention provides a method of identifying sequences in HCV associated with HCV pathogenicity, comprising contacting cells with an isolated nucleic acid molecule encoding an infectious recombinant HCV genome, comprising a chimeric HCV genome, contacting cells with an isolated nucleic acid molecule comprising at least one mutation of the chimeric HCV genome, independently culturing the cells and determining HCV infection, replication, or cell-to-cell spread, in cells contacted with the mutant, versus the chimeric HCV, whereby changes in HCV infection, replication, or cell-to-cell spread in cells contacted with the mutant virus indicates the mutation is in an HCV sequence associated with HCV pathogenicity.

In one embodiment, the invention provides a method of identifying HCV variants with improved growth in cell culture, the method comprising contacting cells with an isolated nucleic acid molecule encoding an infectious recombinant HCV genome, comprising a chimeric HCV genome contacting cells with an isolated nucleic acid molecule comprising at least one mutation of the chimeric HCV genome, independently culturing the cells and determining HCV infection, replication, or cell-to-cell spread, in cells contacted with the chimeric HCV or the mutated virus, whereby enhanced HCV infection, replication, or cell-to-cell spread in cells contacted with the mutated virus indicates that the HCV variant has improved growth in cell culture. In some embodiments, HCV variants are selected for enhanced replication, over a long course of time, in in vitro culture systems. According to this aspect of the invention, and in some embodiments, cells contacted with the variants are characterized by reduced infection, as compared to cells contacted with the chimeric HCV.

Kits

In a related aspect, the invention also provides a test kit for HCV comprising HCV virus components, and a diagnostic test kit for HCV comprising components derived from an HCV virus as described herein.

Furthermore the invention also provide test kits, for screening for new HCV genotype 1a/1b, 2a, 3a, 4a, 5a and 6a inhibitors, neutralizing and cross neutralizing antibodies, comprising HCV virus components.

General

Reference to any prior art in this specification is not, and should not be taken as, an acknowledgment or any form of suggestion that this prior art forms part of the common general knowledge in any country.

All patent and non-patent references cited in the present application, are hereby incorporated by reference in their entirety.

As will be apparent, preferred features and characteristics of one aspect of the invention may be applicable to other aspects of the invention. The invention may be embodied in other specific forms without departing from the spirit or essential characteristics thereof. The foregoing embodiments are therefore to be considered in all respects illustrative rather than limiting on the invention described herein. Scope of the invention is thus indicated be the appended claims rather than by the foregoing description, and all changes that come within the meaning and range of equivalency of the claims are intended to be embraced by reference therein.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In addition, singular reference do not exclude a plurality. Thus, references to "a", "an", "first", "second" etc. do not preclude a plurality.

The invention may be embodied in other specific forms without departing from the spirit or essential characteristics thereof. The foregoing embodiments are therefore to be considered in all respects illustrative rather than limiting on the invention described herein. Scope of the invention is thus indicated be the appended claims rather than by the foregoing description, and all changes that come within the meaning and range of equivalency of the claims are intended to be embraced by reference therein.

The invention will hereinafter be described by way of the following non-limiting Figures and Examples.

Sequences

| Sequence ID | DNA/amino acid(AA) | Name |
| --- | --- | --- |
| SEQ ID NO 1 | DNA | ED43/JFH1-β |
| SEQ ID NO 2 | DNA | ED43/JFH1-γ |
| SEQ ID NO 3 | AA | ED43/JFH1-β |
| SEQ ID NO 4 | AA | ED43/JFH1-γ |
| SEQ ID NO 5 | DNA | ED43/JFH1-α |
| SEQ ID NO 6 | AA | ED43/JFH1-α |
| SEQ ID NO 7 | DNA | pED43/JFH1-$\beta_{A2819G}$ |
| SEQ ID NO 8 | DNA | pED43/JFH1-$\gamma_{A2819G, A3269T}$ |
| SEQ ID NO 9 | DNA | pED43/JFH1-$\gamma_{A2819G}$ |
| SEQ ID NO 10 | DNA | pED43/JFH1-$\gamma_{A3269T}$ |
| SEQ ID NO 11 | DNA | pED43/JFH1-$\gamma_{A1325T, A2819G, A3269T}$ |
| SEQ ID NO 12 | DNA | pED43/JFH1-βT827A, E989K |
| SEQ ID NO 13 | DNA | pED43/JFH1-βT827A, V2436L |
| SEQ ID NO 14 | DNA | pED43/JFH1-βT827A, E989K, T1989I, V2436L |
| SEQ ID NO 15 | DNA | pED43/JFH1-γA216T, T827A, T977S |
| SEQ ID NO 16 | DNA | pED43/JFH1-γT827A, T977S, C2270R |
| SEQ ID NO 17 | DNA | pED43/JFH1-γA216T, T827A, T977S, C2270R |
| SEQ ID NO 18 | AA | pED43/JFH1-$\beta_{A2819G}$ |
| SEQ ID NO 19 | AA | pED43/JFH1-$\gamma_{A2819G, A3269T}$ |
| SEQ ID NO 20 | AA | pED43/JFH1-$\gamma_{A2819G}$ |
| SEQ ID NO 21 | AA | pED43/JFH1-$\gamma_{A3269T}$ |
| SEQ ID NO 22 | AA | pED43/JFH1-$\gamma_{A1325T, A2819G, A3269T}$ |
| SEQ ID NO 23 | AA | pED43/JFH1-βT827A, E989K |
| SEQ ID NO 24 | AA | pED43/JFH1-βT827A, V2436L |
| SEQ ID NO 25 | AA | pED43/JFH1-βT827A, E989K, T1989I, V2436L |
| SEQ ID NO 26 | AA | pED43/JFH1-γA216T, T827A, T977S |
| SEQ ID NO 27 | AA | pED43/JFH1-γT827A, T977S, C2270R |
| SEQ ID NO 28 | AA | pED43/JFH1-γA216T, T827A, T977S, C2270R |
| SEQ ID NO 29 | DNA | 4aF193 |
| SEQ ID NO 30 | DNA | 4aF1G-NotI-T7 |
| SEQ ID NO 31 | DNA | 4aF2676 |
| SEQ ID NO 32 | DNA | 4aF2719 |
| SEQ ID NO 33 | DNA | 4aF309 |
| SEQ ID NO 34 | DNA | 4aF5446 |
| SEQ ID NO 35 | DNA | 4aF741 |
| SEQ ID NO 36 | DNA | 4aF9251 |
| SEQ ID NO 37 | DNA | 4aF9271-HindIII |
| SEQ ID NO 38 | DNA | 4aR262 |
| SEQ ID NO 39 | DNA | 4aR489 |
| SEQ ID NO 40 | DNA | 4aR5664 |
| SEQ ID NO 41 | DNA | 4aR862 |
| SEQ ID NO 42 | DNA | 4aR9406 |
| SEQ ID NO 43 | DNA | 4aR9491-Xba |
| SEQ ID NO 44 | DNA | 4aR9504 |
| SEQ ID NO 45 | DNA | JF2879 |
| SEQ ID NO 46 | DNA | JF2962 |
| SEQ ID NO 47 | DNA | JF3198 |
| SEQ ID NO 48 | DNA | JR345 |
| SEQ ID NO 49 | DNA | JR3593 |
| SEQ ID NO 50 | DNA | JR8368 |
| SEQ ID NO 51 | DNA | JR8688 |
| SEQ ID NO 52 | DNA | RU-O-5720 |
| SEQ ID NO 53 | DNA | RU-O-5721 |
| SEQ ID NO 54 | DNA | JVF12328 |
| SEQ ID NO 55 | DNA | 2aR2905/4aR2866 |
| SEQ ID NO 56 | DNA | 2aR3220/4aR3185 |
| SEQ ID NO 57 | DNA | 2aR3451/4aR3419 |
| SEQ ID NO 58 | DNA | −285s-HCV-MOD |
| SEQ ID NO 59 | DNA | 9470R_JFH1 |
| SEQ ID NO 60 | DNA | consR268 |
| SEQ ID NO 61 | DNA | consR312 |

-continued

| Sequence ID | DNA/amino acid(AA) | Name |
|---|---|---|
| SEQ ID NO 62 | DNA | consR337 |
| SEQ ID NO 63 | DNA | -84S_HCV-MOD |
| SEQ ID NO 64 | DNA | 4aF965 |
| SEQ ID NO 65 | DNA | 4aF1910 |
| SEQ ID NO 66 | DNA | 4aF2719 |
| SEQ ID NO 67 | DNA | 4aR705 |
| SEQ ID NO 68 | DNA | 4aR1080 |
| SEQ ID NO 69 | DNA | 4aR2010 |
| SEQ ID NO 70 | DNA | 4aR2871 |
| SEQ ID NO 71 | DNA | 3329R_JFH1-MOD |
| SEQ ID NO 72 | DNA | 946S_J6 |
| SEQ ID NO 73 | DNA | 1849S_J6 |
| SEQ ID NO 74 | DNA | 2754S_J6 |
| SEQ ID NO 75 | DNA | JR513 |
| SEQ ID NO 76 | DNA | 1109R_J6 |
| SEQ ID NO 77 | DNA | 2111R_J6 |
| SEQ ID NO 78 | DNA | 2763R_J6 |
| SEQ ID NO 79 | DNA | 3774R_J6 |
| SEQ ID NO 80 | DNA | 3081S_J6/JFH1 |
| SEQ ID NO 81 | DNA | 3880S_J6 |
| SEQ ID NO 82 | DNA | 4528S_J6 |
| SEQ ID NO 83 | DNA | 5272S_JFH1 |
| SEQ ID NO 84 | DNA | 6186S_JFH1 |
| SEQ ID NO 85 | DNA | 6862S_JFH1 |
| SEQ ID NO 86 | DNA | 7741S_J6 |
| SEQ ID NO 87 | DNA | 8137S_JFH1 |
| SEQ ID NO 88 | DNA | 4118R_JFH1 |
| SEQ ID NO 89 | DNA | 4796R_JFH1 |
| SEQ ID NO 90 | DNA | 5446R_JFH1 |
| SEQ ID NO 91 | DNA | 6460R_J6 |
| SEQ ID NO 92 | DNA | 7234R_JFH1 |
| SEQ ID NO 93 | DNA | 7848R_JFH1 |
| SEQ ID NO 94 | DNA | 8703R_JFH1 |
| SEQ ID NO 95 | DNA | 9464R(24)_JFH1 |
| SEQ ID NO 96 | DNA | 4aF2261 |

EXAMPLES

Materials and Methods

Source of HCV genotype 4a and HCV plasmids

A plasma pool of strain ED43 was prepared from acute-phase plasmapheresis units collected from an experimentally infected chimpanzee. This plasma pool has an HCV RNA titer of approximately 105.5 IU/ml and an infectivity titer of approximately 105 chimpanzee infectious doses/ml. (Bukh et al, unpublished data). The ED43 strain originated from an Egyptian genotype 4a patient and virus recovered from this patient was originally sequenced by Chamberlain et al 1997.

For construction of the ED43 constructs, a fragment of an ED43 E1 and E2 expression vector (pCMV-ED43(4a-1)) was used to make HCV pseudo particles. pJFH1 and pJFH1/GND used for recombinant 4a/2a constructs was a generous gift from Dr. Wakita RNA Extraction RNA was extracted from plasma and cell culture supernatant using either the High Pure Viral Nucleic Acid Kit (Roche) or the TRIzol (Invitrogen) procedure according to manufacturers protocol. Extracted RNA was diluted in 10 mM DTT with 5% (vol/vol) RNasin (20-40 units/μL) (Promega) and used directly for cDNA synthesis or stored at −80° C.

Reverse Transcription, PCR and Cloning

All reverse transcription-polymerase chain reactions (RT-PCR) were carried out using RNA extracted from 100 μL plasma or cell culture supernatant. Primers (TAG Copenhagen) were 1.25 μM and dNTPs (Invitrogen) were 0.5 mM in RT reactions. For denaturation, RNA was incubated for 2' at 65° C. together with primer and dNTPs and placed on ice. cDNA syntheses was done in a 20 μL volume with enzyme and incubation times as described. The final RT reaction was treated with 1-4U RNase H (Invitrogen) and 1000U RNase T1 (Ambion) for 20' at 37° C. to degrade RNA.

All PCR reactions were done using 2.5 μL cDNA reaction as template in a 50 μL reaction volume. Final concentrations of primer and dNTPs in PCR were 0.2 μM and 0.25 mM respectively. Enzyme and cycle parameters are described. Primer sequences are given in Table 1.

All DNA purification including gel extraction was done using Wizard SV Gel and PCR Clean-Up System (Promega). Restriction endonucleases were from New England Biolabs and ligation reactions were done using Rapid DNA ligation kit (Roche) according to protocol. TOP10 chemically competent bacteria (Invitrogen) were used for all bacterial cloning. After ligation or TA-TOPO reaction (Invitrogen, TA-TOPO cloning kits) 2 μL of the reaction was incubated with 50 μL competent bacteria for 30' on ice before heat-shocking 30' at 42° C. 250 μL SOC-media (Invitrogen) were added to the bacteria and the suspension was incubated for 1 h shaking at 37° C. Bacteria were plated on agar plates with selection as described. DNA preparations were carried out using QIAGEN QIAprep spin miniprep kit or QIAfilter plasmid maxi kit. DNA stocks of plasmids containing the final virus constructs were prepared using QIAGEN Endofree plasmid maxi kit.

Construction of ED43/JFH1 Intergenotypic Recombinants

The ED43 sequence was amplified from the chimpanzee plasma using RT primer 4aR5664 (SEQ ID NO 40) and 200U SuperScriptII (Invitrogen) for 1 h at 42° C.

Enzyme was inactivated for 15' at 70° C. A PCR reaction was set up using the Advantage 2 PCR Enzyme System (Clontech) and primers 4aF1g-NotI-T7 (SEQ ID NO 30) and 4aR5664 (SEQ ID NO 40). Cycling parameters were 1' at 95° C., 35 cycles of 30" at 95° and 9' at 68° C. followed by a final elongation of 9' at 68° C. The PCR product was analyzed by standard agarose gel electrophoresis techniques and TOPO-cloned using TOPO-XL PCR Cloning kit (Invitrogen). From 4 clones we assembled an ED43 sequence deviating from consensus at the two non-coding positions A2458G and A2593G only. pED43/JFH1-γ (SEQ ID NO 2) was constructed by inserting a fusion PCR product containing the ED43 region and the correct junctions directly into pJFH1 8. Templates included a pJFH1 5'UTR PCR fragment, the ED43 consensus sequence and a fusion PCR product containing the ED43/JFH1-γ junction. The JFH1 5'UTR fragment was amplified from pJFH1 using primers JVF12328 (SEQ ID NO 54) (vector sequence) and JR345 (SEQ ID NO 48). Cycling parameters were 45" at 95° C., 20 cycles of 45" at 95° C., 45" at 60° and 1' at 72° followed by a final 10' at 72° C. The γ-junction product was obtained by fusion PCR on two 1st round PCRs. One was using pJFH1 template and forward primer RU-O-5720 (SEQ ID NO 52) at the NS3 5'end and reverse primer RU-O-5721 (SEQ ID NO 53) in NS3. Another was using the ED43 consensus sequence and forward primer 4aF2719 (SEQ ID NO 32) and reverse primer 2aR3451/4aR3419 (SEQ ID NO 57) at the NS2 3'end tailed with 21 nts of the JFH1 NS3 5'end. Cycling parameters in 1st round PCRs were 45" at 95° C., 30 cycles of 45" at 95° C., 45" at 60° and 1'30" at 72° followed by a final 10' at 72° C. Overlapping 1st round PCR products were fused using primers 4aF2719 (SEQ ID NO 32) and RU-O-5721 (SEQ ID NO 53). Cycling parameters were 45" at 95° C., 35 cycles of 45" at 95° C., 45" at 60° and 5' at 72° followed by a final 10' at 72° C. The final fusion PCR was set up using primers JVF12328 (SEQ ID NO 54) and RU-O-5721 (SEQ ID NO 53). Cycle parameters were 45" at 95° C., 35 cycles of 45" at 95° C., 45" at 60° and 5' at 72°, followed by a final 10' at 72° C. The obtained product was directly digested by AgeI and SpeI in the JFH1 5'UTR and NS3 respectively and ligated into pJFH1. All PCR reactions were carried out using proofreading polymerase Pfu (Stratagene).

pED43/JFH1-α and -β (SEQ ID NO 5 and 1) were constructed by inserting a fusion PCR product containing the specific ED43/JFH1 junction into pED43/JFH1-γ. To introduce the correct junction 1st round PCR was done on pJFH1 using forward primer JF2879 (SEQ ID NO 45) (α) or JF3198 (SEQ ID NO 47) (13) and reverse primer RU-O-5721 53. On the ED43 consensus sequence another PCR was done using forward primer F2261 (SEQ ID NO 96) and reverse primer with JFH1 overhang 2aR2905/2aR2866 (SEQ ID NO 55) (α) or 2aR3220/2aR3185 (SEQ ID NO 56) (β). Cycling parameters were 45" at 95° C., 26 cycles of 45" at 95° C., 45" at 62° and 1'30" at 70°, followed by a final 10' at 70° C. Fusion PCR was done on the 1st PCR reactions using primers F2261(SEQ ID NO 96)/RU-O-5721(SEQ ID NO 53) with cycling parameters as above extending cycle-number to 35.

As a negative control a viral polymerase (NS5B) mutant with the active site GDD changed to GND, pED43/JFH1-GND, was created in analogy to pED43/JFH-γ ligating the ED43 containing region into pJFH1/GND digested with AgeI and SpeI. The complete HCV sequence of all final plasmid preparations was sequenced.

ED43/JFH1 (4a/2a) intergenotypic recombinants were constructed to retain the unique cell culture replication abilities of the genotype 2a isolate JFH1, while the structural and part of the non-structural genes were replaced by the genotype 4a reference strain ED43. Three ED43/JFH1 recombinants all containing the amino acid (AA) consensus sequence of Core, E1, E2, p7 and part of or all of NS2 from ED43 were constructed. The 5' untranslated region (UTR, differing from the sequence provided for JFH1 (accession number AB047639) at C301T) as well as the sequence downstream from the NS2-junction, including the nonstructural proteins NS3, NS4A, NS4B, NS5A, NS5B and the 3'UTR was from JFH1 (FIG. 1A). pED43/JFH1-α was constructed with the C-terminal genotype junction between the first and second putative transmembrane (TM) domain of NS2 in analogy to JFH1-based intra- and inter-genotypic recombinants of genotype 1a, 1b, 2a and 3a. pED43/JFH1-β was constructed comprising the internal NS2-junction at a parental hairpin structure in the NS2 protease domain in analogy to the first described natural occurring HCV recombinant. pED43/JFH1-γ contained the entire NS2 gene from ED43. As a negative control, a replication deficient construct mutated in the polymerase active site, pED43/JFH1-GND was constructed. The final ED43 sequences deviated from the consensus sequence at 2 noncoding positions only (A2458G and A2593G).

In Vitro Transcription

For in vitro transcription 5 µg plasmid was XbaI-linearized and treated with mung bean nuclease (New England Biolabs) according to protocol in order to remove XbaI-overhang. This procedure leaves the linearized clone with the exact HCV 3'end. Transcription was carried out for 2 hrs with T7 RNA polymerase (Promega) according to protocol. RNA production was evaluated by gel electrophoresis.

Culturing of Huh7.5 Cells

The human hepatoma cell line Huh7.5 is an INF-α cured clone of the Huh7 hepatoma cell line, with increased HCV replication abilities. Cells were cultured in D-MEM+4500 mg/L Glucose+GlutaMAX-I+Pyruvate (Invitrogen) containing 10% heat inactivated fetal bovine serum (FBS) (Sigma), penicillin at 100 units/ml and streptomycin at 100 mg/ml (Invitrogen) at 5% CO2 and 37° C. Every 2-3 days cells were split after washing with PBS, trypsinizing (Trypsin/EDTA, Invitrogen) and centrifuging for 5' at 1000 rpm. Supernatants were sterile filtered to exclude cells and debris and stored at −80° C.

Transfection of RNA Transcripts into Huh7.5 Cells

Naïve Huh7.5 cells were plated at 3*105/well in 6-well plates the day before transfection. Prior to transfection 1-2.5 µg of unpurified RNA transcripts were incubated with Lipofectamine2000 (Invitrogen) in 500 µL Opti-MEM (Invitrogen) for 20' at room temperature. RNA-Lipofectamine2000 transfection complexes were left on cells for 16-24 hrs before washing.

Infection of Huh7.5 Cells with Supernatants

To prove the production of infectious viruses, sterile filtered supernatant from infected cultures was used to infect naïve Huh7.5 cells. Unless other is described, 1 mL supernatant was used for infection of Huh7.5 cells plated in 6-well plates at 3*105/well the day before. Supernatants were left on cells for 6-24 hrs as described in figure legends.

Immunohistochemistry

For staining, cells grown over night on 4- or 8-well chamberslides (Nunc) were washed 2× with PBS and fixed for 5 minutes with acetone. After washing 2× with PBS and 1× with PBS/Tween-20 (0.1%), slides were incubated with 1° antibody (MAB Murine Anti-Human HCV, Core Protein, Clone B2 (Anogen) used at 1:200 in PBS containing 5% bovine serum albumine (BSA)) for 20' at room temperature. After washing as above, 2° antibody (Alexa Fluor 594 goat anti-mouse IgG (H+L)) and Hoechst33342 (both Invitrogen) for cell nuclei counterstaining, used at 1:500 and 1:10000 dilutions, respectively in PBS/Tween, was added for 5 min.

Finally slides were washed with PBS, mounted with Fluoromount-G (Southern Biotech) and cover slipped. Staining was visualized using a Leica TCS SP5 confocal microscope. Percentage of infected cells was evaluated by assigning values of 0% (no cells infected), 1% (or below), 5%, 10-90% in steps of 10, 95% and 100% (all cells infected).

Infectivity Titration

Viral titers were determined by the tissue culture infectious dose 50 (TCID50). 6*10³/well naïve Huh7.5 cells were plated out in a poly-D-lysine coated 96-well plate (Nunc) the day before infection. Cells were then incubated with 10-fold dilutions of cell culture supernatants in replicates of 6 for 2-3 days. Hereafter cells were washed 2× with PBS and fixed and permeabilized for 5' with cold methanol. After washing 2× with PBS and 1× with PBS/Tween-20, blocking was carried out for 20' with sterile filtered 1% BSA/0.2% skim milk in PBS followed by a 5' blocking of endogenous peroxidase activity using 3% H2O2. Cells were washed as above and a 1:200 dilution of 1° Ab a-NS5A (9E10) in PBS/0.1% tween-20 and incubated on the plate over night at 4° C. After washing, a 1:300 dilution of 2° Ab HRP-goat anti-mouse IgG (H+L) (Amersham Biosciences) in PBS/0.1% tween-20 was added and incubated for 30' at room temperature. Staining was developed using DAB substrate kit (DAKO) for 30' after washing. Wells were scored positive if one or more cells were infected, and the TCID50 was calculated according to the Reed and Muench method.

Real-time PCR (TaqMan) assay for determination of HCV RNA titers. RNA was purified from 200 μL of heat inactivated (56° C. for 30') cell culture supernatant and eluted in a final volume of 50 μL using the Total Nucleic Acid Isolation Kit (Roche) in combination with the Total NA Variable Elution Volume protocol on a MagNA Pure LC Instrument (Roche). As an internal control, Phocine Distemper Virus (PDV) was added to the lysis buffer in a concentration titrated to yield a Ct of ~32 upon real-time PCR analysis. In parallel to RNA purified from cell culture supernatants a quantitative HCV standard panel covering RNA concentrations of 0 to 5×10⁶ IU/mL in one-log increments (OptiQuant HCV Panel, AcroMetrix) was analysed. Real-time PCR analyses of HCV and PDV RNA were carried out in two separate reactions using the TaqMan EZ RT-PCR Kit (Applied Biosystems). For HCV, primers and a FAM-labelled MGB-probe were directed against the 5' UTR and were previously shown to perform equivalently against a panel of the six major HCV genotypes in a different TaqMan assay (Engle R E, Bukh J, and Purcell R H, unpublished data). For PDV, a ready-to-use primer/probe mix was used (Dr. H.G.M. Niesters, Department of Virology, Erasmus Medical Centre, Rotterdam, The Netherlands). The PCR analysis was performed on a 7500 Real-Time PCR System (Applied Biosystems) using 50° C. for 2', 60° C. for 30' and 95° C. for 5' followed by 45 cycles of 94° C. for 20" and 62° C. for 1'. HCV RNA titers (IU/ml) were calculated using a standard curve created from the known concentrations of the standard panel and their corresponding Ct values. The reproducible detection limit of the assay was 500 IU/ml. In order to confirm successful purification, amplification and the absence of PCR inhibitors, the Ct value of the PDV reaction was compared to the expected Ct value (based on a mean of all previous runs; n>9) using the MedLab QC freeware programme. The results of samples with an actual Ct value within ±25D of the expected Ct value were accepted.

Diagnostic PCR and Direct Sequencing of Complete ORF

To confirm the identity of the replicating recombinant viruses a diagnostic PCR was developed. RNA extraction was done as described above and reverse transcription was carried out using 200U SuperScriptIII (Invitrogen) and JFH1 specific RT-primer JR3593 (SEQ ID NO 49) for 1 h at 50° C. in a 20 μL volume. Enzyme was inactivated for 15' at 70° C. The cDNA reaction was treated with 1-4U RNase H (Invitrogen) and 1000U RNase T1 (Ambion) for 20' at 37° C. to degrade RNA. PCR was carried out in 50 μL on 2.5 μL cDNA reaction mixture using AmpliTaq gold (Applied Biosystems) the same reverse primer (JR3593 (SEQ ID NO 49)) and a genotype specific forward primer (JF2962 (SEQ ID NO 46) or 4aF2676 (SEQ ID NO 31)) yielding genotype specific band lengths. Sequencing determined NS2 junction for ED43/JFH1 recombinants.

Direct sequencing of complete ORF was done to identify adaptive mutations. RNA extraction and reverse transcription was done as described above using 400U SuperScriptIII (Invitrogen) and RT-primer 9470R_JFH1 (SEQ ID NO 59). 1st round PCR was performed in a 50 μL volume on 2.5 μL of the cDNA reaction using the Advantage 2 PCR Enzyme System (Clontech), the same reverse primer (9470R_JFH1 (SEQ ID NO 59)) and forward primer −285s-HCV-MOD (SEQ ID NO 58). Cycle parameters were 5 cycles of 35" at 99° C., 30" at 67° C. and 10' at 68° C., 10 cycles of 35" at 99° C., 30" at 67° C. and 11' at 68° C., 10 cycles of 35" at 99° C., 30" at 67° C. and 12' at 68° C. and 10 cycles of 35" at 99° C., 30" at 67° C. and 13' at 68° C. 12~1 kb products were synthesized in a nested PCR covering the entire ORF (nt 297-9427) using primer pairs 1-12 (Table 2). PCR was set up as above using 2.5 μL of the 1st round PCR for each reaction. Initial denaturation was 35 sec at 99° C. followed by 35 cycles with 35 sec at 99° C., 30 sec at 67° C. and 6 min at 68° C. For determination of 5'UTR nt86-296 of selected virus pools another nested reaction was setup using the same 1st round product and primer pair 0 (Table 2). PCR products were agarose gel purified and directly sequenced in both directions.

5'RACE (Rapid Amplification of cDNA Ends)

The extreme 5' end of selected viral genomes was determined following the protocol of the kit '5' RACE System for Rapid Amplification of cDNA Ends, Version 2.0' (Invitrogen) after RNA extraction as above. First strand synthesis was carried out using RT-primer consR337 (SEQ ID NO 62) and by replacing SuperScriptII by SuperscriptIII (Invitrogen), with reverse transcription of 40' at 50° C. and 30' at 55° C. followed by 15' enzyme inactivation at 70° C. To optimize binding on S.N.A.P. cDNA purification columns, samples were reloaded twice, and 16.5 μL of the eluate were used for TdT-tailing according to protocol. 1st round PCR was done according to protocol using reverse primer consR312 (SEQ ID NO 61) and AmpliTaq Gold (Applied Biosystems). Cycle parameters were as following: 10' at 94° C., 40 cycles of 45" at 94° C., 45" at 55° C. and 1'30" at 72° C. followed by a final 10' at 72° C. A nested PCR was done using reverse primer consR268 (SEQ ID NO 60) and cycle parameters as above.

PCR products were agarose gel purified and directly sequenced.

Clonal sequence analysis of 3rd passage ED43/JFH1-β and γ viruses.

RNA extraction was done as described above and reverse transcription was carried out using 400U SuperScriptIII (Invitrogen) and RT-primer JR8688 (SEQ ID NO 51) for 1 h at 50° C. in a 20 μL volume. Enzyme was inactivated for 15' at 70° C. The cDNA reaction was treated with 1-4U RNase H (Invitrogen) and 1000U RNase T1 (Ambion) for 20' at 37° C. to degrade RNA. A long PCR product was generated with primers −285S_HCV-MOD (SEQ ID NO 58) and JR8368 (SEQ ID NO 50) using the Advantage 2 PCR Enzyme System (Clontech) with the following cycling parameters: 1 min at 95° C., 40 cycles with 35 sec at 95° C., 35 sec at 67° C., 9 min at 68° C., and final extension of 9 min at 68° C. The resulting PCR product was gel purified, subcloned into pCR-XL-TOPO (Invitrogen), and 10 clones per construct were sequenced.

Sequencing, Sequence Analysis and Databases

All sequence reactions was performed at Macrogen Inc., Seoul, South Korea. Sequence analysis was performed with Sequencher 4.6, Gene Codes Corporation and freeware Bio-Edit v. 7.0.5. HCV sequences used for alignments were retrieved from The European HCV database (euHCVdb; http://euhcvdb.ibcp.fr/euHCVdb/)(48) and the American HCV database (LANL; http://hcv.lanl.gov/content/hcv-db/index).

Example 1

In Vitro Infectivity of ED43/JFH1 Recombinants Depends on Location of the Recombination Point In vitro transcribed RNA from pED43/JFH1-α, -β, -γ (SEQ ID NO 5, 1 and 2) and -GND as well as pJ6/JFH (positive control), was transfected into Huh7.5 hepatoma cells. ED43/JFH1-α, -β and -γ replicated as evidenced by anti-Core immunostaining at day 1 (FIGS. 1B and C). While J6/JFH infected most Huh7.5 cells (80-100%) within 3 days, the percentage of ED43/JFH1 antigen positive cells decreased. Subsequent viral spread to most cells in the culture was observed for ED43/JHF1-β at day 16 and for ED43/JFH1-γ at day 43 (FIGS. 1B and C). Cytopathic effects followed by proliferation of infection resistant Huh7.5 cells, occurred after infection spread to most cells. Full culture infection was generally seen for approximately 5-10 days. The delayed production of infectious ED43/JFH1-β and -γ viruses was confirmed by infectivity titration using the tissue culture infectious dose-50 method (TCID$_{50}$, Table 3). ED43/JFH1-α replication declined until day 19. Hereafter replication was not observed following the culture until the end of the experiment at day 66. Furthermore, no virus production was observed throughout the experiment, as measured by TCID$_{50}$. 1 mL of filtered supernatant from J6/JFH (day 6, $10^{4,4}$ TCID$_{50}$), ED43/JFH1-β (day 19, $10^{2,9}$ TCID$_{50}$), ED43/JFH1-γ (day 45, $10^{2,9}$ TCID$_{50}$) and ED43/JFH1-GND (day 19) transfection cultures, was used for $1^{st}$ passage to naïve Huh7.5 cells. Both viable ED43/JFH1 constructs readily infected naïve cells, and required only 8 and 10 days respectively to infect the whole culture (FIG. 1C). J6/JFH spread to most cells within 3 days only, reflecting the higher infectious dose of the inoculum.

Example 2

ED43/JFH1 Viral Spread Kinetics Resembles J6/JFH while the Specific Infectivity Titers Appear to be Lower J6/JFH and ED43/JFH1-β and -γ in a total of four cell free passages were serially passaged. Peak genome titers around $10^7$ IU/mL (IU, International Units) were obtained in all experiments, with J6/JFH peaking at $10^{7,7}$ IU/mL in $4^{th}$ passage, ED43/JFH1-β at $10^{7,3}$ IU/mL in $1^{st}$ and $4^{th}$ passage and ED43/JFH1-γ at $10^{7,2}$ IU/mL in $4^{th}$ passage. J6/JFH showed infectivity titers of up to $10^{5,1}$ TCID$_{50}$/mL, while the genotype 4 recombinants peaked at $10^{3,5}$ and $10^{3,6}$ TCID$_{50}$/mL, respectively (Table 4). Inconsistency between genome titers and infectivity titers in J6/JFH and the two genotype 4 recombinants was reflected by a difference in specific infectivity (infectious doses per genomes measured in IU). For J6/JFH specific infectivities of 1:100 were observed. Specific infectivities of 1:1600 only was observed for ED43/JFH1-β and -γ.

In order to directly compare the spread and infectivity of the viruses, approximately $10^3$ TCID$_{50}$ of $1^{st}$ passage J6/JFH and $3^{rd}$ passage J6/JFH, ED43/JFH1-β and -γ were inoculated for 6 hrs on naïve Huh7.5 cells. Similar infection spread kinetics was observed for the four virus cultures, and the spread was reflected in genome titers rising above $10^7$ IU/mL for all cultures (FIG. 2A). Apart from for J6/JFH, $3^{rd}$ passage inoculum, which produced infectious progeny slightly faster, the initial rise in infectivity titer was similar for J6/JFH and the two ED43/JFH1 viruses. The ED43/JFH1 production stagnated and titers peaked at $10^{3,4}$ TCID$_{50}$/mL (γ) and $10^{3,2}$ TCID$_{50}$/mL (γ) while J6/JFH titers continued to rise to $10^{4,9}$ TCID$_{50}$/mL (FIG. 2B), thus confirming observations from earlier passages (Table 4). As the consensus ORF sequence of both J6/JFH pools was confirmed to be identical to the plasmid sequence, the kinetics differences may be ascribed to variation in the assay.

Example 3

Identification of putative adaptive mutations in recovered ED43/JFH1 viruses. The significantly extended time needed for the 4a/2a recombinants to spread in transfection culture relative to subsequent passages may be indicative of requirements of adaptation. Thus, viral RNA was isolated from supernatant at high-titer time points (same used for passage) in $1^{st}$, $2^{nd}$ and $3^{rd}$ passage, and the complete ORF sequences were analyzed by direct sequence analyses of overlapping nested RT-PCR amplicons. Putative adaptive mutations were found as indicated in Table 5 (A-B). Noteworthy regarding recovered ED43/JFH1-β viruses is the occurrence of one coding mutation in the ED43 part of NS2 (A2819G), which changed completely already in $1^{st}$ passage. No other dominating coding mutations where observed, except for an NS5A mutation (G7646T) present only in virus recovered from $3^{rd}$ passage. The NS2 mutation A2819G appeared to be essential for the viability of ED43/JFH1 recombinants, since the same mutation occurred also in ED43/JFH1-γ$1^{st}$ passage virus. Two other dominating coding mutations were observed in $1^{st}$ passage ED43/JFH1-γ; A1325T in the E1 gene and A3269T in the γ-specific ED43 part of NS2. Again, additional dominating coding mutations were only observed in $3^{rd}$ passage (G986A in E1 and T7148C in NS5A). Dominating mutations occurring in $1^{st}$ passage were all consistently seen in $2^{nd}$ and $3^{rd}$ passage viruses, except for the γ-specific A1325T continuing only as a mixture with the original sequence. Additional positions showed co-existence of original and mutant sequence in direct sequencing of $1^{st}$, $2^{nd}$ and $3^{rd}$ passage. The complete 5'UTR of $1^{st}$ passage viruses was sequenced, and no mutations were found.

Clonal Analysis of $3^{rd}$ Passage Viral Quasispecies

Co-existence of different viral quasispecies in the $3^{rd}$ passage was investigated by amplifying nt86-8335 of ED43/JFH1-β and -γ in a single long RT-PCR. 10 clones of each were sequenced (Table 5, A-B).

Analysis confirmed the complete change of A2819G, which was found in all clones from both constructs. 9/10 ED43/JFH1-β clones acquired the coding G7646T NS5A mutation. 5 and 6 of these 9 clones further carried coding mutations G3305A in the JFH1 part of NS2 and C6306T in the NS5A membrane anchor, respectively. Non-coding mutations were observed in Core, E2 and NS3 as indicated in table 5A. All 10 ED43/JFH1-γ clones, in addition to A2819G, confirmed the complete change of A3269T. Furthermore, 7/10 clones carried a distinct pattern of mutations including two coding mutations (G986A in E1 and T7148C in NS5A). By direct sequencing these were observed in $3^{rd}$ passage only. Interestingly, A1325T was not observed in the 10 sequenced $3^{rd}$ passage γ-clones. Non-coding mutations were observed in E1 and NS3.

Example 4

Identification of ED43/JFH1 Vital Adaptive Mutations by Reverse Genetics

Figure 3:
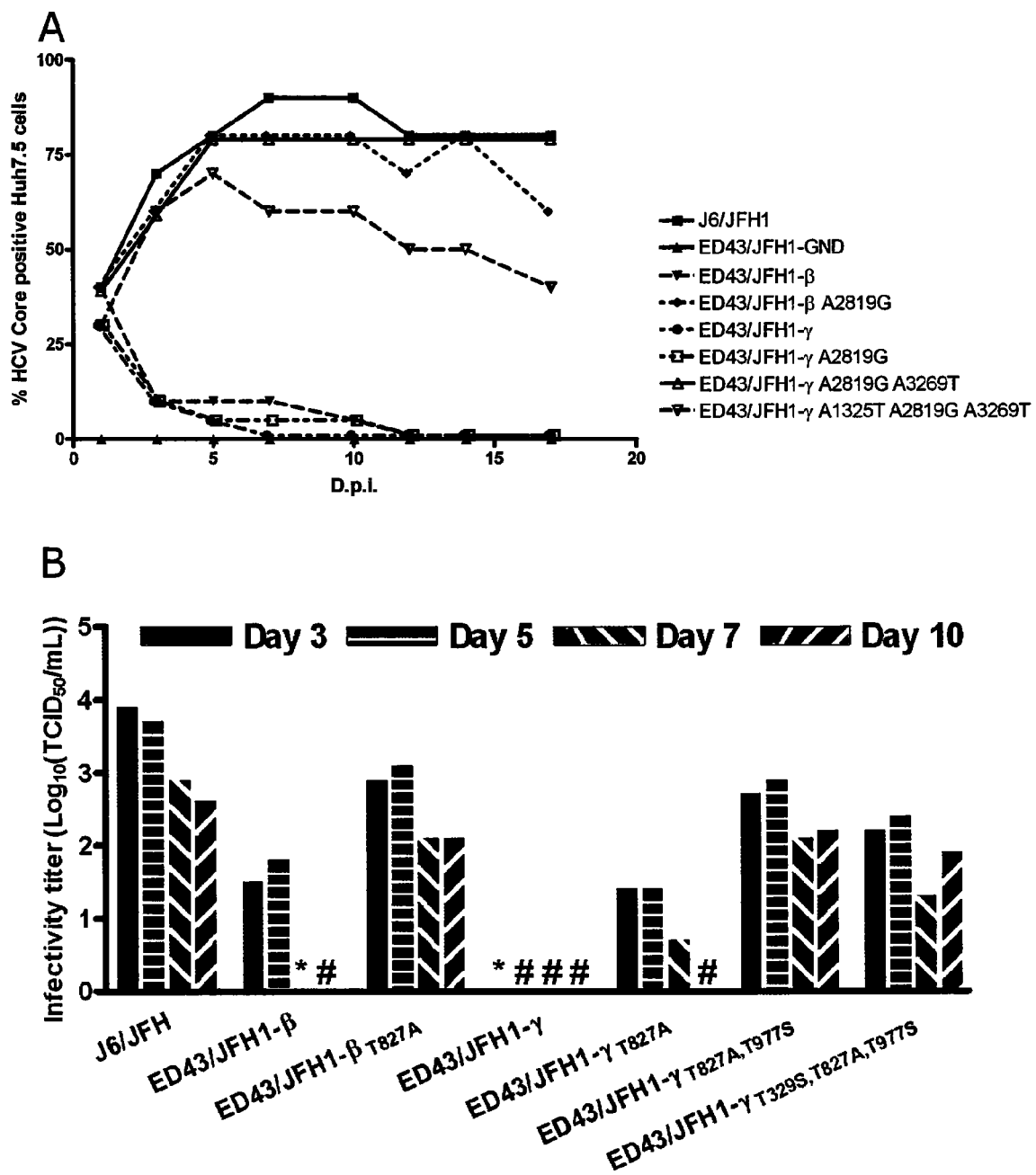

Adaptive mutations were investigated by introducing selected mutations back into the ED43/JFH1-β and -γ cDNA clones. Coding mutations being dominant already in 1$^{st}$ passage virus pools was included as such mutations were likely to prove vital for infectivity. Accordingly pED43/JFH1-$β_{A2819G}$ (SEQ ID NO 7), pED43/JFH1-$γ_{A2819G}$ (SEQ ID NO 9), pED43/JFH1-$γ_{A3269T}$ (SEQ ID NO 10), pED43/JFH1-$γ_{A2819G,A3269T}$ (SEQ ID NO 8) and pED43/JFH1-$γ_{A1325T,A2819G,A3269T}$ (SEQ ID NO 11) were generated. RNA transcripts from mutated plasmids were transfected into Huh7.5 cells along with RNA transcripts from the original ED43/JFH1 plasmids, J6/JFH and ED43/JFH1-GND. While the percentage of cells infected with the original constructs decreased as previously observed, J6/JFH, ED43/JFH1-$β_{A2819G}$, ED43/JFH1-$γ_{A2819G,A3269T}$ and ED43/JFH1-$γ_{A1325T,A2819G,A3269T}$ infection immediately spread in the culture as apparent from FIG. 3A. This was supported by infectivity titers measured on day 3, 5, 7 and 10 (FIG. 3B). J6/JFH titers peaked at approximately $10^4$ TCID$_{50}$/mL, while ED43/JFH1-$β_{A2819G}$ and ED43/JFH1-$γ_{A2819G,A3269T}$ peak titers were approximately 10-fold below the J6/JFH titer.

ED43/JFH1-$γ_{A1325T,A2819G,A3269T}$ peaked at $10^{2.4}$ TCID$_{50}$/mL. Though sufficient for ED43/JFH1-β, single introduction of A2819G into the γ-construct (pED43/JFH1-$γ_{A2819G}$) was not sufficient to confer viability in cell culture (FIGS. 3A and B). In analogy to transfection of the original construct, efficient spread in culture was delayed, here by 42 days. Sequencing of the complete ORF at day 42 revealed the occurrence of the A3269T mutation, thus emphasized the need for the two described NS2 mutations. In addition the virus acquired four completely changed non-coding mutations (G3154A, A4152G, T6184G and T7879C) and two positions with presence of both the original and the mutated sequence (A387C coding and C436A non-coding). The ED43/JFH1-$γ_{T977S}$ transfection culture produced low or undeterminable infectivity titers (FIG. 6), until the virus finally infected most cells on day 30 (FIG. 7) where it had acquired the T827A amino acid change as well as C4944T and T7125C coding for T15351 and L2262P. Introduction of the E1 mutation A1325T indicated a reduction of viral fitness as reflected by percentage of infected cells, infectivity titer (FIGS. 3A and B) and cytopathic effects observed in cell culture (data not shown). At day 5 transfection supernatants of ED43/JFH1-$β_{A2819G}$, ED43/JFH1-$γ_{A2819G,A3269T}$ and ED43/JFH1-$γ_{A1325T,A2819G,A3269T}$ were passed to naïve Huh7.5 cells along with J6/JFH and ED43/JFH1-GND. Infection was confirmed by anti-Core staining. The complete ORF of the infectious progeny from day 17 was sequenced to investigate the genetic stability of the mutated constructs. ED43/JFH1-$β_{A2819G}$ and ED43/JFH1-$γ_{A2819G,A3269T}$ both showed the expected sequence after 17 days of 1$^{st}$ passage infection with no additional mutations. Introduction of A1325T conferred need for genomic adaptation; ED43/JFH1-$γ_{A1325T,A2819G,A3269T}$ acquired two dominating changes (T7809C coding and C781A noncoding) as well as a position with presence of both original and changed sequence (A5592G).

Thus introduction of A2819G into pED43/JFH1-β and A2819G combined with A3269T into pED43/JFH1-γ immediately rescued the production of infectious viruses in Huh7.5 cells. These adapted constructs showed genetic stability during transfection and 1st viral passage. Introduction of A1325T resulted in an attenuated phenotype and requirements for further genomic adaptation.

Figure 6:
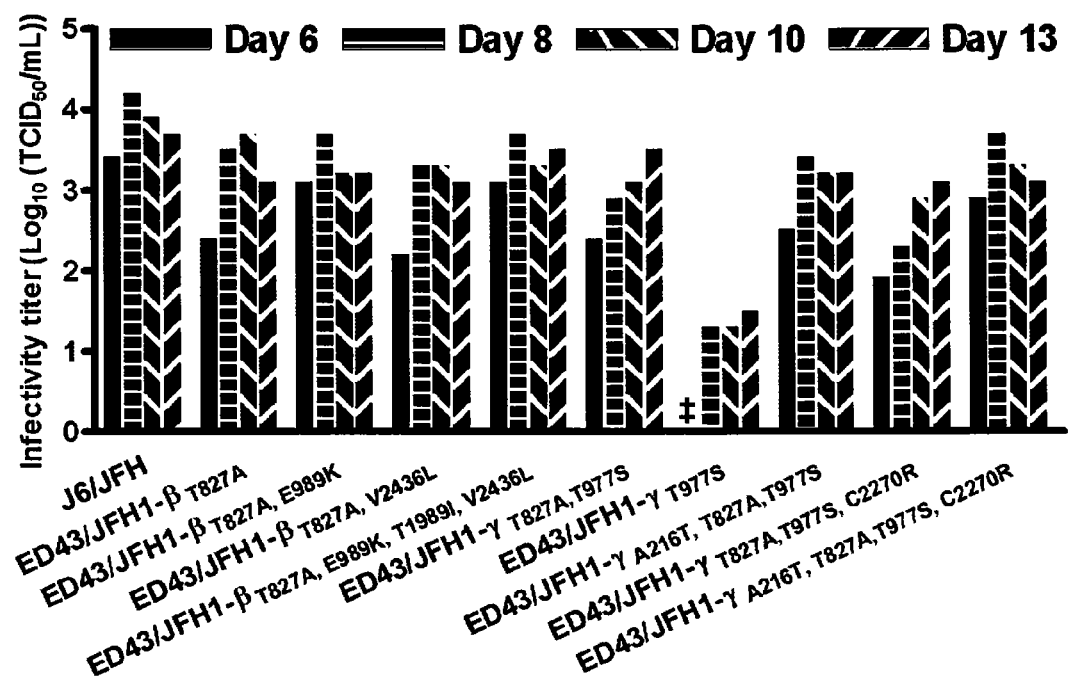
Figure 7:
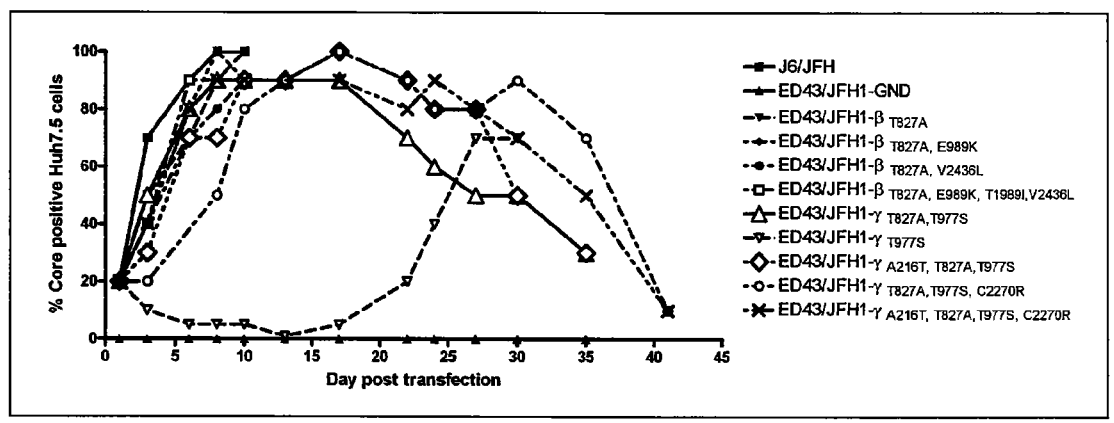

To test whether the additional coding mutations observed in 3$^{rd}$ passage clonal analysis of ED43/JFH1-β and ED43/JFH1-γ (Tables 5A and 5B) could further improve viral infectivity, pED43/JFH1-$β_{T827A,E989K}$ (SEQ ID NO 12), pED43/JFH1-$β_{T827A,V2436L}$ (SEQ ID NO 13) and pED43/JFH1-$β_{T827A,E989K,T1989I,V2436L}$ (SEQ ID NO 14) as well as pED43/JFH1-$γ_{A2161T,T827A,T977S}$ (SEQ ID NO 15), pED43/JFH1-$γ_{T827A,T977S,C2270R}$ (SEQ ID NO 16) and pED43/JFH1-$γ_{A2161T,T827A,T977S,C2270R}$ (SEQ ID NO 17) were constructed. However, no significant increase of peak titers was observed after transfection of Huh7.5 cells (FIG. 6).

Example 5

ED43/JFH1 Infection Depend on CD81

Figure 4:
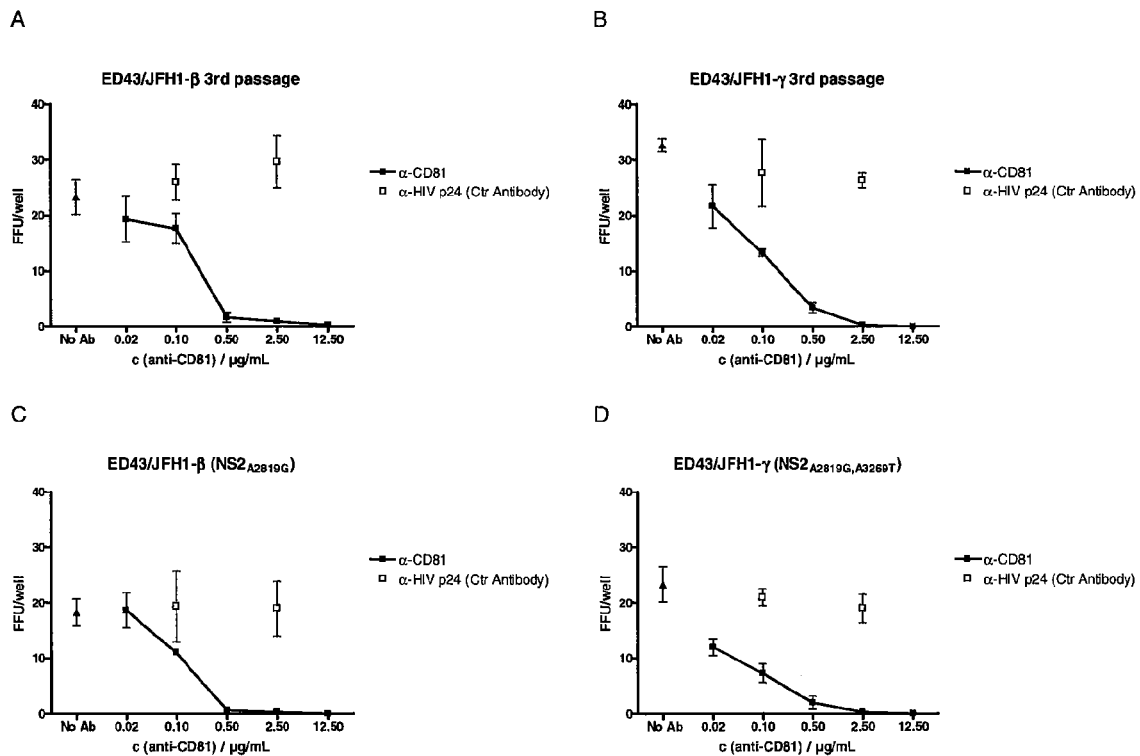

The tetraspanin cell surface molecule CD81 is expressed on various cells including hepatocytes and has been shown to interact with the E2 protein. Studies have shown that CD81 antibodies block infection of Huh7 cells with HCV pseudo particles as well as JFH1 viruses. In order to investigate whether ED43/JFH1 infection depend on CD81, Huh7.5 cells were incubated with CD81 antibodies in different concentrations before infection with approximately 100 TCID$_{50}$ 3$^{rd}$ passage and -γ viruses as well as ED43/JFH1-$β_{A2819G}$ and ED43/JFH1-$γ_{A2819G,A3269T}$ viruses from transfection cultures. CD81 antibodies specifically blocked infection of all viruses, and ≥95% inhibition was achieved by incubation with 2.5 μg/mL CD81 antibody. Except for one of three wells with ED43/JFH1-β infection, 12.5 μg/mL CD81 antibody prevented infection entirely (FIG. 4).

Example 6

Testing of cross-genotype neutralization of genotype 1-6 recombinant viruses with 1a and 4a anti-sera.

To further investigate the biological relevance of ED43/JFH1 viruses, ~100 TCID$_{50}$ ED43/JFH1-γ were incubated with serial 2-fold dilutions of chronic phase serum from a genotype 4a infected patient (AA) before infection of Huh7.5 cells. In contrast to incubation with HCV negative control serum, incubation with AA serum reduced the number of FFUs in a concentration dependent manner, yielding a 50% neutralization titer of 1:6400 (FIG. 5, Table 6). Thus, the 4a/JFH1 viruses could be efficiently neutralized with homologous patient serum.

Homologous neutralization of recombinant H77C/JFH1 virus was demonstrated with serum from Patient H, taken 29 years after acute infection (H06). Serial 2-fold dilutions of H06 serum were used to neutralize ~100 TCID$_{50}$ of H77C/JFH1, yielding a 50% neutralization titer of 1:1600 (Table 6). The H06 1a serum efficiently neutralized ED43/JFH1-γ (4a/JFH1) with a 50% titer of 1:12800, while the AA 4a serum showed low-level neutralization of H77C/JFH1 with a 50% titer of 1:50 (Table 6). To further broaden the investigation of cross-genotype neutralization, serial 2-fold dilutions of 1a and 4a sera were tested against ~100 TCID$_{50}$ of JFH1-based recombinant viruses expressing the envelope proteins of genotype 2a, 3a, 5a, and 6a. Genotype 2a and 3a viruses could not be neutralized at a 1:50 dilution of either serum. However, genotype 5a and 6a viruses were efficiently neutralized by both sera with 50% neutralization titers of at least 1:3200 (Table 6).

Example 7

4a/JFH1 infection depends on SR-BI.

Figure 8:
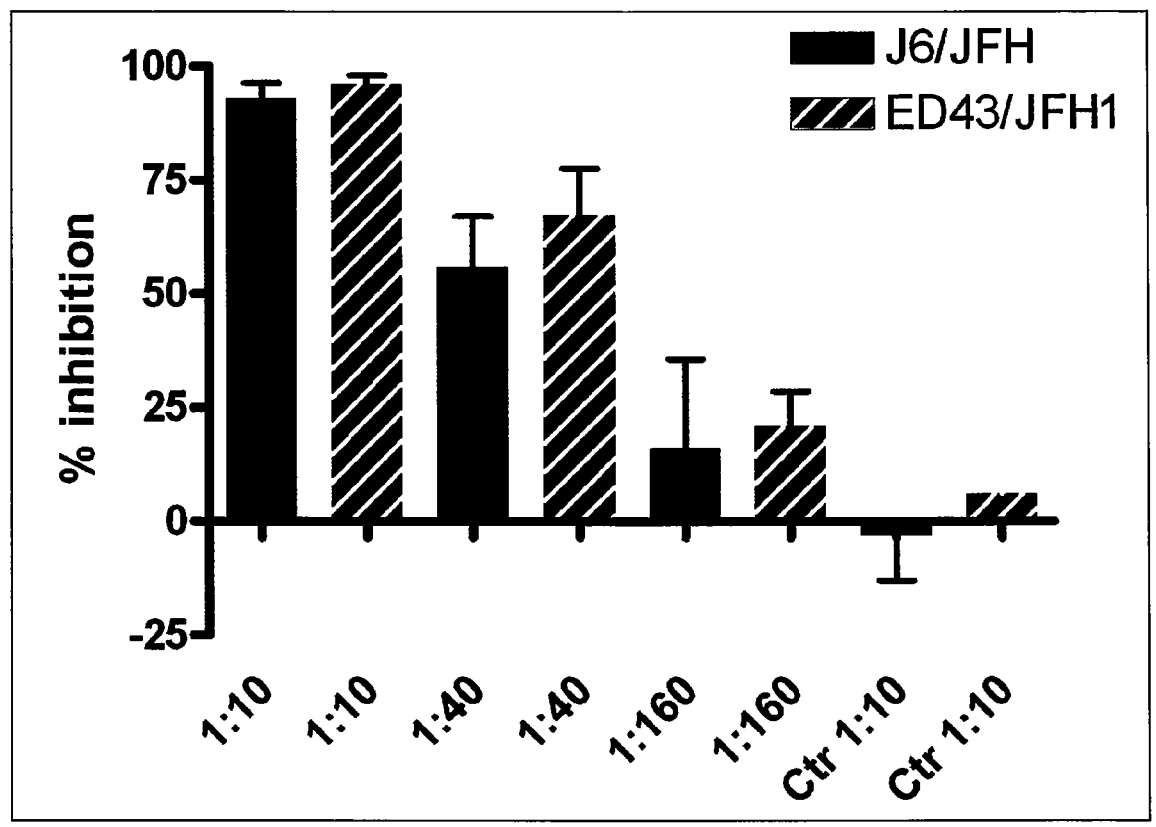

Blockage of the cell surface molecule SR-BI was previously shown to inhibit entry of HCV pseudo particles or cell culture grown virus of genotype 2a into Huh7 and derived cell lines. To investigate the SR-BI dependence of genotype 4a entry, Huh7.5 cells were incubated with anti-SR-BI serum before infection with ~300 TCID50 (150 FFUs) ED43/JFH1-γ. Anti-SR-BI serum but not a control serum reduced the number of focus forming units (FFUs) in a concentration dependent manner (FIG. 8).

Example 8

Use of the 4a/JFH1 system in drug testing: infected cells can be cured using the currently used antiviral IFN-α.

As an example of the use of the 4a/JFH1 system in test of antiviral drugs, the inventors of the present invention applied the antiviral drug IFN-a 2b, which is a constituent of the currently used combination therapy against HCV also involving ribavirin, to 4a/JFH1 infected cell cultures. Huh7.5 cells were infected with 4a/JFH1 (MOI 0.003). On day 5, when infection had spread to approximately 40% of the cells, 500 IU/mL IFN-α were applied every 1-3 days. Already from the third day of the treatment period, the percentage of infected cells was strongly diminished. A complete curing of the culture, as determined by the absence of NS5A antigen positive staining cells, was achieved after 38 days of treatment with 500 IU/mL IFN-α (FIG. 9).

Example 9

Cross-genotype neutralization potential of genotype 5a sera.

The inventors of the present invention found that chronic phase sera from genotype 1a and 4a infected patients could cross-neutralize intergenotypic recombinant viruses of genotype 1a, 4a, 5a and 6a, but failed to neutralize recombinants of genotype 2a and 3a. Thus, the ability of 5a sera (SA1, SA3, SA13, two-fold dilutions starting at 1:100) to cross-neutralize intergenotypic recombinants of the different genotypes were examined. The SA1 serum had the highest reciprocal 50% cross-neutralization titers, being 1,600, 400 and >51,200 against genotype 1a, 4a, and 6a viruses, respectively (Table 7). The SA3 and SA13 sera had limited or no cross-neutralization activity against genotype 1a and 4a viruses, but both sera had relative high titers of neutralizing antibodies against the 6a virus (Table 7). The 5a sera had no detectable cross-neutralizing activity against the genotypes 2a and 3a viruses at the 1:100 dilution. However, when subsequently testing a 1:50 dilution of the SA1 serum, which had the highest homologous neutralization titer, the inventors of the present invention observed >50% neutralization of the genotype 2a and 3a viruses (data not shown).

FIGURE LEGENDS

FIG. 1

Intergenotypic recombinant 2a/2a and 4a/2a constructs and their replication in Huh7.5 cells. (A) Genome map of J6/JFH (genotype 2a/2a) and ED43/JFH1 (genotype 4a/2a) cDNA clones. The 4a/2a constructs contain the Core, E1, E2, p7 and part of or all of NS2 genes from isolate ED43 (genotype 4a). pED43/JFH1-α (SEQ ID NO 5) has its 3' junction between the first and second TM domain (nt2866/2867, H77 reference (AF009606) nt2867/2868) of NS2, while pED43/JFH1-13 (SEQ ID NO 1) has the junction placed in the cytoplasmic part of NS2 (nt 3185/3186H77 reference (AF009606) nt3186/3187) in analogy to a naturally occurring 2k/1b isolate. The complete NS2 gene from ED43 is included in pED43/JFH1-γ (SEQ ID NO 2) and the negative replication control ED43/JFH1-GND. All constructs contain the 5'UTR, NS3 through NS5B and the 3'UTR of the JFH1 genome. (B) After immuno-staining for HCV Core, the percentage of infected cells was scored. Supernatant from day 6 (J6/JFH), day 19 (ED43/JFH1-13) and 45 (ED43/JFH1-γ) was used for 1st passage (arrows). A decreasing number of ED43/JFH1-α Core positive cells was observed until day 19. During continuation of the experiment hereafter and until day 66, no positive cells could be detected. The ED43/JFH1-GND transfected culture remained negative throughout the experiment. (C) Huh7.5 cells were transfected in parallel with 1.5 μg RNA transcripts from pJ6/JFH (positive control), pED43/JFH-GND (negative control) and pED43/JFH1-α, -β and -γ (SEQ ID NO 5, 1 and 2), respectively. Immunostainings for HCV Core in transfection and 1st passage experiments are shown. Core antigen is visualized in red by confocal fluorescence microscopy. Cell nuclei were counterstained using Hoechst reagent (blue).

FIG. 2

Comparison of J6/JFH and ED43/JFH1-β and -γ infection kinetics. Naïve Huh7.5 cells were inoculated for 6 hrs with approximately $10^3$ TCID50 of 1st passage J6/JFH (J6/JFH#, titer measured in 4 replicates) and 3rd passage J6/JFH (J6/JFH§) and ED43/JFH-β and -γ (titers measured in duplicates). (A) Viral RNA titers of culture supernatant were monitored by a quantitative HCV TaqMan RT-PCR assay. nd: not determinable; below assay detection limit of 500 IU/mL. (B) After immuno-staining for Core antigen, the percentage of infected cells was visualized and scored using confocal fluorescence microscopy. (C) Infectivity titers were determined for supernatant collected on day 3, 6, 8 and 10 by the TCID50 assay (dark coloured columns). To visualize the difference between HCV RNA- and infectivity-titers (reciprocal specific infectivity), RNA titers are shown in IU/mL (light coloured columns).

FIG. 3

Transfection of Huh7.5 cells with 2.5 μg RNA transcripts of ED43/JFH1 intergenotypic recombinants with putative adaptive mutations (SEQ ID NO 7, 8, 9, 11). RNA transcripts from J6/JFH (positive control), ED43/JFH1-GND (negative control) and the original pED43/JFH1-β and -γ constructs (SEQ ID NO 1 and 2) were tested in parallel. (A) After immuno-staining for Core antigen the percentage of infected cells was visualized and scored using confocal fluorescence microscopy. As indicated, ED43/JFH1-$γ_{A2819G}$ did not spread within the depicted timeframe. However, the infection spread from below 1% at day 31 to more than 50% at day 42 (data not shown). Day 5 supernatants from J6/JFH, ED43/JFH1-GND, ED43/JFH1-$β_{A2819G}$, ED43/JFH1-$γ_{A2819G,A3269T}$ and ED43/JFH1-$γ_{A1325T,A2819G,A3269T}$ cultures were used for inoculation of the 1st passage (arrow). (B) Comparison of TCID50 values of viruses recovered from supernatant at days 3, 5, 7 and 10 post-transfection. nd: not determined. §: One of six replicates infected by undiluted supernatant only; TCID50 value undeterminable. #: None of 6 replicate wells infected by undiluted supernatant.

FIG. 4

Blocking of CD81 inhibits ED43/JFH1-β and -γ infection. Huh7.5 cells growing in a 96 well plate were incubated for one hour at 37° C. with anti-CD81 antibodies or anti-HIV-p24 isotype-matched control antibodies in concentrations as indicated. Approximately 100 TCID50 (measured in duplicates) of ED43/JFH1-β 3rd passage virus (A), ED43/JFH1-γ 3rd passage virus (B), ED43/JFH1-$β_{A2819G}$ from transfection culture (C) or ED43/JFH1-$γ_{A2819G,A3269T}$ from transfection culture (D) was added and incubated with the cells for 4 hours at 37° C. The count of focus forming units (FFU) per well after 2 days of growth is indicated. Each data point was determined in triplicates. Error bars indicate standard error of the mean.

FIG. 5

Neutralization of ED43/JFH1 virus. ~100 $TCID_{50}$ of ED43/JFH1-γ $1^{st}$ passage virus were incubated with serial 2-fold dilutions of genotype 4a (AA, gray) or genotype 1a (H06, white) chronic phase patient samples or a mixture of sera from four HCV negative controls (black) in final dilutions as indicated, prior to incubation with Huh7.5 cells. The count of FFUs per well after an incubation period of 2 days is indicated. Each data point represents triplicate experiments. Error bars indicate standard errors of the mean.

FIG. 6

Transfection of RNA transcripts from pJ6/JFH, pED43/JFH1-GND and pED43/JFH1-$\gamma_{T977S}$ (SEQ ID NO 10), as well as pED43/JFH1-$\beta_{T827A}$ and pED43/JFH1-$\gamma_{T827A,T977S}$ constructs with or without mutations observed in $3^{rd}$ passage (SEQ ID NO 7, 8, 12, 13, 14, 15, 16 and 17). TCID$_{50}$ determinations on transfection supernatants are shown. ‡, two (TCID$_{50}$<0.7) of 6 replicates infected by undiluted supernatant. ED43/JFH1-GND was confirmed negative.

FIG. 7

Transfection of Huh7.5 cells with ED43/JFH1 recombinants with putative adaptive mutations. ED43/JFH1-$\beta_{T827A}$ (SEQ ID NO 7), ED43/JFH1-$\gamma_{T827A,E989K}$ (SEQ ID NO 12), ED43/JFH1-$\beta_{T827A,V2436L}$ (SEQ ID NO 13) and ED43/JFH1-$\gamma_{T827A,E989K,T1989I,V2436L}$ (SEQ ID NO 14) as well as ED43/JFH1-$\gamma_{T827A,T977S}$ (SEQ ID NO 8), ED43/JFH1-$\gamma_{T977S}$ (SEQ ID NO 10), ED43/JFH1-$\gamma_{A216T,T827A,T977S}$ (SEQ ID NO 15), ED43/JFH1-$\gamma_{T827A,T977S,C2270R}$ (SEQ ID NO 16) and ED43/JFH1-$\gamma_{A216T,T827A,T977S,C2270R}$ (SEQ ID NO 17) RNA transcripts were transfected into naïve Huh7.5 cells. After immunostaining, the percentage of HCV Core positive cells was scored using confocal fluorescence microscopy.

FIG. 8

Blocking of SR-BI inhibits ED43/JFH1 infection.

Huh7.5 cells growing in a 96 well plate were incubated for one hour at 37° C. with SR-BI anti-serum or a control serum in dilutions as indicated. Approximately 300 TCID50 ED43/JFH1-γ were added and incubated with the cells for 3 hours at 37° C. The count of focus forming units (FFU) per well after 2 days of growth is indicated. Each data point was determined in triplicates. Error bars indicate standard error of the mean.

FIG. 9

INF-α treatment significantly reduces 4a/JFH1 infection of Huh7.5 cells. Huh7.5 cells were infected with ED43/JFH1 (MOI 0.003). On day 5, when infection had spread to approximately 40% of the cells, 500 IU/mL IFN-α were applied every 1-3 days. A complete curing of the ED43/JFH1 culture, as determined by the absence of NS5A antigen positive staining cells, was achieved after 38 days of treatment with 500 IU/mL IFN-α.

TABLES

TABLE 1

Primers and primer sequences for PCR

| Primer | SEQ ID NO | 5'-3' Sequence |
|---|---|---|
| 4aF193 | 29 | TTTCTTGGATTAACCCGCTCAATG |
| 4aF1G-NotI-T7 | 30 | TTTTTTTTGCGGCCGC*TAATACGACTCACTATA*GACCTGCTCTCTATGAGAGCAACACTCC |
| 4aF2676 | 31 | AGGGCCGGTTCCCAGCTGCT |
| 4aF2719 | 32 | GTGGCCCTGTTTTCTCCTGCTTC |
| 4aF309 | 33 | AGTGCCCCGGGAGGTCTCGTAG |
| 4aF5446 | 34 | CCAACAGTTCGACGAAATGGAGGAGTGTTC |
| 4aF741 | 35 | TGGGATACATCCCGCTCGTAGG |
| 4aF9251 | 36 | GGCGCCGGCGGGGGAGACATTTATCACAGC |
| 4aF9271-HindIII | 37 | GTCCAAGCTTATCACAGCATGTCTCATGCCCGACCCCG |
| 4aR262 | 38 | ACACTACTCGGCTAGCAGTCTTGC |
| 4aR489 | 39 | CGAGTCGCGCGCACACCCAATC |
| 4aR5664 | 40 | AGATATTGAATGCCGCTGATGAAATTCCACATG |
| 4aR862 | 41 | AAAGGAGCAACCGGGGAGATTC |
| 4aR9406 | 42 | AAAAAACAAGGGGACCCTAAGGTCGGAGTG |
| 4aR9491-Xba | 43 | CGTCTCTAGAGGACCTTTCACAGCTAGCCGTGACTAGGG |
| 4aR9504 | 44 | TCATGCGGCTCACGGACCTTTCACAGCTAG |
| JF2879 | 45 | CTGTGGTGGTTGTGCTATCTCC |
| JF2962 | 46 | TGATGGCATCATATGGGCCGTC |
| JF3198 | 47 | TCTATGACCACCTCACACCTATG |
| JR345 | 48 | CTCATGGTGCACGGTCTACGAGA |
| JR3593 | 49 | TTGCCAGCTCCGTGGTAAAC |
| JR8368 | 50 | CCTGATGTCTCTCTCAGTGAC |
| JR8688 | 51 | TCCGTGAAGGCTCTCAGGTTC |
| RU-O-5720 | 52 | GCTCCCATCACTGCTTATGCC |
| RU-O-5721 | 53 | GCTACCGAGGGGTTAAGCACT |
| JVF12328 | 54 | CGTTGTAAAACGACGGCCAGTGA |
| 2aR2905/4aR2866 | 55 | *GGAGATAGCACAACCACCACAGTCCCCTAGCCAGCCATAACTTG* |
| 2aR3220/4aR3185 | 56 | *CATAGGTGTGAGGTGGTCATAGATGTAAGTACCAGTCAGGGCCCC* |
| 2aR3451/4aR3419 | 57 | *GGCATAAGCAGTGATGGGAGCAAGGAGTCTCCACCCCTTTG* |
| 285s-HCV-MOD | 58 | ACTGTCTTCACGCAGAAAGCGCCTAGCCAT |
| 9470R_JFH1 | 59 | CTATGGAGTGTACCTAGTGTGTGC |
| consR268 | 60 | ACCCAACGCTACTCGGCTA |
| consR312 | 61 | CGCAAGCRCCCTATCAGGCAGTACC |
| consR337 | 62 | GGTCTACGAGRCCTCCCGGGGCAC |

Bold: non-HCV sequence. Bold italics: T7 promotor sequence. Italics: intergenotype primers, genotype 2a sequence. Underlined: Restriction sites.

TABLE 2

Primers and primer sequences used for generation of amplicons for sequencing as described in Materials and Methods

| Primer pair | Forward | 5'-3' Sequence | SEQ ID NO | Reverse | 5'-3' Sequence | SEQ ID NO |
|---|---|---|---|---|---|---|
| ED43/JFH1 | | | | | | |
| 0 | 285S_HCV-MOD | ACTGTCTTCACGCAGAAAGCGCCTAGCCAT | 58 | 4aR705 | ACCTTACCCAAATTGCGGGACCTC | 67 |
| 1 | 84S_HCV-MOD | GTAGCGTTGGGTTGCGAAAGGCCTTGTGGTACTGCCTGAT | 63 | 4aR1080 | GCGACGGTAGGAGTAAGGGCCACCC | 68 |
| 2 | 4aF965 | AATTCAAGCATAGTGTATGAGGCCGAC | 64 | 4aR2010 | TTCATCCACACGCATCCAAACC | 69 |
| 3 | 4aF1910 | GGGGTCCCTACTTACACCTGGGG | 65 | 4aR2871 | CACAATCCCCTAGCCAGCCATAAC | 70 |
| 4 | 4aF2719 | GTGGCCCTGTTTTCTCCTGCTTC | 66 | 3329R_JFH1-MOD | CCCTCAGCACTCGAGTACATCTG | 71 |
| J6/JFH | | | | | | |
| 0 | 285S_HCV-MOD | ACTGTCTTCACGCAGAAAGCGCCTAGCCAT | 58 | JR513 | gctgggaccgctccgaag | 75 |
| 1 | 84S_HCV-MOD | GTAGCGTTGGGTTGCGAAAGGCCTTGTGGTACTGCCTGAT | 63 | 1109R_J6 | TTTGCCCACGCTCCCTGCATAGAGAA | 76 |
| 2 | 946S_J6 | CACCGCATGGCGTGGGACATGATG | 72 | 2111R_J6 | TGCACGTCCACGATGTTTTGGTG | 77 |
| 3 | 1849S_J6 | TACAGGCTCTGGCATTACCCCTGCAC | 73 | 2763R_J6 | AGCGTGAGCCCTGACGAAGTACGG | 78 |
| 4 | 2754S_J6 | TAGCATTGCCCCAACAGGCTTATGCTTATGACG | 74 | 3774R_J6 | GGGATGACATCAGCGTTCCGCGTGACCAG | 79 |
| JFH1 | | | | | | |
| 5 | 3081S_J6/JFH1 | GGGAGTCTTCTCGCTCCCATCACTGC | 80 | 4118R_JFH1 | CGCCCGAGGCCTACCTCTTCTATATC | 88 |
| 6 | 3880S_J6 | CCCATCACGTACTCCACATATGGC | 81 | 4796R_JFH1 | GCGCACACCGTAGCTTGGTAGG | 89 |
| 7 | 4528S_J6 | GAGCGAGCCTCAGGAATGTTTGACA | 82 | 5446R_JFH1 | TGATGTTGAGAAGGATGGTGGTAC | 90 |
| 8 | 5272S_JFH1 | TGGCCCAAAGTGGAACAATTTTGG | 83 | 6460R_J6 | CAACGCAGAACGAGACCTCATCCC | 91 |
| 9 | 6186S_JFH1 | GACCTTTCCTATCAATTGCTACAC | 84 | 7234R_JFH1 | GAAGCTCTACCTGATCAGACTCCA | 92 |
| 10 | 6862S_JFH1 | TGGGCACGGCCTGACTACAA | 85 | 7848R_JFH1 | GGCCATTTTCTCGCAGACCCGGAC | 93 |
| 11 | 7741S_J6 | ATGGCCAAAAATGAGGTGTTCTGC | 86 | 8703R_JFH1 | AAGGTCAAAGGATTCACGGAGTA | 94 |
| 12 | 8137S_JFH1 | GGTCAAACCTGCGGTTACAGACGTTG | 87 | 9464R(24)_JFH1 | GTGTACCTAGTGTGTGCGCTCTA | 95 |

TABLE 3

Tranfection culture of J6/JFH and ED43/JFH1-α, -β and -γ was monitored for viral infectivity by the TCID50 assay. This titration method gives an endpoint, based on the virus dilution infecting half of the six replicates tested (1). Results are given in infectious doses per mL. The infectivity titer for each culture was measured on day 6, 19 and 45 (time points where J6/JFH, ED43/JFH1-β and ED43/JFH1-γ infection, respectively, spread to most cell in the culture) or until percentage of infected cells peaked.

| Infectivity titer/ | Day | | |
|---|---|---|---|
| Log(TCID-50/mL) | 6 | 19 | 45 |
| J6/JFH | 4.4 | nd | nd |
| ED43/JFH1-α | # | # | # |
| ED43/JFH1-β | § | 2.9 | nd |
| ED43/JFH1-γ | # | # | 2.9 | nd: not determined.
§: One of six replicates infected by undiluted supernatant only; TCID50 value undeterminable.
: None of 6 replicate wells infected by undiluted supernatant.

TABLE 4

Infectivity titer, RNA titer and specific infectivity for J6/JFH and ED43/JFH1-β and -γ. Viruses were serially passaged in four cell free passages. In each passage, infectivity titer in supernatant was determined at selected timepoints during the period with most cells infected. For each passage selected samples and correlating RNA titers are shown. The reciprocal specific infectivity (viral genome titer/dose TCID50) is given.

| Virus construct | Passage | Days post infection | Infectivity titer/ log(TCID$_{50}$/mL) | RNA titer/ log(IU/mL) | Reciprocal specific infectivity, log-transformed |
|---|---|---|---|---|---|
| J6/JFH | 1st | 7 | 5.1 | 7.1 | 2.0 |
|  | 2nd | 12 | 4.3 | 6.7 | 2.4 |
|  | 3rd | 6 | 3.5 | 6.9 | 3.4 |
|  | 4th | 8 | 4.9 | 7.6 | 2.7 |
| ED43/JFH-β | 1st | 10 | 3.5 | 6.7 | 3.2 |
|  | 2nd | 7 | 3.3 | 6.8 | 3.5 |
|  | 3rd | 10 | 3.1 | 7.0 | 3.9 |
|  | 4th | 10 | 3.4 | 7.2 | 3.8 |
| ED43/JFH-γ | 1st | 12 | 3.6 | 6.8 | 3.2 |
|  | 2nd | 15 | 2.7 | 6.8 | 4.1 |
|  | 3rd | 19 | 3.4 | 6.8 | 3.4 |
|  | 4th | 10 | 3.2 | 6.6 | 3.4 |

TABLE 5A

Mutations of ED43/JFH1-β during serial passages in Huh7.5 cells.

| HCV gene* | Core | E2 | NS2 | NS2 | NS3 | NS5A | |
|---|---|---|---|---|---|---|---|
| | | | Nucleotide number† | | | | |
| ED43/JFH1-β | 787 | 2206 | 2819 | 3305 | 4222 | 6306 | 7646 |
| H77 abs. ref. | 788 | 2207 | 2820 | 3306 | 4223 | 6307 | 7593 |
| pED43/JFH1-β | G | C | A | G | C | C | G |
| | | | Direct sequencing‡ | | | | |
| 1st passage | — | — | G | — | — | — | — |
| 2nd passage | G/a | — | G | G/a | C/t | — | G/t |
| 3rd passage | A/g | C/T | G | G/A | C/T | C/T | T/g |
| | | | 3rd passage clonal distribution§ | | | | |
| 3/10 | A | T | G | A | T | T | T |
| 2/10 | A | T | G | A | T | — | T |
| 2/10 | — | — | G | — | T | T | T |
| 1/10 | A | — | G | — | — | T | T |
| 1/10 | — | — | G | — | — | — | T |
| 1/10 | — | — | G | — | — | — | — |

| HCV gene* | Core | E2 | NS2 | NS2 | NS3 | NS5A |
|---|---|---|---|---|---|---|
| | | | Amino acid number† | | | |
| ED43/JFH1-β | | | 827 | 989 | 1989 | 2436 |
| H77 abs. ref. | | | 827 | 989 | 1989 | 2418 |
| Change | | | T → A | E → K | T → I | V → L |

*Mutations within the region of nucleotide 341-3185, both incl. are in the ED43 region, others are in the JFH1 region
†Positions are numbered according to the HCV sequence of pED43/JFH1-β. Corresponding H77 reference positions (AF009606) are given.
‡Mutations representing ≧50% of the sequence read in at least one passage. Positions with mixtures are written with the dominant sequence in capital and the minor sequence in lower case letters, or with both capitalized wherever a dominant nucleotide was not determinable. Dots indicate identity with the original plasmid sequence.
§In addition to indicated mutations, G7147C (E2269D) and A7640G (T2434A) were present in 3 clones and C1944G (T535S), T2021C (F561L), A2772G (D811G), T3392C (Y1018H), and T5836C (nc) were present in 2 clones. In each clone a number of single mutations were found, yielding an average of 22 mutations in total per clone. Thus, all clones had unique sequences.

TABLE 5B

Mutations of ED43/JFH1-γ during serial passages in Huh7.5 cells*.

| HCV gene | E1 | | | NS2 | | NS3 | | | NS5A | | |
|---|---|---|---|---|---|---|---|---|---|---|---|
| | | | | Nucleotide number† | | | | | | | |
| ED43/JFH1-γ | 986 | 1325 | 1336 | 2785 | 2819 | 3269 | 4459 | 4918 | 7022 | 7128 | 7148 |
| H77 abs. ref. | 987 | 1326 | 1337 | 2786 | 2820 | 3270 | 4460 | 4919 | 7023 | 7141 | 7161 |
| pED43/JFH-γ | G | A | A | A | A | A | C | G | G | A | T |
| | | | | Direct sequencing | | | | | | | |
| 1st passage | — | T/a | G | A/G | G | T | — | — | G/A | A/g | — |
| 2nd passage | — | A/T | G/a | A/G | G | T | C/T | G/A | G/a | A/G | — |
| 3rd passage | A/g | A/t | G/a | A/g | G | T | T | A | — | — | C |

TABLE 5B-continued

Mutations of ED43/JFH1-γ during serial passages in Huh7.5 cells*.

| HCV gene | E1 | | NS2 | | NS3 | | | | NS5A | | |
|---|---|---|---|---|---|---|---|---|---|---|---|
| | | | 3rd passage clonal distribution‡ | | | | | | | | |
| 7/10 | A | — | G | — | G | T | T | A | — | — | C |
| 2/10 | — | — | G | — | G | T | — | — | — | — | — |
| 1/10 | — | — | — | — | G | T | — | — | — | — | — |
| | | | | Amino Acid number | | | | | | | |
| ED43/JFH1-γ | 216 | 329 | 827 | | 977 | | | | 2228 | 2263 | 2270 |
| H77 abs. ref. | 216 | 329 | 827 | | 977 | | | | 2228 | 2267 | 2274 |
| Change | A → T | T → S | T → A | | T → S | | | | D → N | E → G | C → R |

*Mutations within the region of nucleotide 341-3418, both incl. are in the ED43 region, others are in the JFH1 region. See Table 6 legend for further details.
†Positions are numbered according to the HCV sequence of pED43/JFH1-γ.
‡In addition to indicated mutations, G1026A (C229Y), T1150C (nc), C2480T (L714F), A2995G (nc), C3001G (D887E), G7291A (nc) and T7985C (nc) were present in 3 clones; G723A (C128Y), T1211G (F291V), T1369C (nc), A2114G (T592A), G2251A (nc), T2916C (V859A), T2937C (V866A), G3208A (M956I), T4540C (nc), A5668G (nc), A6248G (I1970V), A7103G (M2255V), G7534A (nc) and G7584A (G2415E) were present in 2 clones.

TABLE 6

Reciprocal titers of neutralizing antibodies in chronic phase serum from patients infected with HCV genotype 1a (H06) and 4a (AA) against JFH1-based viruses representing the 6 HCV genotypes.

| Envelope genotype | 90% reciprocal serum neutralizing antibody titer | | 50% reciprocal serum neutralizing antibody titr | |
|---|---|---|---|---|
| | 1a (H06) | 4a (AA) | 1a (H06) | 4a (AA) |
| 1a | 50 | <50 | 1600 | 50 |
| 2a | <50 | <50 | <50 | <50 |
| 3a | <50 | <50 | <50 | <50 |
| 4a | 800 | 400 | 12800 | 6400 |
| 5a | 3200 | 800 | 25600 | 3200 |
| 6a | 25600 | 3200 | 204800 | 25600 |

~100 TCID$_{50}$ of JFH1-based recombinant virus containing Core-NS2 of each of the 6 major genotypes were incubated in triplicates with a 2-fold dilution series of genotype 1a or 4a chronic phase patient serum or a mixture of sera from four HCV negative controls and tested in Huh7.5 cells. Reciprocal neutralization titers are indicated as the highest dilution showing a reduction in FFUs of at least 90% or 50% compared to HCV negative controls.

TABLE 7

Neutralization of JFH1-based HCV recombinants of genotypes 1-6 with genotype 5a sera.

| | Envelope genotype of JFH1-based recombinants | | | | | |
|---|---|---|---|---|---|---|
| | 1a | 2a | 3a | 4a | 5a | 6a |
| | Reciprocal 50% neutralization titer | | | | | |
| SA1 serum | 1,600 | <100 | <100 | 400 | 25,600 | >51,200# |
| SA3 serum | <100 | <100 | <100 | 200 | 6,400 | 12,800 |
| SA13 serum | <100 | <100 | <100 | <100 | 1,600 | 3,200 |

Neutralization of HCV was performed against 100-200 TCID$_{50}$ of JFH1-based recombinants containing Core-NS2 of genotypes 1-6. The recombinant viruses were incubated in triplicates with 2-fold serial dilutions of chronic phase sera of patients infected with HCV genotype 5a (SA1, SA3 and SA13) or 2-fold serial dilutions of a control serum mixture before testing on Huh7.5 cells. Reciprocal neutralization titers were determined as the highest serum dilution showing a reduction of 50% FFUs compared to the average FFUs counts for the control serum. The average FFUs in the controls in the different genotype experiments ranged from 10 to 70 FFUs/well. In control serum experiments for a particular genotype there was no significant difference in the FFU counts between the different dilutions (data not shown).
<sup>a</sup>Neutralization ~75% at a 1:51,200 dilution.

REFERENCES

Bukh, J., Purcell, R. H., and Miller, R. H. (1993). At least 12 genotypes of hepatitis C virus predicted by sequence analysis of the putative E1 gene of isolates collected worldwide. Proc Natl Acad Sci USA 90, 8234-8238.

Kato, T., T. Date, M. Miyamoto, A. Furusaka, K. Tokushige, M. Mizokami, and T. Wakita. 2003. Efficient replication of the genotype 2a hepatitis C virus subgenomic replicon. Gastroenterology 125:1808-1817.

Kato, T., A. Furusaka, M. Miyamoto, T. Date, K. Yasui, J. Hiramoto, K. Nagayama, T. Tanaka, and T. Wakita. 2001. Sequence analysis of hepatitis C virus isolated from a fulminant hepatitis patient. J Med Virol 64:334-339.

Lindenbach, B. D., M. J. Evans, A. J. Syder, B. Wolk, T. L. Tellinghuisen, C. C. Liu, T. Maruyama, R. O. Hynes, D. R. Burton, J. A. McKeating, and C. M. Rice. 2005. Complete replication of hepatitis C virus in cell culture. Science 309:623-626.

Lindenbach B D, Meuleman P, Ploss A, Vanwolleghem T, Syder A J, McKeating J A, Lanford R E, Feinstone S M, Major M E, Leroux-Roels G, Rice C M. Cell culture-grown hepatitis C virus is infectious in vivo and can be recultured in vitro. Proc Natl Acad Sci USA. 2006 Mar. 7; 103(10): 3805-9. Epub 2006 Feb. 16.

Meunier, J. C. et al. (2005) Evidence for Cross-Genotype Neutralization of Hepatitis C Virus Pseudo-Particles and Enhancement of Infectivity by Apolipoprotein Cl Proc Natl Acad Sci USA 102, 4560-4565.

Pietschmann, T., Kaul, A., Koutsoudakis, G., Shavinskaya, A., Kallis, S., Steinmann, E., Abid, K., Negro, F., Dreux, M., Cosset, F. L., and Bartenschlager, R. (2006). Construction and characterization of infectious intragenotypic and intergenotypic hepatitis C virus chimeras. Proc. Natl. Acad. Sci. U.S. A 103, 7408-7413.

Wakita, T., T. Pietschmann, T. Kato, T. Date, M. Miyamoto, Z. Zhao, K. Murthy, A. Habermann, H. G. Krausslich, M. Mizokami, R. Bartenschlager, and T. J. Liang. 2005. Production of infectious hepatitis C virus in tissue culture from a cloned viral genome. Nat Med 11:791-796.

Zhong, J., P. Gastaminza, G. Cheng, S. Kapadia, T. Kato, D. R. Burton, S. F. Wieland, S. L. Uprichard, T. Wakita, and F. V. Chisari. 2005. Robust hepatitis C virus infection in vitro. Proc Natl Acad Sci USA 102:9294-9299.

The invention claimed is:

1. An isolated nucleic acid molecule which encodes human hepatitis C virus of genotype 4a/JFH1, wherein said molecule:
   (i) is capable of expressing said virus when transfected into cells,
   (ii) is capable of infectivity in vivo, and
   (iii) encodes an amino acid sequence with at least 95% sequence identity to that of SEQ ID NO:3, which
   (iv) comprises an intergenotypic junction in the cytoplasmic part of NS2 and at least one adaptive mutation in the amino acid sequence of E1, NS2 or NS5A, selected from the group consisting of T827A, E989K, T1989I and V2436L, wherein said mutation is numbered according to the HCV sequence of SEQ ID NO:3.

2. The isolated nucleic acid molecule according to claim 1, wherein said molecule:
   (i) comprises a nucleic acid sequence with at least 95% sequence identity to that of SEQ ID NO 1, which
   (ii) comprises at least one adaptive mutation in the nucleic acid sequence of E1, NS2 or NS5A, selected from the group consisting of A2819G, G3305A, C6306T, and G7646T, wherein said mutation is numbered according to the HCV sequence of SEQ ID NO:1.

3. An isolated nucleic acid molecule which encodes human hepatitis C virus of genotype 4a/JFH1, wherein said molecule:
   (i) is capable of expressing said virus when transfected into cells,
   (ii) is capable of infectivity in vivo, and
   (iii) encodes an amino acid sequence with at least 95% sequence identity to that of SEQ ID NO 4, which
   (iv) comprises an intergenotypic NS2/NS3 junction and at least two adaptive mutations consisting of T827A and T977S, wherein said mutations are numbered according to the HCV sequence of SEQ ID NO:4.

4. The isolated nucleic acid molecule according to claim 3, wherein said molecule:

(i) comprises a nucleic acid sequence with at least 95% sequence identity to that of SEQ ID NO 2, which (ii) comprises at least two adaptive mutations consisting of A2819G and A3269T, wherein said mutations are numbered according to the HCV sequence of SEQ ID NO:2.

5. The isolated nucleic acid of claim 1 further comprising a pharmaceutical acceptable diluent or excipient.

6. The isolated nucleic acid of claim 1 further comprising an active promoter and a cassette vector for cloning viral genomes.

7. A method for producing a cell which replicates HCV 4a/JFH1 and produces a virus particle comprising:

(i) introducing a nucleic acid molecule into a cell wherein said nucleic acid molecule comprises at least 95% sequence identity to SEQ ID NO:4, which (ii) comprises a sequence encoding an intergenotypic NS2/NS3 junction and at least two adaptive mutations consisting of T827A and T977S , wherein said mutations are numbered according to the HCV sequence of SEQ ID NO:2.

8. A method for producing a cell which replicates HCV 4a/JFH1 and produces a virus particle comprising:

(i) introducing a nucleic acid molecule into a cell wherein said nucleic acid molecule comprises at least 95% sequence identity to SEQ ID NO: 2, which (ii) comprises a sequence encoding an intergenotypic junction in the cytoplasmic part of NS2 and at least two adaptive mutations consisting of A28190 G and A3269T , wherein said mutations are numbered according to the HCV sequence of SEQ ID NO:1.

9. The method according to claim 7, wherein the cell is Huh7.5.

10. The method of claim 7 further comprising culturing the cell to allow the cell to produce the virus particle.

11. The method of claim 10 further comprising isolating the hepatitis C virus particle.

12. The method of claim 10 further comprising culturing the cell and infecting other cells with the produced virus particle in the culture.

13. A method for screening an anti-hepatitis C virus substance, comprising a) culturing the cell produced by claim 7 with an anti-hepatitis C virus substance and a hepatitis C virus permissive cell, and b) detecting the replicating RNA or the virus particles in the resulting culture.

14. An immunogenic composition comprising a hepatitis C virus particle that comprises the nucleic acid of claim 1.

15. The isolated nucleic acid of claim 3 further comprising a pharmaceutical acceptable diluent or excipient.

16. The isolated nucleic acid of claim 3 further comprising an active promoter and a cassette vector for cloning viral genomes.

17. The method according to claim 8, wherein the cell is Huh7.5.

18. The method of claim 8 further comprising culturing the cell to allow the cell to produce the virus particle.

19. The method of claim 18 further comprising isolating the hepatitis C virus particle.

20. The method of claim 18 further comprising culturing the cell and infecting other cells with the produced virus particle in the culture.

21. The nucleic acid of claim 1, wherein said human hepatitis C virus of genotype 4a/JFH1 comprises a Core-NS2 N-terminal region of a genotype 4a human hepatitis C virus wherein the NS2 junction with a C-terminal region of JFH-1 NS2 is at a parental hairpin structure in the NS2 protease domain.

22. The nucleic acid of claim 1, wherein said nucleic acid encodes an amino acid sequence with at least about 98% identity to SEQ ID NO:3.

23. The nucleic acid of claim 1, wherein said nucleic acid encodes an amino acid sequence with at least about 99% identity to SEQ ID NO:3.

24. The nucleic acid of claim 3, wherein said nucleic acid encodes an amino acid sequence with at least about 98% identity to SEQ ID NO:4.

25. The nucleic acid of claim 3, wherein said nucleic acid encodes an amino acid sequence with at least about 99% identity to SEQ ID NO:4.

* * * * *

SEQUENCE LISTING

<160> NUMBER OF SEQ ID NOS: 96

<210> SEQ ID NO 1
<211> LENGTH: 9666
<212> TYPE: DNA
<213> ORGANISM: Hepatitis C virus

<400> SEQUENCE: 1

| | | | | | |
|---|---|---|---|---|---|
| acctgcccct | aatagggcg | acactccgcc | atgaatcact | cccctgtgag | gaactactgt | 60 |
| cttcacgcag | aaagcgccta | gccatggcgt | tagtatgagt | gtcgtacagc | ctccaggccc | 120 |
| cccctcccg | ggagagccat | agtggtctgc | ggaaccggtg | agtacaccgg | aattgccggg | 180 |
| aagactgggt | cctttcttgg | ataaacccac | tctatgcccg | gccatttggg | cgtgcccccg | 240 |
| caagactgct | agccgagtag | cgttgggttg | cgaaaggcct | tgtggtactg | cctgataggg | 300 |
| cgcttgcgag | tgccccggga | ggtctcgtag | accgtgcacc | atgagcacga | atcctaaacc | 360 |
| tcaaagaaaa | accaaacgta | acaccaaccg | ccgcccaatg | gacgttaagt | tcccgggtgg | 420 |
| tggccagatc | gttggcggag | tttacttgtt | gccgcgcagg | ggcccagat | tgggtgtgcg | 480 |
| cgcgactcgg | aagacttcgg | agcggtcgca | acctcgtgga | agacgccaac | ctatccccaa | 540 |
| ggcgcgtcga | cccgagggaa | ggtcctgggc | acaaccagga | tatccatggc | ctctttacgg | 600 |
| taatgagggt | tgtgggtggg | caggatggct | cttgtccccc | cgtggctctc | gaccgtcttg | 660 |
| gggcccaaat | gatccccggc | ggaggtcccg | caatttgggt | aaggtcatcg | atacctaac | 720 |
| ctgcggcttc | gccgacctca | tgggatacat | cccgctcgta | ggcgccccg | tgggtggcgt | 780 |
| cgccagggcc | ctggcacatg | gtgtcagggc | tttggaggac | gggatcaatt | atgcaacagg | 840 |
| gaatctcccc | ggttgctcct | tttctatctt | cctcttggca | cttctttcgt | gcctgactgt | 900 |
| ccccgcttcg | gccgttaact | atcgcaatgt | ctcgggcatc | taccatgtca | ccaatgactg | 960 |
| cccgaattca | agcatagtgt | atgaggccga | ccatcacatc | ttgcaccttc | caggttgcgt | 1020 |
| gccctgcgtg | agagagggga | atcagtcacg | ctgctgggtg | cccttactc | ctaccgtcgc | 1080 |
| agcgccatac | atcggcgcac | cgcttgagtc | cttacggagt | catgtggatt | tgatggtggg | 1140 |
| ggccgccact | gtttgctcgg | gtcttacat | cggggacctg | tgtggcggct | tgttcctagt | 1200 |
| tggccagatg | tttcattcc | gaccacggcg | ccactggacc | acccaggatt | gcaattgttc | 1260 |
| catctacaca | gggcacatta | caggccacag | aatggcctgg | gacatgatga | tgaactggag | 1320 |
| tccaacaacc | accttagttc | tcgcccaggt | catgaggatc | caaccactc | tggtagactt | 1380 |
| actctctgga | ggccactggg | gtgtcctcgt | gggagtggcc | tatttcagca | tgcaggccaa | 1440 |
| ttgggccaaa | gtcatcttgg | tcctattcct | ctttgcaggg | gttgatgccg | agactcacgt | 1500 |
| gtctggggca | gcagtcggcc | ggagtaccgc | cggcttggct | aacctctttt | cttctgggtc | 1560 |
| taagcagaat | ttacagctca | tcaacagcaa | tgggagctgg | catataaata | ggactgccct | 1620 |
| taactgcaat | gacagcttaa | acactggggtt | cttggctagc | ttgttctaca | cccacaagtt | 1680 |
| taacagctca | ggtgttccg | aacgctcgc | gtgctgcaag | agccttgaca | gctacggcca | 1740 |
| aggctgggc | ccactcgggg | tcgctaacat | cagcggctcg | tctgatgaca | ggccttattg | 1800 |
| ctggcactac | gcgcctcggc | cgtgcgggat | tgtgccagca | tccagtgtgt | gtggcccgt | 1860 |
| gtattgtttc | actcccagcc | ctgtcgtggt | cggtactact | gatcacgtcg | ggtccctac | 1920 |
| ttacacctgg | ggggagaatg | agactgatgt | cttcctttg | aactcgacca | gaccgccgca | 1980 |
| tggtgcgtgg | tttggatgcg | tgtggatgaa | cagtaccggg | ttcaccaaaa | cctgtggcgc | 2040 |

-continued

```
ccctccatgc gaggttaaca ccaataatgg gacctggcac tgccccaccg attgcttcag    2100
gaagcatccg gagactacct acgccaagtg cggatcaggg ccttggatca caccgcgctg    2160
cctgattgat tacccgtacc ggctgtggca tttcccgtgc accgccaact tctccgtctt    2220
taacatcagg acatttgtcg gcggtataga gcatcggatg caagcggcat gcaactggac    2280
caggggggaa gtctgtggct tggagcacag ggatcgcgta gagctatcac ccctgctcct    2340
taccactaca gcgtggcaga tcctcccctg ctctttcacc actttacctg ccctctccac    2400
cggcttgatc cacctccacc aaaatatcgt ggacgtccag tacctctatg gtgttgggtc    2460
tgcagtggta tcttgggccc ttaagtggga atatgtggtg ctcgcgttcc tgcttctcgc    2520
ggacgcgaga gtctctgcct gcctatggat gatgtttatg gtaagtcaag ttgaggcggc    2580
tctgtccaac ctgattaaca tcaatgctgc ttcagccgct ggtgcccaag gcttctggta    2640
cgccatcctc ttcatctgca ttgtctggca tgtcaagggc cggttcccag ctgctgctgc    2700
ctacgcagcc tgcgggctgt ggcccctgtt tctcctgctt ctgatgctgc tgagagggc    2760 ttatgcatac gaccaggaag tggcagggtc ccttggcggc gccatcgttg tcatgctgac    2820
cattctgaca ctgtctccgc actacaagtt atggctggct aggggattgt ggtggatcca    2880 atatttata gctaggaccg aggctgtgct gcatgtctat attccatcct tcaacgtgcg    2940
cgggcctcgc gactcagtga ttgttcttgc agtcctggtc tgtccacacc tagtatttga    3000
catcacaaaa tatcttctgg ccatcttagg gcccctccac atactccagg cctcgctcct    3060
acgcatccct tactttgtga gggcacaagc gctggttaag atctgcagct tgttgcgtgg    3120
ggtagtttat ggcaagtact tccaaatggt cgtgcttaaa gcaggggccc tgactggtac    3180
ttacatctat gaccacctca cacctatgtc ggactgggcc gctagcggcc tgcgcgactt    3240
agcggtcgcc gtggaaccca tcatcttcag tccgatggag aagaaggtca tcgtctgggg    3300
agcggagacg gctgcatgtg gggacattct acatggactt cccgtgtccg cccgactcgg    3360
ccaggagatc ctcctcggcc cagctgatgg ctacacctcc aagggtgga agctccttgc    3420 tcccatcact gcttatgccc agcaaacacg aggcctcctg ggcgccatag tggtgagtat    3480
gacggggcgt gacaggacag aacaggccgg ggaagtccaa atcctgtcca cagtctctca    3540
gtccttcctc ggaacaacca tctcgggggt tttgtggact gtttaccacg gagctggcaa    3600
caagactcta gccggcttac ggggtccggt cacgcagatg tactcgagtg ctgaggggga    3660
cttggtaggc tggcccagcc ccctgggac caagtctttg gagccgtgca agtgtggagc    3720
cgtcgaccta tatctggtca cgcggaacgc tgatgtcatc ccggctcgga gacgcgggga    3780
caagcgggga gcattgctct ccccgagacc catttcgacc ttgaaggggt cctcgggggg    3840
gccggtgctc tgccctaggg gccacgtcgt tgggctcttc cgagcagctg tgtgctctcg    3900
gggcgtggcc aaatccatcg atttcatccc cgttgagaca ctcgacgttg ttacaaggtc    3960
tcccactttc agtgacaaca gcacgccacc ggctgtgccc cagacctatc aggtcgggta    4020
cttgcatgct ccaactggca gtggaaagag caccaaggtc cctgtcgcgt atgccgccca    4080
ggggtacaaa gtactagtgc ttaacccctc ggtagctgcc accctgggt ttggggcgta    4140 cctatccaag gcacatggca tcaatcccaa cattaggact ggagtcagga ccgtgatgac    4200
cggggaggcc atcacgtact ccacatatgg caaatttctc gccgatgggg gctgcgctag    4260
cggcgcctat gacatcatca tatgcgatga atgccacgct gtggatgcta cctccattct    4320
cggcatcgga acggtccttg atcaagcaga gacagccggg gtcagactaa ctgtgctggc    4380
tacggccaca ccccccgggt cagtgacaac cccccatccc gatatagaag aggtaggcct    4440
```

```
cgggcgggag ggtgagatcc ccttctatgg gagggcgatt cccctatcct gcatcaaggg    4500
agggagacac ctgattttct gccactcaaa gaaaaagtgt gacgagctcg cggcggccct    4560
tcggggcatg ggcttgaatg ccgtggcata ctatagaggg ttggacgtct ccataatacc    4620
agctcaggga gatgtggtgg tcgtcgccac cgacgccctc atgacggggt acactggaga    4680
ctttgactcc gtgatcgact gcaatgtagc ggtcacccaa gctgtcgact tcagcctgga    4740
ccccaccttc actataacca cacagactgt cccacaagac gctgtctcac gcagtcagcg    4800
ccgcgggcgc acaggtagag gaagacaggg cacttatagg tatgtttcca ctggtgaacg    4860
agcctcagga atgtttgaca gtgtagtgct ttgtgagtgc tacgacgcag gggctgcgtg    4920
gtacgatctc acaccagcgg agaccaccgt caggcttaga gcgtatttca cacgcccgg    4980 cctaccgtg tgtcaagacc atcttgaatt ttgggaggca gttttcaccg gcctcacaca    5040
catagacgcc cacttcctct cccaaacaaa gcaagcgggg gagaacttcg cgtacctagt    5100
agcctaccaa gctacggtgt gcgccagagc caaggcccct cccccgtcct gggacgccat    5160
gtggaagtgc ctggcccgac tcaagcctac gcttgcgggc cccacacctc tcctgtaccg    5220
tttgggccct attaccaatg aggtcaccct cacacaccct gggacgaagt acatcgccac    5280
atgcatgcaa gctgaccttg aggtcatgac cagcacgtgg gtcctagctg gaggagtcct    5340
ggcagccgtc gccgcatatt gcctggcgac tggatgcgtt tccatcatcg gccgcttgca    5400
cgtcaaccag cgagtcgtcg ttgcgccgga taaggaggtc ctgtatgagg cttttgatga    5460
gatggaggaa tgcgcctcta gggcggctct catcgaagag gggcagcgga tagccgagat    5520
gttgaagtcc aagatccaag gcttgctgca gcaggcctct aagcaggccc aggacataca    5580
acccgctatg caggcttcat ggcccaaagt ggaacaattt ggggccagac acatgtggaa    5640
cttcattagc ggcatccaat acctcgcagg attgtcaaca ctgccaggga ccccgcggt    5700 ggcttccatg atggcattca gtgccgccct caccagtccg ttgtcgacca gtaccaccat    5760
ccttctcaac atcatgggag ctggttagc gtcccagatc gcaccaccccg cggggggccac    5820 cggctttgtc gtcagtggcc tggtgggggc tgccgtgggc agcataggcc tgggtaaggt    5880
gctggtggac atcctggcag gatatggtgc gggcatttcg ggggccctcg tcgcattcaa    5940
gatcatgtct ggcgagaagc cctctatgga agatgtcatc aatctactgc ctgggatcct    6000
gtctccggga gccctggtgg tggggtcat ctgcgcggcc attctgcgcc gccacgtggg    6060
accgggggag ggcgcggtcc aatggatgaa caggcttatt gcctttgctt ccagaggaaa    6120
ccacgtcgcc cctactcact acgtgacgga gtcggatgcg tcgcagcgtg tgacccaact    6180
acttggctct cttactataa ccagcctact cagaagactc cacaattgga taactgagga    6240
ctgccccatc ccatgctccg gatcctggct ccgcgacgtg tgggactggg tttgcaccat    6300
cttgacagac ttcaaaaatt ggctgacctc taaattgttc cccaagctgc ccggcctccc    6360
cttcatctct tgtcaaaagg ggtacaaggg tgtgtgggcc ggcactggca tcatgaccac    6420
gcgctgccct tgcggcgcca acatctctgg caatgtccgc ctgggctcta tgaggatcac    6480
agggcctaaa acctgcatga acacctggca ggggacctttt cctatcaatt gctacacgga    6540
gggccagtgc gcgccgaaac cccccacgaa ctacaagacc gccatctgga gggtggcggc    6600
ctcggagtac gcggaggtga cgcagcatgg gtcgtactcc tatgtaacag gactgaccac    6660
tgacaatctg aaaattcctt gccaactacc ttctccagag ttttttctcct gggtggacgg    6720 tgtgcagatc cataggtttg cacccacacc aaagccgttt ttccgggatg aggtctcgtt    6780
ctgcgttggg cttaattcct atgctgtcgg gtcccagctt ccctgtgaac ctgagcccga    6840
```

-continued

```
cgcagacgta ttgaggtcca tgctaacaga tccgccccac atcacggcgg agactgcggc    6900
gcggcgcttg gcacgggat  cacctccatc tgaggcgagc tcctcagtga gccagctatc    6960
agcaccgtcg ctgcgggcca cctgcaccac ccacagcaac acctatgacg tggacatggt    7020
cgatgccaac ctgctcatgg agggcggtgt ggctcagaca gagcctgagt ccagggtgcc    7080
cgttctggac tttctcgagc caatggccga ggaagagagc gaccttgagc cctcaatacc    7140
atcggagtgc atgctcccca ggagcgggtt tccacgggcc ttaccggctt gggcacggcc    7200
tgactacaac ccgccgctcg tggaatcgtg gaggaggcca gattaccaac cgcccaccgt    7260
tgctggttgt gctctccccc ccccaagaa  ggccccgacg cctcccccaa ggagacgccg    7320
gacagtgggt ctgagcgaga gcaccatatc agaagccctc cagcaactgg ccatcaagac    7380
ctttggccag ccccctcga  gcggtgatgc aggctcgtcc acggggcgg  gcgccgccga    7440
atccggcggt ccgacgtccc ctggtgagcc ggcccctca  gagacaggtt ccgcctcctc    7500
tatgccccc  ctcgagggg  agcctggaga tccggacctg gagtctgatc aggtagagct    7560
tcaacctccc ccccagggg  ggggggtagc tcccggttcg ggctcggggt cttggtctac    7620
ttgctccgag gaggacgata ccaccgtgtg ctgctccatg tcatactcct ggaccggggc    7680
tctaataact ccctgtagcc ccgaagagga aaagttgcca atcaaccctt tgagtaactc    7740
gctgttgcga taccataaca aggtgtactg tacaacatca aagagcgcct cacagagggc    7800
taaaaggta  acttttgaca ggacgcaagt gctcgacgcc cattatgact cagtcttaaa    7860
ggacatcaag ctagcggctt ccaaggtcag cgcaaggctc ctcaccttgg aggaggcgtg    7920
ccagttgact ccacccccatt ctgcaagatc caagtatgga ttcggggcca aggaggtccg    7980
cagcttgtcc gggagggccg ttaaccacat caagtccgtg tggaaggacc tcctggaaga    8040
cccacaaaca ccaattccca caaccatcat ggccaaaaat gaggtgttct gcgtggaccc    8100
cgccaagggg ggtaagaaac cagctcgcct catcgtttac cctgacctcg gcgtccgggt    8160
ctgcgagaaa atggccctct atgacattac acaaaagctt cctcaggcgg taatgggagc    8220
ttcctatggc ttccagtact cccctgccca acgggtggag tatctcttga aagcatgggc    8280
ggaaaagaag gaccccatgg ttttttcgta tgatacccga tgcttcgact caaccgtcac    8340
tgagagagac atcaggaccg aggagtccat ataccaggcc tgctccctgc ccgaggaggc    8400
ccgcactgcc atacactcgc tgactgagag actttacgta ggagggccca tgttcaacag    8460
caagggtcaa acctgcggtt acagacgttg ccgcgccagc ggggtgctaa ccactagcat    8520
gggtaacacc atcacatgct atgtgaaagc cctagcggcc tgcaaggctg cggggatagt    8580
tgcgcccaca atgctggtat gcggcgatga cctagtagtc atctcagaaa gccaggggac    8640
tgaggaggac gagcggaacc tgagagcctt cacggaggcc atgaccaggt actctgcccc    8700
tcctggtgat cccccagac  cggaatatga cctggagcta ataacatcct gttcctcaaa    8760
tgtgtctgtg gcgttgggcc cgcggggccg ccgcagatac tacctgacca gagacccaac    8820
cactccactc gcccgggctg cctgggaaac agttagacac tcccctatca attcatggct    8880
gggaaacatc atccagtatg ctccaaccat atgggttcgc atggtcctaa tgacacactt    8940
cttctccatt ctcatggtcc aagacaccct ggaccagaac ctcaactttg agatgtatgg    9000
atcagtatac tccgtgaatc cttttggacct tccagccata attgagaggt tacacgggct    9060
tgacgccttt tctatgcaca catactctca ccacgaactg acgcgggtgg cttcagccct    9120
cagaaaactt ggggcgccac ccctcagggt gtggaagagt cgggctcgcg cagtcagggc    9180
gtccctcatc tcccgtggag ggaaagcggc cgtttgcggc cgatatctct tcaattgggc    9240
```

```
ggtgaagacc aagctcaaac tcactccatt gccggaggcg cgcctactgg acttatccag    9300
ttggttcacc gtcggcgccg gcgggggcga cattttcac agcgtgtcgc gcgcccgacc    9360
ccgctcatta ctcttcggcc tactcctact tttcgtaggg gtaggcctct tcctactccc    9420
cgctcggtag agcggcacac actaggtaca ctccatagct aactgttcct tttttttttt    9480
tttttttttt tttttttttt tttttttttt ttctttttttt tttttttccc tctttcttcc    9540
cttctcatct tattctactt tctttcttgg tggctccatc ttagccctag tcacggctag    9600
ctgtgaaagg tccgtgagcc gcatgactgc agagagtgcc gtaactggtc tctctgcaga    9660
tcatgt                                                               9666

<210> SEQ ID NO 2
<211> LENGTH: 9666
<212> TYPE: DNA
<213> ORGANISM: Hepatitis C virus

<400> SEQUENCE: 2
acctgcccct aatagggggcg acactccgcc atgaatcact ccctgtgag gaactactgt      60 cttcacgcag aaagcgccta gccatggcgt tagtatgagt gtcgtacagc ctccaggccc     120 cccctcccg ggagagccat agtggtctgc ggaaccggtg agtacaccgg aattgccggg     180
aagactgggt cctttcttgg ataaacccac tctatgcccg gccatttggg cgtgcccccg     240
caagactgct agccgagtag cgttgggttg cgaaaggcct tgtggtactg cctgataggg     300
cgcttgcgag tgccccggga ggtctcgtag accgtgcacc atgagcacga atcctaaacc     360
tcaaagaaaa accaaacgta acaccaaccg ccgcccaatg gacgttaagt tcccgggtgg     420
tggccagatc gttggcggag tttacttgtt gccgcgcagg ggcccagat tgggtgtgcg     480 cgcgactcgg aagacttcgg agcggtcgca acctcgtgga agacgccaac ctatccccaa     540
ggcgcgtcga cccagggaa ggtcctgggc acaaccagga tatccatggc ctctttacgg     600
taatgagggt tgtgggtggg caggatggct cttgtccccc cgtggctctc gaccgtcttg     660
gggcccaaat gatccccggc ggaggtcccg caatttgggt aaggtcatcg atacccctaac    720 ctgcggcttc gccgacctca tgggatacat cccgctcgta ggcgccccg tgggtggcgt     780 cgccagggcc ctggcacatg gtgtcagggc tttggaggac gggatcaatt atgcaacagg     840
gaatctcccc ggttgctcct tttctatctt cctcttggca cttctttcgt gcctgactgt     900
ccccgcttcg gccgttaact atcgcaatgt ctcgggcatc taccatgtca ccaatgactg     960
cccgaattca agcatagtgt atgaggccga ccatcacatc ttgcaccttc caggttgcgt    1020
gccctgcgtg agagagggga atcagtcacg ctgctgggtg gcccttactc ctaccgtcgc    1080
agcgccatac atcggcgcac gcttgagtc cttacggagt catgtggatt tgatggtggg    1140
ggccgccact gtttgctcgg gtctttacat cggggacctg tgtggcggct tgttcctagt    1200
tggccagatg ttttcattcc gaccacggcg ccactggacc acccaggatt gcaattgttc    1260
catctacaca gggcacatta caggccacag aatggcctgg gacatgatga tgaactggag    1320
tccaacaacc accttagttc tcgcccaggt catgaggatc caaccactc tggtagactt    1380 actctctgga ggccactggg gtgtcctcgt gggagtggcc tatttcagca tgcaggccaa    1440
ttgggccaaa gtcatcttgg tcctattcct ctttgcaggg gttgatgccg agactcacgt    1500
gtctggggca gcagtcggcc ggagtaccgc cggcttggct aacctctttt cttctgggtc    1560
taagcagaat ttacagctca tcaacagcaa tgggagctgg catataaata ggactgccct    1620
taactgcaat gacagcttaa acactgggtt cttggctagc ttgttctaca cccacaagtt    1680
```

```
taacagctca gggtgttccg aacggctcgc gtgctgcaag agccttgaca gctacggcca    1740
aggctggggc ccactcgggg tcgctaacat cagcggctcg tctgatgaca ggccttattg    1800
ctggcactac gcgcctcggc cgtgcgggat tgtgccagca tccagtgtgt gtggccccgt    1860
gtattgtttc actcccagcc ctgtcgtggt cggtactact gatcacgtcg gggtccctac    1920
ttacacctgg ggggagaatg agactgatgt cttccttttg aactcgacca gaccgccgca    1980
tggtgcgtgg tttggatgcg tgtggatgaa cagtaccggg ttcaccaaaa cctgtggcgc    2040
ccctccatgc gaggttaaca ccaataatgg gacctggcac tgccccaccg attgcttcag    2100
gaagcatccg gagactacct acgccaagtg cggatcaggg ccttggatca caccgcgctg    2160
cctgattgat tacccgtacc ggctgtggca tttcccgtgc accgccaact tctccgtctt    2220
taacatcagg acatttgtcg gcggtataga gcatcggatg caagcggcat gcaactggac    2280
caggggggaa gtctgtggct tggagcacag ggatcgcgta gagctatcac ccctgctcct    2340
taccactaca gcgtggcaga tcctcccctg ctctttcacc actttacctg ccctctccac    2400
cggcttgatc cacctccacc aaaatatcgt ggacgtccag tacctctatg tgttgggtc     2460 tgcagtggta tcttgggccc ttaagtggga atatgtggtg ctcgcgttcc tgcttctcgc    2520
ggacgcgaga gtctctgcct gcctatggat gatgtttatg gtaagtcaag ttgaggcggc    2580
tctgtccaac ctgattaaca tcaatgctgc ttcagccgct ggtgcccaag gcttctggta    2640
cgccatcctc ttcatctgca ttgtctggca tgtcaagggc cggttcccag ctgctgctgc    2700
ctacgcagcc tgcgggctgt ggcccctgtt tctcctgctt ctgatgctgc tgagagggc     2760 ttatgcatac gaccaggaag tggcagggtc ccttggcggc gccatcgttg tcatgctgac    2820
cattctgaca ctgtctccgc actacaagtt atggctggct aggggattgt ggtggatcca    2880
atattttata gctaggaccg aggctgtgct gcatgtctat attccatcct tcaacgtgcg    2940
cgggcctcgc gactcagtga ttgttcttgc agtcctggtc tgtccacacc tagtatttga    3000
catcacaaaa tatcttctgg ccatcttagg gcccctccac atactccagg cctcgctcct    3060
acgcatccct tactttgtga gggcacaagc gctggttaag atctgcagct tgttgcgtgg    3120
ggtagtttat ggcaagtact tccaaatggt cgtgcttaaa gcaggggccc tgactggtac    3180
ttacatctat gaccacctta ctcccatgtc agattgggcc gctacgggcc tccgcgattt    3240
ggcggtggcc ctagagccag ttgtgttcac gcccatggag aagaaagtca tcgtctgggg    3300
cgctgacacc gctgcgtgcg gagacatcat aagggggatta cctgtttcgg ccaggttggg    3360
caatgaaatc ttgctcggac cagccgatac agaaacatca aaggggtgga gactccttgc    3420
tcccatcact gcttatgccc agcaaacacg aggcctcctg ggcgccatag tggtgagtat    3480
gacggggcgt gacaggacag aacaggccgg ggaagtccaa atcctgtcca cagtctctca    3540
gtccttcctc ggaacaacca tctcgggggt tttgtggact gtttaccacg gagctggcaa    3600
caagactcta gccggcttac ggggtccggt cacgcagatg tactcgagtg ctgaggggga    3660
cttggtaggc tggcccagcc ccctgggac caagtctttg gagccgtgca agtgtggagc     3720
cgtcgaccta tatctggtca cgcggaacgc tgatgtcatc ccggctcgga gacgcgggga    3780
caagcgggga gcattgctct ccccgagacc catttcgacc ttgaagggt cctcggggg      3840 gccggtgctc tgccctaggg gccacgtcgt tgggctcttc cgagcagctg tgtgctctcg    3900
gggcgtggcc aaatccatcg atttcatccc cgttgagaca ctcgacgttg ttacaaggtc    3960 tcccacttc agtgacaaca gcacgccacc ggctgtgccc cagacctatc aggtcggta      4020 cttgcatgct ccaactggca gtggaaagag caccaaggtc cctgtcgcgt atgccgccca    4080
```

```
ggggtacaaa gtactagtgc ttaacccctc ggtagctgcc accctggggt ttggggcgta      4140
cctatccaag gcacatggca tcaatcccaa cattaggact ggagtcagga ccgtgatgac      4200
cggggaggcc atcacgtact ccacatatgg caaatttctc gccgatgggg gctgcgctag      4260
cggcgcctat gacatcatca tatgcgatga atgccacgct gtggatgcta cctccattct      4320
cggcatcgga acggtccttg atcaagcaga gacagccggg gtcagactaa ctgtgctggc      4380
tacgccacca ccccccgggt cagtgacaac ccccatccc gatatagaag aggtaggcct       4440
cgggcgggag ggtgagatcc ccttctatgg gagggcgatt cccctatcct gcatcaaggg      4500
agggagacac ctgattttct gccactcaaa gaaaaagtgt gacgagctcg cggcggccct      4560
tcggggcatg ggcttgaatg ccgtggcata ctatagaggg ttggacgtct ccataatacc      4620
agctcaggga gatgtggtgg tcgtcgccac cgacgccctc atgacggggt acactggaga      4680
ctttgactcc gtgatcgact gcaatgtagc ggtcacccaa gctgtcgact tcagcctgga      4740
ccccaccttc actataacca cacagactgt cccacaagac gctgtctcac gcagtcagcg      4800
ccgcgggcgc acaggtagag aagacaggg cacttatagg tatgtttcca ctggtgaacg       4860
agcctcagga atgtttgaca gtgtagtgct ttgtgagtgc tacgacgcag gggctgcgtg      4920
gtacgatctc acaccagcgg agaccaccgt caggcttaga gcgtatttca acacgcccgg      4980 cctaccgtg tgtcaagacc atcttgaatt ttgggaggca gttttcaccg gcctcacaca       5040
catagacgcc cacttcctct cccaaacaaa gcaagcgggg gagaacttcg cgtacctagt      5100
agcctaccaa gctacggtgt gcgccagagc caaggcccct cccccgtcct gggacgccat      5160
gtggaagtgc ctggcccgac tcaagcctac gcttgcgggc cccacacctc tcctgtaccg      5220
tttgggccct attaccaatg aggtcaccct cacacaccct gggacgaagt acatcgccac      5280
atgcatgcaa gctgaccttg aggtcatgac cagcacgtgg gtcctagctg gaggagtcct      5340
ggcagccgtc gccgcatatt gcctggcgac tggatgcgtt ccatcatcg gccgcttgca       5400 cgtcaaccag cgagtcgtcg ttgcgccgga taaggaggtc ctgtatgagg cttttgatga     5460
gatggaggaa tgcgcctcta gggcggctct catcgaagag gggcagcgga tagccgagat      5520
gttgaagtcc aagatccaag gcttgctgca gcaggcctct aagcaggccc aggacataca      5580
acccgctatg caggcttcat ggccaaagt ggaacaattt tgggccagac acatgtggaa       5640
cttcattagc ggcatccaat acctcgcagg attgtcaaca ctgccaggga ccccgcggt      5700 ggcttccatg atggcattca gtgccgccct caccagtccg ttgtcgacca gtaccaccat      5760
ccttctcaac atcatgggag ctggttagc gtcccagatc gcaccaccg cggggggccac       5820 cggctttgtc gtcagtggcc tggtgggggc tgccgtgggc agcataggcc tgggtaaggt      5880
gctggtggac atcctggcag gatatggtgc gggcatttcg ggggccctcg tcgcattcaa      5940
gatcatgtct ggcgagaagc cctctatgga agatgtcatc aatctactgc tgggatcct      6000 gtctccggga gccctggtgg tggggtcat ctgcgcggcc attctgcgcc gccacgtggg      6060
accgggggag ggcgcggtcc aatggatgaa caggcttatt gcctttgctt ccagaggaaa      6120
ccacgtcgcc cctactcact acgtgacgga gtcggatgcg tcgcagcgtg tgacccaact      6180
acttggctct cttactataa ccagcctact cagaagactc cacaattgga taactgagga      6240
ctgccccatc ccatgctccg gatcctggct ccgcgacgtg tgggactggg tttgcaccat      6300
cttgacagac ttcaaaaatt ggctgacctc taaattgttc cccaagctgc ccggcctccc      6360
cttcatctct tgtcaaaagg ggtacaaggg tgtgtgggcc ggcactggca tcatgaccac      6420
gcgctgccct tgcggcgcca acatctctgg caatgtccgc ctgggctcta tgaggatcac      6480
```

| | |
|---|---|
| agggcctaaa acctgcatga acacctggca ggggaccttt cctatcaatt gctacacgga | 6540 |
| gggccagtgc cgcgccgaaac cccccacgaa ctacaagacc gccatctgga gggtggcggc | 6600 |
| ctcggagtac gcggaggtga cgcagcatgg gtcgtactcc tatgtaacag gactgaccac | 6660 |
| tgacaatctg aaaattcctt gccaactacc ttctccagag ttttttctcct gggtggacgg | 6720 |
| tgtgcagatc cataggtttg cacccacacc aaagccgttt ttccgggatg aggtctcgtt | 6780 |
| ctgcgttggg cttaattcct atgctgtcgg gtcccagctt ccctgtgaac ctgagcccga | 6840 |
| cgcagacgta ttgaggtcca tgctaacaga tccgccccac atcacggcgg agactgcggc | 6900 |
| gcggcgcttg gcacggggat cacctccatc tgaggcgagc tcctcagtga gccagctatc | 6960 |
| agcaccgtcg ctgcgggcca cctgcaccac ccacagcaac acctatgacg tggacatggt | 7020 |
| cgatgccaac ctgctcatgg agggcggtgt ggctcagaca gagcctgagt ccagggtgcc | 7080 |
| cgttctggac tttctcgagc caatggccga ggaagagagc gaccttgagc cctcaatacc | 7140 |
| atcggagtgc atgctcccca ggagcgggtt tccacgggcc ttaccggctt gggcacggcc | 7200 |
| tgactacaac ccgccgctcg tggaatcgtg gaggaggcca gattaccaac cgcccaccgt | 7260 |
| tgctggttgt gctctccccc cccccaagaa ggccccgacg cctcccccaa ggagacgccg | 7320 |
| gacagtgggt ctgagcgaga gcaccatatc agaagccctc cagcaactgg ccatcaagac | 7380 |
| ctttggccag cccccctcga gcggtgatgc aggctcgtcc acgggggcgg gcgccgccga | 7440 |
| atccggcggt ccgacgtccc ctggtgagcc ggcccccttca gagacaggtt ccgcctcctc | 7500 |
| tatgcccccc ctcgagggggg agcctggaga tccggacctg gagtctgatc aggtagagct | 7560 |
| tcaacctccc ccccaggggg gggggtagc tcccggttcg ggctcggggt cttggtctac | 7620 |
| ttgctccgag gaggacgata ccaccgtgtg ctgctccatg tcatactcct ggaccggggc | 7680 |
| tctaataact ccctgtagcc ccgaagagga aaagttgcca atcaacccctt tgagtaactc | 7740 |
| gctgttgcga taccataaca aggtgtactg tacaacatca aagagcgcct cacagagggc | 7800 |
| taaaaaggta acttttgaca ggacgcaagt gctcgacgcc cattatgact cagtcttaaa | 7860 |
| ggacatcaag ctagcggctt ccaaggtcag cgcaaggctc ctcaccttgg aggaggcgtg | 7920 |
| ccagttgact ccacccccatt ctgcaagatc caagtatgga ttcggggcca aggaggtccg | 7980 |
| cagcttgtcc ggggagggccg ttaaccacat caagtccgtg tggaaggacc tcctggaaga | 8040 |
| cccacaaaca ccaattccca caaccatcat ggccaaaaat gaggtgttct gcgtggaccc | 8100 |
| cgccaagggg ggtaagaaac cagctcgcct catcgtttac cctgacctcg cgtccgggt | 8160 |
| ctgcgagaaa atggccctct atgacattac acaaaagctt cctcaggcgg taatgggagc | 8220 |
| ttcctatggc ttccagtact cccctgccca acgggtggag tatctcttga aagcatgggc | 8280 |
| ggaaaagaag gaccccatgg gttttttcgta tgatacccga tgcttcgact caaccgtcac | 8340 |
| tgagagagac atcaggaccg aggagtccat ataccaggcc tgctccctgc ccgaggaggc | 8400 |
| ccgcactgcc atacactcgc tgactgagag actttacgta ggagggccca tgttcaacag | 8460 |
| caagggtcaa acctgcggtt acagacgttg ccgcgccagc ggggtgctaa ccactagcat | 8520 |
| gggtaacacc atcacatgct atgtgaaagc cctagcggcc tgcaaggctg cggggatagt | 8580 |
| tgcgcccaca atgctggtat gcggcgatga cctagtagtc atctcagaaa gccaggggac | 8640 |
| tgaggaggac gagcggaacc tgagagcctt cacggaggcc atgaccaggt actctgcccc | 8700 |
| tcctggtgat ccccccagac cggaatatga cctggagcta ataacatcct gttcctcaaa | 8760 |
| tgtgtctgtg gcgttgggcc cgcggggccg ccgcagatac tacctgacca gagacccaac | 8820 |
| cactccactc gcccgggctg cctgggaaac agttagacac tcccctatca attcatggct | 8880 |

-continued

```
gggaaacatc atccagtatg ctccaaccat atgggttcgc atggtcctaa tgacacactt   8940
cttctccatt tcatggtcc aagacaccct ggaccagaac ctcaactttg agatgtatgg    9000
atcagtatac tccgtgaatc ctttggacct tccagccata attgagaggt tacacgggct    9060
tgacgccttt tctatgcaca catactctca ccacgaactg acgcgggtgg cttcagccct    9120
cagaaaactt ggggcgccac ccctcagggt gtggaagagt cgggctcgcg cagtcagggc    9180
gtccctcatc tcccgtggag ggaaagcggc cgtttgcggc cgatatctct tcaattgggc    9240
ggtgaagacc aagctcaaac tcactccatt gccggaggcg cgcctactgg acttatccag    9300
ttggttcacc gtcggcgccg gcggggggcga catttttcac agcgtgtcgc gcgcccgacc    9360
ccgctcatta ctcttcggcc tactcctact tttcgtaggg gtaggcctct tcctactccc    9420
cgctcggtag agcggcacac actaggtaca ctccatagct aactgttcct ttttttttt    9480 tttttttttt tttttttttt tttttttttt ttcttttttt tttttttccc tctttcttcc    9540
cttctcatct tattctactt tctttcttgg tggctccatc ttagccctag tcacggctag    9600
ctgtgaaagg tccgtgagcc gcatgactgc agagagtgcc gtaactggtc tctctgcaga    9660
tcatgt                                                              9666
```

<210> SEQ ID NO 3
<211> LENGTH: 3029
<212> TYPE: PRT
<213> ORGANISM: Hepatitis C virus

<400> SEQUENCE: 3

```
Met Ser Thr Asn Pro Lys Pro Gln Arg Lys Thr Lys Arg Asn Thr Asn
1               5                   10                  15

Arg Arg Pro Met Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Val
            180                 185                 190

Asn Tyr Arg Asn Val Ser Gly Ile Tyr His Val Thr Asn Asp Cys Pro
        195                 200                 205

Asn Ser Ser Ile Val Tyr Glu Ala Asp His His Ile Leu His Leu Pro
    210                 215                 220

Gly Cys Val Pro Cys Val Arg Glu Gly Asn Gln Ser Arg Cys Trp Val
225                 230                 235                 240
```

```
Ala Leu Thr Pro Thr Val Ala Ala Pro Tyr Ile Gly Ala Pro Leu Glu
            245                 250                 255

Ser Leu Arg Ser His Val Asp Leu Met Val Gly Ala Ala Thr Val Cys
        260                 265                 270

Ser Gly Leu Tyr Ile Gly Asp Leu Cys Gly Gly Leu Phe Leu Val Gly
            275                 280                 285

Gln Met Phe Ser Phe Arg Pro Arg Arg His Trp Thr Thr Gln Asp Cys
    290                 295                 300

Asn Cys Ser Ile Tyr Thr Gly His Ile Thr Gly His Arg Met Ala Trp
305                 310                 315                 320

Asp Met Met Met Asn Trp Ser Pro Thr Thr Leu Val Leu Ala Gln
                325                 330                 335

Val Met Arg Ile Pro Thr Thr Leu Val Asp Leu Leu Ser Gly Gly His
            340                 345                 350

Trp Gly Val Leu Val Gly Val Ala Tyr Phe Ser Met Gln Ala Asn Trp
        355                 360                 365

Ala Lys Val Ile Leu Val Leu Phe Leu Phe Ala Gly Val Asp Ala Glu
    370                 375                 380

Thr His Val Ser Gly Ala Ala Val Gly Arg Ser Thr Ala Gly Leu Ala
385                 390                 395                 400

Asn Leu Phe Ser Ser Gly Ser Lys Gln Asn Leu Gln Leu Ile Asn Ser
                405                 410                 415

Asn Gly Ser Trp His Ile Asn Arg Thr Ala Leu Asn Cys Asn Asp Ser
            420                 425                 430

Leu Asn Thr Gly Phe Leu Ala Ser Leu Phe Tyr Thr His Lys Phe Asn
        435                 440                 445

Ser Ser Gly Cys Ser Glu Arg Leu Ala Cys Cys Lys Ser Leu Asp Ser
    450                 455                 460

Tyr Gly Gln Gly Trp Gly Pro Leu Gly Val Ala Asn Ile Ser Gly Ser
465                 470                 475                 480

Ser Asp Asp Arg Pro Tyr Cys Trp His Tyr Ala Pro Arg Pro Cys Gly
                485                 490                 495

Ile Val Pro Ala Ser Ser Val Cys Gly Pro Val Tyr Cys Phe Thr Pro
            500                 505                 510

Ser Pro Val Val Val Gly Thr Thr Asp His Val Gly Val Pro Thr Tyr
        515                 520                 525

Thr Trp Gly Glu Asn Glu Thr Asp Val Phe Leu Leu Asn Ser Thr Arg
    530                 535                 540

Pro Pro His Gly Ala Trp Phe Gly Cys Val Trp Met Asn Ser Thr Gly
545                 550                 555                 560

Phe Thr Lys Thr Cys Gly Ala Pro Pro Cys Glu Val Asn Thr Asn Asn
                565                 570                 575

Gly Thr Trp His Cys Pro Thr Asp Cys Phe Arg Lys His Pro Glu Thr
            580                 585                 590

Thr Tyr Ala Lys Cys Gly Ser Gly Pro Trp Ile Thr Pro Arg Cys Leu
        595                 600                 605

Ile Asp Tyr Pro Tyr Arg Leu Trp His Phe Pro Cys Thr Ala Asn Phe
    610                 615                 620

Ser Val Phe Asn Ile Arg Thr Phe Val Gly Gly Ile Glu His Arg Met
625                 630                 635                 640

Gln Ala Ala Cys Asn Trp Thr Arg Gly Glu Val Cys Gly Leu Glu His
                645                 650                 655

Arg Asp Arg Val Glu Leu Ser Pro Leu Leu Leu Thr Thr Thr Ala Trp
```

-continued

```
                660                 665                 670
Gln Ile Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
            690                 695                 700

Val Gly Ser Ala Val Val Ser Trp Ala Leu Lys Trp Glu Tyr Val Val
705                 710                 715                 720

Leu Ala Phe Leu Leu Leu Ala Asp Ala Arg Val Ser Ala Cys Leu Trp
            725                 730                 735

Met Met Phe Met Val Ser Gln Val Glu Ala Ala Leu Ser Asn Leu Ile
            740                 745                 750

Asn Ile Asn Ala Ala Ser Ala Ala Gly Ala Gln Gly Phe Trp Tyr Ala
            755                 760                 765

Ile Leu Phe Ile Cys Ile Val Trp His Val Lys Gly Arg Phe Pro Ala
            770                 775                 780

Ala Ala Ala Tyr Ala Ala Cys Gly Leu Trp Pro Leu Phe Leu Leu Leu
785                 790                 795                 800

Leu Met Leu Pro Glu Arg Ala Tyr Ala Tyr Asp Gln Glu Val Ala Gly
            805                 810                 815

Ser Leu Gly Gly Ala Ile Val Val Met Leu Thr Ile Leu Thr Leu Ser
            820                 825                 830

Pro His Tyr Lys Leu Trp Leu Ala Arg Gly Leu Trp Trp Ile Gln Tyr
            835                 840                 845

Phe Ile Ala Arg Thr Glu Ala Val Leu His Val Tyr Ile Pro Ser Phe
            850                 855                 860

Asn Val Arg Gly Pro Arg Asp Ser Val Ile Val Leu Ala Val Leu Val
865                 870                 875                 880

Cys Pro His Leu Val Phe Asp Ile Thr Lys Tyr Leu Leu Ala Ile Leu
            885                 890                 895

Gly Pro Leu His Ile Leu Gln Ala Ser Leu Leu Arg Ile Pro Tyr Phe
            900                 905                 910

Val Arg Ala Gln Ala Leu Val Lys Ile Cys Ser Leu Leu Arg Gly Val
            915                 920                 925

Val Tyr Gly Lys Tyr Phe Gln Met Val Val Leu Lys Ala Gly Ala Leu
            930                 935                 940

Thr Gly Thr Tyr Ile Tyr Asp His Leu Thr Pro Met Ser Asp Trp Ala
945                 950                 955                 960

Ala Ser Gly Leu Arg Asp Leu Ala Val Ala Val Glu Pro Ile Ile Phe
            965                 970                 975

Ser Pro Met Glu Lys Lys Val Ile Val Trp Gly Ala Glu Thr Ala Ala
            980                 985                 990

Cys Gly Asp Ile Leu His Gly Leu Pro Val Ser Ala Arg Leu Gly Gln
            995                 1000                1005

Glu Ile Leu Leu Gly Pro Ala Asp Gly Tyr Thr Ser Lys Gly Trp
            1010                1015                1020

Lys Leu Leu Ala Pro Ile Thr Ala Tyr Ala Gln Gln Thr Arg Gly
            1025                1030                1035

Leu Leu Gly Ala Ile Val Val Ser Met Thr Gly Arg Asp Arg Thr
            1040                1045                1050

Glu Gln Ala Gly Glu Val Gln Ile Leu Ser Thr Val Ser Gln Ser
            1055                1060                1065

Phe Leu Gly Thr Thr Ile Ser Gly Val Leu Trp Thr Val Tyr His
            1070                1075                1080
```

-continued

```
Gly Ala Gly Asn Lys Thr Leu Ala Gly Leu Arg Gly Pro Val Thr
    1085                1090                1095
Gln Met Tyr Ser Ser Ala Glu Gly Asp Leu Val Gly Trp Pro Ser
    1100                1105                1110
Pro Pro Gly Thr Lys Ser Leu Glu Pro Cys Lys Cys Gly Ala Val
    1115                1120                1125
Asp Leu Tyr Leu Val Thr Arg Asn Ala Asp Val Ile Pro Ala Arg
    1130                1135                1140
Arg Arg Gly Asp Lys Arg Gly Ala Leu Leu Ser Pro Arg Pro Ile
    1145                1150                1155
Ser Thr Leu Lys Gly Ser Ser Gly Gly Pro Val Leu Cys Pro Arg
    1160                1165                1170
Gly His Val Val Gly Leu Phe Arg Ala Ala Val Cys Ser Arg Gly
    1175                1180                1185
Val Ala Lys Ser Ile Asp Phe Ile Pro Val Glu Thr Leu Asp Val
    1190                1195                1200
Val Thr Arg Ser Pro Thr Phe Ser Asp Asn Ser Thr Pro Pro Ala
    1205                1210                1215
Val Pro Gln Thr Tyr Gln Val Gly Tyr Leu His Ala Pro Thr Gly
    1220                1225                1230
Ser Gly Lys Ser Thr Lys Val Pro Val Ala Tyr Ala Ala Gln Gly
    1235                1240                1245
Tyr Lys Val Leu Val Leu Asn Pro Ser Val Ala Ala Thr Leu Gly
    1250                1255                1260
Phe Gly Ala Tyr Leu Ser Lys Ala His Gly Ile Asn Pro Asn Ile
    1265                1270                1275
Arg Thr Gly Val Arg Thr Val Met Thr Gly Glu Ala Ile Thr Tyr
    1280                1285                1290
Ser Thr Tyr Gly Lys Phe Leu Ala Asp Gly Gly Cys Ala Ser Gly
    1295                1300                1305
Ala Tyr Asp Ile Ile Ile Cys Asp Glu Cys His Ala Val Asp Ala
    1310                1315                1320
Thr Ser Ile Leu Gly Ile Gly Thr Val Leu Asp Gln Ala Glu Thr
    1325                1330                1335
Ala Gly Val Arg Leu Thr Val Leu Ala Thr Ala Thr Pro Pro Gly
    1340                1345                1350
Ser Val Thr Thr Pro His Pro Asp Ile Glu Glu Val Gly Leu Gly
    1355                1360                1365
Arg Glu Gly Glu Ile Pro Phe Tyr Gly Arg Ala Ile Pro Leu Ser
    1370                1375                1380
Cys Ile Lys Gly Gly Arg His Leu Ile Phe Cys His Ser Lys Lys
    1385                1390                1395
Lys Cys Asp Glu Leu Ala Ala Ala Leu Arg Gly Met Gly Leu Asn
    1400                1405                1410
Ala Val Ala Tyr Tyr Arg Gly Leu Asp Val Ser Ile Ile Pro Ala
    1415                1420                1425
Gln Gly Asp Val Val Val Ala Thr Asp Ala Leu Met Thr Gly
    1430                1435                1440
Tyr Thr Gly Asp Phe Asp Ser Val Ile Asp Cys Asn Val Ala Val
    1445                1450                1455
Thr Gln Ala Val Asp Phe Ser Leu Asp Pro Thr Phe Thr Ile Thr
    1460                1465                1470
Thr Gln Thr Val Pro Gln Asp Ala Val Ser Arg Ser Gln Arg Arg
    1475                1480                1485
```

```
Gly Arg Thr Gly Arg Gly Gln Gly Thr Tyr Arg Tyr Val Ser
    1490            1495                1500

Thr Gly Glu Arg Ala Ser Gly Met Phe Asp Ser Val Val Leu Cys
    1505            1510                1515

Glu Cys Tyr Asp Ala Gly Ala Ala Trp Tyr Asp Leu Thr Pro Ala
    1520            1525                1530

Glu Thr Thr Val Arg Leu Arg Ala Tyr Phe Asn Thr Pro Gly Leu
    1535            1540                1545

Pro Val Cys Gln Asp His Leu Glu Phe Trp Glu Ala Val Phe Thr
    1550            1555                1560

Gly Leu Thr His Ile Asp Ala His Phe Leu Ser Gln Thr Lys Gln
    1565            1570                1575

Ala Gly Glu Asn Phe Ala Tyr Leu Val Ala Tyr Gln Ala Thr Val
    1580            1585                1590

Cys Ala Arg Ala Lys Ala Pro Pro Pro Ser Trp Asp Ala Met Trp
    1595            1600                1605

Lys Cys Leu Ala Arg Leu Lys Pro Thr Leu Ala Gly Pro Thr Pro
    1610            1615                1620

Leu Leu Tyr Arg Leu Gly Pro Ile Thr Asn Glu Val Thr Leu Thr
    1625            1630                1635

His Pro Gly Thr Lys Tyr Ile Ala Thr Cys Met Gln Ala Asp Leu
    1640            1645                1650

Glu Val Met Thr Ser Thr Trp Val Leu Ala Gly Gly Val Leu Ala
    1655            1660                1665

Ala Val Ala Ala Tyr Cys Leu Ala Thr Gly Cys Val Ser Ile Ile
    1670            1675                1680

Gly Arg Leu His Val Asn Gln Arg Val Val Val Ala Pro Asp Lys
    1685            1690                1695

Glu Val Leu Tyr Glu Ala Phe Asp Glu Met Glu Glu Cys Ala Ser
    1700            1705                1710

Arg Ala Ala Leu Ile Glu Glu Gly Gln Arg Ile Ala Glu Met Leu
    1715            1720                1725

Lys Ser Lys Ile Gln Gly Leu Leu Gln Gln Ala Ser Lys Gln Ala
    1730            1735                1740

Gln Asp Ile Gln Pro Ala Met Gln Ala Ser Trp Pro Lys Val Glu
    1745            1750                1755

Gln Phe Trp Ala Arg His Met Trp Asn Phe Ile Ser Gly Ile Gln
    1760            1765                1770

Tyr Leu Ala Gly Leu Ser Thr Leu Pro Gly Asn Pro Ala Val Ala
    1775            1780                1785

Ser Met Met Ala Phe Ser Ala Ala Leu Thr Ser Pro Leu Ser Thr
    1790            1795                1800

Ser Thr Thr Ile Leu Leu Asn Ile Met Gly Gly Trp Leu Ala Ser
    1805            1810                1815

Gln Ile Ala Pro Pro Ala Gly Ala Thr Gly Phe Val Val Ser Gly
    1820            1825                1830

Leu Val Gly Ala Ala Val Gly Ser Ile Gly Leu Gly Lys Val Leu
    1835            1840                1845

Val Asp Ile Leu Ala Gly Tyr Gly Ala Gly Ile Ser Gly Ala Leu
    1850            1855                1860

Val Ala Phe Lys Ile Met Ser Gly Glu Lys Pro Ser Met Glu Asp
    1865            1870                1875

Val Ile Asn Leu Leu Pro Gly Ile Leu Ser Pro Gly Ala Leu Val
```

-continued

```
                 1880                1885                1890
Val Gly Val Ile Cys Ala Ala Ile Leu Arg Arg His Val Gly Pro
    1895                1900                1905
Gly Glu Gly Ala Val Gln Trp Met Asn Arg Leu Ile Ala Phe Ala
    1910                1915                1920
Ser Arg Gly Asn His Val Ala Pro Thr His Tyr Val Thr Glu Ser
    1925                1930                1935
Asp Ala Ser Gln Arg Val Thr Gln Leu Leu Gly Ser Leu Thr Ile
    1940                1945                1950
Thr Ser Leu Leu Arg Arg Leu His Asn Trp Ile Thr Glu Asp Cys
    1955                1960                1965
Pro Ile Pro Cys Ser Gly Ser Trp Leu Arg Asp Val Trp Asp Trp
    1970                1975                1980
Val Cys Thr Ile Leu Thr Asp Phe Lys Asn Trp Leu Thr Ser Lys
    1985                1990                1995
Leu Phe Pro Lys Leu Pro Gly Leu Pro Phe Ile Ser Cys Gln Lys
    2000                2005                2010
Gly Tyr Lys Gly Val Trp Ala Gly Thr Gly Ile Met Thr Thr Arg
    2015                2020                2025
Cys Pro Cys Gly Ala Asn Ile Ser Gly Asn Val Arg Leu Gly Ser
    2030                2035                2040
Met Arg Ile Thr Gly Pro Lys Thr Cys Met Asn Thr Trp Gln Gly
    2045                2050                2055
Thr Phe Pro Ile Asn Cys Tyr Thr Glu Gly Gln Cys Ala Pro Lys
    2060                2065                2070
Pro Pro Thr Asn Tyr Lys Thr Ala Ile Trp Arg Val Ala Ala Ser
    2075                2080                2085
Glu Tyr Ala Glu Val Thr Gln His Gly Ser Tyr Ser Tyr Val Thr
    2090                2095                2100
Gly Leu Thr Thr Asp Asn Leu Lys Ile Pro Cys Gln Leu Pro Ser
    2105                2110                2115
Pro Glu Phe Phe Ser Trp Val Asp Gly Val Gln Ile His Arg Phe
    2120                2125                2130
Ala Pro Thr Pro Lys Pro Phe Phe Arg Asp Glu Val Ser Phe Cys
    2135                2140                2145
Val Gly Leu Asn Ser Tyr Ala Val Gly Ser Gln Leu Pro Cys Glu
    2150                2155                2160
Pro Glu Pro Asp Ala Asp Val Leu Arg Ser Met Leu Thr Asp Pro
    2165                2170                2175
Pro His Ile Thr Ala Glu Thr Ala Ala Arg Arg Leu Ala Arg Gly
    2180                2185                2190
Ser Pro Pro Ser Glu Ala Ser Ser Ser Val Ser Gln Leu Ser Ala
    2195                2200                2205
Pro Ser Leu Arg Ala Thr Cys Thr Thr His Ser Asn Thr Tyr Asp
    2210                2215                2220
Val Asp Met Val Asp Ala Asn Leu Leu Met Glu Gly Gly Val Ala
    2225                2230                2235
Gln Thr Glu Pro Glu Ser Arg Val Pro Val Leu Asp Phe Leu Glu
    2240                2245                2250
Pro Met Ala Glu Glu Glu Ser Asp Leu Glu Pro Ser Ile Pro Ser
    2255                2260                2265
Glu Cys Met Leu Pro Arg Ser Gly Phe Pro Arg Ala Leu Pro Ala
    2270                2275                2280
```

```
Trp Ala Arg Pro Asp Tyr Asn Pro Pro Leu Val Glu Ser Trp Arg
    2285                2290                2295
Arg Pro Asp Tyr Gln Pro Pro Thr Val Ala Gly Cys Ala Leu Pro
2300                2305                2310
Pro Pro Lys Lys Ala Pro Pro Pro Arg Arg Arg Arg Thr
2315                2320                2325
Val Gly Leu Ser Glu Ser Thr Ile Ser Glu Ala Leu Gln Gln Leu
    2330                2335                2340
Ala Ile Lys Thr Phe Gly Gln Pro Pro Ser Ser Gly Asp Ala Gly
    2345                2350                2355
Ser Ser Thr Gly Ala Gly Ala Ala Glu Ser Gly Gly Pro Thr Ser
    2360                2365                2370
Pro Gly Glu Pro Ala Pro Ser Glu Thr Gly Ser Ala Ser Ser Met
    2375                2380                2385
Pro Pro Leu Glu Gly Glu Pro Gly Asp Pro Asp Leu Glu Ser Asp
    2390                2395                2400
Gln Val Glu Leu Gln Pro Pro Gln Gly Gly Gly Val Ala Pro
2405                2410                2415
Gly Ser Gly Ser Gly Ser Trp Ser Thr Cys Ser Glu Glu Asp Asp
    2420                2425                2430
Thr Thr Val Cys Cys Ser Met Ser Tyr Ser Trp Thr Gly Ala Leu
    2435                2440                2445
Ile Thr Pro Cys Ser Pro Glu Glu Lys Leu Pro Ile Asn Pro
    2450                2455                2460
Leu Ser Asn Ser Leu Leu Arg Tyr His Asn Lys Val Tyr Cys Thr
    2465                2470                2475
Thr Ser Lys Ser Ala Ser Gln Arg Ala Lys Lys Val Thr Phe Asp
    2480                2485                2490
Arg Thr Gln Val Leu Asp Ala His Tyr Asp Ser Val Leu Lys Asp
    2495                2500                2505
Ile Lys Leu Ala Ala Ser Lys Val Ser Ala Arg Leu Leu Thr Leu
    2510                2515                2520
Glu Glu Ala Cys Gln Leu Thr Pro Pro His Ser Ala Arg Ser Lys
    2525                2530                2535
Tyr Gly Phe Gly Ala Lys Glu Val Arg Ser Leu Ser Gly Arg Ala
    2540                2545                2550
Val Asn His Ile Lys Ser Val Trp Lys Asp Leu Leu Glu Asp Pro
    2555                2560                2565
Gln Thr Pro Ile Pro Thr Thr Ile Met Ala Lys Asn Glu Val Phe
    2570                2575                2580
Cys Val Asp Pro Ala Lys Gly Gly Lys Lys Pro Ala Arg Leu Ile
    2585                2590                2595
Val Tyr Pro Asp Leu Gly Val Arg Val Cys Glu Lys Met Ala Leu
    2600                2605                2610
Tyr Asp Ile Thr Gln Lys Leu Pro Gln Ala Val Met Gly Ala Ser
    2615                2620                2625
Tyr Gly Phe Gln Tyr Ser Pro Ala Gln Arg Val Glu Tyr Leu Leu
    2630                2635                2640
Lys Ala Trp Ala Glu Lys Lys Asp Pro Met Gly Phe Ser Tyr Asp
    2645                2650                2655
Thr Arg Cys Phe Asp Ser Thr Val Thr Glu Arg Asp Ile Arg Thr
    2660                2665                2670
Glu Glu Ser Ile Tyr Gln Ala Cys Ser Leu Pro Glu Glu Ala Arg
    2675                2680                2685
```

```
Thr Ala Ile His Ser Leu Thr Glu Arg Leu Tyr Val Gly Gly Pro
    2690            2695                2700

Met Phe Asn Ser Lys Gly Gln Thr Cys Gly Tyr Arg Arg Cys Arg
    2705            2710                2715

Ala Ser Gly Val Leu Thr Thr Ser Met Gly Asn Thr Ile Thr Cys
    2720            2725                2730

Tyr Val Lys Ala Leu Ala Ala Cys Lys Ala Ala Gly Ile Val Ala
    2735            2740                2745

Pro Thr Met Leu Val Cys Gly Asp Asp Leu Val Val Ile Ser Glu
    2750            2755                2760

Ser Gln Gly Thr Glu Glu Asp Glu Arg Asn Leu Arg Ala Phe Thr
    2765            2770                2775

Glu Ala Met Thr Arg Tyr Ser Ala Pro Pro Gly Asp Pro Pro Arg
    2780            2785                2790

Pro Glu Tyr Asp Leu Glu Leu Ile Thr Ser Cys Ser Ser Asn Val
    2795            2800                2805

Ser Val Ala Leu Gly Pro Arg Gly Arg Arg Tyr Tyr Leu Thr
    2810            2815                2820

Arg Asp Pro Thr Thr Pro Leu Ala Arg Ala Ala Trp Glu Thr Val
    2825            2830                2835

Arg His Ser Pro Ile Asn Ser Trp Leu Gly Asn Ile Ile Gln Tyr
    2840            2845                2850

Ala Pro Thr Ile Trp Val Arg Met Val Leu Met Thr His Phe Phe
    2855            2860                2865

Ser Ile Leu Met Val Gln Asp Thr Leu Asp Gln Asn Leu Asn Phe
    2870            2875                2880

Glu Met Tyr Gly Ser Val Tyr Ser Val Asn Pro Leu Asp Leu Pro
    2885            2890                2895

Ala Ile Ile Glu Arg Leu His Gly Leu Asp Ala Phe Ser Met His
    2900            2905                2910

Thr Tyr Ser His His Glu Leu Thr Arg Val Ala Ser Ala Leu Arg
    2915            2920                2925

Lys Leu Gly Ala Pro Pro Leu Arg Val Trp Lys Ser Arg Ala Arg
    2930            2935                2940

Ala Val Arg Ala Ser Leu Ile Ser Arg Gly Gly Lys Ala Ala Val
    2945            2950                2955

Cys Gly Arg Tyr Leu Phe Asn Trp Ala Val Lys Thr Lys Leu Lys
    2960            2965                2970

Leu Thr Pro Leu Pro Glu Ala Arg Leu Leu Asp Leu Ser Ser Trp
    2975            2980                2985

Phe Thr Val Gly Ala Gly Gly Gly Asp Ile Phe His Ser Val Ser
    2990            2995                3000

Arg Ala Arg Pro Arg Ser Leu Leu Phe Gly Leu Leu Leu Leu Phe
    3005            3010                3015

Val Gly Val Gly Leu Phe Leu Leu Pro Ala Arg
    3020            3025

<210> SEQ ID NO 4
<211> LENGTH: 3029
<212> TYPE: PRT
<213> ORGANISM: Hepatitis C virus

<400> SEQUENCE: 4

Met Ser Thr Asn Pro Lys Pro Gln Arg Lys Thr Lys Arg Asn Thr Asn
1               5                   10                  15
```

```
Arg Arg Pro Met Asp Val Lys Phe Pro Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Gln Pro
 50                  55                  60

Ile Pro Lys Ala Arg Arg Pro Glu Gly Arg Ser Trp Ala Gln Pro Gly
 65              70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
                100                 105                 110

Arg Arg Arg Ser Arg Asn Leu Gly Lys Val Ile Asp Thr Leu Thr Cys
115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Val
                180                 185                 190

Asn Tyr Arg Asn Val Ser Gly Ile Tyr His Val Thr Asn Asp Cys Pro
                195                 200                 205

Asn Ser Ser Ile Val Tyr Glu Ala Asp His His Ile Leu His Leu Pro
            210                 215                 220

Gly Cys Val Pro Cys Val Arg Glu Gly Asn Gln Ser Arg Cys Trp Val
225                 230                 235                 240

Ala Leu Thr Pro Thr Val Ala Ala Pro Tyr Ile Gly Ala Pro Leu Glu
                245                 250                 255

Ser Leu Arg Ser His Val Asp Leu Met Val Gly Ala Ala Thr Val Cys
                260                 265                 270

Ser Gly Leu Tyr Ile Gly Asp Leu Cys Gly Gly Leu Phe Leu Val Gly
            275                 280                 285

Gln Met Phe Ser Phe Arg Pro Arg Arg His Trp Thr Thr Gln Asp Cys
    290                 295                 300

Asn Cys Ser Ile Tyr Thr Gly His Ile Thr Gly His Arg Met Ala Trp
305                 310                 315                 320

Asp Met Met Met Asn Trp Ser Pro Thr Thr Thr Leu Val Leu Ala Gln
                325                 330                 335

Val Met Arg Ile Pro Thr Thr Leu Val Asp Leu Leu Ser Gly Gly His
                340                 345                 350

Trp Gly Val Leu Val Gly Val Ala Tyr Phe Ser Met Gln Ala Asn Trp
            355                 360                 365

Ala Lys Val Ile Leu Val Leu Phe Leu Phe Ala Gly Val Asp Ala Glu
    370                 375                 380

Thr His Val Ser Gly Ala Ala Val Gly Arg Ser Thr Ala Gly Leu Ala
385                 390                 395                 400

Asn Leu Phe Ser Ser Gly Ser Lys Gln Asn Leu Gln Leu Ile Asn Ser
                405                 410                 415

Asn Gly Ser Trp His Ile Asn Arg Thr Ala Leu Asn Cys Asn Asp Ser
            420                 425                 430

Leu Asn Thr Gly Phe Leu Ala Ser Leu Phe Tyr Thr His Lys Phe Asn
```

```
                435                 440                 445
Ser Ser Gly Cys Ser Glu Arg Leu Ala Cys Cys Lys Ser Leu Asp Ser
450                 455                 460

Tyr Gly Gln Gly Trp Gly Pro Leu Gly Val Ala Asn Ile Ser Gly Ser
465                 470                 475                 480

Ser Asp Asp Arg Pro Tyr Cys Trp His Tyr Ala Pro Arg Pro Cys Gly
                485                 490                 495

Ile Val Pro Ala Ser Ser Val Cys Gly Pro Val Tyr Cys Phe Thr Pro
            500                 505                 510

Ser Pro Val Val Gly Thr Thr Asp His Val Gly Val Pro Thr Tyr
            515                 520                 525

Thr Trp Gly Glu Asn Glu Thr Asp Val Phe Leu Leu Asn Ser Thr Arg
530                 535                 540

Pro Pro His Gly Ala Trp Phe Gly Cys Val Trp Met Asn Ser Thr Gly
545                 550                 555                 560

Phe Thr Lys Thr Cys Gly Ala Pro Pro Cys Glu Val Asn Thr Asn Asn
                565                 570                 575

Gly Thr Trp His Cys Pro Thr Asp Cys Phe Arg Lys His Pro Glu Thr
            580                 585                 590

Thr Tyr Ala Lys Cys Gly Ser Gly Pro Trp Ile Thr Pro Arg Cys Leu
            595                 600                 605

Ile Asp Tyr Pro Tyr Arg Leu Trp His Phe Pro Cys Thr Ala Asn Phe
610                 615                 620

Ser Val Phe Asn Ile Arg Thr Phe Val Gly Gly Ile Glu His Arg Met
625                 630                 635                 640

Gln Ala Ala Cys Asn Trp Thr Arg Gly Glu Val Cys Gly Leu Glu His
                645                 650                 655

Arg Asp Arg Val Glu Leu Ser Pro Leu Leu Thr Thr Ala Trp
            660                 665                 670

Gln Ile Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
690                 695                 700

Val Gly Ser Ala Val Val Ser Trp Ala Leu Lys Trp Glu Tyr Val Val
705                 710                 715                 720

Leu Ala Phe Leu Leu Leu Ala Asp Ala Arg Val Ser Ala Cys Leu Trp
                725                 730                 735

Met Met Phe Met Val Ser Gln Val Glu Ala Ala Leu Ser Asn Leu Ile
            740                 745                 750

Asn Ile Asn Ala Ala Ser Ala Ala Gly Ala Gln Gly Phe Trp Tyr Ala
            755                 760                 765

Ile Leu Phe Ile Cys Ile Val Trp His Val Lys Gly Arg Phe Pro Ala
770                 775                 780

Ala Ala Ala Tyr Ala Ala Cys Gly Leu Trp Pro Leu Phe Leu Leu Leu
785                 790                 795                 800

Leu Met Leu Pro Glu Arg Ala Tyr Ala Tyr Asp Gln Glu Val Ala Gly
                805                 810                 815

Ser Leu Gly Gly Ala Ile Val Val Met Leu Thr Ile Leu Thr Leu Ser
            820                 825                 830

Pro His Tyr Lys Leu Trp Leu Ala Arg Gly Leu Trp Trp Ile Gln Tyr
            835                 840                 845

Phe Ile Ala Arg Thr Glu Ala Val Leu His Val Tyr Ile Pro Ser Phe
850                 855                 860
```

-continued

Asn Val Arg Gly Pro Arg Asp Ser Val Ile Val Leu Ala Val Leu Val
865                 870                 875                 880

Cys Pro His Leu Val Phe Asp Ile Thr Lys Tyr Leu Leu Ala Ile Leu
                885                 890                 895

Gly Pro Leu His Ile Leu Gln Ala Ser Leu Leu Arg Ile Pro Tyr Phe
            900                 905                 910

Val Arg Ala Gln Ala Leu Val Lys Ile Cys Ser Leu Leu Arg Gly Val
        915                 920                 925

Val Tyr Gly Lys Tyr Phe Gln Met Val Val Leu Lys Ala Gly Ala Leu
    930                 935                 940

Thr Gly Thr Tyr Ile Tyr Asp His Leu Thr Pro Met Ser Asp Trp Ala
945                 950                 955                 960

Ala Thr Gly Leu Arg Asp Leu Ala Val Ala Leu Glu Pro Val Val Phe
                965                 970                 975

Thr Pro Met Glu Lys Lys Val Ile Val Trp Gly Ala Asp Thr Ala Ala
            980                 985                 990

Cys Gly Asp Ile Ile Arg Gly Leu Pro Val Ser Ala Arg Leu Gly Asn
        995                 1000                1005

Glu Ile Leu Leu Gly Pro Ala Asp Thr Glu Thr Ser Lys Gly Trp
    1010                1015                1020

Arg Leu Leu Ala Pro Ile Thr Ala Tyr Ala Gln Gln Thr Arg Gly
    1025                1030                1035

Leu Leu Gly Ala Ile Val Val Ser Met Thr Gly Arg Asp Arg Thr
    1040                1045                1050

Glu Gln Ala Gly Glu Val Gln Ile Leu Ser Thr Val Ser Gln Ser
    1055                1060                1065

Phe Leu Gly Thr Thr Ile Ser Gly Val Leu Trp Thr Val Tyr His
    1070                1075                1080

Gly Ala Gly Asn Lys Thr Leu Ala Gly Leu Arg Gly Pro Val Thr
    1085                1090                1095

Gln Met Tyr Ser Ser Ala Glu Gly Asp Leu Val Gly Trp Pro Ser
    1100                1105                1110

Pro Pro Gly Thr Lys Ser Leu Glu Pro Cys Lys Cys Gly Ala Val
    1115                1120                1125

Asp Leu Tyr Leu Val Thr Arg Asn Ala Asp Val Ile Pro Ala Arg
    1130                1135                1140

Arg Arg Gly Asp Lys Arg Gly Ala Leu Leu Ser Pro Arg Pro Ile
    1145                1150                1155

Ser Thr Leu Lys Gly Ser Ser Gly Gly Pro Val Leu Cys Pro Arg
    1160                1165                1170

Gly His Val Val Gly Leu Phe Arg Ala Ala Val Cys Ser Arg Gly
    1175                1180                1185

Val Ala Lys Ser Ile Asp Phe Ile Pro Val Glu Thr Leu Asp Val
    1190                1195                1200

Val Thr Arg Ser Pro Thr Phe Ser Asp Asn Ser Thr Pro Pro Ala
    1205                1210                1215

Val Pro Gln Thr Tyr Gln Val Gly Tyr Leu His Ala Pro Thr Gly
    1220                1225                1230

Ser Gly Lys Ser Thr Lys Val Pro Val Ala Tyr Ala Ala Gln Gly
    1235                1240                1245

Tyr Lys Val Leu Val Leu Asn Pro Ser Val Ala Ala Thr Leu Gly
    1250                1255                1260

Phe Gly Ala Tyr Leu Ser Lys Ala His Gly Ile Asn Pro Asn Ile
    1265                1270                1275

-continued

```
Arg Thr Gly Val Arg Thr Val Met Thr Gly Glu Ala Ile Thr Tyr
    1280            1285            1290

Ser Thr Tyr Gly Lys Phe Leu Ala Asp Gly Gly Cys Ala Ser Gly
    1295            1300            1305

Ala Tyr Asp Ile Ile Ile Cys Asp Glu Cys His Ala Val Asp Ala
    1310            1315            1320

Thr Ser Ile Leu Gly Ile Gly Thr Val Leu Asp Gln Ala Glu Thr
    1325            1330            1335

Ala Gly Val Arg Leu Thr Val Leu Ala Thr Ala Thr Pro Pro Gly
    1340            1345            1350

Ser Val Thr Thr Pro His Pro Asp Ile Glu Glu Val Gly Leu Gly
    1355            1360            1365

Arg Glu Gly Glu Ile Pro Phe Tyr Gly Arg Ala Ile Pro Leu Ser
    1370            1375            1380

Cys Ile Lys Gly Gly Arg His Leu Ile Phe Cys His Ser Lys Lys
    1385            1390            1395

Lys Cys Asp Glu Leu Ala Ala Ala Leu Arg Gly Met Gly Leu Asn
    1400            1405            1410

Ala Val Ala Tyr Tyr Arg Gly Leu Asp Val Ser Ile Ile Pro Ala
    1415            1420            1425

Gln Gly Asp Val Val Val Val Ala Thr Asp Ala Leu Met Thr Gly
    1430            1435            1440

Tyr Thr Gly Asp Phe Asp Ser Val Ile Asp Cys Asn Val Ala Val
    1445            1450            1455

Thr Gln Ala Val Asp Phe Ser Leu Asp Pro Thr Phe Thr Ile Thr
    1460            1465            1470

Thr Gln Thr Val Pro Gln Asp Ala Val Ser Arg Ser Gln Arg Arg
    1475            1480            1485

Gly Arg Thr Gly Arg Gly Arg Gln Gly Thr Tyr Arg Tyr Val Ser
    1490            1495            1500

Thr Gly Glu Arg Ala Ser Gly Met Phe Asp Ser Val Val Leu Cys
    1505            1510            1515

Glu Cys Tyr Asp Ala Gly Ala Ala Trp Tyr Asp Leu Thr Pro Ala
    1520            1525            1530

Glu Thr Thr Val Arg Leu Arg Ala Tyr Phe Asn Thr Pro Gly Leu
    1535            1540            1545

Pro Val Cys Gln Asp His Leu Glu Phe Trp Glu Ala Val Phe Thr
    1550            1555            1560

Gly Leu Thr His Ile Asp Ala His Phe Leu Ser Gln Thr Lys Gln
    1565            1570            1575

Ala Gly Glu Asn Phe Ala Tyr Leu Val Ala Tyr Gln Ala Thr Val
    1580            1585            1590

Cys Ala Arg Ala Lys Ala Pro Pro Pro Ser Trp Asp Ala Met Trp
    1595            1600            1605

Lys Cys Leu Ala Arg Leu Lys Pro Thr Leu Ala Gly Pro Thr Pro
    1610            1615            1620

Leu Leu Tyr Arg Leu Gly Pro Ile Thr Asn Glu Val Thr Leu Thr
    1625            1630            1635

His Pro Gly Thr Lys Tyr Ile Ala Thr Cys Met Gln Ala Asp Leu
    1640            1645            1650

Glu Val Met Thr Ser Thr Trp Val Leu Ala Gly Gly Val Leu Ala
    1655            1660            1665

Ala Val Ala Ala Tyr Cys Leu Ala Thr Gly Cys Val Ser Ile Ile
```

-continued

```
             1670                1675                1680

Gly Arg Leu His Val Asn Gln Arg Val Val Ala Pro Asp Lys
     1685                1690                1695

Glu Val Leu Tyr Glu Ala Phe Asp Glu Met Glu Cys Ala Ser
     1700                1705                1710

Arg Ala Ala Leu Ile Glu Glu Gly Gln Arg Ile Ala Glu Met Leu
     1715                1720                1725

Lys Ser Lys Ile Gln Gly Leu Leu Gln Gln Ala Ser Lys Gln Ala
     1730                1735                1740

Gln Asp Ile Gln Pro Ala Met Gln Ala Ser Trp Pro Lys Val Glu
     1745                1750                1755

Gln Phe Trp Ala Arg His Met Trp Asn Phe Ile Ser Gly Ile Gln
     1760                1765                1770

Tyr Leu Ala Gly Leu Ser Thr Leu Pro Gly Asn Pro Ala Val Ala
     1775                1780                1785

Ser Met Met Ala Phe Ser Ala Ala Leu Thr Ser Pro Leu Ser Thr
     1790                1795                1800

Ser Thr Thr Ile Leu Leu Asn Ile Met Gly Gly Trp Leu Ala Ser
     1805                1810                1815

Gln Ile Ala Pro Pro Ala Gly Ala Thr Gly Phe Val Val Ser Gly
     1820                1825                1830

Leu Val Gly Ala Ala Val Gly Ser Ile Gly Leu Gly Lys Val Leu
     1835                1840                1845

Val Asp Ile Leu Ala Gly Tyr Gly Ala Gly Ile Ser Gly Ala Leu
     1850                1855                1860

Val Ala Phe Lys Ile Met Ser Gly Glu Lys Pro Ser Met Glu Asp
     1865                1870                1875

Val Ile Asn Leu Leu Pro Gly Ile Leu Ser Pro Gly Ala Leu Val
     1880                1885                1890

Val Gly Val Ile Cys Ala Ala Ile Leu Arg Arg His Val Gly Pro
     1895                1900                1905

Gly Glu Gly Ala Val Gln Trp Met Asn Arg Leu Ile Ala Phe Ala
     1910                1915                1920

Ser Arg Gly Asn His Val Ala Pro Thr His Tyr Val Thr Glu Ser
     1925                1930                1935

Asp Ala Ser Gln Arg Val Thr Gln Leu Leu Gly Ser Leu Thr Ile
     1940                1945                1950

Thr Ser Leu Leu Arg Arg Leu His Asn Trp Ile Thr Glu Asp Cys
     1955                1960                1965

Pro Ile Pro Cys Ser Gly Ser Trp Leu Arg Asp Val Trp Asp Trp
     1970                1975                1980

Val Cys Thr Ile Leu Thr Asp Phe Lys Asn Trp Leu Thr Ser Lys
     1985                1990                1995

Leu Phe Pro Lys Leu Pro Gly Leu Pro Phe Ile Ser Cys Gln Lys
     2000                2005                2010

Gly Tyr Lys Gly Val Trp Ala Gly Thr Gly Ile Met Thr Thr Arg
     2015                2020                2025

Cys Pro Cys Gly Ala Asn Ile Ser Gly Asn Val Arg Leu Gly Ser
     2030                2035                2040

Met Arg Ile Thr Gly Pro Lys Thr Cys Met Asn Thr Trp Gln Gly
     2045                2050                2055

Thr Phe Pro Ile Asn Cys Tyr Thr Glu Gly Gln Cys Ala Pro Lys
     2060                2065                2070
```

-continued

```
Pro Pro Thr Asn Tyr Lys Thr Ala Ile Trp Arg Val Ala Ala Ser
2075                2080                2085

Glu Tyr Ala Glu Val Thr Gln His Gly Ser Tyr Ser Tyr Val Thr
2090                2095                2100

Gly Leu Thr Thr Asp Asn Leu Lys Ile Pro Cys Gln Leu Pro Ser
2105                2110                2115

Pro Glu Phe Phe Ser Trp Val Asp Gly Val Gln Ile His Arg Phe
2120                2125                2130

Ala Pro Thr Pro Lys Pro Phe Phe Arg Asp Glu Val Ser Phe Cys
2135                2140                2145

Val Gly Leu Asn Ser Tyr Ala Val Gly Ser Gln Leu Pro Cys Glu
2150                2155                2160

Pro Glu Pro Asp Ala Asp Val Leu Arg Ser Met Leu Thr Asp Pro
2165                2170                2175

Pro His Ile Thr Ala Glu Thr Ala Ala Arg Arg Leu Ala Arg Gly
2180                2185                2190

Ser Pro Pro Ser Glu Ala Ser Ser Val Ser Gln Leu Ser Ala
2195                2200                2205

Pro Ser Leu Arg Ala Thr Cys Thr Thr His Ser Asn Thr Tyr Asp
2210                2215                2220

Val Asp Met Val Asp Ala Asn Leu Leu Met Glu Gly Gly Val Ala
2225                2230                2235

Gln Thr Glu Pro Glu Ser Arg Val Pro Val Leu Asp Phe Leu Glu
2240                2245                2250

Pro Met Ala Glu Glu Ser Asp Leu Glu Pro Ser Ile Pro Ser
2255                2260                2265

Glu Cys Met Leu Pro Arg Ser Gly Phe Pro Arg Ala Leu Pro Ala
2270                2275                2280

Trp Ala Arg Pro Asp Tyr Asn Pro Pro Leu Val Glu Ser Trp Arg
2285                2290                2295

Arg Pro Asp Tyr Gln Pro Pro Thr Val Ala Gly Cys Ala Leu Pro
2300                2305                2310

Pro Pro Lys Lys Ala Pro Thr Pro Pro Pro Arg Arg Arg Arg Thr
2315                2320                2325

Val Gly Leu Ser Glu Ser Thr Ile Ser Glu Ala Leu Gln Gln Leu
2330                2335                2340

Ala Ile Lys Thr Phe Gly Gln Pro Pro Ser Ser Gly Asp Ala Gly
2345                2350                2355

Ser Ser Thr Gly Ala Gly Ala Ala Glu Ser Gly Gly Pro Thr Ser
2360                2365                2370

Pro Gly Glu Pro Ala Pro Ser Glu Thr Gly Ser Ala Ser Ser Met
2375                2380                2385

Pro Pro Leu Glu Gly Glu Pro Gly Asp Pro Asp Leu Glu Ser Asp
2390                2395                2400

Gln Val Glu Leu Gln Pro Pro Gln Gly Gly Val Ala Pro
2405                2410                2415

Gly Ser Gly Ser Gly Ser Trp Ser Thr Cys Ser Glu Glu Asp Asp
2420                2425                2430

Thr Thr Val Cys Cys Ser Met Ser Tyr Ser Trp Thr Gly Ala Leu
2435                2440                2445

Ile Thr Pro Cys Ser Pro Glu Glu Lys Leu Pro Ile Asn Pro
2450                2455                2460

Leu Ser Asn Ser Leu Leu Arg Tyr His Asn Lys Val Tyr Cys Thr
2465                2470                2475
```

-continued

```
Thr Ser Lys Ser Ala Ser Gln Arg Ala Lys Lys Val Thr Phe Asp
    2480                2485                2490
Arg Thr Gln Val Leu Asp Ala His Tyr Asp Ser Val Leu Lys Asp
    2495                2500                2505
Ile Lys Leu Ala Ala Ser Lys Val Ser Ala Arg Leu Leu Thr Leu
    2510                2515                2520
Glu Glu Ala Cys Gln Leu Thr Pro Pro His Ser Ala Arg Ser Lys
    2525                2530                2535
Tyr Gly Phe Gly Ala Lys Glu Val Arg Ser Leu Ser Gly Arg Ala
    2540                2545                2550
Val Asn His Ile Lys Ser Val Trp Lys Asp Leu Leu Glu Asp Pro
    2555                2560                2565
Gln Thr Pro Ile Pro Thr Thr Ile Met Ala Lys Asn Glu Val Phe
    2570                2575                2580
Cys Val Asp Pro Ala Lys Gly Gly Lys Lys Pro Ala Arg Leu Ile
    2585                2590                2595
Val Tyr Pro Asp Leu Gly Val Arg Val Cys Glu Lys Met Ala Leu
    2600                2605                2610
Tyr Asp Ile Thr Gln Lys Leu Pro Gln Ala Val Met Gly Ala Ser
    2615                2620                2625
Tyr Gly Phe Gln Tyr Ser Pro Ala Gln Arg Val Glu Tyr Leu Leu
    2630                2635                2640
Lys Ala Trp Ala Glu Lys Lys Asp Pro Met Gly Phe Ser Tyr Asp
    2645                2650                2655
Thr Arg Cys Phe Asp Ser Thr Val Thr Glu Arg Asp Ile Arg Thr
    2660                2665                2670
Glu Glu Ser Ile Tyr Gln Ala Cys Ser Leu Pro Glu Glu Ala Arg
    2675                2680                2685
Thr Ala Ile His Ser Leu Thr Glu Arg Leu Tyr Val Gly Gly Pro
    2690                2695                2700
Met Phe Asn Ser Lys Gly Gln Thr Cys Gly Tyr Arg Arg Cys Arg
    2705                2710                2715
Ala Ser Gly Val Leu Thr Thr Ser Met Gly Asn Thr Ile Thr Cys
    2720                2725                2730
Tyr Val Lys Ala Leu Ala Ala Cys Lys Ala Ala Gly Ile Val Ala
    2735                2740                2745
Pro Thr Met Leu Val Cys Gly Asp Asp Leu Val Val Ile Ser Glu
    2750                2755                2760
Ser Gln Gly Thr Glu Glu Asp Glu Arg Asn Leu Arg Ala Phe Thr
    2765                2770                2775
Glu Ala Met Thr Arg Tyr Ser Ala Pro Pro Gly Asp Pro Pro Arg
    2780                2785                2790
Pro Glu Tyr Asp Leu Glu Leu Ile Thr Ser Cys Ser Ser Asn Val
    2795                2800                2805
Ser Val Ala Leu Gly Pro Arg Gly Arg Arg Tyr Tyr Leu Thr
    2810                2815                2820
Arg Asp Pro Thr Thr Pro Leu Ala Arg Ala Ala Trp Glu Thr Val
    2825                2830                2835
Arg His Ser Pro Ile Asn Ser Trp Leu Gly Asn Ile Ile Gln Tyr
    2840                2845                2850
Ala Pro Thr Ile Trp Val Arg Met Val Leu Met Thr His Phe Phe
    2855                2860                2865
Ser Ile Leu Met Val Gln Asp Thr Leu Asp Gln Asn Leu Asn Phe
```

|  |  | 2870 |  |  | 2875 |  |  | 2880 |  |  |
|---|---|---|---|---|---|---|---|---|---|---|

Glu Met Tyr Gly Ser Val Tyr Ser Val Asn Pro Leu Asp Leu Pro
           2885                    2890                    2895

Ala Ile Ile Glu Arg Leu His Gly Leu Asp Ala Phe Ser Met His
         2900                    2905                    2910

Thr Tyr Ser His His Glu Leu Thr Arg Val Ala Ser Ala Leu Arg
         2915                    2920                    2925

Lys Leu Gly Ala Pro Pro Leu Arg Val Trp Lys Ser Arg Ala Arg
         2930                    2935                    2940

Ala Val Arg Ala Ser Leu Ile Ser Arg Gly Gly Lys Ala Ala Val
         2945                    2950                    2955

Cys Gly Arg Tyr Leu Phe Asn Trp Ala Val Lys Thr Lys Leu Lys
         2960                    2965                    2970

Leu Thr Pro Leu Pro Glu Ala Arg Leu Leu Asp Leu Ser Ser Trp
         2975                    2980                    2985

Phe Thr Val Gly Ala Gly Gly Asp Ile Phe His Ser Val Ser
         2990                    2995                    3000

Arg Ala Arg Pro Arg Ser Leu Leu Phe Gly Leu Leu Leu Leu Phe
         3005                    3010                    3015

Val Gly Val Gly Leu Phe Leu Leu Pro Ala Arg
         3020                    3025

<210> SEQ ID NO 5
<211> LENGTH: 9666
<212> TYPE: DNA
<213> ORGANISM: Hepatitis C virus

<400> SEQUENCE: 5

```
acctgcccct aataggggcg acactccgcc atgaatcact cccctgtgag gaactactgt     60
cttcacgcag aaagcgccta gccatggcgt tagtatgagt gtcgtacagc ctccaggccc    120
ccccctcccg ggagagccat agtggtctgc ggaaccggtg agtacaccgg aattgccggg    180
aagactgggt cctttcttgg ataaacccac tctatgcccg gccatttggg cgtgcccccg    240
caagactgct agccgagtag cgttgggttg cgaaaggcct tgtggtactg cctgataggg    300
cgcttgcgag tgccccggga ggtctcgtag accgtgcacc atgagcacga atcctaaacc    360
tcaaagaaaa accaaacgta acaccaaccg ccgcccaatg acgttaagt  tcccgggtgg    420
tggccagatc gttggcggag tttacttgtt gccgcgcagg ggccccagat gggtgtgcg     480
cgcgactcgg aagacttcgg agcggtcgca acctcgtgga agacgccaac ctatccccaa    540
ggcgcgtcga cccgagggaa ggtcctgggc acaaccagga tatccatggc ctctttacgg    600
taatgagggt tgtgggtggg caggatggct cttgtccccc cgtggctctc gaccgtcttg    660
gggcccaaat gatccccggc ggaggtcccg caatttgggt aaggtcatcg atacccctaac    720
ctgcggcttc gccgacctca tgggatacat cccgctcgta ggcgccccg tgggtggcgt    780
cgccagggcc ctggcacatg tgtcagggc tttggaggac gggatcaatt atgcaacagg    840
gaatctcccc ggttgctcct tttctatctt cctcttggca cttctttcgt gcctgactgt    900
ccccgcttcg gccgttaact atcgcaatgt ctcgggcatc taccatgtca ccaatgactg   960
cccgaattca agcatagtgt atgaggccga ccatcacatc ttgcacccttc caggttgcgt   1020
gccctgcgtg agagagggga atcagtcacg ctgctgggtg gcccttactc ctaccgtcgc   1080
agcgccatac atcggcgcac cgcttgagtc cttacgagt catgtggatt tgatggtggg   1140
ggccgccact gtttgctcgg gtctttacat cggggacctg tgtggcggct tgttcctagt   1200
```

```
tggccagatg ttttcattcc gaccacggcg ccactggacc acccaggatt gcaattgttc    1260
catctacaca gggcacatta caggccacag aatggcctgg gacatgatga tgaactggag    1320
tccaacaacc accttagttc tcgcccaggt catgaggatc ccaaccactc tggtagactt    1380
actctctgga ggccactggg gtgtcctcgt gggagtggcc tatttcagca tgcaggccaa    1440
ttgggccaaa gtcatcttgg tcctattcct ctttgcaggg gttgatgccg agactcacgt    1500
gtctggggca gcagtcggcc ggagtaccgc cggcttggct aacctctttt cttctgggtc    1560
taagcagaat ttacagctca tcaacagcaa tgggagctgg catataaata ggactgccct    1620
taactgcaat gacagcttaa acactgggtt cttggctagc ttgttctaca cccacaagtt    1680
taacagctca gggtgttccg aacggctcgc gtgctgcaag agccttgaca gctacggcca    1740
aggctggggc ccactcgggg tcgctaacat cagcggctcg tctgatgaca ggccttattg    1800
ctggcactac gcgcctcggc cgtgcgggat tgtgccagca tccagtgtgt gtggccccgt    1860
gtattgtttc actcccagcc ctgtcgtggt cggtactact gatcacgtcg gggtccctac    1920
ttacacctgg ggggagaatg agactgatgt cttccttttg aactcgacca gaccgccgca    1980
tggtgcgtgg tttggatgcg tgtggatgaa cagtaccggg ttcaccaaaa cctgtggcgc    2040
ccctccatgc gaggttaaca ccaataatgg gacctggcac tgccccaccg attgcttcag    2100
gaagcatccg gagactacct acgccaagtg cggatcaggg ccttggatca caccgcgctg    2160
cctgattgat tacccgtacc ggctgtggca tttcccgtgc accgccaact tctccgtctt    2220
taacatcagg acatttgtcg gcggtataga gcatcggatg caagcggcat gcaactggac    2280
caggggggaa gtctgtggct tggagcacag ggatcgcgta gagctatcac ccctgctcct    2340
taccactaca gcgtggcaga tcctcccctg ctctttcacc actttacctg ccctctccac    2400
cggcttgatc cacctccacc aaaatatcgt ggacgtccag tacctctatg tgttgggtc    2460 tgcagtggta tcttgggccc ttaagtggga atatgtggtg ctcgcgttcc tgcttctcgc    2520
ggacgcgaga gtctctgcct gcctatggat gatgtttatg gtaagtcaag ttgaggcggc    2580
tctgtccaac ctgattaaca tcaatgctgc ttcagccgct ggtgcccaag gcttctggta    2640
cgccatcctc ttcatctgca ttgtctggca tgtcaagggc cggttcccag ctgctgctgc    2700
ctacgcagcc tgcgggctgt ggcccctgtt tctcctgctt ctgatgctgc ctgagagggc    2760
ttatgcatac gaccaggaag tggcagggtc ccttggcggc gccatcgttg tcatgctgac    2820
cattctgaca ctgtctccgc actacaagtt atggctggct aggggactgt ggtggttgtg    2880
ctatctcctg accctggggg aagccatgat tcaggagtgg gtaccaccca tgcaggtgcg    2940
cggcggccgc gatggcatcg cgtgggccgt cactatattc tgcccgggtg tggtgtttga    3000
cattaccaaa tggcttttgg cgttgcttgg gcctgcttac ctcttaaggg ccgctttgac    3060
acatgtgccg tacttcgtca gagctcacgc tctgataagg gtatgcgctt tggtgaagca    3120
gctcgcgggg gtaggtatg ttcaggtggc gctattggcc cttggcaggt ggactggcac    3180
ctacatctat gaccacctca cacctatgtc ggactgggcc gctagcggcc tgcgcgactt    3240
agcggtcgcc gtgaacccca tcatcttcag tccgatggag aagaaggtca tcgtctgggg    3300
agcggagacg gctgcatgtg gggacattct acatggactt cccgtgtccg cccgactcgg    3360
ccaggagatc ctcctcggcc cagctgatgg ctacacctcc aagggtgga agctccttgc    3420 tcccatcact gcttatgccc agcaaacacg aggcctcctg ggcgccatag tggtgagtat    3480
gacggggcgt gacaggacag aacaggccgg ggaagtccaa atcctgtcca cagtctctca    3540
gtccttcctc ggaacaacca tctcgggggt tttgtggact gtttaccacg gagctggcaa    3600
```

```
caagactcta gccggcttac ggggtccggt cacgcagatg tactcgagtg ctgaggggga    3660
cttggtaggc tggcccagcc ccctgggac caagtctttg gagccgtgca agtgtggagc     3720
cgtcgaccta tatctggtca cgcggaacgc tgatgtcatc ccggctcgga gacgcgggga   3780
caagcgggga gcattgctct ccccgagacc catttcgacc ttgaagggt cctcgggggg    3840
gccggtgctc tgccctaggg gccacgtcgt tgggctcttc cgagcagctg tgtgctctcg   3900
gggcgtggcc aaatccatcg atttcatccc cgttgagaca ctcgacgttg ttacaaggtc   3960
tcccactttc agtgacaaca gcacgccacc ggctgtgccc cagacctatc aggtcgggta   4020
cttgcatgct ccaactggca gtggaaagag caccaaggtc cctgtcgcgt atgccgccca   4080
ggggtacaaa gtactagtgc ttaacccctc ggtagctgcc accctggggt ttggggcgta   4140
cctatccaag gcacatggca tcaatcccaa cattaggact ggagtcagga ccgtgatgac   4200
cggggaggcc atcacgtact ccacatatgg caaatttctc gccgatgggg gctgcgctag   4260
cggcgcctat gacatcatca tatgcgatga atgccacgct gtggatgcta cctccattct   4320
cggcatcgga acggtccttg atcaagcaga gacagccggg gtcagactaa ctgtgctggc   4380
tacgccaca ccccccgggt cagtgacaac ccccatccc gatatagaag aggtaggcct    4440
cgggcgggag ggtgagatcc ccttctatgg gagggcgatt cccctatcct gcatcaaggg   4500
agggagacac ctgattttct gccactcaaa gaaaaagtgt gacgagctcg cggcggccct   4560
tcggggcatg ggcttgaatg ccgtggcata ctatagaggg ttggacgtct ccataatacc   4620
agctcaggga gatgtggtgg tcgtcgccac cgacgccctc atgacggggt acactgagga   4680
cttttgactcc gtgatcgact gcaatgtagc ggtcacccaa gctgtcgact tcagcctgga   4740
ccccaccttc actataacca cacagactgt cccacaagac gctgtctcac gcagtcagcg   4800
ccgcgggcgc acaggtagag gaagacaggg cacttatagg tatgtttcca ctggtgaacg   4860
agcctcagga atgtttgaca gtgtagtgct ttgtgagtgc tacgacgcag gggctgcgtg   4920
gtacgatctc acaccagcgg agaccaccgt caggcttaga gcgtatttca acacgcccgg   4980
cctacccgtg tgtcaagacc atcttgaatt ttgggaggca gttttcaccg gcctcacaca   5040
catagacgcc cacttcctct cccaaacaaa gcaagcgggg gagaacttcg cgtacctagt   5100
agcctaccaa gctacggtgt gcgccagagc caaggcccct ccccgtcct gggacgccat    5160
gtggaagtgc ctggcccgac tcaagcctac gcttgcgggc cccacacctc tcctgtaccg   5220
tttgggccct attaccaatg aggtcacccc cacacaccct gggacgaagt acatcgccac   5280
atgcatgcaa gctgaccttg aggtcatgac cagcacgtgg gtcctagctg gaggagtcct   5340
ggcagccgtc gccgcatatt gcctggcgac tggatgcgtt tccatcatcg gccgcttgca   5400
cgtcaaccag cgagtcgtcg ttgcgccgga taaggaggtc ctgtatgagg cttttgatga   5460
gatggaggaa tgcgcctcta gggcggctct catcgaagag gggcagcgga tagccgagat   5520
gttgaagtcc aagatccaag gcttgctgca gcaggcctct aagcaggccc aggacataca   5580
acccgctatg caggcttcat ggcccaaagt ggaacaattt tgggccagac acatgtggaa   5640
cttcattagc ggcatccaat acctcgcagg attgtcaaca ctgccaggga ccccgcggt    5700
ggcttccatg atggcattca gtgccgccct caccagtccg ttgtcgacca gtaccaccat   5760
ccttctcaac atcatgggag ctggttagc gtcccagatc gcaccacccg cgggggccac    5820
cggctttgtc gtcagtggcc tggtgggggc tgccgtgggc agcataggcc tgggtaaggt   5880
gctggtggac atcctggcag gatatggtgc gggcatttcg ggggccctcg tcgcattcaa   5940
gatcatgtct ggcgagaagc cctctatgga agatgtcatc aatctactgc ctgggatcct   6000
```

```
gtctccggga gccctggtgg tgggggtcat ctgcgcggcc attctgcgcc gccacgtggg    6060 accggggag ggcgcggtcc aatgatgaa caggcttatt gcctttgctt ccagaggaaa    6120
ccacgtcgcc cctactcact acgtgacgga gtcggatgcg tcgcagcgtg tgacccaact    6180
acttggctct cttactataa ccagcctact cagaagactc cacaattgga taactgagga    6240
ctgccccatc ccatgctccg gatcctggct ccgcgacgtg tgggactggg tttgcaccat    6300
cttgacagac ttcaaaaatt ggctgacctc taaattgttc cccaagctgc ccggcctccc    6360
cttcatctct tgtcaaaagg ggtacaaggg tgtgtgggcc ggcactggca tcatgaccac    6420
gcgctgccct tgcggcgcca acatctctgg caatgtccgc ctgggctcta tgaggatcac    6480
agggcctaaa acctgcatga acacctggca ggggacctt cctatcaatt gctacacgga    6540
gggccagtgc gcgccgaaac cccccacgaa ctacaagacc gccatctgga gggtggcggc    6600
ctcggagtac gcggaggtga cgcagcatgg gtcgtactcc tatgtaacag gactgaccac    6660
tgacaatctg aaaattcctt gccaactacc ttctccagag ttttttctcct gggtggacgg    6720 tgtgcagatc cataggtttg cacccacacc aaagccgttt ttccgggatg aggtctcgtt    6780
ctgcgttggg cttaattcct atgctgtcgg gtcccagctt ccctgtgaac ctgagcccga    6840
cgcagacgta ttgaggtcca tgctaacaga tccgccccac atcacggcgg agactgcggc    6900
gcggcgcttg gcacggggat cacctccatc tgaggcgagc tcctcagtga gccagctatc    6960
agcaccgtcg ctgcgggcca cctgcaccac ccacagcaac acctatgacg tggacatggt    7020
cgatgccaac ctgctcatgg agggcggtgt ggctcagaca gagcctgagt ccagggtgcc    7080
cgttctggac tttctcgagc caatggccga ggaagagagc gaccttgagc cctcaatacc    7140
atcggagtgc atgctcccca ggagcgggtt tccacgggcc ttaccggctt gggcacggcc    7200
tgactacaac ccgccgctcg tggaatcgtg gaggaggcca gattaccaac cgcccaccgt    7260
tgctggttgt gctctccccc cccccaagaa ggccccgacg cctcccccaa ggagacgccg    7320
gacagtgggt ctgagcgaga gcaccatatc agaagccctc cagcaactgg ccatcaagac    7380 cttttggccag ccccccctcga gcggtgatgc aggctcgtcc acggggcgg gcgccgccga    7440 atccggcggt ccgacgtccc ctggtgagcc ggcccccctca gagacaggtt ccgcctcctc    7500
tatgcccccc ctcgagggg agcctggaga tccggacctg gagtctgatc aggtagagct    7560
tcaacctccc cccagggg ggggtagc tcccggttcg ggctcggggt cttggtctac    7620
ttgctccgag gaggacgata ccaccgtgtg ctgctccatg tcatactcct ggaccggggc    7680
tctaataact ccctgtagcc ccgaagagga aaagttgcca atcaacccctt tgagtaactc    7740 gctgttgcga taccataaca aggtgtactg tacaacatca aagagcgcct cacagagggc    7800
taaaaaggta acttttgaca ggacgcaagt gctcgacgcc cattatgact cagtcttaaa    7860
ggacatcaag ctagcggctt ccaaggtcag cgcaaggctc ctcaccttgg aggaggcgtg    7920
ccagttgact ccaccccatt ctgcaagatc caagtatgga ttcggggcca aggaggtccg    7980
cagcttgtcc gggagggccg ttaaccacat caagtccgtg tggaaggacc tcctggaaga    8040
cccacaaaca ccaattccca caaccatcat ggccaaaaat gaggtgttct gcgtggaccc    8100
cgccaagggg ggtaagaaac cagctcgcct catcgtttac cctgacctcg cgtccgggt    8160 ctgcgagaaa atggccctct atgacattac acaaaagctt cctcaggcgg taatgggagc    8220
ttcctatggc ttccagtact cccctgccca acgggtggag tatctcttga aagcatgggc    8280
ggaaaagaag gaccccatgg ttttttcgta tgataccccga tgcttcgact caaccgtcac    8340
tgagagagac atcaggaccg aggagtccat ataccaggcc tgctccctgc ccgaggaggc    8400
```

```
ccgcactgcc atacactcgc tgactgagag actttacgta ggagggccca tgttcaacag    8460
caagggtcaa acctgcggtt acagacgttg ccgcgccagc ggggtgctaa ccactagcat    8520
gggtaacacc atcacatgct atgtgaaagc ctagcggcc tgcaaggctg cggggatagt    8580
tgcgcccaca atgctggtat gcggcgatga cctagtagtc atctcagaaa gccaggggac    8640
tgaggaggac gagcggaacc tgagagcctt cacggaggcc atgaccaggt actctgcccc    8700
tcctggtgat cccccagac cggaatatga cctggagcta ataacatcct gttcctcaaa    8760
tgtgtctgtg gcgttgggcc cgcggggccg ccgcagatac tacctgacca gagacccaac    8820
cactccactc gcccgggctg cctgggaaac agttagacac tcccctatca attcatggct    8880
gggaaacatc atccagtatg ctccaaccat atgggttcgc atggtcctaa tgacacactt    8940
cttctccatt tcatggtcc aagacaccct ggaccagaac tcaactttg agatgtatgg    9000 atcagtatac tccgtgaatc ctttggacct tccagccata attgagaggt tacacgggct    9060
tgacgccttt tctatgcaca catactctca ccacgaactg acgcgggtgg cttcagccct    9120
cagaaaactt ggggcgccac ccctcagggt gtggaagagt cgggctcgcg cagtcagggc    9180
gtccctcatc tcccgtggag ggaaagcggc cgtttgcggc cgatatctct tcaattgggc    9240
ggtgaagacc aagctcaaac tcactccatt gccggaggcg cgcctactgg acttatccag    9300
ttggttcacc gtcggcgccg gcgggggcga cattttttcac agcgtgtcgc gcgcccgacc    9360
ccgctcatta ctcttcggcc tactcctact tttcgtaggg gtaggcctct tcctactccc    9420
cgctcggtag agcggcacac actaggtaca ctccatagct aactgttcct ttttttttt    9480 ttttttttttt tttttttttt ttttttttt ttcttttttt tttttttccc tctttcttcc    9540
cttctcatct tattctactt tctttcttgg tggctccatc ttagccctag tcacggctag    9600
ctgtgaaagg tccgtgagcc gcatgactgc agagagtgcc gtaactggtc tctctgcaga    9660
tcatgt                                                               9666

<210> SEQ ID NO 6
<211> LENGTH: 3029
<212> TYPE: PRT
<213> ORGANISM: Hepatitis C virus

<400> SEQUENCE: 6

Met Ser Thr Asn Pro Lys Pro Gln Arg Lys Thr Lys Arg Asn Thr Asn
1               5                   10                  15

Arg Arg Pro Met Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
```

```
                145                 150                 155                 160
Gly Ile Asn Tyr Ala Thr Gly Asn Leu Pro Gly Cys Ser Phe Ser Ile
                    165                 170                 175

Phe Leu Leu Ala Leu Leu Ser Cys Leu Thr Val Pro Ala Ser Ala Val
                180                 185                 190

Asn Tyr Arg Asn Val Ser Gly Ile Tyr His Val Thr Asn Asp Cys Pro
            195                 200                 205

Asn Ser Ser Ile Val Tyr Glu Ala Asp His His Ile Leu His Leu Pro
        210                 215                 220

Gly Cys Val Pro Cys Val Arg Glu Gly Asn Gln Ser Arg Cys Trp Val
225                 230                 235                 240

Ala Leu Thr Pro Thr Val Ala Ala Pro Tyr Ile Gly Ala Pro Leu Glu
                245                 250                 255

Ser Leu Arg Ser His Val Asp Leu Met Val Gly Ala Ala Thr Val Cys
                260                 265                 270

Ser Gly Leu Tyr Ile Gly Asp Leu Cys Gly Gly Leu Phe Leu Val Gly
                275                 280                 285

Gln Met Phe Ser Phe Arg Pro Arg His Trp Thr Thr Gln Asp Cys
    290                 295                 300

Asn Cys Ser Ile Tyr Thr Gly His Ile Thr Gly His Arg Met Ala Trp
305                 310                 315                 320

Asp Met Met Met Asn Trp Ser Pro Thr Thr Thr Leu Val Leu Ala Gln
                325                 330                 335

Val Met Arg Ile Pro Thr Thr Leu Val Asp Leu Leu Ser Gly Gly His
                340                 345                 350

Trp Gly Val Leu Val Gly Val Ala Tyr Phe Ser Met Gln Ala Asn Trp
            355                 360                 365

Ala Lys Val Ile Leu Val Leu Phe Leu Phe Ala Gly Val Asp Ala Glu
        370                 375                 380

Thr His Val Ser Gly Ala Ala Val Gly Arg Ser Thr Ala Gly Leu Ala
385                 390                 395                 400

Asn Leu Phe Ser Ser Gly Ser Lys Gln Asn Leu Gln Leu Ile Asn Ser
                405                 410                 415

Asn Gly Ser Trp His Ile Asn Arg Thr Ala Leu Asn Cys Asn Asp Ser
                420                 425                 430

Leu Asn Thr Gly Phe Leu Ala Ser Leu Phe Tyr Thr His Lys Phe Asn
            435                 440                 445

Ser Ser Gly Cys Ser Glu Arg Leu Ala Cys Cys Lys Ser Leu Asp Ser
        450                 455                 460

Tyr Gly Gln Gly Trp Gly Pro Leu Gly Val Ala Asn Ile Ser Gly Ser
465                 470                 475                 480

Ser Asp Asp Arg Pro Tyr Cys Trp His Tyr Ala Pro Arg Pro Cys Gly
                485                 490                 495

Ile Val Pro Ala Ser Ser Val Cys Gly Pro Val Tyr Cys Phe Thr Pro
                500                 505                 510

Ser Pro Val Val Val Gly Thr Thr Asp His Val Gly Val Pro Thr Tyr
                515                 520                 525

Thr Trp Gly Glu Asn Glu Thr Asp Val Phe Leu Leu Asn Ser Thr Arg
            530                 535                 540

Pro Pro His Gly Ala Trp Phe Gly Cys Val Trp Met Asn Ser Thr Gly
545                 550                 555                 560

Phe Thr Lys Thr Cys Gly Ala Pro Pro Cys Glu Val Asn Thr Asn Asn
                565                 570                 575
```

-continued

```
Gly Thr Trp His Cys Pro Thr Asp Cys Phe Arg Lys His Pro Glu Thr
            580                 585                 590
Thr Tyr Ala Lys Cys Gly Ser Gly Pro Trp Ile Thr Pro Arg Cys Leu
        595                 600                 605
Ile Asp Tyr Pro Tyr Arg Leu Trp His Phe Pro Cys Thr Ala Asn Phe
610                 615                 620
Ser Val Phe Asn Ile Arg Thr Phe Val Gly Ile Glu His Arg Met
625                 630                 635                 640
Gln Ala Ala Cys Asn Trp Thr Arg Gly Glu Val Cys Gly Leu Glu His
                645                 650                 655
Arg Asp Arg Val Glu Leu Ser Pro Leu Leu Thr Thr Ala Trp
                660                 665                 670
Gln Ile Leu Pro Cys Ser Phe Thr Thr Leu Pro Ala Leu Ser Thr Gly
            675                 680                 685
Leu Ile His Leu His Gln Asn Ile Val Asp Val Gln Tyr Leu Tyr Gly
        690                 695                 700
Val Gly Ser Ala Val Val Ser Trp Ala Leu Lys Trp Glu Tyr Val Val
705                 710                 715                 720
Leu Ala Phe Leu Leu Leu Ala Asp Ala Arg Val Ser Ala Cys Leu Trp
                725                 730                 735
Met Met Phe Met Val Ser Gln Val Glu Ala Ala Leu Ser Asn Leu Ile
                740                 745                 750
Asn Ile Asn Ala Ala Ser Ala Ala Gly Ala Gln Gly Phe Trp Tyr Ala
            755                 760                 765
Ile Leu Phe Ile Cys Ile Val Trp His Val Lys Gly Arg Phe Pro Ala
        770                 775                 780
Ala Ala Ala Tyr Ala Ala Cys Gly Leu Trp Pro Leu Phe Leu Leu Leu
785                 790                 795                 800
Leu Met Leu Pro Glu Arg Ala Tyr Ala Tyr Asp Gln Glu Val Ala Gly
                805                 810                 815
Ser Leu Gly Gly Ala Ile Val Val Met Leu Thr Ile Leu Thr Leu Ser
                820                 825                 830
Pro His Tyr Lys Leu Trp Leu Ala Arg Gly Leu Trp Trp Leu Cys Tyr
        835                 840                 845
Leu Leu Thr Leu Gly Glu Ala Met Ile Gln Glu Trp Val Pro Pro Met
    850                 855                 860
Gln Val Arg Gly Gly Arg Asp Gly Ile Ala Trp Ala Val Thr Ile Phe
865                 870                 875                 880
Cys Pro Gly Val Val Phe Asp Ile Thr Lys Trp Leu Leu Ala Leu Leu
                885                 890                 895
Gly Pro Ala Tyr Leu Leu Arg Ala Ala Leu Thr His Val Pro Tyr Phe
            900                 905                 910
Val Arg Ala His Ala Leu Ile Arg Val Cys Ala Leu Val Lys Gln Leu
        915                 920                 925
Ala Gly Gly Arg Tyr Val Gln Val Ala Leu Leu Ala Leu Gly Arg Trp
    930                 935                 940
Thr Gly Thr Tyr Ile Tyr Asp His Leu Thr Pro Met Ser Asp Trp Ala
945                 950                 955                 960
Ala Ser Gly Leu Arg Asp Leu Ala Val Ala Val Glu Pro Ile Ile Phe
                965                 970                 975
Ser Pro Met Glu Lys Lys Val Ile Val Trp Gly Ala Glu Thr Ala Ala
            980                 985                 990
Cys Gly Asp Ile Leu His Gly Leu  Pro Val Ser Ala Arg  Leu Gly Gln
        995                 1000                1005
```

-continued

Glu Ile Leu Leu Gly Pro Ala Asp Gly Tyr Thr Ser Lys Gly Trp
    1010                1015                1020

Lys Leu Leu Ala Pro Ile Thr Ala Tyr Ala Gln Gln Thr Arg Gly
    1025                1030                1035

Leu Leu Gly Ala Ile Val Val Ser Met Thr Gly Arg Asp Arg Thr
    1040                1045                1050

Glu Gln Ala Gly Glu Val Gln Ile Leu Ser Thr Val Ser Gln Ser
    1055                1060                1065

Phe Leu Gly Thr Thr Ile Ser Gly Val Leu Trp Thr Val Tyr His
    1070                1075                1080

Gly Ala Gly Asn Lys Thr Leu Ala Gly Leu Arg Gly Pro Val Thr
    1085                1090                1095

Gln Met Tyr Ser Ser Ala Glu Gly Asp Leu Val Gly Trp Pro Ser
    1100                1105                1110

Pro Pro Gly Thr Lys Ser Leu Glu Pro Cys Lys Cys Gly Ala Val
    1115                1120                1125

Asp Leu Tyr Leu Val Thr Arg Asn Ala Asp Val Ile Pro Ala Arg
    1130                1135                1140

Arg Arg Gly Asp Lys Arg Gly Ala Leu Leu Ser Pro Arg Pro Ile
    1145                1150                1155

Ser Thr Leu Lys Gly Ser Ser Gly Gly Pro Val Leu Cys Pro Arg
    1160                1165                1170

Gly His Val Val Gly Leu Phe Arg Ala Ala Val Cys Ser Arg Gly
    1175                1180                1185

Val Ala Lys Ser Ile Asp Phe Ile Pro Val Glu Thr Leu Asp Val
    1190                1195                1200

Val Thr Arg Ser Pro Thr Phe Ser Asp Asn Ser Thr Pro Pro Ala
    1205                1210                1215

Val Pro Gln Thr Tyr Gln Val Gly Tyr Leu His Ala Pro Thr Gly
    1220                1225                1230

Ser Gly Lys Ser Thr Lys Val Pro Val Ala Tyr Ala Ala Gln Gly
    1235                1240                1245

Tyr Lys Val Leu Val Leu Asn Pro Ser Val Ala Ala Thr Leu Gly
    1250                1255                1260

Phe Gly Ala Tyr Leu Ser Lys Ala His Gly Ile Asn Pro Asn Ile
    1265                1270                1275

Arg Thr Gly Val Arg Thr Val Met Thr Gly Glu Ala Ile Thr Tyr
    1280                1285                1290

Ser Thr Tyr Gly Lys Phe Leu Ala Asp Gly Gly Cys Ala Ser Gly
    1295                1300                1305

Ala Tyr Asp Ile Ile Ile Cys Asp Glu Cys His Ala Val Asp Ala
    1310                1315                1320

Thr Ser Ile Leu Gly Ile Gly Thr Val Leu Asp Gln Ala Glu Thr
    1325                1330                1335

Ala Gly Val Arg Leu Thr Val Leu Ala Thr Ala Thr Pro Pro Gly
    1340                1345                1350

Ser Val Thr Thr Pro His Pro Asp Ile Glu Glu Val Gly Leu Gly
    1355                1360                1365

Arg Glu Gly Glu Ile Pro Phe Tyr Gly Arg Ala Ile Pro Leu Ser
    1370                1375                1380

Cys Ile Lys Gly Gly Arg His Leu Ile Phe Cys His Ser Lys Lys
    1385                1390                1395

Lys Cys Asp Glu Leu Ala Ala Ala Leu Arg Gly Met Gly Leu Asn

```
                1400                1405                1410
Ala Val Ala Tyr Tyr Arg Gly Leu Asp Val Ser Ile Ile Pro Ala
        1415                1420                1425

Gln Gly Asp Val Val Val Ala Thr Asp Ala Leu Met Thr Gly
    1430                1435                1440

Tyr Thr Gly Asp Phe Asp Ser Val Ile Asp Cys Asn Val Ala Val
        1445                1450                1455

Thr Gln Ala Val Asp Phe Ser Leu Asp Pro Thr Phe Thr Ile Thr
        1460                1465                1470

Thr Gln Thr Val Pro Gln Asp Ala Val Ser Arg Ser Gln Arg Arg
        1475                1480                1485

Gly Arg Thr Gly Arg Gly Arg Gln Gly Thr Tyr Arg Tyr Val Ser
        1490                1495                1500

Thr Gly Glu Arg Ala Ser Gly Met Phe Asp Ser Val Val Leu Cys
        1505                1510                1515

Glu Cys Tyr Asp Ala Gly Ala Ala Trp Tyr Asp Leu Thr Pro Ala
        1520                1525                1530

Glu Thr Thr Val Arg Leu Arg Ala Tyr Phe Asn Thr Pro Gly Leu
        1535                1540                1545

Pro Val Cys Gln Asp His Leu Glu Phe Trp Glu Ala Val Phe Thr
        1550                1555                1560

Gly Leu Thr His Ile Asp Ala His Phe Leu Ser Gln Thr Lys Gln
        1565                1570                1575

Ala Gly Glu Asn Phe Ala Tyr Leu Val Ala Tyr Gln Ala Thr Val
        1580                1585                1590

Cys Ala Arg Ala Lys Ala Pro Pro Pro Ser Trp Asp Ala Met Trp
        1595                1600                1605

Lys Cys Leu Ala Arg Leu Lys Pro Thr Leu Ala Gly Pro Thr Pro
        1610                1615                1620

Leu Leu Tyr Arg Leu Gly Pro Ile Thr Asn Glu Val Thr Leu Thr
        1625                1630                1635

His Pro Gly Thr Lys Tyr Ile Ala Thr Cys Met Gln Ala Asp Leu
        1640                1645                1650

Glu Val Met Thr Ser Thr Trp Val Leu Ala Gly Gly Val Leu Ala
        1655                1660                1665

Ala Val Ala Ala Tyr Cys Leu Ala Thr Gly Cys Val Ser Ile Ile
        1670                1675                1680

Gly Arg Leu His Val Asn Gln Arg Val Val Ala Pro Asp Lys
        1685                1690                1695

Glu Val Leu Tyr Glu Ala Phe Asp Glu Met Glu Glu Cys Ala Ser
        1700                1705                1710

Arg Ala Ala Leu Ile Glu Glu Gly Gln Arg Ile Ala Glu Met Leu
        1715                1720                1725

Lys Ser Lys Ile Gln Gly Leu Leu Gln Gln Ala Ser Lys Gln Ala
        1730                1735                1740

Gln Asp Ile Gln Pro Ala Met Gln Ala Ser Trp Pro Lys Val Glu
        1745                1750                1755

Gln Phe Trp Ala Arg His Met Trp Asn Phe Ile Ser Gly Ile Gln
        1760                1765                1770

Tyr Leu Ala Gly Leu Ser Thr Leu Pro Gly Asn Pro Ala Val Ala
        1775                1780                1785

Ser Met Met Ala Phe Ser Ala Ala Leu Thr Ser Pro Leu Ser Thr
        1790                1795                1800
```

Ser Thr Thr Ile Leu Leu Asn Ile Met Gly Gly Trp Leu Ala Ser
1805                    1810                1815

Gln Ile Ala Pro Pro Ala Gly Ala Thr Gly Phe Val Val Ser Gly
1820                    1825                1830

Leu Val Gly Ala Ala Val Gly Ser Ile Gly Leu Gly Lys Val Leu
1835                    1840                1845

Val Asp Ile Leu Ala Gly Tyr Gly Ala Gly Ile Ser Gly Ala Leu
1850                    1855                1860

Val Ala Phe Lys Ile Met Ser Gly Glu Lys Pro Ser Met Glu Asp
1865                    1870                1875

Val Ile Asn Leu Leu Pro Gly Ile Leu Ser Pro Gly Ala Leu Val
1880                    1885                1890

Val Gly Val Ile Cys Ala Ala Ile Leu Arg Arg His Val Gly Pro
1895                    1900                1905

Gly Glu Gly Ala Val Gln Trp Met Asn Arg Leu Ile Ala Phe Ala
1910                    1915                1920

Ser Arg Gly Asn His Val Ala Pro Thr His Tyr Val Thr Glu Ser
1925                    1930                1935

Asp Ala Ser Gln Arg Val Thr Gln Leu Leu Gly Ser Leu Thr Ile
1940                    1945                1950

Thr Ser Leu Leu Arg Arg Leu His Asn Trp Ile Thr Glu Asp Cys
1955                    1960                1965

Pro Ile Pro Cys Ser Gly Ser Trp Leu Arg Asp Val Trp Asp Trp
1970                    1975                1980

Val Cys Thr Ile Leu Thr Asp Phe Lys Asn Trp Leu Thr Ser Lys
1985                    1990                1995

Leu Phe Pro Lys Leu Pro Gly Leu Pro Phe Ile Ser Cys Gln Lys
2000                    2005                2010

Gly Tyr Lys Gly Val Trp Ala Gly Thr Gly Ile Met Thr Thr Arg
2015                    2020                2025

Cys Pro Cys Gly Ala Asn Ile Ser Gly Asn Val Arg Leu Gly Ser
2030                    2035                2040

Met Arg Ile Thr Gly Pro Lys Thr Cys Met Asn Thr Trp Gln Gly
2045                    2050                2055

Thr Phe Pro Ile Asn Cys Tyr Thr Glu Gly Gln Cys Ala Pro Lys
2060                    2065                2070

Pro Pro Thr Asn Tyr Lys Thr Ala Ile Trp Arg Val Ala Ala Ser
2075                    2080                2085

Glu Tyr Ala Glu Val Thr Gln His Gly Ser Tyr Ser Tyr Val Thr
2090                    2095                2100

Gly Leu Thr Thr Asp Asn Leu Lys Ile Pro Cys Gln Leu Pro Ser
2105                    2110                2115

Pro Glu Phe Phe Ser Trp Val Asp Gly Val Gln Ile His Arg Phe
2120                    2125                2130

Ala Pro Thr Pro Lys Pro Phe Phe Arg Asp Glu Val Ser Phe Cys
2135                    2140                2145

Val Gly Leu Asn Ser Tyr Ala Val Gly Ser Gln Leu Pro Cys Glu
2150                    2155                2160

Pro Glu Pro Asp Ala Asp Val Leu Arg Ser Met Leu Thr Asp Pro
2165                    2170                2175

Pro His Ile Thr Ala Glu Thr Ala Ala Arg Arg Leu Ala Arg Gly
2180                    2185                2190

Ser Pro Pro Ser Glu Ala Ser Ser Ser Val Ser Gln Leu Ser Ala
2195                    2200                2205

-continued

```
Pro Ser Leu Arg Ala Thr Cys Thr Thr His Ser Asn Thr Tyr Asp
    2210                2215                2220

Val Asp Met Val Asp Ala Asn Leu Leu Met Glu Gly Gly Val Ala
    2225                2230                2235

Gln Thr Glu Pro Glu Ser Arg Val Pro Val Leu Asp Phe Leu Glu
    2240                2245                2250

Pro Met Ala Glu Glu Ser Asp Leu Glu Pro Ser Ile Pro Ser
    2255                2260                2265

Glu Cys Met Leu Pro Arg Ser Gly Phe Pro Arg Ala Leu Pro Ala
    2270                2275                2280

Trp Ala Arg Pro Asp Tyr Asn Pro Pro Leu Val Glu Ser Trp Arg
    2285                2290                2295

Arg Pro Asp Tyr Gln Pro Pro Thr Val Ala Gly Cys Ala Leu Pro
    2300                2305                2310

Pro Pro Lys Lys Ala Pro Thr Pro Pro Pro Arg Arg Arg Arg Thr
    2315                2320                2325

Val Gly Leu Ser Glu Ser Thr Ile Ser Glu Ala Leu Gln Gln Leu
    2330                2335                2340

Ala Ile Lys Thr Phe Gly Gln Pro Pro Ser Ser Gly Asp Ala Gly
    2345                2350                2355

Ser Ser Thr Gly Ala Gly Ala Ala Glu Ser Gly Gly Pro Thr Ser
    2360                2365                2370

Pro Gly Glu Pro Ala Pro Ser Glu Thr Gly Ser Ala Ser Ser Met
    2375                2380                2385

Pro Pro Leu Glu Gly Glu Pro Gly Asp Pro Asp Leu Glu Ser Asp
    2390                2395                2400

Gln Val Glu Leu Gln Pro Pro Gln Gly Gly Gly Val Ala Pro
    2405                2410                2415

Gly Ser Gly Ser Gly Ser Trp Ser Thr Cys Ser Glu Glu Asp Asp
    2420                2425                2430

Thr Thr Val Cys Cys Ser Met Ser Tyr Ser Trp Thr Gly Ala Leu
    2435                2440                2445

Ile Thr Pro Cys Ser Pro Glu Glu Lys Leu Pro Ile Asn Pro
    2450                2455                2460

Leu Ser Asn Ser Leu Leu Arg Tyr His Asn Lys Val Tyr Cys Thr
    2465                2470                2475

Thr Ser Lys Ser Ala Ser Gln Arg Ala Lys Lys Val Thr Phe Asp
    2480                2485                2490

Arg Thr Gln Val Leu Asp Ala His Tyr Asp Ser Val Leu Lys Asp
    2495                2500                2505

Ile Lys Leu Ala Ala Ser Lys Val Ser Ala Arg Leu Leu Thr Leu
    2510                2515                2520

Glu Glu Ala Cys Gln Leu Thr Pro Pro His Ser Ala Arg Ser Lys
    2525                2530                2535

Tyr Gly Phe Gly Ala Lys Glu Val Arg Ser Leu Ser Gly Arg Ala
    2540                2545                2550

Val Asn His Ile Lys Ser Val Trp Lys Asp Leu Leu Glu Asp Pro
    2555                2560                2565

Gln Thr Pro Ile Pro Thr Thr Ile Met Ala Lys Asn Glu Val Phe
    2570                2575                2580

Cys Val Asp Pro Ala Lys Gly Gly Lys Lys Pro Ala Arg Leu Ile
    2585                2590                2595

Val Tyr Pro Asp Leu Gly Val Arg Val Cys Glu Lys Met Ala Leu
```

-continued

```
              2600               2605               2610

Tyr Asp Ile Thr Gln Lys Leu Pro Gln Ala Val Met Gly Ala Ser
        2615               2620               2625

Tyr Gly Phe Gln Tyr Ser Pro Ala Gln Arg Val Glu Tyr Leu Leu
        2630               2635               2640

Lys Ala Trp Ala Glu Lys Lys Asp Pro Met Gly Phe Ser Tyr Asp
        2645               2650               2655

Thr Arg Cys Phe Asp Ser Thr Val Thr Glu Arg Asp Ile Arg Thr
        2660               2665               2670

Glu Glu Ser Ile Tyr Gln Ala Cys Ser Leu Pro Glu Glu Ala Arg
        2675               2680               2685

Thr Ala Ile His Ser Leu Thr Glu Arg Leu Tyr Val Gly Gly Pro
        2690               2695               2700

Met Phe Asn Ser Lys Gly Gln Thr Cys Gly Tyr Arg Arg Cys Arg
        2705               2710               2715

Ala Ser Gly Val Leu Thr Thr Ser Met Gly Asn Thr Ile Thr Cys
        2720               2725               2730

Tyr Val Lys Ala Leu Ala Ala Cys Lys Ala Ala Gly Ile Val Ala
        2735               2740               2745

Pro Thr Met Leu Val Cys Gly Asp Asp Leu Val Val Ile Ser Glu
        2750               2755               2760

Ser Gln Gly Thr Glu Glu Asp Glu Arg Asn Leu Arg Ala Phe Thr
        2765               2770               2775

Glu Ala Met Thr Arg Tyr Ser Ala Pro Pro Gly Asp Pro Pro Arg
        2780               2785               2790

Pro Glu Tyr Asp Leu Glu Leu Ile Thr Ser Cys Ser Ser Asn Val
        2795               2800               2805

Ser Val Ala Leu Gly Pro Arg Gly Arg Arg Arg Tyr Tyr Leu Thr
        2810               2815               2820

Arg Asp Pro Thr Thr Pro Leu Ala Arg Ala Ala Trp Glu Thr Val
        2825               2830               2835

Arg His Ser Pro Ile Asn Ser Trp Leu Gly Asn Ile Ile Gln Tyr
        2840               2845               2850

Ala Pro Thr Ile Trp Val Arg Met Val Leu Met Thr His Phe Phe
        2855               2860               2865

Ser Ile Leu Met Val Gln Asp Thr Leu Asp Gln Asn Leu Asn Phe
        2870               2875               2880

Glu Met Tyr Gly Ser Val Tyr Ser Val Asn Pro Leu Asp Leu Pro
        2885               2890               2895

Ala Ile Ile Glu Arg Leu His Gly Leu Asp Ala Phe Ser Met His
        2900               2905               2910

Thr Tyr Ser His His Glu Leu Thr Arg Val Ala Ser Ala Leu Arg
        2915               2920               2925

Lys Leu Gly Ala Pro Pro Leu Arg Val Trp Lys Ser Arg Ala Arg
        2930               2935               2940

Ala Val Arg Ala Ser Leu Ile Ser Arg Gly Gly Lys Ala Ala Val
        2945               2950               2955

Cys Gly Arg Tyr Leu Phe Asn Trp Ala Val Lys Thr Lys Leu Lys
        2960               2965               2970

Leu Thr Pro Leu Pro Glu Ala Arg Leu Leu Asp Leu Ser Ser Trp
        2975               2980               2985

Phe Thr Val Gly Ala Gly Gly Gly Asp Ile Phe His Ser Val Ser
        2990               2995               3000
```

```
Arg Ala  Arg Pro Arg Ser Leu  Leu Phe Gly Leu Leu  Leu Leu Phe
    3005             3010                 3015

Val Gly  Val Gly Leu Phe Leu  Leu Pro Ala Arg
    3020             3025

<210> SEQ ID NO 7
<211> LENGTH: 9666
<212> TYPE: DNA
<213> ORGANISM: Hepatitis C virus

<400> SEQUENCE: 7
acctgcccct aatagggggcg acactccgcc atgaatcact ccctgtgag gaactactgt      60 cttcacgcag aaagcgccta gccatggcgt tagtatgagt gtcgtacagc ctccaggccc     120 cccctcccg ggagagccat agtggtctgc ggaaccggtg agtacaccgg aattgccggg     180
aagactgggt cctttcttgg ataaacccac tctatgcccg gccatttggg cgtgcccccg     240
caagactgct agccgagtag cgttgggttg cgaaaggcct tgtggtactg cctgataggg     300
cgcttgcgag tgccccggga ggtctcgtag accgtgcacc atgagcacga atcctaaacc     360
tcaaagaaaa accaaacgta acaccaaccg ccgcccaatg acgttaagt tcccgggtgg     420 tggccagatc gttggcggag tttacttgtt gccgcgcagg ggccccagat tgggtgtgcg     480
cgcgactcgg aagacttcgg agcggtcgca acctcgtgga agacgccaac ctatccccaa     540
ggcgcgtcga cccgagggaa ggtcctgggc acaaccagga tatccatggc ctctttacgg     600
taatgagggt tgtgggtggg caggatggct cttgtccccc cgtggctctc gaccgtcttg     660
gggcccaaat gatccccggc ggaggtcccg caatttgggt aaggtcatcg ataccctaac     720
ctgcggcttc gccgacctca tgggatacat cccgctcgta ggcgccccg tgggtggcgt     780 cgccagggcc ctggcacatg tgtcagggc tttggaggac gggatcaatt atgcaacagg     840
gaatctcccc ggttgctcct tttctatctt cctcttggca cttctttcgt gcctgactgt     900
ccccgcttcg gccgttaact atcgcaatgt ctcgggcatc taccatgtca ccaatgactg     960
cccgaattca agcatagtgt atgaggccga ccatcacatc ttgcaccttc aggttgcgt    1020 gccctgcgtg agagagggga atcagtcacg ctgctgggtg cccttactc ctaccgtcgc    1080 agcgccatac atcggcgcac cgcttgagtc cttacggagt catgtggatt tgatggtggg    1140
ggccgccact gtttgctcgg tcttttacat cggggacctg tgtggcggct tgttcctagt    1200
tggccagatg tttttcattc c gaccacggcg ccactggacc acccaggatt gcaattgttc    1260
catctacaca gggcacatta caggccacag aatggcctgg gacatgatga tgaactggag    1320
tccaacaacc accttagttc tcgcccaggt catgaggatc ccaaccactc tggtagactt    1380
actctctgga ggccactggg gtgtcctcgt gggagtggcc tatttcagca tgcaggccaa    1440
ttgggccaaa gtcatcttgg tcctattcct ctttgcaggg gttgatgccg agactcacgt    1500
gtctggggca gcagtcggcc ggagtaccgc cggcttggct aacctctttt cttctgggtc    1560
taagcagaat ttacagctca tcaacagcaa tgggagctgg catataaata ggactgccct    1620
taactgcaat gacagcttaa acactgggtt cttggctagc ttgttctaca cccacaagtt    1680
taacagctca gggtgttccg aacggctcgc gtgctgcaag agccttgaca gctacggcca    1740
aggctggggc ccactcgggg tcgctaacat cagcggctcg tctgatgaca ggccttattg    1800
ctggcactac gcgcctcggc cgtgcgggat tgtgccagca tccagtgtgt gtggccccgt    1860
gtattgtttc actcccagcc ctgtcgtggt cggtactact gatcacgtcg gggtccctac    1920
ttacacctgg ggggagaatg agactgatgt cttccttttg aactcgacca ccgccgcaca    1980
```

```
tggtgcgtgg tttggatgcg tgtggatgaa cagtaccggg ttcaccaaaa cctgtggcgc    2040
ccctccatgc gaggttaaca ccaataatgg gacctggcac tgccccaccg attgcttcag    2100
gaagcatccg gagactacct acgccaagtg cggatcaggg ccttggatca caccgcgctg    2160
cctgattgat tacccgtacc ggctgtggca tttcccgtgc accgccaact tctccgtctt    2220
taacatcagg acatttgtcg gcggtataga gcatcggatg caagcggcat gcaactggac    2280
caggggggaa gtctgtggct tggagcacag ggatcgcgta gagctatcac ccctgctcct    2340
taccactaca gcgtggcaga tcctccctg ctctttcacc actttacctg ccctctccac     2400
cggcttgatc cacctccacc aaaatatcgt ggacgtccag tacctctatg tgttgggtc     2460 tgcagtggta tcttgggccc ttaagtggga atatgtggtg ctcgcgttcc tgcttctcgc    2520
ggacgcgaga gtctctgcct gcctatggat gatgtttatg gtaagtcaag ttgaggcggc    2580
tctgtccaac ctgattaaca tcaatgctgc ttcagccgct ggtgcccaag gcttctggta    2640
cgccatcctc ttcatctgca ttgtctggca tgtcaagggc cggttcccag ctgctgctgc    2700
ctacgcagcc tgcgggctgt ggcccctgtt tctcctgctt ctgatgctgc tgagagggc     2760 ttatgcatac gaccaggaag tggcagggtc ccttggcggc gccatcgttg tcatgctggc    2820
cattctgaca ctgtctccgc actacaagtt atggctggct aggggattgt ggtggatcca    2880 atatttata gctaggaccg aggctgtgct gcatgtctat attccatcct caacgtgcg     2940 cgggcctcgc gactcagtga ttgttcttgc agtcctggtc tgtccacacc tagtatttga    3000
catcacaaaa tatcttctgg ccatcttagg gcccctccac atactccagg cctcgctcct    3060
acgcatccct tactttgtga gggcacaagc gctggttaag atctgcagct tgttgcgtgg    3120
ggtagtttat ggcaagtact tccaaatggt cgtgcttaaa gcaggggccc tgactggtac    3180
ttacatctat gaccacctca cacctatgtc ggactgggcc gctagcggcc tgcgcgactt    3240
agcggtcgcc gtggaaccca tcatcttcag tccgatggag aagaaggtca tcgtctgggg    3300
agcggagacg gctgcatgtg gggacattct acatggactt cccgtgtccg cccgactcgg    3360
ccaggagatc ctcctcggcc cagctgatgg ctacacctcc aagggtggaa gctccttgc     3420 tcccatcact gcttatgccc agcaaacacg aggcctcctg ggcgccatag tggtgagtat    3480
gacggggcgt gacaggacag aacaggccgg ggaagtccaa atcctgtcca cagtctctca    3540
gtccttcctc ggaacaacca tctcgggggt tttgtggact gtttaccacg gagctggcaa    3600
caagactcta gccggcttac ggggtccggt cacgcagatg tactcgagtg ctgaggggga    3660
cttggtaggc tggcccagcc ccctgggac caagtctttg gagccgtgca agtgtggagc     3720
cgtcgaccta tatctggtca cgcggaacgc tgatgtcatc ccggctcgga gacgcgggga    3780
caagcgggga gcattgctct ccccgagacc catttcgacc ttgaagggg cctcgggggg     3840 gccggtgctc tgccctaggg gccacgtcgt tgggctcttc cgagcagctg tgtgctctcg    3900
gggcgtggcc aaatccatcg atttcatccc cgttgagaca ctcgacgttg ttacaaggtc    3960
tcccactttc agtgacaaca gcacgccacc ggctgtgccc cagacctatc aggtcgggta    4020
cttgcatgct ccaactggca gtggaaagag caccaaggtc cctgtcgcgt atgccgccca    4080
ggggtacaaa gtactagtgc ttaaccctc ggtagctgcc accctggggt ttggggcgta     4140
cctatccaag gcacatggca tcaatcccaa cattaggact ggagtcagga ccgtgatgac    4200
cggggaggcc atcacgtact ccacatatgg caaatttctc gccgatgggg gctgcgctag    4260
cggcgcctat gacatcatca tatgcgatga atgccacgct gtggatgcta cctccattct    4320
cggcatcgga acggtccttg atcaagcaga gacagccggg gtcagactaa ctgtgctggc    4380
```

```
tacggccaca ccccccgggt cagtgacaac cccccatccc gatatagaag aggtaggcct   4440
cgggcgggag ggtgagatcc ccttctatgg gagggcgatt cccctatcct gcatcaaggg   4500
agggagacac ctgattttct gccactcaaa gaaaaagtgt gacgagctcg cggcggccct   4560
tcggggcatg ggcttgaatg ccgtggcata ctatagaggg ttggacgtct ccataatacc   4620
agctcaggga gatgtggtgg tcgtcgccac cgacgccctc atgacggggt acactggaga   4680
cttgactcc  gtgatcgact gcaatgtagc ggtcacccaa gctgtcgact tcagcctgga    4740
ccccaccttc actataacca cacagactgt cccacaagac gctgtctcac gcagtcagcg   4800
ccgcgggcgc acaggtagag gaagacaggg cacttatagg tatgtttcca ctggtgaacg   4860
agcctcagga atgtttgaca gtgtagtgct tgtgagtgc  tacgacgcag gggctgcgtg   4920
gtacgatctc acaccagcgg agaccaccgt caggcttaga gcgtatttca acacgcccgg   4980
cctacccgtg tgtcaagacc atcttgaatt ttgggaggca gttttcaccg gcctcacaca   5040
catagacgcc cacttcctct cccaaacaaa gcaagcgggg gagaacttcg cgtacctagt   5100
agcctaccaa gctacggtgt gcgccagagc caaggcccct ccccgtcct  gggacgccat    5160
gtggaagtgc ctggcccgac tcaagcctac gcttgcgggc cccacacctc tcctgtaccg   5220
tttgggccct attaccaatg aggtcaccct cacacaccct gggacgaagt acatcgccac   5280
atgcatgcaa gctgaccttg aggtcatgac cagcacgtgg gtcctagctg gaggagtcct   5340
ggcagccgtc gccgcatatt gcctggcgac tggatgcgtt tccatcatcg gccgcttgca   5400
cgtcaaccag cgagtcgtcg ttgcgccgga taaggaggtc ctgtatgagg cttttgatga   5460
gatggaggaa tgcgcctcta gggcggctct catcgaagag gggcagcgga tagccgagat   5520
gttgaagtcc aagatccaag gcttgctgca gcaggcctct aagcaggccc aggacataca   5580
acccgctatg caggcttcat ggcccaaagt ggaacaattt gggccagac  acatgtggaa    5640
cttcattagc ggcatccaat acctcgcagg attgtcaaca ctgccaggga accccgcgt    5700
ggcttccatg atggcattca gtgccgccct caccagtccg ttgtcgacca gtaccaccat   5760
ccttctcaac atcatgggag ctggttagc  gtcccagatc gcaccacccg cgggggccac    5820
cggctttgtc gtcagtggcc tggtggggc  tgccgtgggc agcataggcc tgggtaaggt    5880
gctggtggac atcctggcag gatatggtgc gggcatttcg ggggccctcg tcgcattcaa   5940
gatcatgtct ggcgagaagc cctctatgga agatgtcatc aatctactgc ctgggatcct   6000
gtctccggga gccctggtgg tggggtcat  ctgcgcggcc attctgcgcc gccacgtggg    6060
accggggag  ggcgcggtcc aatggatgaa caggcttatt gcctttgctt ccagaggaaa    6120
ccacgtcgcc cctactcact acgtgacgga gtcggatgcg tcgcagcgtg tgacccaact   6180
acttggctct cttactataa ccagcctact cagaagactc cacaattgga taactgagga   6240
ctgccccatc ccatgctccg gatcctggct ccgcgacgtg tgggactggg tttgcaccat   6300
cttgacagac ttcaaaaatt ggctgacctc taaattgttc cccaagctgc ccggcctccc   6360
cttcatctct tgtcaaaagg ggtacaaggg tgtgtgggcc ggcactggca tcatgaccac   6420
gcgctgccct tgcggcgcca acatctctgg caatgtccgc ctgggctcta tgaggatcac   6480
agggcctaaa acctgcatga acacctggca ggggaccttt cctatcaatt gctacacgga   6540
gggccagtgc gcgccgaaac cccccacgaa ctacaagacc gccatctgga gggtggcggc   6600
ctcggagtac gcggaggtga cgcagcatgg gtcgtactcc tatgtaacag gactgaccac   6660
tgacaatctg aaaattcctt gccaactacc ttctccagag ttttctcct  gggtggacgg    6720
tgtgcagatc cataggtttg cacccacacc aaagccgttt ttccgggatg aggtctcgtt   6780
```

```
ctgcgttggg cttaattcct atgctgtcgg gtcccagctt ccctgtgaac ctgagcccga   6840
cgcagacgta ttgaggtcca tgctaacaga tccgccccac atcacggcgg agactgcggc   6900
gcggcgcttg gcacggggat cacctccatc tgaggcgagc tcctcagtga gccagctatc   6960
agcaccgtcg ctgcgggcca cctgcaccac ccacagcaac acctatgacg tggacatggt   7020
cgatgccaac ctgctcatgg agggcggtgt ggctcagaca gagcctgagt ccagggtgcc   7080
cgttctggac tttctcgagc caatggccga ggaagagagc gaccttgagc cctcaatacc   7140
atcggagtgc atgctcccca ggagcgggtt tccacgggcc ttaccggctt gggcacggcc   7200
tgactacaac ccgccgctcg tggaatcgtg gaggaggcca gattaccaac cgcccaccgt   7260
tgctggttgt gctctccccc cccccaagaa ggccccgacg cctcccccaa ggagacgccg   7320
gacagtgggt ctgagcgaga gcaccatatc agaagccctc cagcaactgg ccatcaagac   7380
ctttggccag ccccccctcga gcggtgatgc aggctcgtcc acggggcgg cgccgccga   7440
atccggcggt ccgacgtccc ctggtgagcc ggcccccctca gagacaggtt ccgcctcctc   7500
tatgcccccc ctcgagggg agcctggaga tccggacctg gagtctgatc aggtagagct   7560
tcaacctccc ccccagggg ggggggtagc tcccggttcg ggctcggggt cttggtctac   7620
ttgctccgag gaggacgata ccaccgtgtg ctgctccatg tcatactcct ggaccggggc   7680
tctaataact ccctgtagcc ccgaagagga aaagttgcca atcaacccctt tgagtaactc   7740
gctgttgcga taccataaca aggtgtactg tacaacatca aagagcgcct cacagagggc   7800
taaaaaggta acttttgaca ggacgcaagt gctcgacgcc cattatgact cagtcttaaa   7860
ggacatcaag ctagcggctt ccaaggtcag cgcaaggctc ctcaccttgg aggaggcgtg   7920
ccagttgact ccaccccatt ctgcaagatc caagtatgga ttcggggcca aggaggtccg   7980
cagcttgtcc gggagggccg ttaaccacat caagtccgtg tggaaggacc tcctggaaga   8040
cccacaaaca ccaattccca caaccatcat ggccaaaaat gaggtgttct gcgtggaccc   8100
cgccaagggg ggtaagaaac cagctcgcct catcgtttac cctgacctcg cgtccgggt   8160
ctgcgagaaa atggccctct atgacattac acaaaagctt cctcaggcgg taatgggagc   8220
ttcctatggc ttccagtact ccctgcccca acgggtggag tatctcttga aagcatgggc   8280
ggaaagaag accccatgg gttttcgta tgatacccga tgcttcgact caaccgtcac   8340
tgagagagac atcaggaccg aggagtccat ataccaggcc tgctccctgc ccgaggaggc   8400
ccgcactgcc atacactcgc tgactgagag actttacgta ggagggccca tgttcaacag   8460
caagggtcaa acctgcggtt acagacgttg ccgcgccagc ggggtgctaa ccactagcat   8520
gggtaacacc atcacatgct atgtgaaagc cctagcggcc tgcaaggctg cggggatagt   8580
tgcgcccaca atgctggtat gcggcgatga cctagtagtc atctcagaaa gccagggac   8640
tgaggaggac gagcggaacc tgagagcctt cacggaggcc atgaccaggt actctgcccc   8700
tcctggtgat cccccagac cggaatatga cctggagcta ataacatcct gttcctcaaa   8760
tgtgtctgtg gcgttgggcc cgcggggccg ccgcagatac tacctgacca gagacccaac   8820
cactccactc gccggggctg cctgggaaac agttagacac tcccctatca attcatggct   8880
gggaaacatc atccagtatg ctccaaccat atgggttcgc atggtcctaa tgacacactt   8940
cttctccatt ctcatggtcc aagacaccct ggaccagaac ctcaactttg agatgtatgg   9000
atcagtatac tccgtgaatc ctttggacct tccagccata attgagaggt tacacgggct   9060
tgacgccttt tctatgcaca catactctca ccacgaactg acgcgggtgg cttcagcct   9120
cagaaaactt ggggcgccac ccctcagggt gtggaagagt cgggctcgcg cagtcagggc   9180
```

| | |
|---|---|
| gtccctcatc tcccgtggag ggaaagcggc cgtttgcggc cgatatctct tcaattgggc | 9240 |
| ggtgaagacc aagctcaaac tcactccatt gccggaggcg cgcctactgg acttatccag | 9300 |
| ttggttcacc gtcggcgccg gcggggcga catttttcac agcgtgtcgc gcgcccgacc | 9360 |
| ccgctcatta ctcttcggcc tactcctact tttcgtaggg gtaggcctct tcctactccc | 9420 |
| cgctcggtag agcggcacac actaggtaca ctccatagct aactgttcct tttttttttt | 9480 |
| tttttttttt tttttttttt tttttttttt ttctttttttt tttttttccc tcttcttcc | 9540 |
| cttctcatct tattctactt tctttcttgg tggctccatc ttagccctag tcacggctag | 9600 |
| ctgtgaaagg tccgtgagcc gcatgactgc agagagtgcc gtaactggtc tctctgcaga | 9660 |
| tcatgt | 9666 |

<210> SEQ ID NO 8
<211> LENGTH: 9666
<212> TYPE: DNA
<213> ORGANISM: Hepatitis C virus

<400> SEQUENCE: 8

| | |
|---|---|
| acctgcccct aatagggggcg acactccgcc atgaatcact ccctgtgag gaactactgt | 60 |
| cttcacgcag aaagcgccta gccatggcgt tagtatgagt gtcgtacagc ctccaggccc | 120 |
| cccctcccg ggagagccat agtggtctgc ggaaccggtg agtacaccgg aattgccggg | 180 |
| aagactgggt cctttcttgg ataaacccac tctatgcccg gccatttggg cgtgcccccg | 240 |
| caagactgct agccgagtag cgttgggttg cgaaaggcct tgtggtactg cctgataggg | 300 |
| cgcttgcgag tgccccggga ggtctcgtag accgtgcacc atgagcacga atcctaaacc | 360 |
| tcaaagaaaa accaaacgta acaccaaccg ccgcccaatg acgttaagt tcccgggtgg | 420 |
| tggccagatc gttggcggag tttacttgtt gccgcgcagg ggcccagat gggtgtgcg | 480 |
| cgcgactcgg aagacttcgg agcggtcgca acctcgtgga agacgccaac ctatccccaa | 540 |
| ggcgcgtcga cccgagggaa ggtcctgggc acaaccagga tatccatggc ctctttacgg | 600 |
| taatgagggt tgtgggtggg caggatggct cttgtccccc cgtggctctc gaccgtcttg | 660 |
| gggcccaaat gatccccggc ggaggtcccg caatttgggt aaggtcatcg ataccctaac | 720 |
| ctgcggcttc gccgacctca tgggatacat cccgctcgta ggcgcccccg tgggtggcgt | 780 |
| cgccagggcc ctggcacatg tgtcagggc tttgaggac gggatcaatt atgcaacagg | 840 |
| gaatctcccc ggttgctcct tttctatctt cctcttggca cttctttcgt gcctgactgt | 900 |
| ccccgcttcg gccgttaact atcgcaatgt ctcgggcatc taccatgtca ccaatgactg | 960 |
| cccgaattca agcatagtgt atgaggccga ccatcacatc ttgcaccttc caggttgcgt | 1020 |
| gccctgcgtg agagagggga atcagtcacg ctgctgggtg gcccttactc ctaccgtcgc | 1080 |
| agcgccatac atcggcgcac cgcttgagtc cttacggagt catgtggatt tgatggtggg | 1140 |
| ggccgccact gtttgctcgg tcttttacat cggggacctg tgtggcggct tgttcctagt | 1200 |
| tggccagatg tttttcattcc gaccacggcg ccactggacc acccaggatt gcaattgttc | 1260 |
| catctacaca gggcacatta caggccacag aatggcctgg gacatgatga tgaactggag | 1320 |
| tccaacaacc accttagttc tcgcccaggt catgaggatc caaccactc tggtagactt | 1380 |
| actctctgga ggccactggg gtgtcctcgt gggagtggcc tatttcagca tgcaggccaa | 1440 |
| ttgggccaaa gtcatcttgg tcctattcct ctttgcaggg gttgatgccg agactcacgt | 1500 |
| gtctggggca gcagtcggcc ggagtaccgc cggcttggct aacctctttt cttctgggtc | 1560 |
| taagcagaat ttacagctca tcaacagcaa tgggagctgg catataaata ggactgccct | 1620 |

```
taactgcaat gacagcttaa acactgggtt cttggctagc ttgttctaca cccacaagtt    1680
taacagctca gggtgttccg aacggctcgc gtgctgcaag agccttgaca gctacggcca    1740
aggctggggc ccactcgggg tcgctaacat cagcggctcg tctgatgaca ggccttattg    1800
ctggcactac gcgcctcggc cgtgcggat tgtgccagca tccagtgtgt gtggcccgt     1860
gtattgtttc actcccagcc ctgtcgtggt cggtactact gatcacgtcg gggtccctac    1920
ttacacctgg ggggagaatg agactgatgt cttcctttg aactcgacca gaccgccgca    1980
tggtgcgtgg tttggatgcg tgtggatgaa cagtaccggg ttcaccaaaa cctgtggcgc    2040
ccctccatgc gaggttaaca ccaataatgg gacctggcac tgccccaccg attgcttcag    2100
gaagcatccg gagactacct acgccaagtg cggatcaggg ccttggatca caccgcgctg    2160
cctgattgat tacccgtacc ggctgtggca tttcccgtgc accgccaact ctccgtctt    2220
taacatcagg acatttgtcg gcggtataga gcatcggatg caagcggcat gcaactggac    2280
caggggggaa gtctgtggct tggagcacag ggatcgcgta gagctatcac ccctgctcct    2340
taccactaca gcgtggcaga tcctcccctg ctctttcacc actttacctg ccctctccac    2400
cggcttgatc cacctccacc aaaatatcgt ggacgtccag tacctctatg gtgttgggtc    2460
tgcagtggta tcttgggccc ttaagtggga atatgtggtg ctcgcgttcc tgcttctcgc    2520
ggacgcgaga gtctctgcct gcctatggat gatgtttatg gtaagtcaag ttgaggcggc    2580
tctgtccaac ctgattaaca tcaatgctgc ttcagccgct ggtgcccaag gcttctggta    2640
cgccatcctc ttcatctgca ttgtctggca tgtcaagggc cggttcccag ctgctgctgc    2700
ctacgcagcc tgcgggctgt ggcccctgtt tctcctgctt ctgatgctgc tgagagggc    2760
ttatgcatac gaccaggaag tggcaggtc ccttggcggc gccatcgttg tcatgctggc    2820
cattctgaca ctgtctccgc actacaagtt atggctggct aggggattgt ggtggatcca    2880
atatttata gctaggaccg aggctgtgct gcatgtctat attccatcct tcaacgtgcg    2940
cgggcctcgc gactcagtga ttgttcttgc agtcctggtc tgtccacacc tagtatttga    3000
catcacaaaa tatcttctgg ccatcttagg gcccctccac atactccagg cctcgctcct    3060
acgcatccct tactttgtga gggcacaagc gctggttaag atctgcagct tgttgcgtgg    3120
ggtagtttat ggcaagtact tccaaatggt cgtgcttaaa gcaggggccc tgactggtac    3180
ttacatctat gaccacctta ctcccatgtc agattgggcc gctacgggcc tccgcgattt    3240
ggcggtggcc ctagagccag ttgtgttctc gcccatggag aagaaagtca tcgtctgggg    3300
cgctgacacc gctgcgtgcg gagacatcat aaggggatta cctgtttcgg ccaggttggg    3360
caatgaaatc ttgctcggac cagccgatac agaaacatca aaggggtgga gactccttgc    3420
tcccatcact gcttatgccc agcaaacacg aggcctcctg ggcgccatag tggtgagtat    3480
gacggggcgt gacaggacag aacaggccgg ggaagtccaa atcctgtcca cagtctctca    3540
gtccttcctc ggaacaacca tctcgggggt tttgtggact gtttaccacg gagctggcaa    3600
caagactcta gccggcttac ggggtccggt cacgcagatg tactcgagtg ctgaggggga    3660
cttggtaggc tggcccagcc ccctgggac caagtctttg gagccgtgca gtgtggagc    3720
cgtcgaccta tatctggtca cgcggaacgc tgatgtcatc ccggctcgga gacgcgggga    3780
caagcgggga gcattgctct ccccgagacc catttcgacc ttgaagggggt cctcgggggg    3840
gccggtgctc tgccctaggg gccacgtcgt tgggctcttc gagcagctg tgtgctctcg    3900
gggcgtggga aaatccatcg atttcatccc cgttgagaca ctcgacgttg ttacaaggtc    3960
tcccactttc agtgacaaca gcacgccacc ggctgtgccc cagacctatc aggtcgggta    4020
```

```
cttgcatgct ccaactggca gtggaaagag caccaaggtc cctgtcgcgt atgccgccca   4080
ggggtacaaa gtactagtgc ttaacccctc ggtagctgcc accctggggt ttggggcgta   4140
cctatccaag gcacatggca tcaatcccaa cattaggact ggagtcagga ccgtgatgac   4200
cggggaggcc atcacgtact ccacatatgg caaatttctc gccgatgggg gctgcgctag   4260
cggcgcctat gacatcatca tatgcgatga atgccacgct gtggatgcta cctccattct   4320
cggcatcgga acgtccttg atcaagcaga cacagccggg gtcagactaa ctgtgctggc    4380
tacggccaca ccccccgggt cagtgacaac ccccatccc gatatagaag aggtaggcct    4440
cgggcgggag ggtgagatcc ccttctatgg gagggcgatt cccctatcct gcatcaaggg   4500
agggagacac ctgattttct gccactcaaa gaaaaagtgt gacgagctcg cggcggccct   4560
tcggggcatg ggcttgaatg ccgtggcata ctatagaggg ttggacgtct ccataatacc   4620
agctcaggga gatgtggtgg tcgtcgccac cgacgccctc atgacggggt acactggaga   4680
ctttgactcc gtgatcgact gcaatgtagc ggtcacccaa gctgtcgact tcagcctgga   4740
ccccaccttc actataacca cacagactgt cccacaagac gctgtctcac gcagtcagcg   4800
ccgcgggcgc acaggtagag gaagacaggg cacttatagg tatgtttcca ctggtgaacg   4860
agcctcagga atgtttgaca gtgtagtgct tgtgagtgc tacgacgcag gggctgcgtg    4920
gtacgatctc acaccagcgg agaccaccgt caggcttaga gcgtatttca acacgcccgg   4980
cctacccgtg tgtcaagacc atcttgaatt tgggaggca gttttcaccg gcctcacaca    5040
catagacgcc cacttcctct cccaaacaaa gcaagcgggg gagaacttcg cgtacctagt   5100
agcctaccaa gctacggtgt gcgccagagc caaggcccct ccccgtcct gggacgccat    5160 gtggaagtgc ctggcccgac tcaagcctac gcttgcgggc cccacacctc tcctgtaccg   5220
tttgggccct attaccaatg aggtcaccct cacacaccct gggacgaagt acatcgccac   5280
atgcatgcaa gctgaccttg aggtcatgac cagcacgtgg gtcctagctg gaggagtcct   5340
ggcagccgtc gccgcatatt gcctggcgac tggatgcgtt ccatcatcg gccgcttgca    5400 cgtcaaccag cgagtcgtcg ttgcgccgga taaggaggtc ctgtatgagg cttttgatga   5460
gatggaggaa tgcgcctcta gggcggctct catcgaagag gggcagcgga tagccgagat   5520
gttgaagtcc aagatccaag gcttgctgca gcaggcctct aagcaggccc aggacataca   5580
acccgctatg caggcttcat ggcccaaagt ggaacaattt gggccagac acatgtggaa    5640 cttcattagc ggcatccaat acctcgcagg attgtcaaca ctgccaggga accccgcggt   5700
ggcttccatg atggcattca gtgccgccct caccagtccg ttgtcgacca gtaccaccat   5760
ccttctcaac atcatgggag ctggttagc gtcccagatc gcaccacccg cgggggccac    5820
cggctttgtc gtcagtggcc tggtggggc tgccgtgggc agcataggcc tgggtaaggt   5880
gctggtggac atcctggcag gatatggtgc gggcatttcg ggggccctcg tcgcattcaa   5940
gatcatgtct ggcgagaagc cctctatgga agatgtcatc aatctactgc ctgggatcct   6000
gtctccggga gccctggtgg tggggtcat ctgcgcggcc attctgcgcc gccacgtggg    6060
accgggggag ggcgcggtcc aatgatgaa caggcttatt gcctttgctt ccagaggaaa    6120
ccacgtcgcc cctactcact acgtgacgga gtcggatgcg tcgcagcgtg tgacccaact   6180
acttggctct cttactataa ccagcctact cagaagactc cacaattgga taactgagga   6240
ctgccccatc ccatgctccg gatcctggct ccgcgacgtg tgggactggg tttgcaccat   6300
cttgacagac ttcaaaaatt ggctgacctc taaattgttc cccaagctgc ccggcctccc   6360
cttcatctct tgtcaaaagg ggtacaaggg tgtgtgggcc ggcactggca tcatgaccac   6420
```

```
gcgctgccct tgcggcgcca acatctctgg caatgtccgc ctgggctcta tgaggatcac    6480
agggcctaaa acctgcatga acacctggca ggggaccttt cctatcaatt gctacacgga    6540
gggccagtgc gcgccgaaac cccccacgaa ctacaagacc gccatctgga gggtggcggc    6600
ctcggagtac gcggaggtga cgcagcatgg gtcgtactcc tatgtaacag gactgaccac    6660
tgacaatctg aaaattcctt gccaactacc ttctccagag ttttctcct gggtggacgg     6720 tgtgcagatc cataggtttg cacccacacc aaagccgttt ttccgggatg aggtctcgtt    6780
ctgcgttggg cttaattcct atgctgtcgg gtcccagctt ccctgtgaac ctgagcccga    6840
cgcagacgta ttgaggtcca tgctaacaga tccgccccac atcacggcgg agactgcggc    6900
gcggcgcttg cacggggat caccctccatc tgaggcgagc tcctcagtga ccagctatc     6960 agcaccgtcg ctgcgggcca cctgcaccac ccacagcaac acctatgacg tggacatggt    7020
cgatgccaac ctgctcatgg agggcggtgt ggctcagaca gagcctgagt ccagggtgcc    7080
cgttctggac tttctcgagc caatggccga ggaagagagc gaccttgagc cctcaatacc    7140
atcggagtgc atgctcccca ggagcgggtt tccacgggcc ttaccggctt gggcacggcc    7200
tgactacaac ccgccgctcg tggaatcgtg gaggaggcca gattaccaac cgcccaccgt    7260
tgctggttgt gctctccccc cccccaagaa ggccccgacg cctcccccaa ggagacgccg    7320
gacagtgggt ctgagcgaga gcaccatatc agaagccctc cagcaactgg ccatcaagac    7380 cttttggccag cccccctcga cggtgatgc aggctcgtcc acggggggcgg gcgccgccga    7440 atccggcggt ccgacgtccc ctggtgagcc ggccccctca gagacaggtt ccgcctcctc    7500 tatgccccc ctcgaggggg agcctggaga tccggacctg gagtctgatc aggtagagct     7560
tcaacctccc ccccagggggg gggggtagc tcccggttcg ggctcggggt cttggtctac    7620
ttgctccgag gaggacgata ccaccgtgtg ctgctccatg tcatactcct ggaccggggc    7680
tctaataact ccctgtagcc ccgaagagga aaagttgcca atcaacccctt tgagtaactc    7740 gctgttgcga taccataaca aggtgtactg tacaacatca aagagcgcct cacagagggc    7800
taaaaaggta acttttgaca ggacgcaagt gctcgacgcc cattatgact cagtcttaaa    7860
ggacatcaag ctagcggctt ccaaggtcag cgcaaggctc ctcaccttgg aggaggcgtg    7920
ccagttgact ccaccccatt ctgcaagatc caagtatgga ttcggggcca aggaggtccg    7980
cagcttgtcc ggggagggccg ttaaccacat caagtccgtg tggaaggacc tcctggaaga    8040
cccacaaaca ccaattccca caaccatcat ggccaaaaat gaggtgttct gcgtggaccc    8100
cgccaagggg gtaagaaac cagctcgcct catcgtttac cctgacctcg cgtccgggt     8160 ctgcgagaaa atggccctct atgacattac acaaaagctt cctcaggcgg taatgggagc    8220
ttcctatggc ttccagtact cccctgccca acggtggag tatctcttga agcatgggc      8280 ggaaaagaag accccatgg ttttttcgta tgatacccga tgcttcgact caaccgtcac     8340
tgagagagac atcaggaccg aggagtccat ataccaggcc tgctccctgc ccgaggaggc    8400
ccgcactgcc atacactcgc tgactgagag actttacgta ggagggccca tgttcaacag    8460
caagggtcaa acctgcggtt acagacgttg ccgcgccagc ggggtgctaa ccactagcat    8520
gggtaacacc atcacatgct atgtgaaagc cctagcggcc tgcaaggctg cggggatagt    8580
tgcgcccaca atgctggtat gcggcgatga cctagtagtc atctcagaaa gccagggac    8640 tgaggaggac gagcggaacc tgagagcctt cacggaggcc atgaccaggt actctgcccc    8700
tcctggtgat ccccccagac cggaaatatga cctggagcta ataacatcct gttcctcaaa    8760
tgtgtctgtg gcgttgggcc cgcggggccg ccgcagatac tacctgacca gagacccaac    8820
```

| | |
|---|---|
| cactccactc gcccgggctg cctgggaaac agttagacac tcccctatca attcatggct | 8880 |
| gggaaacatc atccagtatg ctccaaccat atgggttcgc atggtcctaa tgacacactt | 8940 |
| cttctccatt ctcatggtcc aagacaccct ggaccagaac ctcaactttg agatgtatgg | 9000 |
| atcagtatac tccgtgaatc ctttggacct tccagccata attgagaggt tacacgggct | 9060 |
| tgacgccttt tctatgcaca catactctca ccacgaactg acgcgggtgg cttcagccct | 9120 |
| cagaaaactt ggggcgccac ccctcagggt gtggaagagt cgggctcgcg cagtcagggc | 9180 |
| gtccctcatc tcccgtggag ggaaagcggc cgtttgcggc cgatatctct tcaattgggc | 9240 |
| ggtgaagacc aagctcaaac tcactccatt gccggaggcg cgcctactgg acttatccag | 9300 |
| ttggttcacc gtcggcgccg gcggggggcga cattttttcac agcgtgtcgc gcgcccgacc | 9360 |
| ccgctcatta ctcttcggcc tactcctact tttcgtaggg gtaggcctct tcctactccc | 9420 |
| cgctcggtag agcggcacac actaggtaca ctccatagct aactgttcct tttttttttt | 9480 |
| tttttttttt tttttttttt tttttttttt ttcttttttt tttttttccc tctttcttcc | 9540 |
| cttctcatct tattctactt tctttcttgg tggctccatc ttagccctag tcacggctag | 9600 |
| ctgtgaaagg tccgtgagcc gcatgactgc agagagtgcc gtaactggtc tctctgcaga | 9660 |
| tcatgt | 9666 |

<210> SEQ ID NO 9
<211> LENGTH: 9666
<212> TYPE: DNA
<213> ORGANISM: Hepatitis C virus

<400> SEQUENCE: 9

| | |
|---|---|
| acctgcccct aatagggggcg acactccgcc atgaatcact cccctgtgag gaactactgt | 60 |
| cttcacgcag aaagcgccta gccatggcgt tagtatgagt gtcgtacagc ctccaggccc | 120 |
| cccctcccg ggagagccat agtggtctgc ggaaccggtg agtacaccgg aattgccggg | 180 |
| aagactgggt cctttcttgg ataaacccac tctatgcccg gccatttggg cgtgcccccg | 240 |
| caagactgct agccgagtag cgttgggttg cgaaaggcct tgtggtactg cctgataggg | 300 |
| cgcttgcgag tgccccggga ggtctcgtag accgtgcacc atgagcacga atcctaaacc | 360 |
| tcaaagaaaa accaaacgta acaccaaccg ccgcccaatg gacgttaagt tcccgggtgg | 420 |
| tggccagatc gttggcggag tttacttgtt gccgcgcagg ggcccagat tgggtgtgcg | 480 |
| cgcgactcgg aagacttcgg agcggtcgca acctcgtgga agacgccaac ctatccccaa | 540 |
| ggcgcgtcga cccgagggaa ggtcctgggc acaaccagga tatccatggc ctctttacgg | 600 |
| taatgagggt tgtgggtggg caggatggct cttgtccccc cgtggctctc gaccgtcttg | 660 |
| gggcccaaat gatcccggc ggaggtcccg caatttgggt aaggtcatcg atacctaac | 720 |
| ctgcggcttc gccgacctca tgggatacat cccgctcgta ggcgcccccg tgggtggcgt | 780 |
| cgccagggcc ctggcacatg gtgtcagggc tttggaggac gggatcaatt atgcaacagg | 840 |
| gaatctcccc ggttgctcct tttctatctt cctcttggca cttctttcgt gcctgactgt | 900 |
| ccccgcttcg gccgttaact atcgcaatgt ctcgggcatc taccatgtca ccaatgactg | 960 |
| cccgaattca agcatagtgt atgaggccga ccatcacatc ttgcaccttc caggttgcgt | 1020 |
| gccctgcgtg agagagggga atcagtcacg ctgctgggtg gcccttactc ctaccgtcgc | 1080 |
| agcgccatac atcggcgcac cgcttgagtc cttacggagt catgtggatt tgatggtggg | 1140 |
| ggccgccact gtttgctcgg gtctttacat cgggggacctg tgtggcggct tgttcctagt | 1200 |
| tggccagatg ttttcattcc gaccacggcg ccactgacc acccaggatt gcaattgttc | 1260 |

```
catctacaca gggcacatta caggccacag aatggcctgg acatgatga tgaactggag      1320 tccaacaacc accttagttc tcgcccaggt catgaggatc ccaaccactc tggtagactt      1380
actctctgga ggccactggg gtgtcctcgt gggagtggcc tatttcagca tgcaggccaa      1440
ttgggccaaa gtcatcttgg tcctattcct ctttgcaggg gttgatgccg agactcacgt      1500
gtctggggca gcagtcggcc ggagtaccgc cggcttggct aacctctttt cttctgggtc      1560
taagcagaat ttacagctca tcaacagcaa tgggagctgg catataaata ggactgccct      1620
taactgcaat gacagcttaa acactgggtt cttggctagc ttgttctaca cccacaagtt      1680
taacagctca gggtgttccg aacgctcgc gtgctgcaag agccttgaca gctacggcca      1740
aggctggggc ccactcgggg tcgctaacat cagcggctcg tctgatgaca ggccttattg      1800
ctggcactac gcgcctcggc cgtgcggat tgtgccagca tccagtgtgt gtggccccgt      1860
gtattgtttc actcccagcc ctgtcgtggt cggtactact gatcacgtcg gggtccctac      1920
ttacacctgg ggggagaatg agactgatgt cttccttttg aactcgacca gaccgccgca      1980
tggtgcgtgg tttggatgcg tgtggatgaa cagtaccggg ttcaccaaaa cctgtggcgc      2040
ccctccatgc gaggttaaca ccaataatgg gacctggcac tgcccaccg attgcttcag      2100 gaagcatccg gagactacct acgccaagtg cggatcaggg ccttggatca caccgcgctg      2160
cctgattgat tacccgtacc ggctgtggca tttcccgtgc accgcaaact tctccgtctt      2220
taacatcagg acatttgtcg gcggtataga gcatcggatg caagcggcat gcaactggac      2280 cagggggaa gtctgtggct tggagcacag ggatcgcgta gagctatcac ccctgctcct      2340
taccactaca gcgtggcaga tcctcccctg ctctttcacc actttacctg ccctctccac      2400
cggcttgatc cacctccacc aaaatatcgt ggacgtccag tacctctatg gtgttgggtc      2460
tgcagtggta tcttgggccc ttaagtggga atatgtggtg ctcgcgttcc tgcttctcgc      2520
ggacgcgaga gtctctgcct gcctatggat gatgtttatg gtaagtcaag ttgaggcggc      2580
tctgtccaac ctgattaaca tcaatgctgc ttcagccgct ggtgcccaag gcttctggta      2640
cgccatcctc ttcatctgca ttgtctggca tgtcaagggc cggttcccag ctgctgctgc      2700
ctacgcagcc tgcgggctgt ggccccctgtt tctcctgctt ctgatgctgc ctgagagggc      2760
ttatgcatac gaccaggaag tggcagggtc ccttggcggc gccatcgttg tcatgctggc      2820
cattctgaca ctgtctccgc actacaagtt atggctggct aggggattgt ggtggatcca      2880 atatttata gctaggaccg aggctgtgct gcatgtctat attccatcct tcaacgtgcg      2940
cgggcctcgc gactcagtga ttgttcttgc agtcctggtc tgtccacacc tagtatttga      3000
catcacaaaa tatcttctgg ccatcttagg gcccctccac atactccagg cctcgctcct      3060
acgcatccct tactttgtga gggcacaagc gctggttaag atctgcagct tgttgcgtgg      3120
ggtagtttat ggcaagtact tccaaatggt cgtgcttaaa gcaggggccc tgactggtac      3180
ttacatctat gaccacctta ctcccatgtc agattgggcc gctacgggcc tccgcgattt      3240
ggcggtggcc ctagagccag ttgtgttcac gcccatggag aagaaagtca tcgtctgggg      3300
cgctgacacc gctgcgtgcg gagacatcat aaggggatta cctgtttcgg ccaggttggg      3360
caatgaaatc ttgctcggac cagccgatac agaaacatca aaggggtgga gactccttgc      3420
tcccatcact gcttatgccc agcaaacacg aggcctcctg ggcgccatag tggtgagtat      3480
gacggggcgt gacaggacag aacaggccgg ggaagtccaa atcctgtcca cagtctctca      3540
gtccttcctc ggaacaacca tctcgggggt tttgtggact gtttaccacg agctggcaa       3600 caagactcta gccggcttac ggggtccggt cacgcagatg tactcgagtg ctgaggggga      3660
```

```
cttggtaggc tggcccagcc ccctgggac caagtctttg gagccgtgca agtgtggagc    3720
cgtcgaccta tatctggtca cgcggaacgc tgatgtcatc ccggctcgga gacgcgggga    3780
caagcgggga gcattgctct cccgagacc catttcgacc ttgaagggt cctcgggggg     3840 gccggtgctc tgccctaggg gccacgtcgt tgggctcttc cgagcagctg tgtgctctcg   3900
gggcgtggcc aaatccatcg atttcatccc cgttgagaca ctcgacgttg ttacaaggtc   3960
tcccactttc agtgacaaca gcacgccacc ggctgtgccc cagacctatc aggtcggta   4020 cttgcatgct ccaactggca gtggaaagag caccaaggtc cctgtcgcgt atgccgccca   4080
ggggtacaaa gtactagtgc ttaacccctc ggtagctgcc accctggggt ttggggcgta   4140
cctatccaag gcacatggca tcaatcccaa cattaggact ggagtcagga ccgtgatgac   4200
cggggaggcc atcacgtact ccacatatgg caaatttctc gccgatgggg gctgcgctag   4260
cggcgcctat gacatcatca tatgcgatga atgccacgct gtggatgcta cctccattct   4320
cggcatcgga acggtccttg atcaagcaga gacagccggg gtcagactaa ctgtgctggc   4380
tacggccaca ccccccgggt cagtgacaac cccccatccc gatatagaag aggtaggcct   4440
cgggcgggag ggtgagatcc ccttctatgg gagggcgatt cccctatcct gcatcaaggg   4500
agggagacac ctgattttct gccactcaaa gaaaaagtgt gacgagctcg cggcggccct   4560
tcggggcatg gcttgaatg ccgtggcata ctatagaggg ttggacgtct ccataatacc    4620
agctcaggga gatgtggtgg tcgtcgccac cgacgccctc atgacggggt acactggaga   4680
ctttgactcc gtgatcgact gcaatgtagc ggtcacccaa gctgtcgact tcagcctgga   4740
ccccaccttc actataacca cacagactgt cccacaagac gctgtctcac gcagtcagcg   4800
ccgcgggcgc acaggtagag gaagacaggg cacttatagg tatgtttcca ctggtgaacg   4860
agcctcagga atgtttgaca gtgtagtgct ttgtgagtgc tacgacgcag gggctgcgtg   4920
gtacgatctc acaccagcgg agaccaccgt caggcttaga gcgtatttca acacgcccgg   4980
cctacccgtg tgtcaagacc atcttgaatt ttgggaggca gttttcaccg gcctcacaca   5040
catagacgcc cacttcctct cccaaacaaa gcaagcgggg gagaacttcg cgtacctagt   5100
agcctaccaa gctacggtgt gcgccagagc caaggcccct ccccgtcct gggacgccat    5160 gtggaagtgc ctggcccgac tcaagcctac gcttgcgggc ccacacctc tcctgtaccg    5220 tttgggccct attaccaatg aggtcaccct cacacaccct gggacgaagt acatcgccac   5280
atgcatgcaa gctgaccttg aggtcatgac cagcacgtgg gtcctagctg gaggagtcct   5340
ggcagccgtc gccgcatatt gcctggcgac tggatgcgtt ccatcatcg gccgcttgca    5400 cgtcaaccag cgagtcgtcg ttgcgccgga taaggaggtc ctgtatgagg cttttgatga   5460
gatggaggaa tgcgcctcta gggcggctct catcgaagag gggcagcgga tagccgagat   5520
gttgaagtcc aagatccaag gcttgctgca gcaggcctct aagcaggccc aggacataca   5580
acccgctatg caggcttcat ggcccaaagt ggaacaattt gggccagac acatgtggaa    5640 cttcattagc ggcatccaat acctcgcagg attgtcaaca ctgccaggga acccgcggt    5700 ggcttccatg atggcattca gtgccgccct caccagtccg ttgtcgacca gtaccaccat   5760
ccttctcaac atcatgggag ctggttagc gtcccagatc gcaccacccg cggggccac     5820 cggctttgtc gtcagtggcc tggtggggc tgccgtgggc agcataggcc tgggtaaggt    5880
gctggtggac atcctggcag gatatggtgc gggcatttcg ggggccctcg tcgcattcaa   5940
gatcatgtct ggcgagaagc cctctatgga agatgtcatc aatctactgc ctgggatcct   6000
gtctccggga gccctggtgg tgggggtcat ctgcgcggcc attctgcgcc gccacgtggg   6060
```

```
accgggggag ggcgcggtcc aatggatgaa caggcttatt gcctttgctt ccagaggaaa    6120
ccacgtcgcc cctactcact acgtgacgga gtcggatgcg tcgcagcgtg tgacccaact    6180
acttggctct cttactataa ccagcctact cagaagactc cacaattgga taactgagga    6240
ctgccccatc ccatgctccg gatcctggct ccgcgacgtg tgggactggg tttgcaccat    6300
cttgacagac ttcaaaaatt ggctgacctc taaattgttc cccaagctgc ccggcctccc    6360
cttcatctct tgtcaaaagg ggtacaaggg tgtgtgggcc ggcactggca tcatgaccac    6420
gcgctgccct tgcggcgcca acatctctgg caatgtccgc ctgggctcta tgaggatcac    6480
agggcctaaa acctgcatga acacctggca ggggaccttt cctatcaatt gctacacgga    6540
gggccagtgc gcgccgaaac cccccacgaa ctacaagacc gccatctgga gggtggcggc    6600
ctcggagtac gcggaggtga cgcagcatgg gtcgtactcc tatgtaacag gactgaccac    6660
tgacaatctg aaaattcctt gccaactacc ttctccagag ttttttctcct gggtggacgg    6720
tgtgcagatc cataggtttg cacccacacc aaagccgttt ttccgggatg aggtctcgtt    6780
ctgcgttggg cttaattcct atgctgtcgg gtcccagctt ccctgtgaac ctgagcccga    6840
cgcagacgta ttgaggtcca tgctaacaga tccgccccac atcacggcgg agactgcggc    6900
gcggcgcttg gcacggggat cacctccatc tgaggcgagc tcctcagtga gccagctatc    6960
agcaccgtcg ctgcgggcca cctgcaccac ccacagcaac acctatgacg tggacatggt    7020
cgatgccaac ctgctcatgg agggcggtgt ggctcagaca gagcctgagt ccagggtgcc    7080
cgttctggac tttctcgagc caatggccga ggaagagagc gaccttgagc cctcaatacc    7140
atcggagtgc atgctcccca ggagcgggtt tccacgggcc ttaccggctt gggcacggcc    7200
tgactacaac ccgccgctcg tggaatcgtg gaggaggcca gattaccaac cgcccaccgt    7260
tgctggttgt gctctccccc ccccaagaa ggccccgacg cctcccccaa ggagacgccg    7320
gacagtgggt ctgagcgaga gcaccatatc agaagccctc cagcaactgg ccatcaagac    7380
cttttggccag ccccccctcga gcggtgatgc aggctcgtcc acggggcgg gcgccgccga    7440
atccggcggt ccgacgtccc ctggtgagcc ggccccctca gagacaggtt ccgcctcctc    7500
tatgccccc ctcgaggggg agcctggaga tccggacctg gagtctgatc aggtagagct    7560
tcaacctccc ccccaggggg gggggtagc tcccggttcg ggctcggggt cttggtctac    7620
ttgctccgag gaggacgata ccaccgtgtg ctgctccatg tcatactcct ggaccggggc    7680
tctaataact ccctgtagcc ccgaagagga aaagttgcca atcaaccctt tgagtaactc    7740
gctgttgcga taccataaca aggtgtactg tacaacatca aagagcgcct cacagagggc    7800
taaaaaggta acttttgaca ggacgcaagt gctcgacgcc cattatgact cagtcttaaa    7860
ggacatcaag ctagcggctt ccaaggtcag cgcaaggctc ctcaccttgg aggaggcgtg    7920
ccagttgact ccaccccatt ctgcaagatc caagtatgga ttcggggcca aggaggtccg    7980
cagcttgtcc gggagggccg ttaaccacat caagtccgtg tggaaggacc tcctggaaga    8040
cccacaaaca ccaattccca caaccatcat ggccaaaaat gaggtgttct gcgtggaccc    8100
cgccaagggg ggtaagaaac cagctcgcct catcgtttac cctgacctcg gcgtccgggt    8160
ctgcgagaaa atggcgctct atgacattac acaaaagctt cctcaggcgg taatgggagc    8220
ttcctatggc ttccagtact cccctgccca acgggtggag tatctcttga agcatgggc    8280
ggaaaagaag gaccccatgg gttttttcgta tgatacccga tgcttcgact caaccgtcac    8340
tgagagagac atcaggaccg aggagtccat ataccaggcc tgctccctgc ccgaggaggc    8400
ccgcactgcc atacactcgc tgactgagag actttacgta ggagggccca tgttcaacag    8460
```

| | | | | | |
|---|---|---|---|---|---|
| caagggtcaa | acctgcggtt | acagacgttg | ccgcgccagc | ggggtgctaa | ccactagcat | 8520 |
| gggtaacacc | atcacatgct | atgtgaaagc | cctagcggcc | tgcaaggctg | cggggatagt | 8580 |
| tgcgcccaca | atgctggtat | gcggcgatga | cctagtagtc | atctcagaaa | gccaggggac | 8640 |
| tgaggaggac | gagcggaacc | tgagagcctt | cacggaggcc | atgaccaggt | actctgcccc | 8700 |
| tcctggtgat | cccccagac | cggaatatga | cctggagcta | ataacatcct | gttcctcaaa | 8760 |
| tgtgtctgtg | gcgttgggcc | cgcggggccg | ccgcagatac | tacctgacca | gagacccaac | 8820 |
| cactccactc | gcccgggctg | cctgggaaac | agttagacac | tccctatca | attcatggct | 8880 |
| gggaaacatc | atccagtatg | ctccaaccat | atgggttcgc | atggtcctaa | tgacacactt | 8940 |
| cttctccatt | ctcatggtcc | aagacaccct | ggaccagaac | ctcaactttg | agatgtatgg | 9000 |
| atcagtatac | tccgtgaatc | ctttggacct | tccagccata | attgagaggt | tacacgggct | 9060 |
| tgacgccttt | tctatgcaca | catactctca | ccacgaactg | acgcgggtgg | cttcagccct | 9120 |
| cagaaaactt | ggggcgccac | ccctcagggt | gtggaagagt | cgggctcgcg | cagtcagggc | 9180 |
| gtccctcatc | tcccgtggag | ggaaagcggc | cgtttgcggc | cgatatctct | tcaattgggc | 9240 |
| ggtgaagacc | aagctcaaac | tcactccatt | gccggaggcg | cgcctactgg | acttatccag | 9300 |
| ttggttcacc | gtcggcgccg | gcggggggcga | catttttcac | agcgtgtcgc | gcgcccgacc | 9360 |
| ccgctcatta | ctcttcggcc | tactcctact | tttcgtaggg | gtaggcctct | tcctactccc | 9420 |
| cgctcggtag | agcggcacac | actaggtaca | ctccatagct | aactgttcct | tttttttttt | 9480 |
| tttttttttt | tttttttttt | tttttttttt | tctttttttt | ttttttttccc | tctttcttcc | 9540 |
| cttctcatct | tattctactt | tctttcttgg | tggctccatc | ttagccctag | tcacggctag | 9600 |
| ctgtgaaagg | tccgtgagcc | gcatgactgc | agagagtgcc | gtaactggtc | tctctgcaga | 9660 |
| tcatgt | | | | | | 9666 |

<210> SEQ ID NO 10
<211> LENGTH: 9666
<212> TYPE: DNA
<213> ORGANISM: Hepatitis C virus

<400> SEQUENCE: 10

| | | | | | |
|---|---|---|---|---|---|
| acctgcccct | aatagggggcg | acactccgcc | atgaatcact | cccctgtgag | gaactactgt | 60 |
| cttcacgcag | aaagcgccta | gccatggcgt | tagtatgagt | gtcgtacagc | ctccaggccc | 120 |
| cccctcccg | ggagagccat | agtggtctgc | ggaaccggtg | agtacaccgg | aattgccggg | 180 |
| aagactgggt | cctttcttgg | ataaacccac | tctatgcccg | gccatttggg | cgtgcccccg | 240 |
| caagactgct | agccgagtag | cgttgggttg | cgaaaggcct | tgtggtactg | cctgataggg | 300 |
| cgcttgcgag | tgccccggga | ggtctcgtag | accgtgcacc | atgagcacga | atcctaaacc | 360 |
| tcaaagaaaa | accaaacgta | acaccaaccg | ccgcccaatg | gacgttaagt | tcccgggtgg | 420 |
| tggccagatc | gttggcggag | tttacttgtt | gccgcgcagg | ggccccagat | tgggtgtgcg | 480 |
| cgcgactcgg | aagacttcgg | agcggtcgca | acctcgtgga | agacgccaac | ctatccccaa | 540 |
| ggcgcgtcga | cccgagggaa | ggtcctgggc | acaaccagga | tatccatggc | ctctttacgg | 600 |
| taatgagggt | tgtgggtggg | caggatggct | cttgtccccc | cgtggctctc | gaccgtcttg | 660 |
| gggcccaaat | gatccccggc | ggaggtcccg | caatttgggt | aaggtcatcg | ataccctaac | 720 |
| ctgcggcttc | gccgacctca | tgggatacat | cccgctcgta | ggcgccccg | tgggtggcgt | 780 |
| cgccagggcc | ctggcacatg | gtgtcagggc | tttggaggac | gggatcaatt | atgcaacagg | 840 |
| gaatctcccc | ggttgctcct | tttctatctt | cctcttggca | cttctttcgt | gcctgactgt | 900 |

```
ccccgcttcg gccgttaact atcgcaatgt ctcgggcatc taccatgtca ccaatgactg      960
cccgaattca agcatagtgt atgaggccga ccatcacatc ttgcaccttc caggttgcgt     1020
gccctgcgtg agagagggga atcagtcacg ctgctgggtg gcccttactc ctaccgtcgc     1080
agcgccatac atcggcgcac cgcttgagtc cttacgagt catgtggatt tgatggtggg      1140
ggccgccact gtttgctcgg gtctttacat cggggacctg tgtggcggct tgttcctagt     1200
tggccagatg ttttcattcc gaccacggcg ccactggacc acccaggatt gcaattgttc     1260
catctacaca gggcacatta caggccacag aatggcctgg gacatgatga tgaactggag     1320
tccaacaacc accttagttc tcgcccaggt catgaggatc caaccactc tggtagactt      1380 actctctgga ggccactggg gtgtcctcgt gggagtggcc tatttcagca tgcaggccaa     1440
ttgggccaaa gtcatcttgg tcctattcct ctttgcaggg gttgatgccg agactcacgt     1500
gtctggggca gcagtcggcc ggagtaccgc cggcttggct aacctctttt cttctgggtc     1560
taagcagaat ttacagctca tcaacagcaa tgggagctgg catataaata ggactgccct     1620
taactgcaat gacagcttaa acactgggtt cttggctagc ttgttctaca cccacaagtt     1680
taacagctca gggtgttccg aacggctcgc gtgctgcaag agccttgaca gctacggcca     1740
aggctggggc ccactcgggg tcgctaacat cagcggctcg tctgatgaca ggccttattg     1800
ctggcactac gcgcctcggc cgtgcggat tgtgccagca tccagtgtgt gtggccccgt      1860
gtattgtttc actcccagcc ctgtcgtggt cggtactact gatcacgtcg gggtccctac     1920
ttacacctgg ggggagaatg agactgatgt cttccttttg aactcgacca gaccgccgca     1980
tggtgcgtgg tttggatgcg tgtggatgaa cagtaccggg ttccaccaaaa cctgtggcgc    2040 ccctccatgc gaggttaaca ccaataatgg gacctggcac tgccccaccg attgcttcag     2100
gaagcatccg gagactacct acgccaagtg cggatcaggg ccttggatca caccgcgctg     2160
cctgattgat tacccgtacc ggctgtggca tttcccgtgc accgccaact tctccgtctt     2220
taacatcagg acatttgtcg gcggtataga gcatcggatg caagcggcat gcaactggac     2280
caggggggaa gtctgtggct tggagcacag ggatcgcgta gagctatcac ccctgctcct     2340
taccactaca gcgtggcaga tcctcccctg ctctttcacc actttacctg ccctctccac     2400
cggcttgatc cacctccacc aaaatatcgt ggacgtccag tacctctatg gtgttgggtc     2460
tgcagtggta tcttgggccc ttaagtggga atatgtggtg ctcgcgttcc tgcttctcgc     2520
ggacgcgaga gtctctgcct gcctatggat gatgtttatg gtaagtcaag ttgaggcggc     2580
tctgtccaac ctgattaaca tcaatgctgc ttcagccgct ggtgcccaag gcttctggta     2640
cgccatcctc ttcatctgca ttgtctggca tgtcaagggc cggttcccag ctgctgctgc     2700
ctacgcagcc tgcgggctgt ggcccctgtt tctcctgctt ctgatgctgc tgagagggc     2760 ttatgcatac gaccaggaag tggcagggtc ccttggcggc gccatcgttg tcatgctgac     2820
cattctgaca ctgtctccgc actacaagtt atggctggct aggggattgt ggtggatcca     2880 atatttata gctaggaccg aggctgtgct gcatgtctat attccatcct tcaacgtgcg      2940
cgggcctcgc gactcagtga ttgttcttgc agtcctggtc tgtccacacc tagtatttga     3000
catcacaaaa tatcttctgg ccatcttagg gccctccac atactccagg cctcgctcct      3060
acgcatccct tactttgtga gggcacaagc gctggttaag atctgcagct tgttgcgtgg     3120
ggtagtttat ggcaagtact tccaaatggt cgtgcttaaa gcaggggccc tgactggtac     3180
ttacatctat gaccacctta ctcccatgtc agattgggcc gctacgggcc tccgcgattt     3240
ggcggtggcc ctagagccag ttgtgttctc gcccatggag aagaaagtca tcgtctgggg     3300
```

```
cgctgacacc gctgcgtgcg gagacatcat aaggggatta cctgtttcgg ccaggttggg    3360
caatgaaatc ttgctcggac cagccgatac agaaacatca aagggggtgga gactccttgc   3420
tcccatcact gcttatgccc agcaaacacg aggcctcctg ggcgccatag tggtgagtat    3480
gacgggcgt  gacaggacag aacaggccgg ggaagtccaa atcctgtcca cagtctctca    3540
gtccttcctc ggaacaacca tctcgggggt tttgtggact gtttaccacg gagctggcaa    3600
caagactcta gccggcttac ggggtccggt cacgcagatg tactcgagtg ctgaggggga    3660
cttggtaggc tggcccagcc ccctgggac  caagtctttg gagccgtgca agtgtggagc    3720
cgtcgaccta tatctggtca cgcggaacgc tgatgtcatc ccggctcgga dacgcgggga   3780
caagcgggga gcattgctct ccccgagacc catttcgacc ttgaagggt  cctcggggg    3840
gccggtgctc tgccctaggg gccacgtcgt tgggctcttc cgagcagctg tgtgctctcg    3900
ggcgtggcc  aaatccatcg atttcatccc cgttgagaca ctcgacgttg ttacaaggtc    3960
tcccactttc agtgacaaca gcacgccacc ggctgtgccc cagacctatc aggtcgggta    4020
cttgcatgct ccaactggca gtggaaagag caccaaggtc cctgtcgcgt atgccgccca    4080
ggggtacaaa gtactagtgc ttaacccctc ggtagctgcc accctggggt ttggggcgta    4140
cctatccaag gcacatggca tcaatcccaa cattaggact ggagtcagga ccgtgatgac    4200
cggggaggcc atcacgtact ccacatatgg caaatttctc gccgatgggg gctgcgctag    4260
cggcgcctat gacatcatca tatgcgatga atgccacgct gtggatgcta cctccattct    4320
cggcatcgga acggtccttg atcaagcaga dacagccggg gtcagactaa ctgtgctggc    4380
tacggccaca ccccccgggt cagtgacaac ccccccatccc gatatagaag aggtaggcct   4440
cgggcgggag ggtgagatcc ccttctatgg gagggcgatt cccctatcct gcatcaaggg    4500
agggagacac ctgatttcct gccactcaaa gaaaaagtgt gacgagctcg cggcggccct    4560
tcggggcatg gcttgaatg  ccgtggcata ctatagaggg ttggacgtct ccataatacc    4620
agctcaggga gatgtggtgg tcgtcgccac cgacgccctc atgacggggt acactggaga    4680
ctttgactcc gtgatcgact gcaatgtagc ggtcacccaa gctgtcgact tcagcctgga    4740
ccccaccttc actataacca cacagactgt cccacaagac gctgtctcac gcagtcagcg    4800
ccgcgggcgc acaggtagag aagacagggg cacttatagg tatgtttcca ctggtgaacg    4860
agcctcagga atgtttgaca gtgtagtgct ttgtgagtgc tacgacgcag gggctgcgtg    4920
gtacgatctc acaccagcgg agaccaccgt caggcttaga gcgtatttca cacgcccgg    4980
cctacccgtg tgtcaagacc atcttgaatt ttgggaggca gttttcaccg gcctcacaca    5040
catagacgcc cacttcctct cccaaacaaa gcaagcgggg gagaacttcg cgtacctagt    5100
agcctaccaa gctacggtgt gcgccagagc caaggcccct cccccgtcct gggacgccat    5160
gtggaagtgc ctggcccgac tcaagcctac gcttgcgggc cccacacctc tcctgtaccg    5220
tttgggccct attaccaatg aggtcacccc cacacaccct gggacgaagt acatcgccac    5280
atgcatgcaa gctgaccttg aggtcatgac cagcacgtgg gtcctagctg gaggagtcct    5340
ggcagccgtc gccgcatatt gcctggcgac tggatgcgtt tccatcatcg gccgcttgca    5400
cgtcaaccag cgagtcgtcg ttgcgccgga taaggaggtc ctgtatgagg cttttgatga    5460
gatgaaggaa tgcgcctcta gggcggctct catcgaagag gggcagcgga tagccgagat    5520
gttgaagtcc aagatccaag cttgctgca  gcaggcctct aagcaggccc aggacataca    5580
acccgctatg caggcttcat ggcccaaagt ggaacaattt tgggcagac  acatgtggaa    5640
cttcattagc ggcatccaat acctcgcagg attgtcaaca ctgccaggga accccgcggt    5700
```

```
ggcttccatg atggcattca gtgccgccct caccagtccg ttgtcgacca gtaccaccat   5760
ccttctcaac atcatgggag ctggttagc gtcccagatc gcaccacccg cgggggccac    5820
cggctttgtc gtcagtggcc tggtgggggc tgccgtgggc agcataggcc tgggtaaggt   5880
gctggtggac atcctggcag gatatggtgc gggcatttcg ggggccctcg tcgcattcaa   5940
gatcatgtct ggcgagaagc cctctatgga agatgtcatc aatctactgc ctgggatcct   6000
gtctccggga gccctggtgg tggggtcat ctgcgcggcc attctgcgcc gccacgtggg    6060
accgggggag ggcgcggtcc aatggatgaa caggcttatt gcctttgctt ccagaggaaa   6120
ccacgtcgcc cctactcact acgtgacgga gtcggatgcg tcgcagcgtg tgacccaact   6180
acttggctct cttactataa ccagcctact cagaagactc cacaattgga taactgagga   6240
ctgccccatc ccatgctccg gatcctggct ccgcgacgtg tgggactggg tttgcaccat   6300
cttgacagac ttcaaaaatt ggctgacctc taaattgttc cccaagctgc ccggcctccc   6360
cttcatctct tgtcaaaagg ggtacaaggg tgtgtgggcc ggcactggca tcatgaccac   6420
gcgctgccct tgcggcgcca acatctctgg caatgtccgc ctgggctcta tgaggatcac   6480
agggcctaaa acctgcatga acacctggca ggggacctt cctatcaatt gctacacgga    6540
gggccagtgc gcgccgaaac cccccacgaa ctacaagacc gccatctgga gggtggcggc   6600
ctcggagtac gcggaggtga cgcagcatgg gtcgtactcc tatgtaacag gactgaccac   6660
tgacaatctg aaaattcctt gccaactacc ttctccagag ttttctcct gggtggacgg    6720 tgtgcagatc cataggtttg cacccacacc aaagccgttt ttccgggatg aggtctcgtt   6780
ctgcgttggg cttaattcct atgctgtcgg gtcccagctt ccctgtgaac ctgagcccga   6840
cgcagacgta ttgaggtcca tgctaacaga tccgccccac atcacggcgg agactgcggc   6900
gcggcgcttg cacggggat cacctccatc tgaggcgagc tcctcagtga gccagctatc    6960
agcaccgtcg ctgcgggcca cctgcaccac ccacagcaac acctatgacg tggacatggt   7020
cgatgccaac ctgctcatgg agggcggtgt ggctcagaca gagcctgagt ccagggtgcc   7080
cgttctggac tttctcgagc caatggccga ggaagagagc gaccttgagc cctcaatacc   7140
atcggagtgc atgctcccca ggagcgggtt tccacgggcc ttaccggctt gggcacggcc   7200
tgactacaac ccgccgctcg tggaatcgtg gaggaggcca gattaccaac cgcccaccgt   7260
tgctggttgt gctctccccc ccccaagaa ggccccgacg cctcccccaa ggagacgccg    7320
gacagtgggt ctgagcgaga gcaccatatc agaagccctc cagcaactgg ccatcaagac   7380
ctttggccag ccccctcga gcggtgatgc aggctcgtcc acggggcgg gcgccgccga    7440 atccggcggt ccgacgtccc ctggtgagcc ggcccctca gagacaggtt ccgcctcctc    7500 tatgccccc ctcgaggggg agcctggaga tccggacctg gagtctgatc aggtagagct    7560
tcaacctccc ccccagggggg gggggtagc tcccggttcg ggctcggggt cttggtctac   7620
ttgctccgag gaggacgata ccaccgtgtg ctgctccatg tcatactcct ggaccgggc    7680 tctaataact ccctgtagcc ccgaagagga aaagttgcca atcaaccctt tgagtaactc   7740
gctgttgcga taccataaca aggtgtactg tacaacatca aagagcgcct cacagagggc   7800
taaaaaggta acttttgaca ggacgcaagt gctcgacgcc cattatgact cagtcttaaa   7860
ggacatcaag ctagcggctt ccaaggtcag cgcaaggctc ctcaccttgg aggaggcgtg   7920
ccagttgact ccaccccatt ctgcaagatc caagtatgga ttcggggcca aggaggtccg   7980
cagcttgtcc ggaggccg ttaaccacat caagtccgtg tggaaggacc tcctggaaga    8040
cccacaaaca ccaattccca caaccatcat ggccaaaaat gaggtgttct gcgtggaccc   8100
```

-continued

```
cgccaagggg ggtaagaaac cagctcgcct catcgtttac cctgacctcg gcgtccgggt    8160
ctgcgagaaa atggccctct atgacattac acaaaagctt cctcaggcgg taatgggagc    8220
ttcctatggc ttccagtact cccctgccca acgggtggag tatctcttga agcatgggc     8280 ggaaaagaag gaccccatgg ttttttcgta tgatacccga tgcttcgact caaccgtcac    8340
tgagagagac atcaggaccg aggagtccat ataccaggcc tgctccctgc ccgaggaggc    8400
ccgcactgcc atacactcgc tgactgagag actttacgta ggagggccca tgttcaacag    8460
caagggtcaa acctgcggtt acagacgttg ccgcgccagc ggggtgctaa ccactagcat    8520
gggtaacacc atcacatgct atgtgaaagc cctagcggcc tgcaaggctg cggggatagt    8580
tgcgcccaca atgctggtat gcggcgatga cctagtagtc atctcagaaa gccaggggac    8640
tgaggaggac gagcggaacc tgagagcctt cacggaggcc atgaccaggt actctgcccc    8700
tcctggtgat cccccagac cggaatatga cctggagcta ataacatcct gttcctcaaa    8760
tgtgtctgtg gcgttgggcc cgcggggccg ccgcagatac tacctgacca gagacccaac    8820
cactccactc gcccgggctg cctgggaaac agttagacac tcccctatca attcatggct    8880
gggaaacatc atccagtatg ctccaaccat atgggttcgc atggtcctaa tgacacactt    8940
cttctccatt ctcatggtcc aagacaccct ggaccagaac ctcaactttg agatgtatgg    9000
atcagtatac tccgtgaatc cttggacct tccagccata attgagaggt tacacgggct    9060
tgacgccttt tctatgcaca catactctca ccacgaactg acgcgggtgg cttcagccct    9120
cagaaaactt ggggcgccac ccctcagggt gtggaagagt cgggctcgcg cagtcagggc    9180
gtccctcatc tcccgtggag ggaaagcggc cgtttgcggc cgatatctct tcaattgggc    9240
ggtgaagacc aagctcaaac tcactccatt gccggaggcg cgcctactgg acttatccag    9300
ttggttcacc gtcggcgccg gcgggggcga cattttttcac agcgtgtcgc gcgcccgacc    9360
ccgctcatta ctcttcggcc tactcctact tttcgtaggg gtaggcctct tcctactccc    9420
cgctcggtag agcggcacac actaggtaca ctccatagct aactgttcct ttttttttt    9480 tttttttttt tttttttttt tttttttttt tcttttttt ttttttcccc tcttttcttcc    9540 cttctcatct tattctactt tctttcttgg tggctccatc ttagccctag tcacggctag    9600
ctgtgaaagg tccgtgagcc gcatgactgc agagagtgcc gtaactggtc tctctgcaga    9660
tcatgt                                                               9666
```

<210> SEQ ID NO 11
<211> LENGTH: 9666
<212> TYPE: DNA
<213> ORGANISM: Hepatitis C virus

<400> SEQUENCE: 11

```
acctgcccct aatagggcg acactccgcc atgaatcact cccctgtgag gaactactgt     60
cttcacgcag aaagcgccta gccatggcgt tagtatgagt gtcgtacagc ctccaggccc    120
ccccctcccg ggagagccat agtggtctgc ggaaccggtg agtacaccgg aattgccggg    180
aagactgggt cctttcttgg ataaacccac tctatgcccg gccatttggg cgtgcccccg    240
caagactgct agccgagtag cgttggggttg cgaaaggcct tgtggtactg cctgataggg    300
cgcttgcgag tgccccggga ggtctcgtag accgtgcacc atgagcacga atcctaaacc    360
tcaaagaaaa accaaacgta acaccaaccg ccgcccaatg acgttaagt tcccgggtgg    420 tggccagatc gttggcggag tttacttgtt gccgcgcagg ggcccagat tgggtgtgcg    480 cgcgactcgg aagacttcgg agcggtcgca acctcgtgga agacgccaac ctatccccaa    540
```

```
ggcgcgtcga cccgagggaa ggtcctgggc acaaccagga tatccatggc ctctttacgg    600
taatgagggt tgtgggtggg caggatggct cttgtccccc cgtggctctc gaccgtcttg    660
gggcccaaat gatccccggc ggaggtcccg caatttgggt aaggtcatcg atacccctaac   720
ctgcggcttc gccgacctca tgggatacat cccgctcgta ggcgcccccg tgggtggcgt    780
cgccagggcc ctggcacatg gtgtcagggc tttggaggac gggatcaatt atgcaacagg    840
gaatctcccc ggttgctcct tttctatctt cctcttggca cttctttcgt gcctgactgt    900
ccccgcttcg gccgttaact atcgcaatgt ctcgggcatc taccatgtca ccaatgactg    960
cccgaattca agcatagtgt atgaggccga ccatcacatc ttgcaccttc caggttgcgt   1020
gccctgcgtg agagagggga atcagtcacg ctgctgggtg gcccttactc ctaccgtcgc   1080
agcgccatac atcggcgcac cgcttgagtc cttacggagt catgtggatt tgatggtggg   1140
ggccgccact gtttgctcgg gtctttacat cggggacctg tgtggcggct tgttcctagt   1200
tggccagatg ttttcattcc gaccacggcg ccactggacc acccaggatt gcaattgttc   1260
catctacaca gggcacatta caggccacag aatggcctgg gacatgatga tgaactggag   1320
tccatcaacc accttagttc tcgcccaggt catgaggatc caaccactc tggtagactt    1380
actctctgga ggccactggg gtgtcctcgt gggagtggcc tatttcagca tgcaggccaa   1440
ttgggccaaa gtcatcttgg tcctattcct ctttgcaggg gttgatgccg agactcacgt   1500
gtctggggca gcagtcggcc ggagtaccgc cggcttggct aacctctttt cttctgggtc   1560
taagcagaat ttacagctca tcaacagcaa tgggagctgg catataaata ggactgccct   1620
taactgcaat gacagcttaa acactgggtt cttggctagc ttgttctaca cccacaagtt   1680
taacagctca gggtgttccg aacggctcgc gtgctgcaag agccttgaca gctacggcca   1740
aggctggggc ccactcgggg tcgctaacat cagcggctcg tctgatgaca ggccttattg   1800
ctggcactac gcgcctcggc cgtgcggat tgtgccagca tccagtgtgt gtggccccgt    1860
gtattgtttc actcccagcc ctgtcgtggt cggtactact gatcacgtcg gggtccctac   1920
ttacacctgg ggggagaatg agactgatgt cttccttttg aactcgacca gaccgccgca   1980
tggtgcgtgg tttggatgcg tgtggatgaa cagtaccggg ttcaccaaaa cctgtggcgc   2040
ccctccatgc gaggttaaca ccaataatgg gacctggcac tgccccaccg attgcttcag   2100
gaagcatccg gagactacct acgccaagtg cggatcaggg ccttggatca caccgcgctg   2160
cctgattgat tacccgtacc ggctgtggca tttcccgtgc accgccaact tctccgtctt   2220
taacatcagg acatttgtcg gcggtataga gcatcggatg caagcggcat gcaactggac   2280
caggggggaa gtctgtggct tggagcacag ggatcgcgta gagctatcac ccctgctcct   2340
taccactaca gcgtggcaga tcctcccctg ctctttcacc actttacctg ccctctccac   2400
cggcttgatc cacctccacc aaaatatcgt ggacgtccag tacctctatg gtgttgggtc   2460
tgcagtggta tcttgggccc ttaagtggga atatgtggtg ctcgcgttcc tgcttctcgc   2520
ggacgcgaga gtctctgcct gcctatggat gatgtttatg gtaagtcaag ttgaggcggc   2580
tctgtccaac ctgattaaca tcaatgctgc ttcagccgct ggtgcccaag gcttctggta   2640
cgccatcctc ttcatctgca ttgtctggca tgtcaagggc cggttcccag ctgctgctgc   2700
ctacgcagcc tgcgggctgt ggcccctgtt tctcctgctt ctgatgctgc tgagagggc   2760
ttatgcatac gaccaggaag tggcagggtc ccttggcggc gccatcgttg tcatgctggc   2820
cattctgaca ctgtctccgc actacaagtt atggctggct aggggattgt ggtgatcca   2880
atattttata gctaggaccg aggctgtgct gcatgtctat attccatcct tcaacgtgcg   2940
```

```
cgggcctcgc gactcagtga ttgttcttgc agtcctggtc tgtccacacc tagtatttga   3000
catcacaaaa tatcttctgg ccatcttagg gcccctccac atactccagg cctcgctcct   3060
acgcatccct tactttgtga gggcacaagc gctggttaag atctgcagct tgttgcgtgg   3120
ggtagtttat ggcaagtact tccaaatggt cgtgcttaaa gcaggggccc tgactggtac   3180
ttacatctat gaccacctta ctcccatgtc agattgggcc gctacgggcc tccgcgattt   3240
ggcggtggcc ctagagccag ttgtgttctc gcccatggaa agaaagtca tcgtctgggg   3300
cgctgacacc gctgcgtgcg gagacatcat aaggggatta cctgtttcgg ccaggttggg   3360
caatgaaatc ttgctcggac cagccgatac agaaacatca aagggtgga gactccttgc   3420
tcccatcact gcttatgccc agcaaacacg aggcctcctg ggcgccatag tggtgagtat   3480
gacgggggcgt gacaggacag aacaggccgg ggaagtccaa atcctgtcca cagtctctca   3540
gtccttcctc ggaacaacca tctcgggggt tttgtggact gtttaccacg gagctggcaa   3600
caagactcta gccggcttac ggggtccggt cacgcagatg tactcgagtg ctgaggggga   3660
cttggtaggc tggcccagcc ccctgggac caagtctttg gagccgtgca gtgtggagc    3720
cgtcgaccta tatctggtca cgcggaacg tgatgtcatc ccggctcgga gacgcgggga   3780
caagcgggga gcattgctct ccccgagacc catttcgacc ttgaaggggt cctcgggggg   3840
gccggtgctc tgccctaggg gccacgtcgt tgggctcttc cgagcagctg tgtgctctcg   3900
gggcgtggcc aaatccatcg atttcatccc cgttgagaca ctcgacgttg ttacaaggtc   3960
tcccactttc agtgacaaca gcacgccacc ggctgtgccc cagacctatc aggtcgggta   4020
cttgcatgct ccaactggca gtggaaagag caccaaggtc cctgtcgcgt atgccgccca   4080
ggggtacaaa gtactagtgc ttaacccctc ggtagctgcc accctggggt ttggggcgta   4140
cctatccaag gcacatggca tcaatcccaa cattaggact ggagtcagga ccgtgatgac   4200
cggggaggcc atcacgtact ccacatatgg caaatttctc gccgatgggg gctgcgctag   4260
cggcgcctat gacatcatca tatgcgatga atgccacgct gtggatgcta cctccattct   4320
cggcatcgga acggtccttg atcaagcaga cagccgggg gtcagactaa ctgtgctggc   4380
tacgccaca ccccccgggt cagtgacaac cccccatccc gatatagaag aggtaggcct   4440
cgggcgggag ggtgagatcc ccttctatgg gagggcgatt ccctatcct gcatcaaggg   4500
agggagacac ctgattttct gccactcaaa gaaaaagtgt gacgagctcg cggcggccct   4560
tcggggcatg ggcttgaatg ccgtggcata ctatagaggg ttggacgtct ccataatacc   4620
agctcaggga gatgtggtgg tcgtcgccac cgacgccctc atgacgggt acactggaga   4680
ctttgactcc gtgatcgact gcaatgtagc ggtcacccaa gctgtcgact tcagcctgga   4740
ccccaccttc actataacca cacagactgt cccacaagac gctgtctcac gcagtcagcg   4800
ccgcgggcgc acaggtagag aagacaggg cacttatagg tatgtttcca ctggtgaacg   4860
agcctcagga atgtttgaca gtgtagtgct ttgtgagtgc tacgacgcag ggctgcgtg   4920
gtacgatctc acaccagcgg agaccaccgt caggcttaga gcgtatttca acacgcccgg   4980
cctacccgtg tgtcaagacc atcttgaatt ttgggaggca gttttcaccg gcctcacaca   5040
catagacgcc cacttcctct cccaaacaaa gcaagcgggg gagaacttcg cgtacctagt   5100
agcctaccaa gctacggtgt gcgccagagc caaggcccct cccccgtcct gggacgccat   5160
gtggaagtgc ctggccggac tcaagcctac gcttgcgggc cccacacctc tcctgtaccg   5220
tttgggccct attaccaatg aggtcacccc cacacaccct gggacgaagt acatcgccac   5280
atgcatgcaa gctgaccttg aggtcatgac cagcacgtgg gtcctagctg gaggagtcct   5340
```

```
ggcagccgtc gccgcatatt gcctggcgac tggatgcgtt tccatcatcg gccgcttgca    5400
cgtcaaccag cgagtcgtcg ttgcgccgga taaggaggtc ctgtatgagg cttttgatga    5460
gatggaggaa tgcgcctcta gggcggctct catcgaagag gggcagcgga tagccgagat    5520
gttgaagtcc aagatccaag gcttgctgca gcaggcctct aagcaggccc aggacataca    5580
acccgctatg caggcttcat ggcccaaagt ggaacaattt ggggccagac acatgtggaa    5640
cttcattagc ggcatccaat acctcgcagg attgtcaaca ctgccaggga ccccgcggt    5700
ggcttccatg atggcattca gtgccgccct caccagtccg ttgtcgacca gtaccaccat    5760
ccttctcaac atcatgggag ctggttagc gtcccagatc gcaccaccg cggggggccac     5820
cggctttgtc gtcagtggcc tggtggggggc tgccgtgggc agcataggcc tgggtaaggt    5880
gctggtggac atcctggcag gatatggtgc gggcatttcg ggggccctcg tcgcattcaa    5940
gatcatgtct ggcgagaagc cctctatgga agatgtcatc aatctactgc tgggatcct    6000
gtctccggga gccctggtgg tgggggtcat ctgcgcggcc attctgcgcc gccacgtggg    6060
accgggggag ggcgcggtcc aatggatgaa caggcttatt gcctttgctt ccagaggaaa    6120
ccacgtcgcc cctactcact acgtgacgga gtcggatgcg tcgcagcgtg tgacccaact    6180
acttggctct cttactataa ccagcctact cagaagactc cacaattgga taactgagga    6240
ctgccccatc ccatgctccg gatcctggct ccgcgacgtg tgggactggg tttgcaccat    6300
cttgacagac ttcaaaaatt ggctgacctc taaattgttc cccaagctgc ccggcctccc    6360
cttcatctct tgtcaaaagg ggtacaaggg tgtgtgggcc ggcactggca tcatgaccac    6420
gcgctgccct tgcggcgcca acatctctgg caatgtccgc ctgggctcta tgaggatcac    6480
agggcctaaa acctgcatga acacctggca ggggaccttt cctatcaatt gctacacgga    6540
gggccagtgc gcgccgaaac cccccacgaa ctacaagacc gccatctgga gggtggcggc    6600
ctcggagtac gcggaggtga cgcagcatgg gtcgtactcc tatgtaacag gactgaccac    6660
tgacaatctg aaaattcctt gccaactacc ttctccagag ttttttctcct gggtggacgg    6720
tgtgcagatc cataggtttg cacccacacc aaagccgttt ttccgggatg aggtctcgtt    6780
ctgcgttggg cttaattcct atgctgtcgg gtcccagctt ccctgtgaac ctgagcccga    6840
cgcagacgta ttgaggtcca tgctaacaga tccgccccac atcacggcgg agactgcggc    6900
gcggcgcttg gcacggggat cacctccatc tgaggcgagc tcctcagtga gccagctatc    6960
agcaccgtcg ctgcgggcca cctgcaccac ccacagcaac acctatgacg tggacatggt    7020
cgatgccaac ctgctcatgg agggcggtgt ggctcagaca gagcctgagt ccagggtgcc    7080
cgttctggac tttctcgagc caatggccga ggaagagagc gaccttgagc cctcaatacc    7140
atcggagtgc atgctcccca ggagcgggtt tccacgggcc ttaccggctt gggcacggcc    7200
tgactacaac ccgccgctcg tggaatcgtg gaggaggcca gattaccaac cgcccaccgt    7260
tgctggttgt gctctccccc cccccaagaa ggccccgacg cctcccccaa ggagacgccg    7320
gacagtgggt ctgagcgaga gcaccatatc agaagccctc cagcaactgg ccatcaagac    7380
ctttggccag ccccctcga gcggtgatgc aggctcgtcc acgggggcgg gcgccgccga    7440
atccggcggt ccgacgtccc ctggtgagcc ggccccctca gagacaggtt ccgcctcctc    7500
tatgcccccc ctcgaggggg agcctggaga tccggacctg gagtctgatc aggtagagct    7560
tcaacctccc cccagggggg gggggtagc tcccggttcg ggctcggggt cttggtctac    7620
ttgctccgag gaggacgata ccaccgtgtg ctgctccatg tcatactcct ggaccggggc    7680
tctaataact ccctgtagcc ccgaagagga aaagttgcca atcaacccct tgagtaactc    7740
```

-continued

```
gctgttgcga taccataaca aggtgtactg tacaacatca agagcgcct cacagagggc      7800 taaaaaggta acttttgaca ggacgcaagt gctcgacgcc cattatgact cagtcttaaa     7860
ggacatcaag ctagcggctt ccaaggtcag cgcaaggctc ctcaccttgg aggaggcgtg     7920
ccagttgact ccacccccatt ctgcaagatc caagtatgga ttcggggcca aggaggtccg    7980
cagcttgtcc gggagggccg ttaaccacat caagtccgtg tggaaggacc tcctggaaga    8040
cccacaaaca ccaattccca caaccatcat ggccaaaaat gaggtgttct gcgtggaccc    8100
cgccaagggg ggtaagaaac cagctcgcct catcgtttac cctgacctcg gcgtccgggt   8160
ctgcgagaaa atggccctct atgacattac acaaaagctt cctcaggcgg taatgggagc    8220
ttcctatggc ttccagtact cccctgccca acgggtggag tatctcttga agcatgggc     8280 ggaaaagaag gacccccatgg gttttttcgta tgatacccga tgcttcgact caaccgtcac  8340
tgagagagac atcaggaccg aggagtccat ataccaggcc tgctccctgc ccgaggaggc    8400
ccgcactgcc atacactcgc tgactgagag actttacgta ggagggccca tgttcaacag   8460
caagggtcaa acctgcggtt acagacgttg ccgcgccagc ggggtgctaa ccactagcat   8520
gggtaacacc atcacatgct atgtgaaagc cctagcggcc tgcaaggctg cggggatagt   8580
tgcgcccaca atgctggtat gcggcgatga cctagtagtc atctcagaaa gccaggggac   8640
tgaggaggac gagcggaacc tgagagcctt cacggaggcc atgaccaggt actctgcccc   8700
tcctggtgat ccccccagac cggaatatga cctggagcta ataacatcct gttcctcaaa   8760
tgtgtctgtg gcgttgggcc cgcggggccg ccgcagatac tacctgacca gagacccaac   8820
cactccactc gcccgggctg cctgggaaac agttagacac tcccctatca attcatggct   8880
gggaaacatc atccagtatg ctccaaccat atgggttcgc atggtcctaa tgacacactt   8940
cttctccatt ctcatggtcc aagacacccct ggaccagaac ctcaactttg agatgtatgg   9000
atcagtatac tccgtgaatc ctttggacct tccagccata attgagaggt acacgggct    9060 tgacgccttt tctatgcaca catactctca ccacgaactg acgcgggtgg cttcagccct   9120
cagaaaactt ggggcgccac ccctcagggt gtggaagagt cgggctcgcg cagtcagggc   9180
gtccctcatc tcccgtggag ggaaagcggc cgtttgcggc cgatatctct tcaattgggc   9240
ggtgaagacc aagctcaaac tcactccatt gccggaggcg cgcctactgg acttatccag   9300
ttggttcacc gtcggcgccg gcgggggcga catttttcac agcgtgtcgc gcgcccgacc   9360
ccgctcatta ctcttcggcc tactcctact tttcgtaggg gtaggcctct tcctactccc   9420
cgctcggtag agcggcacac actaggtaca ctccatagct aactgttcct ttttttttt    9480 ttttttttt  ttttttttt  ttttttttt  ttctttttt  tttttttccc  tcttcttcc    9540 cttctcatct tattctactt tctttcttgg tggctccatc ttagccctag tcacggctag    9600
ctgtgaaagg tccgtgagcc gcatgactgc agagagtgcc gtaactggtc tctctgcaga    9660
tcatgt                                                              9666
```

<210> SEQ ID NO 12
<211> LENGTH: 9666
<212> TYPE: DNA
<213> ORGANISM: Hepatitis C virus

<400> SEQUENCE: 12

```
acctgcccct aatagggcg acactccgcc atgaatcact cccctgtgag gaactactgt      60
cttcacgcag aaagcgccta gccatggcgt tagtatgagt gtcgtacagc ctccaggccc    120
ccccctcccg ggagagccat agtggtctgc ggaaccggtg agtacaccgg aattgccggg   180
```

```
aagactgggt cctttcttgg ataaacccac tctatgcccg gccatttggg cgtgcccccg    240
caagactgct agccgagtag cgttgggttg cgaaaggcct tgtggtactg cctgataggg    300
cgcttgcgag tgccccggga ggtctcgtag accgtgcacc atgagcacga atcctaaacc    360
tcaaagaaaa accaaacgta acaccaaccg ccgcccaatg gacgttaagt tcccgggtgg    420
tggccagatc gttggcggag tttacttgtt gccgcgcagg ggcccagat tgggtgtgcg     480 cgcgactcgg aagacttcgg agcggtcgca acctcgtgga agacgccaac ctatccccaa    540
ggcgcgtcga cccgagggaa ggtcctgggc acaaccagga tatccatggc ctctttacgg    600
taatgagggt tgtgggtggg caggatggct cttgtccccc cgtggctctc gaccgtcttg    660
gggcccaaat gatccccggc ggaggtcccg caatttgggt aaggtcatcg atacccctaac   720 ctgcggcttc gccgacctca tgggatacat cccgctcgta ggcgccccg tgggtggcgt     780 cgccagggcc ctggcacatg gtgtcagggc tttggaggac gggatcaatt atgcaacagg    840
gaatctcccc ggttgctcct tttctatctt cctcttggca cttctttcgt gcctgactgt    900
ccccgcttcg gccgttaact atcgcaatgt ctcgggcatc taccatgtca ccaatgactg    960
cccgaattca agcatagtgt atgaggccga ccatcacatc ttgcaccttc caggttgcgt   1020
gccctgcgtg agagagggga atcagtcacg ctgctgggtg gcccttactc ctaccgtcgc   1080
agcgccatac atcggcgcac cgcttgagtc cttacggagt catgtggatt tgatggtggg   1140
ggccgccact gtttgctcgg gtctttacat cggggacctg tgtggcggct tgttcctagt   1200
tggccagatg ttttcattcc gaccacggcg ccactggacc acccaggatt gcaattgttc   1260
catctacaca gggcacatta caggccacag aatggcctgg gacatgatga tgaactggag   1320
tccaacaacc accttagttc tcgcccaggt catgaggatc caaccactc tggtagactt    1380 actctctgga ggccactggg gtgtcctcgt gggagtggcc tatttcagca tgcaggccaa   1440
ttgggccaaa gtcatcttgg tcctattcct ctttgcaggg gttgatgccg agactcacgt   1500
gtctggggca gcagtcggcc ggagtaccgc cggcttggct aacctctttt cttctgggtc   1560
taagcagaat ttacagctca tcaacagcaa tgggagctgg catataaata ggactgccct   1620
taactgcaat gacagcttaa acactgggtt cttggctagc ttgttctaca cccacaagtt   1680
taacagctca gggtgttccg aacggctcgc gtgctgcaag agccttgaca gctacggcca   1740
aggctggggc ccactcgggg tcgctaacat cagcggctcg tctgatgaca ggccttattg   1800
ctggcactac gcgcctcggc cgtgcgggat tgtgccagca tccagtgtgt gtggccccgt   1860
gtattgtttc actcccagcc ctgtcgtggt cggtactact gatcacgtcg gggtccctac   1920
ttacacctgg ggggagaatg agactgatgt cttccttttg aactcgacca daccgccgca   1980
tggtgcgtgt tttggatgcg tgtggatgaa cagtaccggg ttcaccaaaa cctgtggcgc   2040
ccctccatgc gaggttaaca ccaataatgg gacctggcac tgccccaccg attgcttcag   2100
gaagcatccg gagactacct acgccaagtg cggatcaggg ccttggatca caccgcgctg   2160
cctgattgat tacccgtacc ggctgtggca tttcccgtgc accgccaact tctccgtctt   2220
taacatcagg acatttgtcg gcggtataga gcatcggatg caagcggcat gcaactggac   2280
caggggggaa gtctgtggct tggagcacag ggatcgcgta gagctatcac ccctgctcct   2340
taccactaca gcgtggcaga tcctccccctg ctctttcacc actttacctg ccctctccac   2400
cggcttgatc cacctccacc aaaatatcgt ggacgtccag tacctctatg gtgttgggtc   2460
tgcagtggta tcttgggccc ttaagtggga atatgtggtg ctcgcgttcc tgcttctcgc   2520
ggacgcgaga gtctctgcct gcctatggat gatgtttatg gtaagtcaag ttgaggcggc   2580
```

```
tctgtccaac ctgattaaca tcaatgctgc ttcagccgct ggtgcccaag gcttctggta   2640
cgccatcctc ttcatctgca ttgtctggca tgtcaagggc cggttcccag ctgctgctgc   2700
ctacgcagcc tgcgggctgt ggcccctgtt tctcctgctt ctgatgctgc ctgagagggc   2760
ttatgcatac gaccaggaag tggcagggtc ccttggcggc gccatcgttg tcatgctggc   2820
cattctgaca ctgtctccgc actacaagtt atggctggct aggggattgt ggtggatcca   2880
atattttata gctaggaccg aggctgtgct gcatgtctat attccatcct caacgtgcg   2940
cgggcctcgc gactcagtga ttgttcttgc agtcctggtc tgtccacacc tagtatttga   3000
catcacaaaa tatcttctgg ccatcttagg gcccctccac atactccagg cctcgctcct   3060
acgcatccct tactttgtga gggcacaagc gctggttaag atctgcagct tgttgcgtgg   3120
ggtagtttat ggcaagtact tccaaatggt cgtgcttaaa gcaggggccc tgactggtac   3180
ttacatctat gaccacctca cacctatgtc ggactgggcc gctagcggcc tgcgcgactt   3240
agcggtcgcc gtggaaccca tcatcttcag tccgatggag aagaaggtca tcgtctgggg   3300
agcgaagacg gctgcatgtg gggacattct acatggactt cccgtgtccg cccgactcgg   3360
ccaggagatc ctcctcggcc cagctgatgg ctacacctcc aagggtgga agctccttgc   3420
tcccatcact gcttatgccc agcaaacacg aggcctcctg ggcgccatag tggtgagtat   3480
gacggggcgt gacaggacag aacaggccgg ggaagtccaa atcctgtcca cagtctctca   3540
gtccttcctc ggaacaacca tctcgggggt tttgtggact gtttaccacg gagctggcaa   3600
caagactcta gccggcttac ggggtccggt cacgcagatg tactcgagtg ctgaggggga   3660
cttggtaggc tggcccagcc ccctgggac caagtctttg gagccgtgca agtgtggagc   3720
cgtcgaccta tatctggtca cgcggaacg tgatgtcatc ccggctcgga gacgcgggga   3780
caagcgggga gcattgctct ccccgagacc catttcgacc ttgaagggt cctcgggggg   3840
gccggtgctc tgccctaggg gccacgtcgt tgggctcttc cgagcagctg tgtgctctcg   3900
gggcgtggcc aaatccatcg atttcatccc cgttgagaca ctcgacgttg ttacaaggtc   3960
tcccactttc agtgacaaca gcacgccacc ggctgtgccc cagacctatc aggtcgggta   4020
cttgcatgct ccaactggca gtggaaagag caccaaggtc cctgtcgcgt atgccgccca   4080
ggggtacaaa gtactagtgc ttaacccctc ggtagctgcc accctggggt ttggggcgta   4140
cctatccaag gcacatggca tcaatcccaa cattaggact ggagtcagga ccgtgatgac   4200
cgggagcc atcacgtact ccacatatgg caaatttctc gccgatgggg gctgcgctag   4260
cggcgcctat gacatcatca tatgcgatga atgccacgct gtggatgcta cctccattct   4320
cggcatcgga acggtccttg atcaagcaga gacagccggg gtcagactaa ctgtgctggc   4380
tacgccaca cccccgggt cagtgacaac ccccatccc gatatagaag aggtaggcct   4440
cgggcgggag ggtgagatcc ccttctatgg gagggcgatt cccctatcct gcatcaaggg   4500
agggagacac ctgattttct gccactcaaa gaaaaagtgt gacgagctcg cggcggccct   4560
tcggggcatg ggcttgaatg ccgtggcata ctatagaggg ttggacgtct ccataatacc   4620
agctcaggga gatgtggtgg tcgtcgccac cgacgccctc atgacgggt acactggaga   4680
cttgactcc gtgatcgact gcaatgtagc ggtcacccaa gctgtcgact tcagcctgga   4740
ccccaccttc actataacca cacagactgt cccacaagac gctgtctcac gcagtcagcg   4800
ccgcgggcgc acaggtagag aagacaggg cacttatagg tatgtttcca ctggtgaacg   4860
agcctcagga atgtttgaca gtgtagtgct ttgtgagtgc tacgacgcag gggctgcgtg   4920
gtacgatctc acaccagcgg agaccaccgt caggcttaga gcgtatttca acacgcccgg   4980
```

```
cctacccgtg tgtcaagacc atcttgaatt ttgggaggca gttttcaccg gcctcacaca    5040
catagacgcc cacttcctct cccaaacaaa gcaagcgggg gagaacttcg cgtacctagt    5100
agcctaccaa gctacggtgt gcgccagagc caaggcccct cccccgtcct gggacgccat    5160
gtggaagtgc ctggcccgac tcaagcctac gcttgcgggc cccacacctc tcctgtaccg    5220
tttgggccct attaccaatg aggtcaccct cacacaccct gggacgaagt acatcgccac    5280
atgcatgcaa gctgaccttg aggtcatgac cagcacgtgg gtcctagctg gaggagtcct    5340
ggcagccgtc gccgcatatt gcctggcgac tggatgcgtt tccatcatcg gccgcttgca    5400
cgtcaaccag cgagtcgtcg ttgcgccgga taaggaggtc ctgtatgagg cttttgatga    5460
gatggaggaa tgcgcctcta gggcggctct catcgaagag gggcagcgga tagccgagat    5520
gttgaagtcc aagatccaag gcttgctgca gcaggcctct aagcaggccc aggacataca    5580
acccgctatg caggcttcat ggcccaaagt ggaacaattt gggccagac acatgtggaa    5640 cttcattagc ggcatccaat acctcgcagg attgtcaaca ctgccaggga accccgcggt    5700
ggcttccatg atggcattca gtgccgccct caccagtccg ttgtcgacca gtaccaccat    5760
ccttctcaac atcatgggag ctggttagc gtcccagatc gcaccacccg cgggggccac    5820
cggctttgtc gtcagtggcc tggtggggc tgccgtgggc agcataggcc tgggtaaggt    5880
gctggtggac atcctggcag atatggtgc gggcatttcg ggggccctcg tcgcattcaa    5940
gatcatgtct ggcgagaagc cctctatgga agatgtcatc aatctactgc tgggatcct    6000 gtctccggga gccctggtgg tgggggtcat ctgcgcggcc attctgcgcc gccacgtggg    6060
accgggggag ggcgcggtcc aatggatgaa caggcttatt gcctttgctt ccagaggaaa    6120
ccacgtcgcc cctactcact acgtgacgga gtcggatgcg tcgcagcgtg tgacccaact    6180
acttggctct cttactataa ccagcctact cagaagactc cacaattgga taactgagga    6240
ctgccccatc ccatgctccg gatcctggct ccgcgacgtg tgggactggg tttgcaccat    6300
cttgacagac ttcaaaaatt ggctgacctc taaattgttc cccaagctgc ccggcctccc    6360
cttcatctct tgtcaaaagg ggtacaaggg tgtgtgggcc ggcactggca tcatgaccac    6420
gcgctgccct tgcggcgcca acatctctgg caatgtccgc ctgggctcta tgaggatcac    6480
agggcctaaa acctgcatga acacctggca ggggacctt cctatcaatt gctacacgga    6540
gggccagtgc gcgccgaaac cccccacgaa ctacaagacc gccatctgga gggtggcggc    6600
ctcggagtac gcggaggtga cgcagcatgg gtcgtactcc tatgtaacag gactgaccac    6660
tgacaatctg aaaattcctt gccaactacc ttctccagag ttttctcct gggtggacgg    6720 tgtgcagatc cataggttg cacccacacc aaagccgttt ttccgggatg aggtctcgtt    6780
ctgcgttggg cttaattcct atgctgtcgg gtcccagctt cctgtgaac ctgagcccga    6840 cgcagacgta ttgaggtcca tgctaacaga tccgcccac atcacggcgg agactgcggc    6900
gcggcgcttg gcacggggat cacctccatc tgaggcgagc tcctcagtga gccagctatc    6960
agcaccgtcg ctgcgggcca cctgcaccac ccacagcaac acctatgacg tggacatggt    7020
cgatgccaac ctgctcatgg agggcggtgt ggctcagaca gagcctgagt ccagggtgcc    7080
cgttctggac tttctcgagc caatggccga ggaagagagc gaccttgagc cctcaatacc    7140
atcggagtgc atgctcccca ggagcggtt tccacgggcc ttaccggctt gggcacggcc    7200
tgactacaac ccgccgctcg tggaatcgtg gaggaggcca gattaccaac cgcccaccgt    7260
tgctggttgt gctctccccc cccccaagaa ggccccgacg cctcccccaa ggagacgccg    7320
gacagtgggt ctgagcgaga gcaccatatc agaagccctc cagcaactgg ccatcaagac    7380
```

```
ctttggccag ccccctcga gcggtgatgc aggctcgtcc acggggggcgg gcgccgccga  7440
atccggcggt ccgacgtccc ctggtgagcc ggcccctca gagacaggtt ccgcctcctc    7500
tatgccccc  ctcgagggg  agcctggaga tccggacctg gagtctgatc aggtagagct    7560
tcaacctccc cccagggg  gggggtagc tcccggttcg ggctcgggt cttggtctac      7620
ttgctccgag gaggacgata ccaccgtgtg ctgctccatg tcatactcct ggaccggggc   7680
tctaataact ccctgtagcc ccgaagagga aaagttgcca atcaacctt tgagtaactc    7740
gctgttgcga taccataaca aggtgtactg tacaacatca aagagcgcct cacagagggc   7800
taaaaaggta acttttgaca ggacgcaagt gctcgacgcc cattatgact cagtcttaaa   7860
ggacatcaag ctagcggctt ccaaggtcag cgcaaggctc ctcaccttgg aggaggcgtg   7920
ccagttgact ccaccccatt ctgcaagatc caagtatgga ttcgggcca aggaggtccg    7980
cagcttgtcc gggagggccg ttaaccacat caagtccgtg tggaaggacc tcctggaaga   8040
cccacaaaca ccaattccca caaccatcat ggccaaaaat gaggtgttct gcgtggaccc   8100
cgccaagggg ggtaagaaac cagctcgcct catcgtttac cctgacctcg cgtccgggt    8160
ctgcgagaaa atggccctct atgacattac acaaaagctt cctcaggcgg taatgggagc   8220
ttcctatggc ttccagtact cccctgccca acgggtggag tatctcttga aagcatgggc   8280
ggaaaagaag gaccccatgg ttttttcgta tgatacccga tgcttcgact caaccgtcac   8340
tgagagagac atcaggaccg aggagtccat ataccaggcc tgctccctgc ccgaggaggc   8400
ccgcactgcc atacactcgc tgactgagag actttacgta ggagggccca tgttcaacag   8460
caagggtcaa acctgcggtt acagacgttg ccgcgccagc ggggtgctaa ccactagcat   8520
gggtaacacc atcacatgct atgtgaaagc cctagcggcc tgcaaggctg cggggatagt   8580
tgcgcccaca atgctggtat gcggcgatga cctagtagtc atctcagaaa gccagggac    8640
tgaggaggac gagcggaacc tgagagcctt cacggaggcc atgaccaggt actctgcccc   8700
tcctggtgat ccccccagac cggaatatga cctggagcta ataacatcct gttcctcaaa   8760
tgtgtctgtg gcgttgggcc cgcgggggccg ccgcagatac tacctgacca gagacccaac   8820
cactccactc gcccgggctg cctgggaaac agttagacac tcccctatca attcatggct   8880
gggaaacatc atccagtatg ctccaaccat atgggttcgc atggtcctaa tgacacactt   8940
cttctccatt ctcatggtcc aagacacct ggaccgaaac ctcaactttg agatgtatgg    9000
atcagtatac tccgtgaatc ctttggacct tccagccata attgagaggt tacacgggct   9060
tgacgccttt tctatgcaca catactctca ccacgaactg acgcgggtgg cttcagccc    9120
cagaaaactt ggggcgccac ccctcaggt gtggaagagt cgggctcgcg cagtcagggc    9180
gtccctcatc tcccgtggag ggaaagcggc cgtttgcggc cgatatctct tcaattgggc   9240
ggtgaagacc aagctcaaac tcactccatt gccggaggcg cgcctactgg acttatccag   9300
ttggttcacc gtcggcgccg gcgggggcga cattttcac agcgtgtcgc gcgcccgacc    9360
ccgctcatta ctcttcggcc tactcctact tttcgtaggg gtaggcctct cctactccc    9420
cgctcggtag agcggcacac actaggtaca ctccatagct aactgttcct ttttttttt    9480
tttttttttt tttttttttt tttttttttt ttcttttttt ttttttccc tctttcttcc    9540
cttctcatct tattctactt tctttcttgg tggctccatc ttagccctag tcacggctag   9600
ctgtgaaagg tccgtgagcc gcatgactgc agagagtgcc gtaactggtc tctctgcaga   9660
tcatgt                                                              9666
```

<210> SEQ ID NO 13

<211> LENGTH: 9666
<212> TYPE: DNA
<213> ORGANISM: Hepatitis C virus

<400> SEQUENCE: 13
acctgcccct aataggggcg acactccgcc atgaatcact cccctgtgag gaactactgt 60
cttcacgcag aaagcgccta gccatggcgt tagtatgagt gtcgtacagc ctccaggccc 120
ccccctcccg ggagagccat agtggtctgc ggaaccggtg agtacaccgg aattgccggg 180
aagactgggt cctttcttgg ataaacccac tctatgcccg gccatttggg cgtgcccccg 240
caagactgct agccgagtag cgttgggttg cgaaaggcct tgtggtactg cctgataggg 300
cgcttgcgag tgccccggga ggtctcgtag accgtgcacc atgagcacga atcctaaacc 360
tcaaagaaaa accaaacgta acaccaaccg ccgcccaatg gacgttaagt tcccgggtgg 420
tggccagatc gttggcggag tttacttgtt gccgcgcagg ggccccagat tgggtgtgcg 480
cgcgactcgg aagacttcgg agcggtcgca acctcgtgga agacgccaac ctatccccaa 540
ggcgcgtcga cccgagggaa ggtcctgggc acaaccagga tatccatggc ctctttacgg 600
taatgagggt tgtgggtggg caggatggct cttgtccccc cgtggctctc gaccgtcttg 660
gggcccaaat gatccccggc ggaggtcccg caatttgggt aaggtcatcg ataccctaac 720
ctgcggcttc gccgacctca tgggatacat cccgctcgta ggcgcccccg tgggtggcgt 780
cgccagggcc ctggcacatg gtgtcagggc tttggaggac gggatcaatt atgcaacagg 840
gaatctcccc ggttgctcct tttctatctt cctcttggca cttctttcgt gcctgactgt 900
ccccgcttcg gccgttaact atcgcaatgt ctcgggcatc taccatgtca ccaatgactg 960
cccgaattca agcatagtgt atgaggccga ccatcacatc ttgcaccttc caggttgcgt 1020
gccctgcgtg agagagggga atcagtcacg ctgctgggtg gcccttactc ctaccgtcgc 1080
agcgccatac atcggcgcac cgcttgagtc cttacggagt catgtggatt tgatggtggg 1140
ggccgccact gtttgctcgg gtctttacat cggggacctg tgtggcggct tgttcctagt 1200
tggccagatg ttttcattcc gaccacggcg ccactggacc acccaggatt gcaattgttc 1260
catctacaca gggcacatta caggccacag aatggcctgg gacatgatga tgaactggag 1320
tccaacaacc accttagttc tcgcccaggt catgaggatc ccaaccactc tggtagactt 1380
actctctgga ggccactggg gtgtcctcgt gggagtggcc tatttcagca tgcaggccaa 1440
ttgggccaaa gtcatcttgg tcctattcct ctttgcaggg gttgatgccg agactcacgt 1500
gtctggggca gcagtcggcc ggagtaccgc cggcttggct aacctctttt cttctgggtc 1560
taagcagaat ttacagctca tcaacagcaa tgggagctgg catataaata ggactgccct 1620
taactgcaat gacagcttaa acactgggtt cttggctagc ttgttctaca cccacaagtt 1680
taacagctca gggtgttccg aacggctcgc gtgctgcaag agccttgaca gctacggcca 1740
aggctggggc ccactcgggg tcgctaacat cagcggctcg tctgatgaca ggccttattg 1800
ctggcactac gcgcctcggc cgtgcgggat tgtgccagca tccagtgtgt gtggccccgt 1860
gtattgtttc actcccagcc ctgtcgtggt cggtactact gatcacgtcg gggtccctac 1920
ttacacctgg ggggagaatg agactgatgt cttccttttg aactcgacca gaccgccgca 1980
tggtgcgtgg tttggatgcg tgtggatgaa cagtaccggg ttcaccaaaa cctgtggcgc 2040
ccctccatgc gaggttaaca ccaataatgg gacctggcac tgccccaccg attgcttcag 2100
gaagcatccg gagactacct acgccaagtg cggatcaggg ccttggatca caccgcgctg 2160
cctgattgat tacccgtacc ggctgtggca tttcccgtgc accgccaact tctccgtctt 2220

```
taacatcagg acatttgtcg gcggtataga gcatcggatg caagcggcat gcaactggac    2280
caggggggaa gtctgtggct tggagcacag ggatcgcgta gagctatcac ccctgctcct    2340
taccactaca gcgtggcaga tcctcccctg ctctttcacc actttacctg ccctctccac    2400
cggcttgatc cacctccacc aaaatatcgt ggacgtccag tacctctatg gtgttgggtc    2460
tgcagtggta tcttgggccc ttaagtggga atatgtggtg ctcgcgttcc tgcttctcgc    2520
ggacgcgaga gtctctgcct gcctatggat gatgtttatg gtaagtcaag ttgaggcggc    2580
tctgtccaac ctgattaaca tcaatgctgc ttcagccgct ggtgcccaag gcttctggta    2640
cgccatcctc ttcatctgca ttgtctggca tgtcaagggc cggttcccag ctgctgctgc    2700
ctacgcagcc tgcgggctgt ggcccctgtt tctcctgctt ctgatgctgc tgagagggc    2760
ttatgcatac gaccaggaag tggcagggtc ccttggcggc gccatcgttg tcatgctggc    2820
cattctgaca ctgtctccgc actacaagtt atggctggct aggggattgt ggtggatcca    2880
atatttata gctaggaccg aggctgtgct gcatgtctat attccatcct caacgtgcg    2940
cgggcctcgc gactcagtga ttgttcttgc agtcctggtc tgtccacacc tagtatttga    3000
catcacaaaa tatcttctgg ccatcttagg gcccctccac atactccagg cctgctcct    3060
acgcatccct tactttgtga gggcacaagc gctggttaag atctgcagct tgttgcgtgg    3120
ggtagtttat ggcaagtact tccaaatggt cgtgcttaaa gcaggggccc tgactggtac    3180
ttacatctat gaccacctca cacctatgtc ggactgggcc gctagcggcc tgcgcgactt    3240
agcggtcgcc gtggaaccca tcatcttcag tccgatggag aagaaggtca tcgtctgggg    3300
agcggagacg gctgcatgtg gggacattct acatggactt cccgtgtccg cccgactcgg    3360
ccaggagatc ctcctcggcc cagctgatgg ctacacctcc aagggtgga agctccttgc    3420
tcccatcact gcttatgccc agcaaacacg aggcctcctg ggcgccatag tggtgagtat    3480
gacggggcgt gacaggacag aacaggccgg ggaagtccaa atcctgtcca cagtctctca    3540
gtccttcctc ggaacaacca tctcggggt tttgtggact gtttaccacg gagctggcaa    3600
caagactcta gccggcttac ggggtccggt cacgcagatg tactcgagtg ctgaggggga    3660
cttggtaggc tggcccagcc cctgggac caagtctttg gagccgtgca agtgtggagc    3720
cgtcgaccta tatctggtca cgcggaacgc tgatgtcatc ccggctcgga gacgcgggga    3780
caagcgggga gcattgctct ccccgagacc catttcgacc ttgaaggggt cctcgggggg    3840
gccggtgctc tgccctaggg gccacgtcgt tgggctcttc cgagcagctg tgtgctctcg    3900
gggcgtggcc aaatccatcg atttcatccc cgttgagaca ctcgacgttg ttacaaggtc    3960
tcccactttc agtgacaaca gcacgccacc ggctgtgccc cagacctatc aggtcgggta    4020
cttgcatgct ccaactggca gtggaaagag caccaaggtc cctgtcgcgt atgccgccca    4080
ggggtacaaa gtactagtgc ttaacccctc ggtagctgcc accctggggt ttgggggcgta    4140
cctatccaag gcacatggca tcaatcccaa cattaggact ggagtcagga ccgtgatgac    4200
cggggaggcc atcacgtact ccacatatgg caaatttctc gccgatgggg gctgcgctag    4260
cggcgcctat gacatcatca tatgcgatga atgccacgct gtggatgcta cctccattct    4320
cggcatcgga acggtccttg atcaagcaga gacagccggg gtcagactaa ctgtgctggc    4380
tacgccaca ccccccgggt cagtgacaac ccccccatcc cgatatagaag aggtaggcct    4440
cgggcgggag ggtgagatcc ccttctatgg gagggcgatt cccctatcct gcatcaaggg    4500
agggagacac ctgattttct gccactcaaa gaaaaagtgt gacagagctcg cggcggccct    4560
tcggggcatg ggcttgaatg ccgtggcata ctatagaggg ttggacgtct ccataatacc    4620
```

```
agctcaggga gatgtggtgg tcgtcgccac cgacgccctc atgacggggt acactggaga    4680 cttttgactcc gtgatcgact gcaatgtagc ggtcacccaa gctgtcgact tcagcctgga    4740
ccccaccttc actataacca cacagactgt cccacaagac gctgtctcac gcagtcagcg    4800
ccgcgggcgc acaggtagag gaagacaggg cacttatagg tatgtttcca ctggtgaacg    4860
agcctcagga atgtttgaca gtgtagtgct ttgtgagtgc tacgacgcag gggctgcgtg    4920
gtacgatctc acaccagcgg agaccaccgt caggcttaga gcgtatttca acacgcccgg    4980 cctaccgtg tgtcaagacc atcttgaatt ttgggaggca gttttcaccg gcctcacaca    5040
catagacgcc cacttcctct cccaaacaaa gcaagcgggg gagaacttcg cgtacctagt    5100
agcctaccaa gctacggtgt gcgccagagc caaggcccct cccccgtcct gggacgccat    5160
gtggaagtgc ctggcccgac tcaagcctac gcttgcgggc cccacacctc tcctgtaccg    5220
tttgggccct attaccaatg aggtcaccct cacacaccct gggacgaagt acatcgccac    5280
atgcatgcaa gctgaccttg aggtcatgac cagcacgtgg gtcctagctg gaggagtcct    5340
ggcagccgtc gccgcatatt gcctggcgac tggatgcgtt ccatcatcg gccgcttgca    5400 cgtcaaccag cgagtcgtcg ttgcgccgga taaggaggtc ctgtatgagg cttttgatga    5460
gatggaggaa tgcgcctcta gggcggctct catcgaagag gggcagcgga tagccgagat    5520
gttgaagtcc aagatccaag gcttgctgca gcaggcctct aagcaggccc aggacataca    5580
acccgctatg caggcttcat ggcccaaagt ggaacaattt gggccagac acatgtggaa    5640 cttcattagc ggcatccaat acctcgcagg attgtcaaca ctgccaggga accccgcggt    5700
ggcttccatg atggcattca gtgccgccct caccagtccg ttgtcgacca gtaccaccat    5760
ccttctcaac atcatgggag gctggttagc gtcccagatc gcaccacccg cgggggccac    5820
cggctttgtc gtcagtggcc tggtggggc tgccgtgggc agcataggcc tgggtaaggt    5880
gctggtggac atcctggcag gatatggtgc gggcatttcg ggggccctcg tcgcattcaa    5940
gatcatgtct ggcgagaagc cctctatgga agatgtcatc aatctactgc ctgggatcct    6000
gtctccggga gccctggtgg tggggtcat ctgcgcggcc attctgcgcc gccacgtggg    6060 accggggag ggcgcggtcc aatggatgaa caggcttatt gcctttgctt ccagaggaaa    6120
ccacgtcgcc cctactcact acgtgacgga gtcggatgcg tcgcagcgtg tgacccaact    6180
acttggctct cttactataa ccagcctact cagaagactc cacaattgga taactgagga    6240
ctgccccatc ccatgctccg gatcctggct ccgcgacgtg tgggactggg tttgcaccat    6300
cttgacagac ttcaaaaatt ggctgacctc taaattgttc cccaagctgc ccggcctccc    6360
cttcatctct tgtcaaaagg ggtacaaggg tgtgtgggcc ggcactggca tcatgaccac    6420
gcgctgccct tgcggcgcca acatctctgg caatgtccgc ctgggctcta tgaggatcac    6480
agggcctaaa acctgcatga acacctggca ggggacctt cctatcaatt gctacacgga    6540
gggccagtgc gcgccgaaac cccccacgaa ctacaagacc gccatctgga gggtggcggc    6600
ctcggagtac gcggaggtga cgcagcatgg gtcgtactcc tatgtaacag gactgaccac    6660
tgacaatctg aaaattcctt gccaactacc ttctccagag ttttttctcct gggtggacgg    6720 tgtgcagatc cataggtttg cacccacacc aaagccgttt ttccgggatg aggtctcgtt    6780
ctgcgttggg cttaattcct atgctgtcgg gtcccagctt ccctgtgaac ctgagcccga    6840
cgcagacgta ttgaggtcca tgctaacaga tccgccccac atcacggcgg agactgcggc    6900
gcggcgcttg gcacggggat cacctccatc tgaggcgagc tcctcagtga gccagctatc    6960
agcaccgtcg ctgcgggcca cctgcaccac ccacagcaac acctatgacg tggacatggt    7020
```

-continued

```
cgatgccaac ctgctcatgg agggcggtgt ggctcagaca gagcctgagt ccagggtgcc      7080
cgttctggac tttctcgagc caatggccga ggaagagagc gaccttgagc cctcaatacc      7140
atcggagtgc atgctcccca ggagcgggtt tccacgggcc ttaccggctt gggcacggcc      7200
tgactacaac ccgccgctcg tggaatcgtg gaggaggcca gattaccaac cgcccaccgt      7260
tgctggttgt gctctccccc cccccaagaa ggccccgacg cctcccccaa ggagacgccg      7320
gacagtgggc tgagcgagag gcaccatatc agaagccctc cagcaactgg ccatcaagac      7380
cttcggccag ccccccctcga gcggtgatgc aggctcgtcc acggggggcgg gcgccgccga     7440
atccggcggt ccgacgtccc ctggtgagcc ggcccccctca gagacaggtt ccgcctcctc      7500
tatgcccccc ctcgagggggg agcctggaga tccggacctg gagtctgatc aggtagagct      7560
tcaacctccc ccccagggggg gggggtagc tcccggttcg ggctcggggt cttggtctac       7620
ttgctccgag gaggacgata ccaccttgtg ctgctccatg tcatactcct ggaccggggc      7680
tctaataact ccctgtagcc ccgaagagga aaagttgcca atcaacccctt tgagtaactc     7740
gctgttgcga taccataaca aggtgtactg tacaacatca aagagcgcct cacagagggc      7800
taaaaaggta acttttgaca ggacgcaagt gctcgacgcc cattatgact cagtcttaaa      7860
ggacatcaag ctagcggctt ccaaggtcag cgcaaggctc ctcaccttgg aggaggcgtg      7920
ccagttgact ccaccccatt ctgcaagatc caagtatgga ttcggggcca aggaggtccg      7980
cagcttgtcc gggagggccg ttaaccacat caagtccgtg tggaaggacc tcctggaaga      8040
cccacaaaca ccaattccca caaccatcat ggccaaaaat gaggtgttct gcgtggaccc      8100
cgccaagggg ggtaagaaac cagctcgcct catcgtttac cctgacctcg gcgtccgggt      8160
ctgcgagaaa atggccctct atgacattac acaaaagctt cctcaggcgg taatgggagc      8220
ttcctatggc ttccagtact cccctgccca acgggtggag tatctcttga aagcatgggc      8280
ggaaaagaag gaccccatgg ttttttcgta tgatacccga tgcttcgact caaccgtcac      8340
tgagagagac atcaggaccg aggagtccat ataccaggcc tgctccctgc ccgaggaggc      8400
ccgcactgcc atacactcgc tgactgagag actttacgta ggagggccca tgttcaacag      8460
caagggtcaa acctgcggtt acagacgttg ccgcgccagc ggggtgctaa ccactagcat      8520
gggtaacacc atcacatgct atgtgaaagc cctagcggcc tgcaaggctg cggggatagt      8580
tgcgcccaca atgctggtat gcggcgatga cctagtagtc atctcagaaa gccagggggac     8640
tgaggaggac gagcggaacc tgagagcctt cacggaggcc atgaccaggt actctgcccc      8700
tcctggtgat ccccccagac cggaatatga cctggagcta ataacatcct gttcctcaaa      8760
tgtgtctgtg gcgttgggcc cgcggggccg ccgcagatac tacctgacca gagacccaac      8820
cactccactc gccgggctg cctgggaaac agttagacac tccccctatca attcatggct       8880
gggaaacatc atccagtatg ctccaaccat atgggttcgc atggtcctaa tgacacactt      8940
cttctccatt ctcatggtcc aagacaccct ggaccagaac ctcaactttg agatgtatgg      9000
atcagtatac tccgtgaatc ctttggacct tccagccata attgagaggt tacacgggct      9060
tgacgccttt tctatgcaca catactctca ccacgaactg acgcgggtgg cttcagccct      9120
cagaaaactt ggggcgccac ccctcagggt gtggaagagt cgggctcgcg cagtcagggc      9180
gtccctcatc tcccgtggag ggaaagcggc cgtttgcggc cgatatctct tcaattgggc      9240
ggtgaagacc aagctcaaac tcactccatt gccggaggcg cgcctactgg acttatccag      9300
ttggttcacc gtcggcgccg gcgggggcga cattttttcac agcgtgtcgc gcgcccgacc      9360
ccgctcatta ctcttcggcc tactcctact tttcgtaggg gtaggcctct tcctactccc      9420
```

-continued

| | |
|---|---|
| cgctcggtag agcggcacac actaggtaca ctccatagct aactgttcct tttttttttt | 9480 |
| tttttttttt tttttttttt tttttttttt ttctttttttt ttttttttccc tctttcttcc | 9540 |
| cttctcatct tattctactt tctttcttgg tggctccatc ttagccctag tcacggctag | 9600 |
| ctgtgaaagg tccgtgagcc gcatgactgc agagagtgcc gtaactggtc tctctgcaga | 9660 |
| tcatgt | 9666 |

<210> SEQ ID NO 14
<211> LENGTH: 9666
<212> TYPE: DNA
<213> ORGANISM: Hepatitis C virus

<400> SEQUENCE: 14

| | |
|---|---|
| acctgcccct aatagggcg acactccgcc atgaatcact cccctgtgag gaactactgt | 60 |
| cttcacgcag aaagcgccta gccatggcgt tagtatgagt gtcgtacagc ctccaggccc | 120 |
| cccctcccg ggagagccat agtggtctgc ggaaccggtg agtacaccgg aattgccggg | 180 |
| aagactgggt cctttcttgg ataaacccac tctatgcccg gccatttggg cgtgccccg | 240 |
| caagactgct agccgagtag cgttgggttg cgaaaggcct tgtggtactg cctgataggg | 300 |
| cgcttgcgag tgccccggga ggtctcgtag accgtgcacc atgagcacga atcctaaacc | 360 |
| tcaaagaaaa accaaacgta acaccaaccg ccgcccaatg acgttaagt tcccgggtgg | 420 |
| tggccagatc gttggcggag tttacttgtt gccgcgcagg ggccccagat gggtgtgcg | 480 |
| cgcgactcgg aagacttcgg agcggtcgca acctcgtgga agacgccaac ctatccccaa | 540 |
| ggcgcgtcga cccgagggaa ggtcctgggc acaaccagga tatccatggc ctctttacgg | 600 |
| taatgagggt tgtgggtggg caggatggct cttgtccccc cgtggctctc gaccgtcttg | 660 |
| gggcccaaat gatccccggc ggaggtcccg caatttgggt aaggtcatcg ataccctaac | 720 |
| ctgcggcttc gccgacctca tgggatacat cccgctcgta ggcgccccg tgggtggcgt | 780 |
| cgccagggcc ctggcacatg gtgtcagggc tttgaggac gggatcaatt atgcaacagg | 840 |
| gaatctcccc ggttgctcct tttctatctt cctcttggca cttctttcgt gcctgactgt | 900 |
| ccccgcttcg gccgttaact atcgcaatgt ctcgggcatc taccatgtca ccaatgactg | 960 |
| cccgaattca gcatagtgt atgaggccga ccatcacatc ttgcacctc caggttgcgt | 1020 |
| gccctgcgtg agagagggga atcagtcacg ctgctgggtg gcccttactc ctaccgtcgc | 1080 |
| agcgccatac atcggcgcac cgcttgagtc cttacggagt catgtggatt tgatggtggg | 1140 |
| ggccgccact gtttgctcgg tcttttacat cggggacctg tgtggcggct tgttcctagt | 1200 |
| tggccagatg ttttcattcc gaccacggcg ccactggacc acccaggatt gcaattgttc | 1260 |
| catctacaca gggcacatta caggccacag aatggcctgg gacatgatga tgaactggag | 1320 |
| tccaacaacc accttagttc tcgcccaggt catgaggatc caaccactc tggtagactt | 1380 |
| actctctgga ggccactggg gtgtcctcgt gggagtggcc tatttcagca tgcaggccaa | 1440 |
| ttgggccaaa gtcatcttgg tcctattcct ctttgcaggg gttgatgccg agactcacgt | 1500 |
| gtctggggca gcagtcggcc ggagtaccgc cggcttggct aacctctttt cttctgggtc | 1560 |
| taagcagaat ttacagctca tcaacagcaa tgggagctgg catataaata ggactgccct | 1620 |
| taactgcaat gacagcttaa acactggggtt cttggctagc ttgttctaca cccacaagtt | 1680 |
| taacagctca gggtgttccg aacggctcgc gtgctgcaag agccttgaca gctacggcca | 1740 |
| aggctggggc ccactcgggg tcgctaacat cagcggctcg tctgatgaca ggccttattg | 1800 |
| ctggcactac gcgcctcggc cgtgcgggat tgtgccagca tccagtgtgt gtggccccgt | 1860 |

```
gtattgtttc actcccagcc ctgtcgtggt cggtactact gatcacgtcg gggtccctac    1920
ttacacctgg gggagaatg agactgatgt cttccttttg aactcgacca gaccgccgca    1980
tggtgcgtgg tttggatgcg tgtggatgaa cagtaccggg ttcaccaaaa cctgtggcgc    2040
ccctccatgc gaggttaaca ccaataatgg gacctggcac tgccccaccg attgcttcag    2100
gaagcatccg gagactacct acgccaagtg cggatcaggg ccttggatca caccgcgctg    2160
cctgattgat tacccgtacc ggctgtggca tttcccgtgc accgccaact tctccgtctt    2220
taacatcagg acatttgtcg gcggtataga gcatcggatg caagcggcat gcaactggac    2280
caggggggaa gtctgtggct tggagcacag ggatcgcgta gagctatcac ccctgctcct    2340
taccactaca gcgtggcaga tcctcccctg ctctttcacc actttacctg ccctctccac    2400
cggcttgatc cacctccacc aaaatatcgt ggacgtccag tacctctatg gtgttgggtc    2460
tgcagtggta tcttgggccc ttaagtggga atatgtggtg ctcgcgttcc tgcttctcgc    2520
ggacgcgaga gtctctgcct gcctatggat gatgtttatg gtaagtcaag ttgaggcggc    2580
tctgtccaac ctgattaaca tcaatgctgc ttcagccgct ggtgcccaag gcttctggta    2640
cgccatcctc ttcatctgca ttgtctggca tgtcaagggc cggttcccag ctgctgctgc    2700
ctacgcagcc tgcgggctgt ggcccctgtt tctcctgctt ctgatgctgc tgagagggc    2760 ttatgcatac gaccaggaag tggcagggtc ccttggcggc gccatcgttg tcatgctggc    2820
cattctgaca ctgtctccgc actacaagtt atggctggct aggggattgt ggtggatcca    2880 atatttata gctaggaccg aggctgtgct gcatgtctat attccatcct caacgtgcg    2940 cgggcctcgc gactcagtga ttgttcttgc agtcctggtc tgtccacacc tagtatttga    3000
catcacaaaa tatcttctgg ccatcttagg gcccctccac atactccagg cctcgctcct    3060
acgcatccct tactttgtga gggcacaagc gctggttaag atctgcagct tgttgcgtgg    3120
ggtagtttat ggcaagtact tccaaatggt cgtgcttaaa gcaggggccc tgactggtac    3180
ttacatctat gaccacctca cacctatgtc ggactgggcc gctagcggcc tgcgcgactt    3240
agcggtcgcc gtggaaccca tcatcttcag tccgatggag aagaaggtca tcgtctgggg    3300
agcgaagacg gctgcatgtg gggacattct acatggactt cccgtgtccg cccgactcgg    3360
ccaggagatc ctcctcggcc cagctgatgg ctacacctcc aaggggtgga agctccttgc    3420
tcccatcact gcttatgccc agcaaacacg aggcctcctg ggcgccatag tggtgagtat    3480
gacggggcgt gacaggacag aacaggccgg ggaagtccaa atcctgtcca cagtctctca    3540
gtccttcctc ggaacaacca tctcgggggt tttgtggact gtttaccacg gagctggcaa    3600
caagactcta gccggcttac ggggtccggt cacgcagatg tactcgagtg ctgaggggga    3660
cttggtaggc tggcccagcc cccctgggac caagtctttg gagccgtgca agtgtggagc    3720
cgtcgaccta tatctggtca cgcggaacgc tgatgtcatc ccggctcgga gacgcgggga    3780
caagcgggga gcattgctct ccccgagacc catttcgacc ttgaaggggt cctcgggggg    3840
gccggtgctc tgccctaggg gccacgtcgt tgggctcttc cgagcagctg tgtgctctcg    3900
gggcgtggcc aaatccatcg atttcatccc cgttgagaca ctcgacgttg ttacaaggtc    3960
tcccactttc agtgacaaca gcacgccacc ggctgtgccc cagacctatc aggtcgggta    4020
cttgcatgct ccaactggca gtggaaagag caccaaggtc cctgtcgcgt atgccgccca    4080
ggggtacaaa gtactagtgc ttaaccctc ggtagctgcc accctggggt tggggcgta    4140 cctatccaag gcatggcca tcaatcccaa cattaggact ggagtcagga ccgtgatgac    4200
cggggaggcc atcacgtact ccacatatgg caaatttctc gccgatgggg gctgcgctag    4260
```

```
cggcgcctat gacatcatca tatgcgatga atgccacgct gtggatgcta cctccattct    4320
cggcatcgga acggtccttg atcaagcaga gacagccggg gtcagactaa ctgtgctggc    4380
tacggccaca ccccccgggt cagtgacaac cccccatccc gatatagaag aggtaggcct    4440
cgggcgggag ggtgagatcc ccttctatgg gagggcgatt cccctatcct gcatcaaggg    4500
agggagacac ctgattttct gccactcaaa gaaaagtgt gacgagctcg cggcggccct     4560
tcggggcatg ggcttgaatg ccgtggcata ctatagaggg ttggacgtct ccataatacc    4620
agctcaggga gatgtggtgg tcgtcgccac cgacgccctc atgacggggt acactggaga    4680 cttgactcc gtgatcgact gcaatgtagc ggtcacccaa gctgtcgact tcagcctgga     4740
ccccaccttc actataacca cacagactgt cccacaagac gctgtctcac gcagtcagcg    4800
ccgcgggcgc acaggtagag gaagacaggg cacttatagg tatgtttcca ctggtgaacg    4860
agcctcagga atgtttgaca gtgtagtgct ttgtgagtgc tacgacgcag gggctgcgtg    4920
gtacgatctc acaccagcgg agaccaccgt caggcttaga gcgtatttca acacgcccgg    4980
cctacccgtg tgtcaagacc atcttgaatt ttgggaggca gttttcaccg gcctcacaca    5040
catagacgcc cacttcctct cccaaacaaa gcaagcgggg gagaacttcg cgtacctagt    5100
agcctaccaa gctacggtgt gcgccagagc caaggcccct cccccgtcct gggacgccat    5160
gtggaagtgc ctggcccgac tcaagcctac gcttgcgggc cccacacctc tcctgtaccg    5220 tttgggcccct attaccaatg aggtcaccct cacacaccct gggacgaagt acatcgccac    5280
atgcatgcaa gctgaccttg aggtcatgac cagcacgtgg gtcctagctg gaggagtcct    5340
ggcagccgtc gccgcatatt gcctggcgac tggatgcgtt ccatcatcg ccgcttgca     5400 cgtcaaccag cgagtcgtcg ttgcgccgga taaggaggtc ctgtatgagg cttttgatga    5460
gatgaaggaa tgcgcctcta gggcggctct catcgaagag gggcagcgga tagccgagat    5520
gttgaagtcc aagatccaag gcttgctgca gcaggcctct aagcaggccc aggacataca    5580
acccgctatg caggcttcat ggcccaaagt ggaacaattt gggccagac acatgtggaa     5640 cttcattagc ggcatccaat acctcgcagg attgtcaaca ctgccaggga accccgcggt    5700
ggcttccatg atggcattca gtgccgccct caccagtccg ttgtcgacca gtaccaccat    5760
ccttctcaac atcatgggag ctggttagc gtcccagatc gcaccacccg cggggggccac    5820 cggctttgtc gtcagtggcc tggtgggggc tgccgtgggc agcataggcc tgggtaaggt    5880
gctggtggac atcctggcag gatatggtgc gggcatttcg ggggccctcg tcgcattcaa    5940
gatcatgtct ggcgagaagc cctctatgga agatgtcatc aatctactgc ctgggatcct    6000
gtctccggga gccctggtgg tggggtcat ctgcgcggcc attctgcgcc gccacgtggg     6060 accggggag ggcgcggtcc aatggatgaa caggcttatt gcctttgctt ccagaggaaa     6120
ccacgtcgcc cctactcact acgtgacgga gtcggatgcg tcgcagcgtg tgacccaact    6180
acttggctct cttactataa ccagcctact cagaagactc cacaattgga taactgagga    6240
ctgccccatc ccatgctccg atcctggct ccgcgacgtg tgggactggg tttgcaccat     6300
cttgatagac ttcaaaaatt ggctgacctc taaattgttc cccaagctgc ccggcctccc    6360
cttcatctct tgtcaaaagg ggtacaaggg tgtgtgggcc ggcactggca tcatgaccac    6420
gcgctgccct tgcggcgcca acatctctgg caatgtccgc ctgggctcta tgaggatcac    6480
agggcctaaa acctgcatga acacctggca ggggacctt cctatcaatt gctacacgga     6540
gggccagtgc gcgccgaaac cccccacgaa ctacaagacc gccatctgga gggtggcggc    6600
ctcggagtac gcggaggtga cgcagcatgg gtcgtactcc tatgtaacag gactgaccac    6660
```

```
tgacaatctg aaaattcctt gccaactacc ttctccagag ttttctcct gggtggacgg    6720 tgtgcagatc cataggtttg cacccacacc aaagccgttt ttccgggatg aggtctcgtt    6780
ctgcgttggg cttaattcct atgctgtcgg gtcccagctt ccctgtgaac ctgagcccga    6840
cgcagacgta ttgaggtcca tgctaacaga tccgcccac atcacggcgg agactgcggc    6900
gcggcgcttg cacggggat cacctccatc tgaggcgagc tcctcagtga gccagctatc    6960
agcaccgtcg ctgcgggcca cctgcaccac ccacagcaac acctatgacg tggacatggt    7020
cgatgccaac tgctcatgg agggcggtgt ggctcagaca gagcctgagt ccagggtgcc    7080
cgttctggac tttctcgagc caatggccga ggaagagagc gaccttgagc cctcaatacc    7140
atcggagtgc atgctcccca ggagcgggtt tccacgggcc ttaccggctt gggcacggcc    7200
tgactacaac ccgccgctcg tggaatcgtg gaggaggcca gattaccaac cgcccaccgt    7260
tgctggttgt gctctccccc cccccaagaa ggccccgacg cctcccccaa ggagacgccg    7320
gacagtgggc ctgagcgaga gcaccatatc agaagccctc cagcaactgg ccatcaagac    7380
ctttggccag cccccctcga gcggtgatgc aggctcgtcc acggggcgg gcgccgccga    7440 atccggcggt ccgacgtccc ctggtgagcc ggcccctca gagacaggtt ccgcctcctc    7500 tatgccccc ctcgaggggg agcctggaga tccggacctg gagtctgatc aggtagagct    7560
tcaacctccc ccccaggggg gggggtagc tcccggttcg ggctcggggt cttggtctac    7620
ttgctccgag gaggacgata ccaccttgtg ctgctccatg tcatactcct ggaccggggc    7680
tctaataact ccctgtagcc ccgaagagga aaagttgcca atcaaccctt tgagtaactc    7740
gctgttgcga taccataaca aggtgtactg tacaacatca aagagcgcct cacagagggc    7800
taaaaaggta acttttgaca ggacgcaagt gctcgacgcc cattatgact cagtcttaaa    7860
ggacatcaag ctagcggctt ccaaggtcag cgcaaggctc ctcaccttgg aggaggcgtg    7920
ccagttgact ccaccccatt ctgcaagatc caagtatgga ttcggggcca aggaggtccg    7980
cagcttgtcc gggagggccg ttaaccacat caagtccgtg tggaaggacc tcctggaaga    8040
cccacaaaca ccaattccca caaccatcat ggccaaaaat gaggtgttct gcgtggaccc    8100
cgccaagggg ggtaagaaac cagctcgcct catcgtttac cctgacctcg cgtccgggt    8160 ctgcgagaaa atggccctct atgacattac acaaaagctt cctcaggcgg taatgggagc    8220
ttcctatggc ttccagtact cccctgccca acgggtggag tatctcttga agcatgggc    8280 ggaaaagaag accccatgg gttttcgta tgatacccga tgcttcgact caaccgtcac    8340
tgagagagac atcaggaccg aggagtccat ataccaggcc tgctccctgc cgaggaggc    8400 ccgcactgcc atacactcgc tgactgagag actttacgta ggagggccca tgttcaacag    8460
caagggtcaa acctgcggtt acagacgttg ccgcgccagc ggggtgctaa ccactagcat    8520
gggtaacacc atcacatgct atgtgaaagc cctagcggcc tgcaaggctg cggggatagt    8580
tgcgcccaca atgctggtat gcggcgatga cctagtagtc atctcagaaa gccagggac    8640 tgaggaggac gagcggaacc tgagagcctt cacggaggcc atgaccaggt actctgcccc    8700
tcctggtgat cccccagac cggaatatga cctggagcta ataacatcct gttcctcaaa    8760
tgtgtctgtg gcgttgggcc cgcggggccg ccgcagatac tacctgacca gagacccaac    8820
cactccactc gccgggctg cctgggaaac agttagacac tcccctatca attcatggct    8880
gggaaacatc atccagtatg ctccaaccat atgggttcgc atggtcctaa tgacacactt    8940
cttctccatt ctcatggtcc aagacaccct ggaccgaaac ctcaactttg agatgtatgg    9000
atcagtatac tccgtgaatc ctttggacct tccagccata attgagaggt tacacggct    9060
```

```
tgacgccttt tctatgcaca catactctca ccacgaactg acgcgggtgg cttcagccct    9120
cagaaaactt ggggcgccac ccctcagggt gtggaagagt cgggctcgcg cagtcagggc    9180
gtccctcatc tcccgtggag ggaaagcggc cgtttgcggc cgatatctct tcaattgggc    9240
ggtgaagacc aagctcaaac tcactccatt gccggaggcg cgcctactgg acttatccag    9300
ttggttcacc gtcggcgccg gcggggcga cattttcac agcgtgtcgc gcgcccgacc    9360
ccgctcatta ctcttcggcc tactcctact tttcgtaggg gtaggcctct tcctactccc    9420
cgctcggtag agcggcacac actaggtaca ctccatagct aactgttcct tttttttttt    9480
tttttttttt tttttttttt tttttttttt ttctttttttt tttttttccc tctttcttcc    9540
cttctcatct tattctactt tctttcttgg tggctccatc ttagccctag tcacggctag    9600
ctgtgaaagg tccgtgagcc gcatgactgc agagagtgcc gtaactggtc tctctgcaga    9660
tcatgt                                                              9666

<210> SEQ ID NO 15
<211> LENGTH: 9666
<212> TYPE: DNA
<213> ORGANISM: Hepatitis C virus

<400> SEQUENCE: 15
acctgcccct aatagggggcg acactccgcc atgaatcact cccctgtgag gaactactgt     60
cttcacgcag aaagcgccta gccatggcgt tagtatgagt gtcgtacagc ctccaggccc    120
cccctcccg ggagagccat agtggtctgc ggaaccggtg agtacaccgg aattgccggg    180
aagactgggt cctttcttgg ataaacccac tctatgcccg gccatttggg cgtgcccccg    240
caagactgct agccgagtag cgttgggttg cgaaaggcct tgtggtactg cctgataggg    300
cgcttgcgag tgccccggga ggtctcgtag accgtgcacc atgagcacga atcctaaacc    360
tcaaagaaaa accaaacgta acaccaaccg ccgcccaatg gacgttaagt tcccgggtgg    420
tggccagatc gttggcggag tttacttgtt gccgcgcagg ggcccagat tgggtgtgcg    480
cgcgactcgg aagacttcgg agcggtcgca acctcgtgga agacgccaac ctatccccaa    540
ggcgcgtcga cccgagggaa ggtcctgggc acaaccagga tatccatggc ctctttacgg    600
taatgagggt tgtgggtggg caggatggct cttgtccccc cgtggctctc gaccgtcttg    660
gggcccaaat gatccccggc ggaggtcccg caatttgggt aaggtcatcg atacctaac    720
ctgcggcttc gccgacctca tgggatacat cccgctcgta ggcgccccg tgggtggcgt    780
cgccagggcc ctggcacatg gtgtcagggc tttggaggac gggatcaatt atgcaacagg    840
gaatctcccc ggttgctcct tttctatctt cctcttggca cttctttcgt gcctgactgt    900
ccccgcttcg gccgttaact atcgcaatgt ctcgggcatc taccatgtca ccaatgactg    960
cccgaattca agcatagtgt atgagaccga ccatcacatc ttgcaccttc caggttgcgt   1020
gccctgcgtg agagagggga atcagtcacg ctgctgggtg gcccttactc ctaccgtcgc   1080
agcgccatac atcggcgcac cgcttgagtc cttacggagt catgtggatt tgatggtggg   1140
ggccgccact gtttgctcgg tctttacat cggggacctg tgtggcggct tgttcctagt   1200
tggccagatg tttcattcc gaccacggcg ccactggacc acccaggatt gcaattgttc   1260
catctacaca gggcacatta caggccacag aatggcctgg gacatgatga tgaactggag   1320
tccaacaacc accttagttc tcgcccaggt catgaggatc caaccactc tggtagactt   1380
actctctgga ggccactggg gtgtcctcgt gggagtggcc tatttcagca tgcaggccaa   1440
ttgggccaaa gtcatcttgg tcctattcct ctttgcaggg gttgatgccg agactcacgt   1500
```

```
gtctggggca gcagtcggcc ggagtaccgc cggcttggct aacctctttt cttctgggtc    1560
taagcagaat ttacagctca tcaacagcaa tgggagctgg catataaata ggactgccct    1620
taactgcaat gacagcttaa acactgggtt cttggctagc ttgttctaca cccacaagtt    1680
taacagctca gggtgttccg aacgctcgc gtgctgcaag agccttgaca gctacggcca     1740
aggctggggc ccactcgggg tcgctaacat cagcggctcg tctgatgaca ggccttattg    1800
ctggcactac gcgcctcggc cgtgcggat tgtgccagca tccagtgtgt gtggccccgt     1860
gtattgtttc actcccagcc ctgtcgtggt cggtactact gatcacgtcg gggtccctac    1920
ttacacctgg ggggagaatg agactgatgt cttccttttg aactcgacca gaccgccgca    1980
tggtgcgtgg tttggatgcg tgtggatgaa cagtaccggg ttcaccaaaa cctgtggcgc    2040
ccctccatgc gaggttaaca ccaataatgg gacctggcac tgccccaccg attgcttcag    2100
gaagcatccg gagactacct acgccaagtg cggatcaggg ccttggatca caccgcgctg    2160
cctgattgat tacccgtacc ggctgtggca tttcccgtgc accgcaaact tctccgtctt    2220
taacatcagg acatttgtcg gcggtataga gcatcggatg caagcggcat gcaactggac    2280
caggggggaa gtctgtggct tggagcacag ggatcgcgta gagctatcac ccctgctcct    2340
taccactaca gcgtggcaga tcctcccctg ctctttcacc actttacctg ccctctccac    2400
cggcttgatc cacctccacc aaaatatcgt ggacgtccag tacctctatg gtgttgggtc    2460
tgcagtggta tctgggccc ttaagtggga atatgtggtg ctcgcgttcc tgcttctcgc     2520
ggacgcgaga gtctctgcct gcctatggat gatgtttatg gtaagtcaag ttgaggcggc    2580
tctgtccaac ctgattaaca tcaatgctgc ttcagccgct ggtgcccaag gcttctggta    2640
cgccatcctc ttcatctgca ttgtctggca tgtcaagggc cggttcccag ctgctgctgc    2700
ctacgcagcc tgcgggctgt ggcccctgtt tctcctgctt ctgatgctgc tgagagggc     2760
ttatgcatac gaccaggaag tggcagggtc ccttggcggc ccatcgttg tcatgctggc     2820
cattctgaca ctgtctccgc actacaagtt atggctggct aggggattgt ggtggatcca    2880
atatttata gctaggaccg aggctgtgct gcatgtctat attccatcct tcaacgtgcg     2940
cgggcctcgc gactcagtga ttgttcttgc agtcctggtc tgtccacacc tagtatttga    3000
catcacaaaa tatcttctgg ccatcttagg gcccctccac atactccagg cctcgctcct    3060
acgcatccct tactttgtga gggcacaagc gctggttaag atctgcagct tgttgcgtgg    3120
ggtagtttat ggcaagtact tccaaatggt cgtgcttaaa gcaggggccc tgactggtac    3180
ttacatctat gaccacctta ctcccatgtc agattgggcc gctacgggcc tccgcgattt    3240
ggcggtggcc ctagagccag ttgtgttctc gcccatggag aagaaagtca tcgtctgggg    3300
cgctgacacc gctgcgtgcg gagacatcat aagggattac cctgtttcgg ccaggttggg    3360
caatgaaatc ttgctcggac cagccgatac agaaacatca aaggggtgga gactccttgc    3420
tcccatcact gcttatgccc agcaaacacg aggcctcctg ggcgccatag tggtgagtat    3480
gacggggcgt gacaggacag aacaggccgg ggaagtccaa atcctgtcca cagtctctca    3540
gtccttcctc ggaacaacca tctcgggggt tttgtggact gtttaccacg gagctggcaa    3600
caagactcta gccggcttac ggggtccggt cacgcagatg tactcgagtg ctgaggggga    3660
cttggtaggc tggcccagcc cccctgggac caagtctttg gagccgtgca agtgtggagc    3720
cgtcgaccta tatctggtca cgcggaacgc tgatgtcatc ccggctcgga acgcggggga    3780
caagcgggga gcattgctct ccccgagacc catttcgacc ttgaagggt cctcgggggg     3840
gccggtgctc tgccctaggg gccacgtcgt tgggctcttc cgagcagctg tgtgctctcg    3900
```

```
gggcgtggcc aaatccatcg atttcatccc cgttgagaca ctcgacgttg ttacaaggtc    3960
tcccactttc agtgacaaca gcacgccacc ggctgtgccc cagacctatc aggtcgggta    4020
cttgcatgct ccaactggca gtggaaagag caccaaggtc cctgtcgcgt atgccgccca    4080
ggggtacaaa gtactagtgc ttaacccctc ggtagctgcc accctggggt ttggggcgta    4140
cctatccaag gcacatggca tcaatcccaa cattaggact ggagtcagga ccgtgatgac    4200
cggggaggcc atcacgtact ccacatatgg caaatttctc gccgatgggg gctgcgctag    4260
cggcgcctat gacatcatca tatgcgatga atgccacgct gtggatgcta cctccattct    4320
cggcatcgga acggtccttg atcaagcaga gacagccggg gtcagactaa ctgtgctggc    4380
tacggccaca ccccccgggt cagtgacaac ccccatccc gatatagaag aggtaggcct    4440
cgggcgggag ggtgagatcc ccttctatgg gagggcgatt cccctatcct gcatcaaggg    4500
agggagacac ctgattttct gccactcaaa gaaaaagtgt gacgagctcg cggcggccct    4560
tcggggcatg ggcttgaatg ccgtggcata ctatagaggg ttggacgtct ccataatacc    4620
agctcaggga gatgtggtgg tcgtcgccac cgacgccctc atgacggggt acactggaga    4680
ctttgactcc gtgatcgact gcaatgtagc ggtcacccaa gctgtcgact tcagcctgga    4740
ccccaccttc actataacca cacagactgt cccacaagac gctgtctcac gcagtcagcg    4800
ccgcgggcgc acaggtagag gaagacaggg cacttatagg tatgtttcca ctggtgaacg    4860
agcctcagga atgtttgaca gtgtagtgct ttgtgagtgc tacgacgcag gggctgcgtg    4920
gtacgatctc acaccagcgg agaccaccgt caggcttaga gcgtatttca acacgccgg    4980
cctacccgtg tgtcaagacc atcttgaatt ttgggaggca gttttcaccg gcctcacaca    5040
catagacgcc cacttcctct cccaaacaaa gcaagcgggg gagaacttcg cgtacctagt    5100
agcctaccaa gctacggtgt gcgccagagc caaggcccct cccccgtcct gggacgccat    5160
gtggaagtgc ctggcccgac tcaagcctac gcttgcgggc cccacacctc tcctgtaccg    5220
tttgggccct attaccaatg aggtcaccct cacacaccct gggacgaagt catccgccac    5280
atgcatgcaa gctgaccttg aggtcatgac cagcacgtgg gtcctagctg gaggagtcct    5340
ggcagccgtc gccgcatatt gcctggcgac tggatgcgtt tccatcatcg gccgcttgca    5400
cgtcaaccag cgagtcgtcg ttgcgccgga taaggaggtc ctgtatgagg cttttgatga    5460
gatgaaggaa tgcgcctcta gggcggctct catcgaagag gggcagcgga tagccgagat    5520
gttgaagtcc aagatccaag gcttgctgca gcaggcctct aagcaggccc aggacataca    5580
acccgctatg caggcttcat ggcccaaagt ggaacaattt tgggccagac acatgtggaa    5640
cttcattagc ggcatccaat acctcgcagg attgtcaaca ctgccaggga accccgcggt    5700
ggcttccatg atggcattca gtgccgccct caccagtccg ttgtcgacca gtaccaccat    5760
ccttctcaac atcatgggag ctggttagc gtcccagatc gcaccacccg cggggccac    5820
cggctttgtc gtcagtggcc tggtgggggc tgccgtgggc agcataggcc tgggtaaggt    5880
gctggtggac atcctggcag atatggtgc gggcatttcg ggggccctcg tcgcattcaa    5940
gatcatgtct ggcgagaagc cctctatgga agatgtcatc aatctactgc ctgggatcct    6000
gtctccggga gccctggtgg tgggggtcat ctgcgcggcc attctgcgcc gccacgtggg    6060
accggggagg ggcgcggtcc aatgatgaa caggcttatt gcctttgctt ccagaggaaa    6120
ccacgtcgcc cctactcact acgtgacgga gtcggatgcg tcgcagcgtg tgacccaact    6180
acttggctct cttactataa ccagcctact cagaagactc cacaattgga taactgagga    6240
ctgccccatc ccatgctccg gatcctggct ccgcgacgtg tgggactggg tttgcaccat    6300
```

```
cttgacagac ttcaaaaatt ggctgacctc taaattgttc cccaagctgc ccggcctccc    6360
cttcatctct tgtcaaaagg ggtacaaggg tgtgtgggcc ggcactggca tcatgaccac    6420
gcgctgccct tgcggcgcca acatctctgg caatgtccgc ctgggctcta tgaggatcac    6480
agggcctaaa acctgcatga acacctggca ggggaccttt cctatcaatt gctacacgga    6540
gggccagtgc gcgccgaaac cccccacgaa ctacaagacc gccatctgga gggtggcggc    6600
ctcggagtac gcggaggtga cgcagcatgg gtcgtactcc tatgtaacag gactgaccac    6660
tgacaatctg aaaattcctt gccaactacc ttctccagag ttttctcct gggtggacgg    6720 tgtgcagatc cataggtttg cacccacacc aaagccgttt ttccgggatg aggtctcgtt    6780
ctgcgttggg cttaattcct atgctgtcgg gtcccagctt ccctgtgaac ctgagcccga    6840
cgcagacgta ttgaggtcca tgctaacaga tccgccccac atcacggcgg agactgcggc    6900
gcggcgcttg cacggggat cacctccatc tgaggcgagc tcctcagtga ccagctatc    6960 agcaccgtcg ctgcgggcca cctgcaccac ccacagcaac acctatgacg tggacatggt    7020
cgatgccaac ctgctcatgg agggcggtgt ggctcagaca gagcctgagt ccagggtgcc    7080
cgttctggac tttctcgagc caatggccga ggaagagagc gaccttgagc cctcaatacc    7140
atcggagtgc atgctcccca ggagcgggtt tccacgggcc ttaccggctt gggcacggcc    7200
tgactacaac ccgccgctcg tggaatcgtg gaggaggcca gattaccaac cgcccaccgt    7260
tgctggttgt gctctccccc ccccaagaa ggccccgacg cctcccccaa ggagacgccg    7320
gacagtgggt ctgagcgaga gcaccatatc agaagccctc cagcaactgg ccatcaagac    7380 cttggccag cccccctcga gcggtgatgc aggctcgtcc acggggcgg gcgccgccga    7440 atccggcggt ccgacgtccc ctggtgagcc ggcccctca gagacaggtt ccgcctcctc    7500 tatgccccc ctcgagggg agcctggaga tccggacctg gagtctgatc aggtagagct    7560
tcaacctccc cccaggggg ggggtagc tccggttcg ggctcgggt cttggtctac    7620 ttgctccgag gaggacgata ccaccgtgtg ctgctccatg tcatactcct ggaccggggc    7680
tctaataact ccctgtagcc ccgaagagga aaagttgcca atcaaccctt tgagtaactc    7740
gctgttgcga taccataaca aggtgtactg tacaacatca aagagcgcct cacagagggc    7800
taaaaaggta actttttgaca ggacgcaagt gctcgacgcc cattatgact cagtcttaaa    7860
ggacatcaag ctagcggctt ccaaggtcag cgcaaggctc ctcaccttgg aggaggcgtg    7920
ccagttgact ccaccccatt ctgcaagatc caagtatgga ttcggggcca aggaggtccg    7980
cagcttgtcc gggagggccg ttaaccacat caagtccgtg tggaaggacc tcctggaaga    8040
cccacaaaca ccaattccca caaccatcat ggccaaaaat gaggtgttct gcgtggaccc    8100
cgccaagggg gtaagaaac cagctcgcct catcgtttac cctgacctcg cgtccgggt    8160 ctgcgagaaa atggccctct atgacattac acaaaagctt cctcaggcgg taatgggagc    8220
ttcctatggc ttccagtact cccctgccca acggtggag tatctcttga agcatgggc    8280 ggaaaagaag gaccccatgg gtttttcgta tgatacccga tgcttcgact caaccgtcac    8340
tgagagagac atcaggaccg aggagtccat ataccaggcc tgctccctgc cgaggaggcc    8400
ccgcactgcc atacactcgc tgactgagag actttacgta ggagggccca tgttcaacag    8460
caagggtcaa acctgcggtt acagacgttg ccgcgcagc ggggtgctaa ccactagcat    8520
gggtaacacc atcacatgct atgtgaaagc cctagcggcc tgcaaggctg cggggatagt    8580
tgcgcccaca atgctggtat gcggcgatga cctagtagtc atctcagaaa gccagggac    8640 tgaggaggac gagcggaacc tgagagcctt cacggaggcc atgaccaggt actctgcccc    8700
```

```
tcctggtgat ccccccagac cggaatatga cctggagcta ataacatcct gttcctcaaa    8760
tgtgtctgtg gcgttgggcc cgcggggccg ccgcagatac tacctgacca gagacccaac    8820
cactccactc gcccgggctg cctgggaaac agttagacac tcccctatca attcatggct    8880
gggaaacatc atccagtatg ctccaaccat atgggttcgc atggtcctaa tgacacactt    8940
cttctccatt ctcatggtcc aagacaccct ggaccagaac ctcaactttg agatgtatgg    9000
atcagtatac tccgtgaatc ctttggacct tccagccata attgagaggt tacacgggct    9060
tgacgccttt tctatgcaca catactctca ccacgaactg acgcgggtgg cttcagccct    9120
cagaaaactt ggggcgccac ccctcagggt gtggaagagt cgggctcgcg cagtcagggc    9180
gtccctcatc tcccgtggag ggaaagcggc cgtttgcggc cgatatctct tcaattgggc    9240
ggtgaagacc aagctcaaac tcactccatt gccggaggcg cgcctactgg acttatccag    9300
ttggttcacc gtcggcgccg gcgggggcga catttttcac agcgtgtcgc gcgcccgacc    9360
ccgctcatta ctcttcggcc tactcctact tttcgtaggg gtaggcctct tcctactccc    9420
cgctcggtag agcggcacac actaggtaca ctccatagct aactgttcct ttttttttt    9480 tttttttttt tttttttttt tttttttttt ttctttttttt tttttttccc tcttcttcc    9540 cttctcatct tattctactt tctttcttgg tggctccatc ttagccctag tcacggctag    9600
ctgtgaaagg tccgtgagcc gcatgactgc agagagtgcc gtaactggtc tctctgcaga    9660
tcatgt                                                               9666
```

<210> SEQ ID NO 16
<211> LENGTH: 9666
<212> TYPE: DNA
<213> ORGANISM: Hepatitis C virus

<400> SEQUENCE: 16

```
acctgcccct aatagggggcg acactccgcc atgaatcact cccctgtgag gaactactgt    60
cttcacgcag aaagcgccta gccatggcgt tagtatgagt gtcgtacagc ctccaggccc    120 cccctcccg ggagagccat agtggtctgc ggaaccggtg agtacaccgg aattgccggg    180
aagactgggt cctttcttgg ataaacccac tctatgcccg gccatttggg cgtgcccccg    240
caagactgct agccgagtag cgttgggttg cgaaaggcct tgtggtactg cctgataggg    300
cgcttgcgag tgccccggga ggtctcgtag accgtgcacc atgagcacga atcctaaacc    360
tcaaagaaaa accaaacgta acaccaaccg ccgcccaatg gacgttaagt tcccgggtgg    420
tggccagatc gttggcggag tttacttgtt gccgcgcagg ggcccagat gggtgtgcg    480 cgcgactcgg aagacttcgg agcggtcgca acctcgtgga agacgccaac ctatccccaa    540
ggcgcgtcga cccgagggaa ggtcctgggc acaaccagga tatccatggc ctctttacgg    600
taatgagggt tgtgggtggg caggatggct cttgtccccc cgtggctctc gaccgtcttg    660
gggcccaaat gatccccggc ggaggtcccg caatttgggt aaggtcatcg atacccctaac   720 ctgcggcttc gccgacctca tgggatacat cccgctcgta ggcgccccg tgggtggcgt    780 cgccagggcc ctggcacatg gtgtcagggc tttggaggac gggatcaatt atgcaacagg    840
gaatctcccc ggttgctcct tttctatctt cctcttggca cttctttcgt gcctgactgt    900
ccccgcttcg gccgttaact atcgcaatgt ctcgggcatc taccatgtca ccaatgactg    960
cccgaattca agcatagtgt atgaggccga ccatcacatc ttgcaccttc caggttgcgt    1020
gccctgcgtg agagagggga atcagtcacg ctgctgggtg gcccttactc ctaccgtcgc    1080
agcgccatac atcggcgcac cgcttgagtc cttacggagt catgtggatt tgatggtggg    1140
```

```
ggccgccact gtttgctcgg gtctttacat cggggacctg tgtggcggct tgttcctagt    1200
tggccagatg ttttcattcc gaccacggcg ccactggacc acccaggatt gcaattgttc    1260
catctacaca gggcacatta caggccacag aatggcctgg acatgatga tgaactggag     1320
tccaacaacc accttagttc tcgcccaggt catgaggatc ccaaccactc tggtagactt    1380
actctctgga ggccactggg gtgtcctcgt gggagtggcc tatttcagca tgcaggccaa    1440
ttgggccaaa gtcatcttgg tcctattcct ctttgcaggg gttgatgccg agactcacgt    1500
gtctggggca gcagtcggcc ggagtaccgc cggcttggct aacctctttt cttctgggtc    1560
taagcagaat ttacagctca tcaacagcaa tgggagctgg catataaata ggactgccct    1620
taactgcaat gacagcttaa acactgggtt cttggctagc ttgttctaca cccacaagtt    1680
taacagctca gggtgttccg aacggctcgc gtgctgcaag agccttgaca gctacggcca    1740
aggctggggc ccactcgggg tcgctaacat cagcggctcg tctgatgaca ggccttattg    1800
ctggcactac gcgcctcggc cgtgcgggat tgtgccagca tccagtgtgt gtggcccgt     1860
gtattgtttc actcccagcc ctgtcgtggt cggtactact gatcacgtcg gggtccctac    1920
ttacacctgg ggggagaatg agactgatgt cttccttttg aactcgacca gaccgccgca    1980
tggtgcgtgg tttggatgcg tgtggatgaa cagtaccggg ttcaccaaaa cctgtggcgc    2040
ccctccatgc gaggttaaca ccaataatgg gacctggcac tgccccaccg attgcttcag    2100
gaagcatccg gagactacct acgccaagtg cggatcaggg ccttggatca caccgcgctg    2160
cctgattgat tacccgtacc ggctgtggca tttcccgtgc accgcaact tctccgtctt     2220
taacatcagg acatttgtcg gcggtataga gcatcggatg caagcggcat gcaactggac    2280
caggggggaa gtctgtggct tggagcacag ggatcgcgta gagctatcac ccctgctcct    2340
taccactaca gcgtggcaga tcctcccctg ctctttcacc actttacctg ccctctccac    2400
cggcttgatc cacctccacc aaaatatcgt ggacgtccag tacctctatg gtgttgggtc    2460
tgcagtggta tcttgggccc ttaagtggga atatgtggtg ctcgcgttcc tgcttctcgc    2520
ggacgcgaga gtctctgcct gcctatggat gatgtttatg gtaagtcaag ttgaggcggc    2580
tctgtccaac ctgattaaca tcaatgctgc ttcagccgct ggtgcccaag gcttctggta    2640
cgccatcctc ttcatctgca ttgtctggca tgtcaagggc cggttcccag ctgctgctgc    2700
ctacgcagcc tgcgggctgt ggccccctgtt tctcctgctt ctgatgctgc tgagagggc    2760
ttatgcatac gaccaggaag tggcagggtc ccttggcggc gccatcgttg tcatgctggc    2820
cattctgaca ctgtctccgc actacaagtt atggctggct aggggattgt ggtggatcca    2880
atattttata gctaggaccg aggctgtgct gcatgtctat attccatcct tcaacgtgcg    2940
cggcctcgc gactcagtga ttgttcttgc agtcctggtc tgtccacacc tagtatttga     3000
catcacaaaa tatcttctgg ccatcttagg gccccctccac atactccagg cctcgctcct    3060
acgcatccct tactttgtga gggcacaagc gctggttaag atctgcagct tgttgcgtgg    3120
ggtagtttat ggcaagtact ccaaatggt cgtgcttaaa gcaggggccc tgactggtac      3180
ttacatctat gaccacctta ctcccatgtc agattgggcc gctacgggcc tccgcgattt    3240
ggcggtggcc ctagagccag ttgtgttctc gcccatggag aagaaagtca tcgtctgggg    3300
cgctgacacc gctgcgtgcg gagacatcat aaggggatta cctgtttcgg ccaggttggg    3360
caatgaaatc ttgctcggac cagccgatac agaaacatca aaggggtgga gactccttgc    3420
tcccatcact gcttatgccc agcaaacacg aggcctcctg ggcgccatag tggtgagtat    3480
gacggggcgt gacaggacag aacaggccgg ggaagtccaa atcctgtcca cagtctctca    3540
```

```
gtccttcctc ggaacaacca tctcgggggt tttgtggact gtttaccacg gagctggcaa    3600
caagactcta gccggcttac ggggtccggt cacgcagatg tactcgagtg ctgagggga     3660 cttggtaggc tggcccagcc ccctgggac caagtctttg gagccgtgca agtgtggagc    3720
cgtcgaccta tatctggtca cgcggaacgc tgatgtcatc ccggctcgga gacgcgggga   3780
caagcgggga gcattgctct ccccgagacc catttcgacc ttgaaggggt cctcgggggg   3840
gccggtgctc tgccctaggg gccacgtcgt tgggctcttc cgagcagctg tgtgctctcg   3900
gggcgtggcc aaatccatcg atttcatccc cgttgagaca ctcgacgttg ttacaaggtc   3960
tcccactttc agtgacaaca gcacgccacc ggctgtgccc cagacctatc aggtcgggta   4020
cttgcatgct ccaactggca gtggaaagag caccaaggtc cctgtcgcgt atgccgccca   4080
ggggtacaaa gtactagtgc ttaacccctc ggtagctgcc accctgggt ttggggcgta    4140 cctatccaag gcacatggca tcaatcccaa cattaggact ggagtcagga ccgtgatgac   4200
cggggaggcc atcacgtact ccacatatgg caaatttctc gccgatgggg gctgcgctag   4260
cggcgcctat gacatcatca tatgcgatga atgccacgct gtggatgcta cctccattct   4320
cggcatcgga acggtccttg atcaagcaga gacagccggg gtcagactaa ctgtgctggc   4380 tacgccaca ccccccgggt cagtgacaac ccccatccc gatatagaag aggtaggcct     4440
cgggcgggag ggtgagatcc ccttctatgg gagggcgatt ccctatcct gcatcaaggg    4500 agggagacac ctgattttct gccactcaaa gaaaagtgt gacgagctcg cggcggccct    4560
tcggggcatg gcttgaatg ccgtggcata ctatagaggg ttggacgtct ccataatacc    4620
agctcaggga gatgtggtgg tcgtcgccac cgacgccctc atgacggggt acactggaga   4680
ctttgactcc gtgatcgact gcaatgtagc ggtcacccaa gctgtcgact tcagcctgga   4740
ccccaccttc actataacca cacagactgt cccacaagac gctgtctcac gcagtcagcg   4800
ccgcgggcgc acaggtagag gaagacaggg cacttatagg tatgtttcca ctggtgaacg   4860
agcctcagga atgtttgaca gtgtagtgct ttgtgagtgc tacgacgcag ggctgcgtg    4920 gtacgatctc acaccagcgg agaccaccgt caggcttaga gcgtatttca acacgcccgg   4980
cctacccgtg tgtcaagacc atcttgaatt ttgggaggca gttttcaccg gcctcacaca   5040
catagacgcc cacttcctct cccaaacaaa gcaagcgggg gagaacttcg cgtacctagt   5100
agcctaccaa gctacggtgt gcgccagagc caaggcccct ccccgtcct gggacgccat    5160 gtggaagtgc ctggcccgac tcaagcctac gcttgcgggc cccacacctc tcctgtaccg   5220
tttgggccct attaccaatg aggtcacct cacacaccct gggacgaagt acatcgccac    5280
atgcatgcaa gctgaccttg aggtcatgac cagcacgtgg gtcctagctg gaggagtcct   5340
ggcagccgtc gccgcatatt gcctggcgac tggatgcgtt tccatcatcg gccgcttgca   5400
cgtcaaccag cgagtcgtcg ttgcgccgga taaggaggtc ctgtatgagg cttttgatga   5460
gatggaggaa tgcgcctcta gggcggctct catcgaagag gggcagcgga tagccgagat   5520
gttgaagtcc aagatccaag gcttgctgca gcaggcctct aagcaggccc aggacataca   5580
acccgctatg caggcttcat ggcccaaagt ggaacaattt tgggcagac acatgtggaa    5640 cttcattagc ggcatccaat acctcgcagg attgtcaaca ctgccaggga ccccgcggt    5700 ggcttccatg atggcattca gtgccgccct caccagtccg ttgtcgacca gtaccaccat   5760
ccttctcaac atcatgggag ctggttagc gtcccagatc gcaccaccg cggggggccac   5820 cggctttgtc gtcagtggcc tggtgggggc tgccgtgggc agcataggcc tgggtaaggt   5880
gctggtggac atcctggcag gatatggtgc gggcatttcg ggggccctcg tcgcattcaa   5940
```

```
gatcatgtct ggcgagaagc cctctatgga agatgtcatc aatctactgc ctgggatcct    6000
gtctccggga gccctggtgg tgggggtcat ctgcgcggcc attctgcgcc gccacgtggg    6060
accgggggag ggcgcggtcc aatggatgaa caggcttatt gcctttgctt ccagaggaaa    6120
ccacgtcgcc cctactcact acgtgacgga gtcggatgcg tcgcagcgtg tgacccaact    6180
acttggctct cttactataa ccagcctact cagaagactc cacaattgga taactgagga    6240
ctgccccatc ccatgctccg gatcctggct ccgcgacgtg tgggactggg tttgcaccat    6300
cttgacagac ttcaaaaatt ggctgacctc taaattgttc cccaagctgc ccggcctccc    6360
cttcatctct tgtcaaaagg ggtacaaggg tgtgtgggcc ggcactggca tcatgaccac    6420
gcgctgccct tgcggcgcca acatctctgg caatgtccgc ctgggctcta tgaggatcac    6480
agggcctaaa acctgcatga acacctgcca ggggacctt cctatcaatt gctacacgga    6540
gggccagtgc gcgccgaaac cccccacgaa ctacaagacc gccatctgga gggtggcggc    6600
ctcggagtac gcggaggtga cgcagcatgg gtcgtactcc tatgtaacag gactgaccac    6660
tgacaatctg aaaattcctt gccaactacc ttctccagag ttttttctcct gggtggacgg    6720 tgtgcagatc cataggtttg cacccacacc aaagccgttt ttccgggatg aggtctcgtt    6780
ctgcgttggg cttaattcct atgctgtcgg gtcccagctt ccctgtgaac ctgagcccga    6840
cgcagacgta ttgaggtcca tgctaacaga tccgccccac atcacggcgg agactgcggc    6900
gcggcgcttg gcacggggat cacctccatc tgaggcgagc tcctcagtga gccagctatc    6960
agcaccgtcg ctgcgggcca cctgcaccac ccacagcaac acctatgacg tggacatggt    7020
cgatgccaac ctgctcatgg agggcggtgt ggctcagaca gagcctgagt ccagggtgcc    7080
cgttctggac tttctcgagc caatggccga ggaagagagc gaccttgagc cctcaatacc    7140
atcggagcgc atgctcccca ggagcgggtt tccacgggcc ttaccggctt gggcacggcc    7200
tgactacaac ccgccgctcg tggaatcgtg gaggaggcca gattaccaac cgcccaccgt    7260
tgctggttgt gctctccccc cccccaagaa ggccccgacg cctcccccaa ggagacgccg    7320
gacagtgggt ctgagcgaga gcaccatatc agaagccctc cagcaactgg ccatcaagac    7380
ctttggccag cccccctcga gcggtgatgc aggctcgtcc acggggcgg gcgccgccga    7440 atccggcggt ccgacgtccc ctggtgagcc ggcccctca gagacaggtt ccgcctcctc    7500 tatgccccc ctcgagggg agcctggaga tccggacctg gagtctgatc aggtagagct    7560
tcaacctccc ccccagggg ggggggtagc tcccggttcg ggctcggggt cttggtctac    7620
ttgctccgag gaggacgata ccaccgtgtg ctgctccatg tcatactcct ggaccggggc    7680
tctaataact ccctgtagcc ccgaagagga aaagttgcca atcaacccctt tgagtaactc    7740 gctgttgcga taccataaca aggtgtactg tacaacatca aagagcgcct cacagagggc    7800
taaaaaggta acttttgaca ggacgcaagt gctcgacgcc cattatgact cagtcttaaa    7860
ggacatcaag ctagcggctt ccaaggtcag cgcaaggctc ctcaccttgg aggaggcgtg    7920
ccagttgact ccaccccatt ctgcaagatc caagtatgga ttcgggcca aggaggtccg    7980 cagcttgtcc gggagggccg ttaaccacat caagtccgtg tggaaggacc tcctggaaga    8040
cccacaaaca ccaattccca caaccatcat ggccaaaaat gaggtgttct gcgtggaccc    8100
cgccaagggg ggtaagaaac cagctcgcct catcgtttac cctgacctcg gcgtccgggt    8160
ctgcgagaaa atggccctct atgacattac acaaaagctt cctcaggcgg taatgggagc    8220
ttcctatggc ttccagtact cccctgccca acgggtggag tatctcttga agcatgggc    8280 ggaaaagaag gaccccatgg gttttttcgta tgatacccga tgcttcgact caaccgtcac    8340
```

```
tgagagagac atcaggaccg aggagtccat ataccaggcc tgctccctgc ccgaggaggc    8400
ccgcactgcc atacactcgc tgactgagag actttacgta ggagggccca tgttcaacag    8460
caagggtcaa acctgcggtt acagacgttg ccgcgccagc ggggtgctaa ccactagcat    8520
gggtaacacc atcacatgct atgtgaaagc cctagcggcc tgcaaggctg cggggatagt    8580
tgcgcccaca atgctggtat gcggcgatga cctagtagtc atctcagaaa gccaggggac    8640
tgaggaggac gagcggaacc tgagagcctt cacggaggcc atgaccaggt actctgcccc    8700
tcctggtgat ccccccagac cggaatatga cctggagcta ataacatcct gttcctcaaa    8760
tgtgtctgtg gcgttgggcc cgcggggccg ccgcagatac tacctgacca gagacccaac    8820
cactccactc gcccgggctg cctgggaaac agttagacac tcccctatca attcatggct    8880
gggaaacatc atccagtatg ctccaaccat atgggttcgc atggtcctaa tgacacactt    8940
cttctccatt ctcatggtcc aagacaccct ggaccagaac ctcaactttg agatgtatgg    9000
atcagtatac tccgtgaatc cttttggacct tccagccata attgagaggt tacacgggct    9060
tgacgccttt tctatgcaca catactctca ccacgaactg acgcgggtgg cttcagccct    9120
cagaaaactt ggggcgccac ccctcagggt gtggaagagt cgggctcgcg cagtcagggc    9180
gtccctcatc tcccgtggag ggaaagcggc cgtttgcggc cgatatctct tcaattgggc    9240
ggtgaagacc aagctcaaac tcactccatt gccggaggcg cgcctactgg acttatccag    9300
ttggttcacc gtcggcgccg gcgggggcga catttttcac agcgtgtcgc gcgcccgacc    9360
ccgctcatta ctcttcggcc tactcctact tttcgtaggg gtaggcctct tcctactccc    9420
cgctcggtag agcggcacac actaggtaca ctccatagct aactgttcct ttttttttt    9480 tttttttttt tttttttttt tttttttttt tcttttttt tttttttccc tctttcttcc    9540
cttctcatct tattctactt tctttcttgg tggctccatc ttagccctag tcacggctag    9600
ctgtgaaagg tccgtgagcc gcatgactgc agagagtgcc gtaactggtc tctctgcaga    9660
tcatgt                                                               9666
```

<210> SEQ ID NO 17
<211> LENGTH: 9666
<212> TYPE: DNA
<213> ORGANISM: Hepatitis C virus

<400> SEQUENCE: 17

```
acctgcccct aatagggccg acactccgcc atgaatcact cccctgtgag gaactactgt     60
cttcacgcag aaagcgccta gccatggcgt tagtatgagt gtcgtacagc ctccaggccc    120 cccctcccg ggagagccat agtggtctgc ggaaccggtg agtacaccgg aattgccggg    180
aagactgggt cctttcttgg ataaacccac tctatgcccg gccatttggg cgtgcccccg    240
caagactgct agccgagtag cgttgggttg cgaaaggcct tgtggtactg cctgataggg    300
cgcttgcgag tgccccggga ggtctcgtag accgtgcacc atgagcacga atcctaaacc    360
tcaaagaaaa accaaacgta acaccaaccg ccgcccaatg gacgttaagt tcccgggtgg    420
tggccagatc gttggcggag tttacttgtt gccgcgcagg ggcccagat tgggtgtgcg    480 cgcgactcgg aagacttcgg agcggtcgca acctcgtgga agacgccaac ctatccccaa    540
ggcgcgtcga cccgagggaa ggtcctgggc acaaccagga tatccatggc ctctttacgg    600
taatgagggt tgtgggtggg caggatggct cttgtccccc cgtggctctc gaccgtcttg    660
gggcccaaat gatccccggc ggaggtcccg caatttgggt aaggtcatcg ataccctaac    720
ctgcggcttc gccgacctca tgggatacat cccgctcgta ggcgccccg tgggtggcgt    780
```

-continued

| | |
|---|---|
| cgccagggcc ctggcacatg gtgtcagggc tttggaggac gggatcaatt atgcaacagg | 840 |
| gaatctcccc ggttgctcct tttctatctt cctcttggca cttctttcgt gcctgactgt | 900 |
| ccccgcttcg gccgttaact atcgcaatgt ctcgggcatc taccatgtca ccaatgactg | 960 |
| cccgaattca agcatagtgt atgagaccga ccatcacatc ttgcaccttc caggttgcgt | 1020 |
| gccctgcgtg agagagggga atcagtcacg ctgctgggtg gcccttactc ctaccgtcgc | 1080 |
| agcgccatac atcggcgcac cgcttgagtc cttacggagt catgtggatt tgatggtggg | 1140 |
| ggccgccact gtttgctcgg gtctttacat cggggacctg tgtggcggct tgttcctagt | 1200 |
| tggccagatg ttttcattcc gaccacggcg ccactggacc acccaggatt gcaattgttc | 1260 |
| catctacaca gggcacatta caggccacag aatggcctgg gacatgatga tgaactggag | 1320 |
| tccaacaacc accttagttc tcgcccaggt catgaggatc ccaaccactc tggtagactt | 1380 |
| actctctgga ggccactggg gtgtcctcgt gggagtggcc tatttcagca tgcaggccaa | 1440 |
| ttgggccaaa gtcatcttgg tcctattcct ctttgcaggg gttgatgccg agactcacgt | 1500 |
| gtctggggca gcagtcggcc ggagtaccgc cggcttggct aacctctttt cttctgggtc | 1560 |
| taagcagaat ttacagctca tcaacagcaa tgggagctgg catataaata ggactgccct | 1620 |
| taactgcaat gacagcttaa acactgggtt cttggctagc ttgttctaca cccacaagtt | 1680 |
| taacagctca gggtgttccg aacggctcgc gtgctgcaag agccttgaca gctacggcca | 1740 |
| aggctggggc ccactcgggg tcgctaacat cagcggctcg tctgatgaca ggccttattg | 1800 |
| ctggcactac gcgcctcggc cgtgcgggat tgtgccagca tccagtgtgt gtggccccgt | 1860 |
| gtattgtttc actcccagcc ctgtcgtggt cggtactact gatcacgtcg gggtccctac | 1920 |
| ttacacctgg ggggagaatg agactgatgt cttcctttg aactcgacca gaccgccgca | 1980 |
| tggtgcgtgg tttggatgcg tgtggatgaa cagtaccggg ttcaccaaaa cctgtggcgc | 2040 |
| ccctccatgc gaggttaaca ccaataatgg gacctggcac tgccccaccg attgcttcag | 2100 |
| gaagcatccg gagactacct acgccaagtg cggatcaggg ccttggatca caccgcgctg | 2160 |
| cctgattgat tacccgtacc ggctgtggca tttcccgtgc accgccaact tctccgtctt | 2220 |
| taacatcagg acatttgtcg gcggtataga gcatcggatg caagcggcat gcaactggac | 2280 |
| caggggggaa gtctgtggct tggagcacag ggatcgcgta gagctatcac ccctgctcct | 2340 |
| taccactaca gcgtggcaga tcctcccctg ctctttcacc actttacctg ccctctccac | 2400 |
| cggcttgatc cacctccacc aaaatatcgt ggacgtccag tacctctatg tgttgggtc | 2460 |
| tgcagtggta tcttgggccc ttaagtggga atatgtggtg ctcgcgttcc tgcttctcgc | 2520 |
| ggacgcgaga gtctctgcct gcctatggat gatgtttatg gtaagtcaag ttgaggcggc | 2580 |
| tctgtccaac ctgattaaca tcaatgctgc ttcagccgct ggtgcccaag gcttctggta | 2640 |
| cgccatcctc ttcatctgca ttgtctggca tgtcaagggc cggttcccag ctgctgctgc | 2700 |
| ctacgcagcc tgcgggctgt ggcccctgtt tctcctgctt ctgatgctgc tgagagggc | 2760 |
| ttatgcatac gaccaggaag tggcagggtc ccttggcggc gccatcgttg tcatgctggc | 2820 |
| cattctgaca ctgtctccgc actacaagtt atggctggct aggggattgt ggtgatcca | 2880 |
| atatttata gctaggaccg aggctgtgct gcatgtctat attccatcct tcaacgtgcg | 2940 |
| cgggcctcgc gactcagtga ttgttcttgc agtcctggtc tgtccacacc tagtatttga | 3000 |
| catcacaaaa tatcttctgg ccatcttagg gccccctcca atactccagg cctcgctcct | 3060 |
| acgcatccct tactttgtga gggcacaagc gctggtaag atctgcagct tgttgcgtgg | 3120 |
| ggtagtttat ggcaagtact tccaaatggt cgtgcttaaa gcaggggccc tgactggtac | 3180 |

```
ttacatctat gaccacctta ctcccatgtc agattgggcc gctacgggcc tccgcgattt   3240
ggcggtggcc ctagagccag ttgtgttctc gcccatggag aagaaagtca tcgtctgggg   3300
cgctgacacc gctgcgtgcg gagacatcat aaggggatta cctgtttcgg ccaggttggg   3360
caatgaaatc ttgctcggac cagccgatac agaaacatca aaggggtgga gactccttgc   3420
tcccatcact gcttatgccc agcaaacacg aggcctcctg ggcgccatag tggtgagtat   3480
gacggggcgt gacaggacag aacaggccgg ggaagtccaa atcctgtcca cagtctctca   3540
gtccttcctc ggaacaacca tctcgggggt tttgtggact gtttaccacg gagctggcaa   3600
caagactcta gccggcttac ggggtccggt cacgcagatg tactcgagtg ctgaggggga   3660
cttggtaggc tggcccagcc ccctgggac caagtctttg gagccgtgca agtgtggagc   3720
cgtcgaccta tatctggtca gcggaaacgc tgatgtcatc ccggctcgga gacgcgggga   3780
caagcgggga gcattgctct ccccgagacc catttcgacc ttgaagggt cctcgggggg    3840 gccggtgctc tgccctaggg gccacgtcgt tgggctcttc cgagcagctg tgtgctctcg   3900
gggcgtggcc aaatccatcg atttcatccc cgttgagaca ctcgacgttg ttacaaggtc   3960
tcccactttc agtgacaaca gcacgccacc ggctgtgccc cagacctatc aggtcgggta   4020
cttgcatgct ccaactggca gtggaaagag caccaaggtc cctgtcgcgt atgccgccca   4080
ggggtacaaa gtactagtgc ttaacccctc ggtagctgcc accctggggt ttggggcgta   4140
cctatccaag gcacatggca tcaatcccaa cattaggact ggagtcagga ccgtgatgac   4200
cggggaggcc atcacgtact ccacatatgg caaatttctc gccgatgggg gctgcgctag   4260
cggcgcctat gacatcatca tatgcgatga atgccacgct gtggatgcta cctccattct   4320
cggcatcgga acggtccttg atcaagcaga gacagccggg gtcagactaa ctgtgctggc   4380
tacgcccaca cccccccggt cagtgacaac cccccatccc gatatagaag aggtaggcct   4440
cgggcgggag ggtgagatcc ccttctatgg gagggcgatt cccctatcct gcatcaaggg   4500
agggagacac ctgatttct gccactcaaa gaaaaagtgt gacgagctcg cggcggccct    4560
tcggggcatg ggcttgaatg ccgtggcata ctatagaggg ttggacgtct ccataatacc   4620
agctcaggga gatgtggtgg tcgtcgccac cgacgcccct atgacggggt acactggaga   4680 cttttgactcc gtgatcgact gcaatgtagc ggtcacccaa gctgtcgact tcagcctgga   4740
cccccacttc actataacca cacagactgt cccacaagac gctgtctcac gcagtcagcg   4800
ccgcgggcgc acaggtagag gaagacaggg cacttatagg tatgtttcca ctggtgaacg   4860
agcctcagga atgtttgaca gtgtagtgct ttgtgagtgc tacgacgcag gggctgcgtg   4920
gtacgatctc acaccagcgg agaccaccgt caggcttaga gcgtatttca acacgcccgg   4980
cctacccgtg tgtcaagacc atcttgaatt ttgggaggca gttttcaccg gcctcacaca   5040
catagacgcc cacttcctct cccaaacaaa gcaagcgggg gagaacttcg cgtacctagt   5100
agcctaccaa gctacggtgt gcgccagagc caaggcccct cccccgtcct gggacgccat   5160
gtggaagtgc ctggcccgac tcaagcctac gcttgcgggc cccacacctc tcctgtaccg   5220
tttgggccct attaccaatg aggtcaccct cacacaccct gggacgaagt acatcgccac   5280
atgcatgcaa gctgaccttg aggtcatgac cagcacgtgg gtcctagctg gaggagtcct   5340
ggcagccgtc gccgcatatt gcctggcgac tggatgcgtt tccatcatcg gccgcttgca   5400
cgtcaaccag cgagtcgtcg ttgcgccgga taaggaggtc ctgtatgagg cttttgatga   5460
gatggaggaa tgcgcctcta gggcggctct catcgaagag gggcagcgga tagccgagat   5520
gttgaagtcc aagatccaag gcttgctgca gcaggcctct aagcaggccc aggacataca   5580
```

```
acccgctatg caggcttcat ggcccaaagt ggaacaattt tgggccagac acatgtggaa    5640
cttcattagc ggcatccaat acctcgcagg attgtcaaca ctgccaggga accccgcggt    5700
ggcttccatg atggcattca gtgccgccct caccagtccg ttgtcgacca gtaccaccat    5760
ccttctcaac atcatgggag gctggttagc gtcccagatc gcaccacccg cgggggccac    5820
cggctttgtc gtcagtggcc tggtgggggc tgccgtgggc agcataggcc tgggtaaggt    5880
gctggtggac atcctggcag gatatggtgc gggcatttcg ggggccctcg tcgcattcaa    5940
gatcatgtct ggcgagaagc cctctatgga agatgtcatc aatctactgc tgggatcct    6000
gtctccggga gccctggtgg tggggtcat ctgcgcggcc attctgcgcc gccacgtggg    6060
accgggggag ggcgcggtcc aatggatgaa caggcttatt gcctttgctt ccagaggaaa    6120
ccacgtcgcc cctactcact acgtgacgga gtcggatgcg tcgcagcgtg tgacccaact    6180
acttggctct cttactataa ccagcctact cagaagactc cacaattgga taactgagga    6240
ctgccccatc ccatgctccg gatcctggct ccgcgacgtg tgggactggg tttgcaccat    6300
cttgacagac ttcaaaaatt ggctgacctc taaattgttc cccaagctgc ccggcctccc    6360
cttcatctct tgtcaaaagg ggtacaaggg tgtgtgggcc ggcactggca tcatgaccac    6420
gcgctgccct tgcggcgcca acatctctgg caatgtccgc ctgggctcta tgaggatcac    6480
agggcctaaa acctgcatga acacctggca ggggacctt cctatcaatt gctacacgga    6540
gggccagtgc gcgccgaaac cccccacgaa ctacaagacc gccatctgga gggtggcggc    6600
ctcggagtac gcggaggtga cgcagcatgg gtcgtactcc tatgtaacag gactgaccac    6660
tgacaatctg aaaattcctt gccaactacc ttctccagag tttttctcct gggtggacgg    6720
tgtgcagatc cataggtttg cacccacacc aaagccgttt ttccgggatg aggtctcgtt    6780
ctgcgttggg cttaattcct atgctgtcgg gtcccagctt ccctgtgaac ctgagcccga    6840
cgcagacgta ttgaggtcca tgctaacaga tccgccccac atcacggcgg agactgcggc    6900
gcggcgcttg gcacggggat cacctccatc tgaggcgagc tcctcagtga gccagctatc    6960
agcaccgtcg ctgcgggcca cctgcaccac ccacagcaac acctatgacg tggacatggt    7020
cgatgccaac ctgctcatgg agggcggtgt ggctcagaca gagcctgagt ccagggtgcc    7080
cgttctggac tttctcgagc caatggccga ggaagagagc gaccttgagc cctcaatacc    7140
atcggagcgc atgctcccca ggagcgggtt tccacgggcc ttaccggctt gggcacggcc    7200
tgactacaac ccgccgctcg tggaatcgtg gaggaggcca gattaccaac cgcccaccgt    7260
tgctggttgt gctctccccc cccccaagaa ggccccgacg cctccccaa ggagacgccg    7320
gacagtgggt ctgagcgaga gcaccatatc agaagccctc cagcaactgg ccatcaagac    7380
cttggccag cccccctcga gcggtgatgc aggctcgtcc acggggcgg gcgccgccga    7440
atccggcggt ccgacgtccc ctggtgagcc ggccccctca gagacaggtt ccgcctcctc    7500
tatgccccc ctcgagggg agcctggaga tccggacctg gagtctgatc aggtagagct    7560
tcaacctccc cccaggggg gggggtagc tcccggttcg ggctcggggt cttggtctac    7620
ttgctccgag gaggacgata ccaccgtgtg ctgctccatg tcatactcct ggaccggggc    7680
tctaataact ccctgtagcc ccgaagagga aaagttgcca atcaacccct tgagtaactc    7740
gctgttgcga taccataaca aggtgtactg tacaacatca aagagcgcct cacagagggc    7800
taaaaaggta acttttgaca ggacgcaagt gctcgacgcc cattatgact cagtcttaaa    7860
ggacatcaag ctagcggctt ccaaggtcag cgcaaggctc tcaccttgg aggaggcgtg    7920
ccagttgact ccaccccatt ctgcaagatc caagtatgga ttcggggcca aggaggtccg    7980
```

-continued

```
cagcttgtcc gggagggccg ttaaccacat caagtccgtg tggaaggacc tcctggaaga    8040
cccacaaaca ccaattccca caaccatcat ggccaaaaat gaggtgttct gcgtggaccc    8100
cgccaagggg ggtaagaaac cagctcgcct catcgtttac cctgacctcg cgtccgggt    8160
ctgcgagaaa atggccctct atgacattac acaaaagctt cctcaggcgg taatgggagc    8220
ttcctatggc ttccagtact cccctgccca acgggtggag tatctcttga agcatgggc    8280
ggaaaagaag gaccccatgg ttttttcgta tgatacccga tgcttcgact caaccgtcac    8340
tgagagagac atcaggaccg aggagtccat ataccaggcc tgctccctgc ccgaggaggc    8400
ccgcactgcc atacactcgc tgactgagag actttacgta ggagggccca tgttcaacag    8460
caagggtcaa acctgcggtt acagacgttg ccgcgccagc ggggtgctaa ccactagcat    8520
gggtaacacc atcacatgct atgtgaaagc cctagcggcc tgcaaggctg cggggatagt    8580
tgcgcccaca atgctggtat gcggcgatga cctagtagtc atctcagaaa gccaggggac    8640
tgaggaggac gagcggaacc tgagagcctt cacggaggcc atgaccaggt actctgcccc    8700
tcctggtgat ccccccagac cggaatatga cctggagcta ataacatcct gttcctcaaa    8760
tgtgtctgtg gcgttgggcc cgcggggccg ccgcagatac tacctgacca gagacccaac    8820
cactccactc gcccgggctg cctgggaaac agttagacac tcccctatca attcatggct    8880
gggaaacatc atccagtatg ctccaaccat atgggttcgc atggtcctaa tgacacactt    8940
cttctccatt ctcatggtcc aagacaccct ggaccagaac ctcaactttg agatgtatgg    9000
atcagtatac tccgtgaatc ctttggacct tccagccata attgagaggt acacgggct    9060
tgacgccttt tctatgcaca catactctca ccacgaactg acgcgggtgg cttcagccct    9120
cagaaaactt ggggcgccac ccctcagggt gtggaagagt cgggctcgcg cagtcagggc    9180
gtccctcatc tcccgtggag ggaaagcggc cgtttgcggc cgatatctct tcaattgggc    9240
ggtgaagacc aagctcaaac tcactccatt gccggaggcg cgcctactgg acttatccag    9300
ttggttcacc gtcggcgccg gcgggggcga catttttcac agcgtgtcgc gcgcccgacc    9360
ccgctcatta ctcttcggcc tactccact tttcgtaggg gtaggcctct tcctactccc    9420
cgctcggtag agcggcacac actaggtaca ctccatagct aactgttcct tttttttttt    9480
tttttttttt tttttttttt tttttttttt ttctttttttt ttttttttcc tctttcttcc    9540
cttctcatct tattctactt tctttcttgg tggctccatc ttagccctag tcacggctag    9600
ctgtgaaagg tccgtgagcc gcatgactgc agagagtgcc gtaactggtc tctctgcaga    9660
tcatgt                                                                 9666
```

<210> SEQ ID NO 18
<211> LENGTH: 3029
<212> TYPE: PRT
<213> ORGANISM: Hepatitis C virus

<400> SEQUENCE: 18

Met Ser Thr Asn Pro Lys Pro Gln Arg Lys Thr Lys Arg Asn Thr Asn
1               5                   10                  15

Arg Arg Pro Met Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Ser Trp Ala Gln Pro Gly
65                  70                  75                  80

```
Tyr Pro Trp Pro Leu Tyr Gly Asn Glu Gly Cys Gly Trp Ala Gly Trp
             85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Val
        130                 135                 140

Gly Gly Val Ala Arg Ala Leu Ala His Gly Val Arg Ala Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Val
            180                 185                 190

Asn Tyr Arg Asn Val Ser Gly Ile Tyr His Val Thr Asn Asp Cys Pro
        195                 200                 205

Asn Ser Ser Ile Val Tyr Glu Ala Asp His His Ile Leu His Leu Pro
210                 215                 220

Gly Cys Val Pro Cys Val Arg Glu Gly Asn Gln Ser Arg Cys Trp Val
225                 230                 235                 240

Ala Leu Thr Pro Thr Val Ala Ala Pro Tyr Ile Gly Ala Pro Leu Glu
                245                 250                 255

Ser Leu Arg Ser His Val Asp Leu Met Val Gly Ala Ala Thr Val Cys
            260                 265                 270

Ser Gly Leu Tyr Ile Gly Asp Leu Cys Gly Gly Leu Phe Leu Val Gly
        275                 280                 285

Gln Met Phe Ser Phe Arg Pro Arg Arg His Trp Thr Thr Gln Asp Cys
    290                 295                 300

Asn Cys Ser Ile Tyr Thr Gly His Ile Thr Gly His Arg Met Ala Trp
305                 310                 315                 320

Asp Met Met Met Asn Trp Ser Pro Thr Thr Thr Leu Val Leu Ala Gln
                325                 330                 335

Val Met Arg Ile Pro Thr Thr Leu Val Asp Leu Leu Ser Gly Gly His
            340                 345                 350

Trp Gly Val Leu Val Gly Val Ala Tyr Phe Ser Met Gln Ala Asn Trp
        355                 360                 365

Ala Lys Val Ile Leu Val Leu Phe Leu Phe Ala Gly Val Asp Ala Glu
    370                 375                 380

Thr His Val Ser Gly Ala Ala Val Gly Arg Ser Thr Ala Gly Leu Ala
385                 390                 395                 400

Asn Leu Phe Ser Ser Gly Ser Lys Gln Asn Leu Gln Leu Ile Asn Ser
                405                 410                 415

Asn Gly Ser Trp His Ile Asn Arg Thr Ala Leu Asn Cys Asn Asp Ser
            420                 425                 430

Leu Asn Thr Gly Phe Leu Ala Ser Leu Phe Tyr Thr His Lys Phe Asn
        435                 440                 445

Ser Ser Gly Cys Ser Glu Arg Leu Ala Cys Cys Lys Ser Leu Asp Ser
    450                 455                 460

Tyr Gly Gln Gly Trp Gly Pro Leu Gly Val Ala Asn Ile Ser Gly Ser
465                 470                 475                 480

Ser Asp Asp Arg Pro Tyr Cys Trp His Tyr Ala Pro Arg Pro Cys Gly
                485                 490                 495

Ile Val Pro Ala Ser Ser Val Cys Gly Pro Val Tyr Cys Phe Thr Pro
```

-continued

```
            500                 505                 510
Ser Pro Val Val Gly Thr Thr Asp His Val Gly Pro Thr Tyr
        515                 520                 525

Thr Trp Gly Glu Asn Glu Thr Asp Val Phe Leu Leu Asn Ser Thr Arg
    530                 535                 540

Pro Pro His Gly Ala Trp Phe Gly Cys Val Trp Met Asn Ser Thr Gly
545                 550                 555                 560

Phe Thr Lys Thr Cys Gly Ala Pro Pro Cys Glu Val Asn Thr Asn Asn
                565                 570                 575

Gly Thr Trp His Cys Pro Thr Asp Cys Phe Arg Lys His Pro Glu Thr
            580                 585                 590

Thr Tyr Ala Lys Cys Gly Ser Gly Pro Trp Ile Thr Pro Arg Cys Leu
            595                 600                 605

Ile Asp Tyr Pro Tyr Arg Leu Trp His Phe Pro Cys Thr Ala Asn Phe
        610                 615                 620

Ser Val Phe Asn Ile Arg Thr Phe Val Gly Gly Ile Glu His Arg Met
625                 630                 635                 640

Gln Ala Ala Cys Asn Trp Thr Arg Gly Glu Val Cys Gly Leu Glu His
                645                 650                 655

Arg Asp Arg Val Glu Leu Ser Pro Leu Leu Leu Thr Thr Thr Ala Trp
            660                 665                 670

Gln Ile Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
        690                 695                 700

Val Gly Ser Ala Val Val Ser Trp Ala Leu Lys Trp Glu Tyr Val Val
705                 710                 715                 720

Leu Ala Phe Leu Leu Leu Ala Asp Ala Arg Val Ser Ala Cys Leu Trp
                725                 730                 735

Met Met Phe Met Val Ser Gln Val Glu Ala Ala Leu Ser Asn Leu Ile
            740                 745                 750

Asn Ile Asn Ala Ala Ser Ala Ala Gly Ala Gln Gly Phe Trp Tyr Ala
            755                 760                 765

Ile Leu Phe Ile Cys Ile Val His Val Lys Gly Arg Phe Pro Ala
        770                 775                 780

Ala Ala Ala Tyr Ala Ala Cys Gly Leu Trp Pro Leu Phe Leu Leu Leu
785                 790                 795                 800

Leu Met Leu Pro Glu Arg Ala Tyr Ala Tyr Asp Gln Glu Val Ala Gly
                805                 810                 815

Ser Leu Gly Gly Ala Ile Val Val Met Leu Ala Ile Leu Thr Leu Ser
            820                 825                 830

Pro His Tyr Lys Leu Trp Leu Ala Arg Gly Leu Trp Trp Ile Gln Tyr
            835                 840                 845

Phe Ile Ala Arg Thr Glu Ala Val Leu His Val Tyr Ile Pro Ser Phe
        850                 855                 860

Asn Val Arg Gly Pro Arg Asp Ser Val Ile Val Leu Ala Val Leu Val
865                 870                 875                 880

Cys Pro His Leu Val Phe Asp Ile Thr Lys Tyr Leu Leu Ala Ile Leu
                885                 890                 895

Gly Pro Leu His Ile Leu Gln Ala Ser Leu Leu Arg Ile Pro Tyr Phe
            900                 905                 910

Val Arg Ala Gln Ala Leu Val Lys Ile Cys Ser Leu Leu Arg Gly Val
            915                 920                 925
```

```
Val Tyr Gly Lys Tyr Phe Gln Met Val Val Leu Lys Ala Gly Ala Leu
        930                 935                 940
Thr Gly Thr Tyr Ile Tyr Asp His Leu Thr Pro Met Ser Asp Trp Ala
945                 950                 955                 960
Ala Ser Gly Leu Arg Asp Leu Ala Val Ala Val Glu Pro Ile Ile Phe
                965                 970                 975
Ser Pro Met Glu Lys Lys Val Ile Val Trp Gly Ala Glu Thr Ala Ala
                980                 985                 990
Cys Gly Asp Ile Leu His Gly Leu Pro Val Ser Ala Arg Leu Gly Gln
            995                 1000                1005
Glu Ile Leu Leu Gly Pro Ala Asp Gly Tyr Thr Ser Lys Gly Trp
    1010                1015                1020
Lys Leu Leu Ala Pro Ile Thr Ala Tyr Ala Gln Gln Thr Arg Gly
    1025                1030                1035
Leu Leu Gly Ala Ile Val Val Ser Met Thr Gly Arg Asp Arg Thr
    1040                1045                1050
Glu Gln Ala Gly Glu Val Gln Ile Leu Ser Thr Val Ser Gln Ser
    1055                1060                1065
Phe Leu Gly Thr Thr Ile Ser Gly Val Leu Trp Thr Val Tyr His
    1070                1075                1080
Gly Ala Gly Asn Lys Thr Leu Ala Gly Leu Arg Gly Pro Val Thr
    1085                1090                1095
Gln Met Tyr Ser Ser Ala Glu Gly Asp Leu Val Gly Trp Pro Ser
    1100                1105                1110
Pro Pro Gly Thr Lys Ser Leu Glu Pro Cys Lys Cys Gly Ala Val
    1115                1120                1125
Asp Leu Tyr Leu Val Thr Arg Asn Ala Asp Val Ile Pro Ala Arg
    1130                1135                1140
Arg Arg Gly Asp Lys Arg Gly Ala Leu Leu Ser Pro Arg Pro Ile
    1145                1150                1155
Ser Thr Leu Lys Gly Ser Ser Gly Gly Pro Val Leu Cys Pro Arg
    1160                1165                1170
Gly His Val Val Gly Leu Phe Arg Ala Ala Val Cys Ser Arg Gly
    1175                1180                1185
Val Ala Lys Ser Ile Asp Phe Ile Pro Val Glu Thr Leu Asp Val
    1190                1195                1200
Val Thr Arg Ser Pro Thr Phe Ser Asp Asn Ser Thr Pro Pro Ala
    1205                1210                1215
Val Pro Gln Thr Tyr Gln Val Gly Tyr Leu His Ala Pro Thr Gly
    1220                1225                1230
Ser Gly Lys Ser Thr Lys Val Pro Val Ala Tyr Ala Ala Gln Gly
    1235                1240                1245
Tyr Lys Val Leu Val Leu Asn Pro Ser Val Ala Ala Thr Leu Gly
    1250                1255                1260
Phe Gly Ala Tyr Leu Ser Lys Ala His Gly Ile Asn Pro Asn Ile
    1265                1270                1275
Arg Thr Gly Val Arg Thr Val Met Thr Gly Glu Ala Ile Thr Tyr
    1280                1285                1290
Ser Thr Tyr Gly Lys Phe Leu Ala Asp Gly Gly Cys Ala Ser Gly
    1295                1300                1305
Ala Tyr Asp Ile Ile Ile Cys Asp Glu Cys His Ala Val Asp Ala
    1310                1315                1320
Thr Ser Ile Leu Gly Ile Gly Thr Val Leu Asp Gln Ala Glu Thr
    1325                1330                1335
```

```
Ala Gly Val Arg Leu Thr Val Leu Ala Thr Ala Thr Pro Pro Gly
    1340                1345                1350

Ser Val Thr Thr Pro His Pro Asp Ile Glu Glu Val Gly Leu Gly
    1355                1360                1365

Arg Glu Gly Glu Ile Pro Phe Tyr Gly Arg Ala Ile Pro Leu Ser
    1370                1375                1380

Cys Ile Lys Gly Gly Arg His Leu Ile Phe Cys His Ser Lys Lys
    1385                1390                1395

Lys Cys Asp Glu Leu Ala Ala Ala Leu Arg Gly Met Gly Leu Asn
    1400                1405                1410

Ala Val Ala Tyr Tyr Arg Gly Leu Asp Val Ser Ile Ile Pro Ala
    1415                1420                1425

Gln Gly Asp Val Val Val Ala Thr Asp Ala Leu Met Thr Gly
    1430                1435                1440

Tyr Thr Gly Asp Phe Asp Ser Val Ile Asp Cys Asn Val Ala Val
    1445                1450                1455

Thr Gln Ala Val Asp Phe Ser Leu Asp Pro Thr Phe Thr Ile Thr
    1460                1465                1470

Thr Gln Thr Val Pro Gln Asp Ala Val Ser Arg Ser Gln Arg Arg
    1475                1480                1485

Gly Arg Thr Gly Arg Gly Arg Gln Gly Thr Tyr Arg Tyr Val Ser
    1490                1495                1500

Thr Gly Glu Arg Ala Ser Gly Met Phe Asp Ser Val Val Leu Cys
    1505                1510                1515

Glu Cys Tyr Asp Ala Gly Ala Ala Trp Tyr Asp Leu Thr Pro Ala
    1520                1525                1530

Glu Thr Thr Val Arg Leu Arg Ala Tyr Phe Asn Thr Pro Gly Leu
    1535                1540                1545

Pro Val Cys Gln Asp His Leu Glu Phe Trp Glu Ala Val Phe Thr
    1550                1555                1560

Gly Leu Thr His Ile Asp Ala His Phe Leu Ser Gln Thr Lys Gln
    1565                1570                1575

Ala Gly Glu Asn Phe Ala Tyr Leu Val Ala Tyr Gln Ala Thr Val
    1580                1585                1590

Cys Ala Arg Ala Lys Ala Pro Pro Ser Trp Asp Ala Met Trp
    1595                1600                1605

Lys Cys Leu Ala Arg Leu Lys Pro Thr Leu Ala Gly Pro Thr Pro
    1610                1615                1620

Leu Leu Tyr Arg Leu Gly Pro Ile Thr Asn Glu Val Thr Leu Thr
    1625                1630                1635

His Pro Gly Thr Lys Tyr Ile Ala Thr Cys Met Gln Ala Asp Leu
    1640                1645                1650

Glu Val Met Thr Ser Thr Trp Val Leu Ala Gly Gly Val Leu Ala
    1655                1660                1665

Ala Val Ala Ala Tyr Cys Leu Ala Thr Gly Cys Val Ser Ile Ile
    1670                1675                1680

Gly Arg Leu His Val Asn Gln Arg Val Val Val Ala Pro Asp Lys
    1685                1690                1695

Glu Val Leu Tyr Glu Ala Phe Asp Glu Met Glu Glu Cys Ala Ser
    1700                1705                1710

Arg Ala Ala Leu Ile Glu Glu Gly Gln Arg Ile Ala Glu Met Leu
    1715                1720                1725

Lys Ser Lys Ile Gln Gly Leu Leu Gln Gln Ala Ser Lys Gln Ala
```

|  |  |  |
|---|---|---|
| 1730 | 1735 | 1740 |

Gln Asp Ile Gln Pro Ala Met Gln Ala Ser Trp Pro Lys Val Glu
    1745                    1750               1755

Gln Phe Trp Ala Arg His Met Trp Asn Phe Ile Ser Gly Ile Gln
    1760                    1765               1770

Tyr Leu Ala Gly Leu Ser Thr Leu Pro Gly Asn Pro Ala Val Ala
    1775                    1780               1785

Ser Met Met Ala Phe Ser Ala Ala Leu Thr Ser Pro Leu Ser Thr
    1790                    1795               1800

Ser Thr Thr Ile Leu Leu Asn Ile Met Gly Gly Trp Leu Ala Ser
    1805                    1810               1815

Gln Ile Ala Pro Pro Ala Gly Ala Thr Gly Phe Val Val Ser Gly
    1820                    1825               1830

Leu Val Gly Ala Ala Val Gly Ser Ile Gly Leu Gly Lys Val Leu
    1835                    1840               1845

Val Asp Ile Leu Ala Gly Tyr Gly Ala Gly Ile Ser Gly Ala Leu
    1850                    1855               1860

Val Ala Phe Lys Ile Met Ser Gly Glu Lys Pro Ser Met Glu Asp
    1865                    1870               1875

Val Ile Asn Leu Leu Pro Gly Ile Leu Ser Pro Gly Ala Leu Val
    1880                    1885               1890

Val Gly Val Ile Cys Ala Ala Ile Leu Arg Arg His Val Gly Pro
    1895                    1900               1905

Gly Glu Gly Ala Val Gln Trp Met Asn Arg Leu Ile Ala Phe Ala
    1910                    1915               1920

Ser Arg Gly Asn His Val Ala Pro Thr His Tyr Val Thr Glu Ser
    1925                    1930               1935

Asp Ala Ser Gln Arg Val Thr Gln Leu Leu Gly Ser Leu Thr Ile
    1940                    1945               1950

Thr Ser Leu Leu Arg Arg Leu His Asn Trp Ile Thr Glu Asp Cys
    1955                    1960               1965

Pro Ile Pro Cys Ser Gly Ser Trp Leu Arg Asp Val Trp Asp Trp
    1970                    1975               1980

Val Cys Thr Ile Leu Thr Asp Phe Lys Asn Trp Leu Thr Ser Lys
    1985                    1990               1995

Leu Phe Pro Lys Leu Pro Gly Leu Pro Phe Ile Ser Cys Gln Lys
    2000                    2005               2010

Gly Tyr Lys Gly Val Trp Ala Gly Thr Gly Ile Met Thr Thr Arg
    2015                    2020               2025

Cys Pro Cys Gly Ala Asn Ile Ser Gly Asn Val Arg Leu Gly Ser
    2030                    2035               2040

Met Arg Ile Thr Gly Pro Lys Thr Cys Met Asn Thr Trp Gln Gly
    2045                    2050               2055

Thr Phe Pro Ile Asn Cys Tyr Thr Glu Gly Gln Cys Ala Pro Lys
    2060                    2065               2070

Pro Pro Thr Asn Tyr Lys Thr Ala Ile Trp Arg Val Ala Ala Ser
    2075                    2080               2085

Glu Tyr Ala Glu Val Thr Gln His Gly Ser Tyr Ser Tyr Val Thr
    2090                    2095               2100

Gly Leu Thr Thr Asp Asn Leu Lys Ile Pro Cys Gln Leu Pro Ser
    2105                    2110               2115

Pro Glu Phe Phe Ser Trp Val Asp Gly Val Gln Ile His Arg Phe
    2120                    2125               2130

-continued

| | | | | | | | | | | | |
|---|---|---|---|---|---|---|---|---|---|---|---|
|Ala|Pro|Thr|Pro|Lys|Pro|Phe|Phe|Arg|Asp|Glu|Val|Ser|Phe|Cys|
|2135| | | | |2140| | | | |2145| | | | |
|Val|Gly|Leu|Asn|Ser|Tyr|Ala|Val|Gly|Ser|Gln|Leu|Pro|Cys|Glu|
|2150| | | | |2155| | | | |2160| | | | |
|Pro|Glu|Pro|Asp|Ala|Asp|Val|Leu|Arg|Ser|Met|Leu|Thr|Asp|Pro|
|2165| | | | |2170| | | | |2175| | | | |
|Pro|His|Ile|Thr|Ala|Glu|Thr|Ala|Ala|Arg|Arg|Leu|Ala|Arg|Gly|
|2180| | | | |2185| | | | |2190| | | | |
|Ser|Pro|Pro|Ser|Glu|Ala|Ser|Ser|Ser|Val|Ser|Gln|Leu|Ser|Ala|
|2195| | | | |2200| | | | |2205| | | | |
|Pro|Ser|Leu|Arg|Ala|Thr|Cys|Thr|Thr|His|Ser|Asn|Thr|Tyr|Asp|
|2210| | | | |2215| | | | |2220| | | | |
|Val|Asp|Met|Val|Asp|Ala|Asn|Leu|Leu|Met|Glu|Gly|Gly|Val|Ala|
|2225| | | | |2230| | | | |2235| | | | |
|Gln|Thr|Glu|Pro|Glu|Ser|Arg|Val|Pro|Val|Leu|Asp|Phe|Leu|Glu|
|2240| | | | |2245| | | | |2250| | | | |
|Pro|Met|Ala|Glu|Glu|Glu|Ser|Asp|Leu|Glu|Pro|Ser|Ile|Pro|Ser|
|2255| | | | |2260| | | | |2265| | | | |
|Glu|Cys|Met|Leu|Pro|Arg|Ser|Gly|Phe|Pro|Arg|Ala|Leu|Pro|Ala|
|2270| | | | |2275| | | | |2280| | | | |
|Trp|Ala|Arg|Pro|Asp|Tyr|Asn|Pro|Pro|Leu|Val|Glu|Ser|Trp|Arg|
|2285| | | | |2290| | | | |2295| | | | |
|Arg|Pro|Asp|Tyr|Gln|Pro|Pro|Thr|Val|Ala|Gly|Cys|Ala|Leu|Pro|
|2300| | | | |2305| | | | |2310| | | | |
|Pro|Pro|Lys|Lys|Ala|Pro|Thr|Pro|Pro|Arg|Arg|Arg|Arg|Thr|
|2315| | | | |2320| | | | |2325| | | | |
|Val|Gly|Leu|Ser|Glu|Ser|Thr|Ile|Ser|Glu|Ala|Leu|Gln|Gln|Leu|
|2330| | | | |2335| | | | |2340| | | | |
|Ala|Ile|Lys|Thr|Phe|Gly|Gln|Pro|Pro|Ser|Ser|Gly|Asp|Ala|Gly|
|2345| | | | |2350| | | | |2355| | | | |
|Ser|Ser|Thr|Gly|Ala|Gly|Ala|Ala|Glu|Ser|Gly|Gly|Pro|Thr|Ser|
|2360| | | | |2365| | | | |2370| | | | |
|Pro|Gly|Glu|Pro|Ala|Pro|Ser|Glu|Thr|Gly|Ser|Ala|Ser|Ser|Met|
|2375| | | | |2380| | | | |2385| | | | |
|Pro|Pro|Leu|Glu|Gly|Glu|Pro|Gly|Asp|Pro|Asp|Leu|Glu|Ser|Asp|
|2390| | | | |2395| | | | |2400| | | | |
|Gln|Val|Glu|Leu|Gln|Pro|Pro|Gln|Gly|Gly|Val|Ala|Pro|
|2405| | | | |2410| | | | |2415| | | | |
|Gly|Ser|Gly|Ser|Gly|Ser|Trp|Ser|Thr|Cys|Ser|Glu|Glu|Asp|Asp|
|2420| | | | |2425| | | | |2430| | | | |
|Thr|Thr|Val|Cys|Cys|Ser|Met|Ser|Tyr|Ser|Trp|Thr|Gly|Ala|Leu|
|2435| | | | |2440| | | | |2445| | | | |
|Ile|Thr|Pro|Cys|Ser|Pro|Glu|Glu|Glu|Lys|Leu|Pro|Ile|Asn|Pro|
|2450| | | | |2455| | | | |2460| | | | |
|Leu|Ser|Asn|Ser|Leu|Leu|Arg|Tyr|His|Asn|Lys|Val|Tyr|Cys|Thr|
|2465| | | | |2470| | | | |2475| | | | |
|Thr|Ser|Lys|Ser|Ala|Ser|Gln|Arg|Ala|Lys|Lys|Val|Thr|Phe|Asp|
|2480| | | | |2485| | | | |2490| | | | |
|Arg|Thr|Gln|Val|Leu|Asp|Ala|His|Tyr|Asp|Ser|Val|Leu|Lys|Asp|
|2495| | | | |2500| | | | |2505| | | | |
|Ile|Lys|Leu|Ala|Ala|Ser|Lys|Val|Ser|Ala|Arg|Leu|Leu|Thr|Leu|
|2510| | | | |2515| | | | |2520| | | | |
|Glu|Glu|Ala|Cys|Gln|Leu|Thr|Pro|Pro|His|Ser|Ala|Arg|Ser|Lys|
|2525| | | | |2530| | | | |2535| | | | |

Tyr Gly Phe Gly Ala Lys Glu Val Arg Ser Leu Ser Gly Arg Ala
    2540            2545            2550

Val Asn His Ile Lys Ser Val Trp Lys Asp Leu Leu Glu Asp Pro
    2555            2560            2565

Gln Thr Pro Ile Pro Thr Thr Ile Met Ala Lys Asn Glu Val Phe
    2570            2575            2580

Cys Val Asp Pro Ala Lys Gly Gly Lys Lys Pro Ala Arg Leu Ile
    2585            2590            2595

Val Tyr Pro Asp Leu Gly Val Arg Val Cys Glu Lys Met Ala Leu
    2600            2605            2610

Tyr Asp Ile Thr Gln Lys Leu Pro Gln Ala Val Met Gly Ala Ser
    2615            2620            2625

Tyr Gly Phe Gln Tyr Ser Pro Ala Gln Arg Val Glu Tyr Leu Leu
    2630            2635            2640

Lys Ala Trp Ala Glu Lys Lys Asp Pro Met Gly Phe Ser Tyr Asp
    2645            2650            2655

Thr Arg Cys Phe Asp Ser Thr Val Thr Glu Arg Asp Ile Arg Thr
    2660            2665            2670

Glu Glu Ser Ile Tyr Gln Ala Cys Ser Leu Pro Glu Glu Ala Arg
    2675            2680            2685

Thr Ala Ile His Ser Leu Thr Glu Arg Leu Tyr Val Gly Gly Pro
    2690            2695            2700

Met Phe Asn Ser Lys Gly Gln Thr Cys Gly Tyr Arg Arg Cys Arg
    2705            2710            2715

Ala Ser Gly Val Leu Thr Thr Ser Met Gly Asn Thr Ile Thr Cys
    2720            2725            2730

Tyr Val Lys Ala Leu Ala Ala Cys Lys Ala Ala Gly Ile Val Ala
    2735            2740            2745

Pro Thr Met Leu Val Cys Gly Asp Asp Leu Val Val Ile Ser Glu
    2750            2755            2760

Ser Gln Gly Thr Glu Glu Asp Glu Arg Asn Leu Arg Ala Phe Thr
    2765            2770            2775

Glu Ala Met Thr Arg Tyr Ser Ala Pro Pro Gly Asp Pro Pro Arg
    2780            2785            2790

Pro Glu Tyr Asp Leu Glu Leu Ile Thr Ser Cys Ser Ser Asn Val
    2795            2800            2805

Ser Val Ala Leu Gly Pro Arg Gly Arg Arg Tyr Tyr Leu Thr
    2810            2815            2820

Arg Asp Pro Thr Thr Pro Leu Ala Arg Ala Ala Trp Glu Thr Val
    2825            2830            2835

Arg His Ser Pro Ile Asn Ser Trp Leu Gly Asn Ile Ile Gln Tyr
    2840            2845            2850

Ala Pro Thr Ile Trp Val Arg Met Val Leu Met Thr His Phe Phe
    2855            2860            2865

Ser Ile Leu Met Val Gln Asp Thr Leu Asp Gln Asn Leu Asn Phe
    2870            2875            2880

Glu Met Tyr Gly Ser Val Tyr Ser Val Asn Pro Leu Asp Leu Pro
    2885            2890            2895

Ala Ile Ile Glu Arg Leu His Gly Leu Asp Ala Phe Ser Met His
    2900            2905            2910

Thr Tyr Ser His His Glu Leu Thr Arg Val Ala Ser Ala Leu Arg
    2915            2920            2925

Lys Leu Gly Ala Pro Pro Leu Arg Val Trp Lys Ser Arg Ala Arg

-continued

```
                 2930                2935                2940

Ala Val Arg Ala Ser Leu Ile Ser Arg Gly Gly Lys Ala Ala Val
    2945                2950                2955

Cys Gly Arg Tyr Leu Phe Asn Trp Ala Val Lys Thr Lys Leu Lys
    2960                2965                2970

Leu Thr Pro Leu Pro Glu Ala Arg Leu Leu Asp Leu Ser Ser Trp
    2975                2980                2985

Phe Thr Val Gly Ala Gly Gly Asp Ile Phe His Ser Val Ser
    2990                2995                3000

Arg Ala Arg Pro Arg Ser Leu Leu Phe Gly Leu Leu Leu Leu Phe
    3005                3010                3015

Val Gly Val Gly Leu Phe Leu Leu Pro Ala Arg
    3020                3025

<210> SEQ ID NO 19
<211> LENGTH: 3029
<212> TYPE: PRT
<213> ORGANISM: Hepatitis C virus

<400> SEQUENCE: 19

Met Ser Thr Asn Pro Lys Pro Gln Arg Lys Thr Lys Arg Asn Thr Asn
1               5                   10                  15

Arg Arg Pro Met Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Val
            180                 185                 190

Asn Tyr Arg Asn Val Ser Gly Ile Tyr His Val Thr Asn Asp Cys Pro
        195                 200                 205

Asn Ser Ser Ile Val Tyr Glu Ala Asp His His Ile Leu His Leu Pro
    210                 215                 220

Gly Cys Val Pro Cys Val Arg Glu Gly Asn Gln Ser Arg Cys Trp Val
225                 230                 235                 240

Ala Leu Thr Pro Thr Val Ala Ala Pro Tyr Ile Gly Ala Pro Leu Glu
                245                 250                 255

Ser Leu Arg Ser His Val Asp Leu Met Val Gly Ala Ala Thr Val Cys
            260                 265                 270

Ser Gly Leu Tyr Ile Gly Asp Leu Cys Gly Gly Leu Phe Leu Val Gly
```

-continued

```
                275                 280                 285
Gln Met Phe Ser Phe Arg Pro Arg Arg His Trp Thr Thr Gln Asp Cys
290                 295                 300
Asn Cys Ser Ile Tyr Thr Gly His Ile Thr Gly His Arg Met Ala Trp
305                 310                 315                 320
Asp Met Met Met Asn Trp Ser Pro Thr Thr Thr Leu Val Leu Ala Gln
                325                 330                 335
Val Met Arg Ile Pro Thr Thr Leu Val Asp Leu Leu Ser Gly Gly His
            340                 345                 350
Trp Gly Val Leu Val Gly Val Ala Tyr Phe Ser Met Gln Ala Asn Trp
        355                 360                 365
Ala Lys Val Ile Leu Val Leu Phe Leu Phe Ala Gly Val Asp Ala Glu
    370                 375                 380
Thr His Val Ser Gly Ala Ala Val Gly Arg Ser Thr Ala Gly Leu Ala
385                 390                 395                 400
Asn Leu Phe Ser Ser Gly Ser Lys Gln Asn Leu Gln Leu Ile Asn Ser
                405                 410                 415
Asn Gly Ser Trp His Ile Asn Arg Thr Ala Leu Asn Cys Asn Asp Ser
            420                 425                 430
Leu Asn Thr Gly Phe Leu Ala Ser Leu Phe Tyr Thr His Lys Phe Asn
        435                 440                 445
Ser Ser Gly Cys Ser Glu Arg Leu Ala Cys Cys Lys Ser Leu Asp Ser
    450                 455                 460
Tyr Gly Gln Gly Trp Gly Pro Leu Gly Val Ala Asn Ile Ser Gly Ser
465                 470                 475                 480
Ser Asp Asp Arg Pro Tyr Cys Trp His Tyr Ala Pro Arg Pro Cys Gly
                485                 490                 495
Ile Val Pro Ala Ser Ser Val Cys Gly Pro Val Tyr Cys Phe Thr Pro
            500                 505                 510
Ser Pro Val Val Val Gly Thr Thr Asp His Val Gly Val Pro Thr Tyr
        515                 520                 525
Thr Trp Gly Glu Asn Glu Thr Asp Val Phe Leu Leu Asn Ser Thr Arg
    530                 535                 540
Pro Pro His Gly Ala Trp Phe Gly Cys Val Trp Met Asn Ser Thr Gly
545                 550                 555                 560
Phe Thr Lys Thr Cys Gly Ala Pro Pro Cys Glu Val Asn Thr Asn Asn
                565                 570                 575
Gly Thr Trp His Cys Pro Thr Asp Cys Phe Arg Lys His Pro Glu Thr
            580                 585                 590
Thr Tyr Ala Lys Cys Gly Ser Gly Pro Trp Ile Thr Pro Arg Cys Leu
        595                 600                 605
Ile Asp Tyr Pro Tyr Arg Leu Trp His Phe Pro Cys Thr Ala Asn Phe
    610                 615                 620
Ser Val Phe Asn Ile Arg Thr Phe Val Gly Gly Ile Glu His Arg Met
625                 630                 635                 640
Gln Ala Ala Cys Asn Trp Thr Arg Gly Glu Val Cys Gly Leu Glu His
                645                 650                 655
Arg Asp Arg Val Glu Leu Ser Pro Leu Leu Leu Thr Thr Thr Ala Trp
            660                 665                 670
Gln Ile Leu Pro Cys Ser Phe Thr Thr Leu Pro Ala Leu Ser Thr Gly
        675                 680                 685
Leu Ile His Leu His Gln Asn Ile Val Asp Val Gln Tyr Leu Tyr Gly
    690                 695                 700
```

-continued

Val Gly Ser Ala Val Val Ser Trp Ala Leu Lys Trp Glu Tyr Val Val
705                 710                 715                 720

Leu Ala Phe Leu Leu Leu Ala Asp Ala Arg Val Ser Ala Cys Leu Trp
            725                 730                 735

Met Met Phe Met Val Ser Gln Val Glu Ala Ala Leu Ser Asn Leu Ile
        740                 745                 750

Asn Ile Asn Ala Ala Ser Ala Ala Gly Ala Gln Gly Phe Trp Tyr Ala
    755                 760                 765

Ile Leu Phe Ile Cys Ile Val Trp His Val Lys Gly Arg Phe Pro Ala
770                 775                 780

Ala Ala Ala Tyr Ala Ala Cys Gly Leu Trp Pro Leu Phe Leu Leu Leu
785                 790                 795                 800

Leu Met Leu Pro Glu Arg Ala Tyr Ala Tyr Asp Gln Glu Val Ala Gly
            805                 810                 815

Ser Leu Gly Gly Ala Ile Val Val Met Leu Ala Ile Leu Thr Leu Ser
        820                 825                 830

Pro His Tyr Lys Leu Trp Leu Ala Arg Gly Leu Trp Trp Ile Gln Tyr
    835                 840                 845

Phe Ile Ala Arg Thr Glu Ala Val Leu His Val Tyr Ile Pro Ser Phe
850                 855                 860

Asn Val Arg Gly Pro Arg Asp Ser Val Ile Val Leu Ala Val Leu Val
865                 870                 875                 880

Cys Pro His Leu Val Phe Asp Ile Thr Lys Tyr Leu Leu Ala Ile Leu
            885                 890                 895

Gly Pro Leu His Ile Leu Gln Ala Ser Leu Leu Arg Ile Pro Tyr Phe
        900                 905                 910

Val Arg Ala Gln Ala Leu Val Lys Ile Cys Ser Leu Leu Arg Gly Val
    915                 920                 925

Val Tyr Gly Lys Tyr Phe Gln Met Val Val Leu Lys Ala Gly Ala Leu
930                 935                 940

Thr Gly Thr Tyr Ile Tyr Asp His Leu Thr Pro Met Ser Asp Trp Ala
945                 950                 955                 960

Ala Thr Gly Leu Arg Asp Leu Ala Val Ala Leu Glu Pro Val Val Phe
            965                 970                 975

Ser Pro Met Glu Lys Lys Val Ile Val Trp Gly Ala Asp Thr Ala Ala
        980                 985                 990

Cys Gly Asp Ile Ile Arg Gly Leu Pro Val Ser Ala Arg Leu Gly Asn
    995                 1000                1005

Glu Ile Leu Leu Gly Pro Ala Asp Thr Glu Thr Ser Lys Gly Trp
    1010                1015                1020

Arg Leu Leu Ala Pro Ile Thr Ala Tyr Ala Gln Gln Thr Arg Gly
    1025                1030                1035

Leu Leu Gly Ala Ile Val Val Ser Met Thr Gly Arg Asp Arg Thr
    1040                1045                1050

Glu Gln Ala Gly Glu Val Gln Ile Leu Ser Thr Val Ser Gln Ser
    1055                1060                1065

Phe Leu Gly Thr Thr Ile Ser Gly Val Leu Trp Thr Val Tyr His
    1070                1075                1080

Gly Ala Gly Asn Lys Thr Leu Ala Gly Leu Arg Gly Pro Val Thr
    1085                1090                1095

Gln Met Tyr Ser Ser Ala Glu Gly Asp Leu Val Gly Trp Pro Ser
    1100                1105                1110

Pro Pro Gly Thr Lys Ser Leu Glu Pro Cys Lys Cys Gly Ala Val
    1115                1120                1125

-continued

Asp Leu Tyr Leu Val Thr Arg Asn Ala Asp Val Ile Pro Ala Arg
    1130                1135                1140

Arg Arg Gly Asp Lys Arg Gly Ala Leu Leu Ser Pro Arg Pro Ile
    1145                1150                1155

Ser Thr Leu Lys Gly Ser Ser Gly Gly Pro Val Leu Cys Pro Arg
    1160                1165                1170

Gly His Val Val Gly Leu Phe Arg Ala Ala Val Cys Ser Arg Gly
    1175                1180                1185

Val Ala Lys Ser Ile Asp Phe Ile Pro Val Glu Thr Leu Asp Val
    1190                1195                1200

Val Thr Arg Ser Pro Thr Phe Ser Asp Asn Ser Thr Pro Pro Ala
    1205                1210                1215

Val Pro Gln Thr Tyr Gln Val Gly Tyr Leu His Ala Pro Thr Gly
    1220                1225                1230

Ser Gly Lys Ser Thr Lys Val Pro Val Ala Tyr Ala Ala Gln Gly
    1235                1240                1245

Tyr Lys Val Leu Val Leu Asn Pro Ser Val Ala Ala Thr Leu Gly
    1250                1255                1260

Phe Gly Ala Tyr Leu Ser Lys Ala His Gly Ile Asn Pro Asn Ile
    1265                1270                1275

Arg Thr Gly Val Arg Thr Val Met Thr Gly Glu Ala Ile Thr Tyr
    1280                1285                1290

Ser Thr Tyr Gly Lys Phe Leu Ala Asp Gly Gly Cys Ala Ser Gly
    1295                1300                1305

Ala Tyr Asp Ile Ile Ile Cys Asp Glu Cys His Ala Val Asp Ala
    1310                1315                1320

Thr Ser Ile Leu Gly Ile Gly Thr Val Leu Asp Gln Ala Glu Thr
    1325                1330                1335

Ala Gly Val Arg Leu Thr Val Leu Ala Thr Ala Thr Pro Pro Gly
    1340                1345                1350

Ser Val Thr Thr Pro His Pro Asp Ile Glu Glu Val Gly Leu Gly
    1355                1360                1365

Arg Glu Gly Glu Ile Pro Phe Tyr Gly Arg Ala Ile Pro Leu Ser
    1370                1375                1380

Cys Ile Lys Gly Gly Arg His Leu Ile Phe Cys His Ser Lys Lys
    1385                1390                1395

Lys Cys Asp Glu Leu Ala Ala Ala Leu Arg Gly Met Gly Leu Asn
    1400                1405                1410

Ala Val Ala Tyr Tyr Arg Gly Leu Asp Val Ser Ile Ile Pro Ala
    1415                1420                1425

Gln Gly Asp Val Val Val Ala Thr Asp Ala Leu Met Thr Gly
    1430                1435                1440

Tyr Thr Gly Asp Phe Asp Ser Val Ile Asp Cys Asn Val Ala Val
    1445                1450                1455

Thr Gln Ala Val Asp Phe Ser Leu Asp Pro Thr Phe Thr Ile Thr
    1460                1465                1470

Thr Gln Thr Val Pro Gln Asp Ala Val Ser Arg Ser Gln Arg Arg
    1475                1480                1485

Gly Arg Thr Gly Arg Gly Arg Gln Gly Thr Tyr Arg Tyr Val Ser
    1490                1495                1500

Thr Gly Glu Arg Ala Ser Gly Met Phe Asp Ser Val Val Leu Cys
    1505                1510                1515

Glu Cys Tyr Asp Ala Gly Ala Ala Trp Tyr Asp Leu Thr Pro Ala

```
                1520                1525                1530

Glu Thr Thr Val Arg Leu Arg Ala Tyr Phe Asn Thr Pro Gly Leu
    1535                1540                1545

Pro Val Cys Gln Asp His Leu Glu Phe Trp Glu Ala Val Phe Thr
    1550                1555                1560

Gly Leu Thr His Ile Asp Ala His Phe Leu Ser Gln Thr Lys Gln
    1565                1570                1575

Ala Gly Glu Asn Phe Ala Tyr Leu Val Ala Tyr Gln Ala Thr Val
    1580                1585                1590

Cys Ala Arg Ala Lys Ala Pro Pro Ser Trp Asp Ala Met Trp
    1595                1600                1605

Lys Cys Leu Ala Arg Leu Lys Pro Thr Leu Ala Gly Pro Thr Pro
    1610                1615                1620

Leu Leu Tyr Arg Leu Gly Pro Ile Thr Asn Glu Val Thr Leu Thr
    1625                1630                1635

His Pro Gly Thr Lys Tyr Ile Ala Thr Cys Met Gln Ala Asp Leu
    1640                1645                1650

Glu Val Met Thr Ser Thr Trp Val Leu Ala Gly Val Leu Ala
    1655                1660                1665

Ala Val Ala Ala Tyr Cys Leu Ala Thr Gly Cys Val Ser Ile Ile
    1670                1675                1680

Gly Arg Leu His Val Asn Gln Arg Val Val Val Ala Pro Asp Lys
    1685                1690                1695

Glu Val Leu Tyr Glu Ala Phe Asp Glu Met Glu Glu Cys Ala Ser
    1700                1705                1710

Arg Ala Ala Leu Ile Glu Glu Gly Gln Arg Ile Ala Glu Met Leu
    1715                1720                1725

Lys Ser Lys Ile Gln Gly Leu Leu Gln Gln Ala Ser Lys Gln Ala
    1730                1735                1740

Gln Asp Ile Gln Pro Ala Met Gln Ala Ser Trp Pro Lys Val Glu
    1745                1750                1755

Gln Phe Trp Ala Arg His Met Trp Asn Phe Ile Ser Gly Ile Gln
    1760                1765                1770

Tyr Leu Ala Gly Leu Ser Thr Leu Pro Gly Asn Pro Ala Val Ala
    1775                1780                1785

Ser Met Met Ala Phe Ser Ala Ala Leu Thr Ser Pro Leu Ser Thr
    1790                1795                1800

Ser Thr Thr Ile Leu Leu Asn Ile Met Gly Gly Trp Leu Ala Ser
    1805                1810                1815

Gln Ile Ala Pro Pro Ala Gly Ala Thr Gly Phe Val Val Ser Gly
    1820                1825                1830

Leu Val Gly Ala Ala Val Gly Ser Ile Gly Leu Gly Lys Val Leu
    1835                1840                1845

Val Asp Ile Leu Ala Gly Tyr Gly Ala Gly Ile Ser Gly Ala Leu
    1850                1855                1860

Val Ala Phe Lys Ile Met Ser Gly Glu Lys Pro Ser Met Glu Asp
    1865                1870                1875

Val Ile Asn Leu Leu Pro Gly Ile Leu Ser Pro Gly Ala Leu Val
    1880                1885                1890

Val Gly Val Ile Cys Ala Ala Ile Leu Arg Arg His Val Gly Pro
    1895                1900                1905

Gly Glu Gly Ala Val Gln Trp Met Asn Arg Leu Ile Ala Phe Ala
    1910                1915                1920
```

```
Ser Arg Gly Asn His Val Ala Pro Thr His Tyr Val Thr Glu Ser
1925                1930                1935

Asp Ala Ser Gln Arg Val Thr Gln Leu Leu Gly Ser Leu Thr Ile
1940                1945                1950

Thr Ser Leu Leu Arg Arg Leu His Asn Trp Ile Thr Glu Asp Cys
1955                1960                1965

Pro Ile Pro Cys Ser Gly Ser Trp Leu Arg Asp Val Trp Asp Trp
1970                1975                1980

Val Cys Thr Ile Leu Thr Asp Phe Lys Asn Trp Leu Thr Ser Lys
1985                1990                1995

Leu Phe Pro Lys Leu Pro Gly Leu Pro Phe Ile Ser Cys Gln Lys
2000                2005                2010

Gly Tyr Lys Gly Val Trp Ala Gly Thr Gly Ile Met Thr Thr Arg
2015                2020                2025

Cys Pro Cys Gly Ala Asn Ile Ser Gly Asn Val Arg Leu Gly Ser
2030                2035                2040

Met Arg Ile Thr Gly Pro Lys Thr Cys Met Asn Thr Trp Gln Gly
2045                2050                2055

Thr Phe Pro Ile Asn Cys Tyr Thr Glu Gly Gln Cys Ala Pro Lys
2060                2065                2070

Pro Pro Thr Asn Tyr Lys Thr Ala Ile Trp Arg Val Ala Ala Ser
2075                2080                2085

Glu Tyr Ala Glu Val Thr Gln His Gly Ser Tyr Ser Tyr Val Thr
2090                2095                2100

Gly Leu Thr Thr Asp Asn Leu Lys Ile Pro Cys Gln Leu Pro Ser
2105                2110                2115

Pro Glu Phe Phe Ser Trp Val Asp Gly Val Gln Ile His Arg Phe
2120                2125                2130

Ala Pro Thr Pro Lys Pro Phe Phe Arg Asp Glu Val Ser Phe Cys
2135                2140                2145

Val Gly Leu Asn Ser Tyr Ala Val Gly Ser Gln Leu Pro Cys Glu
2150                2155                2160

Pro Glu Pro Asp Ala Asp Val Leu Arg Ser Met Leu Thr Asp Pro
2165                2170                2175

Pro His Ile Thr Ala Glu Thr Ala Ala Arg Arg Leu Ala Arg Gly
2180                2185                2190

Ser Pro Pro Ser Glu Ala Ser Ser Ser Val Ser Gln Leu Ser Ala
2195                2200                2205

Pro Ser Leu Arg Ala Thr Cys Thr Thr His Ser Asn Thr Tyr Asp
2210                2215                2220

Val Asp Met Val Asp Ala Asn Leu Leu Met Glu Gly Gly Val Ala
2225                2230                2235

Gln Thr Glu Pro Glu Ser Arg Val Pro Val Leu Asp Phe Leu Glu
2240                2245                2250

Pro Met Ala Glu Glu Glu Ser Asp Leu Glu Pro Ser Ile Pro Ser
2255                2260                2265

Glu Cys Met Leu Pro Arg Ser Gly Phe Pro Arg Ala Leu Pro Ala
2270                2275                2280

Trp Ala Arg Pro Asp Tyr Asn Pro Pro Leu Val Glu Ser Trp Arg
2285                2290                2295

Arg Pro Asp Tyr Gln Pro Pro Thr Val Ala Gly Cys Ala Leu Pro
2300                2305                2310

Pro Pro Lys Lys Ala Pro Thr Pro Pro Pro Arg Arg Arg Arg Thr
2315                2320                2325
```

```
Val Gly Leu Ser Glu Ser Thr Ile Ser Glu Ala Leu Gln Gln Leu
    2330                2335                2340

Ala Ile Lys Thr Phe Gly Gln Pro Pro Ser Ser Gly Asp Ala Gly
    2345                2350                2355

Ser Ser Thr Gly Ala Gly Ala Glu Ser Gly Gly Pro Thr Ser
    2360                2365                2370

Pro Gly Glu Pro Ala Pro Ser Glu Thr Gly Ser Ala Ser Ser Met
    2375                2380                2385

Pro Pro Leu Glu Gly Glu Pro Gly Asp Pro Asp Leu Glu Ser Asp
    2390                2395                2400

Gln Val Glu Leu Gln Pro Pro Gln Gly Gly Val Ala Pro
    2405                2410                2415

Gly Ser Gly Ser Gly Ser Trp Ser Thr Cys Ser Glu Glu Asp Asp
    2420                2425                2430

Thr Thr Val Cys Cys Ser Met Ser Tyr Ser Trp Thr Gly Ala Leu
    2435                2440                2445

Ile Thr Pro Cys Ser Pro Glu Glu Lys Leu Pro Ile Asn Pro
    2450                2455                2460

Leu Ser Asn Ser Leu Leu Arg Tyr His Asn Lys Val Tyr Cys Thr
    2465                2470                2475

Thr Ser Lys Ser Ala Ser Gln Arg Ala Lys Lys Val Thr Phe Asp
    2480                2485                2490

Arg Thr Gln Val Leu Asp Ala His Tyr Asp Ser Val Leu Lys Asp
    2495                2500                2505

Ile Lys Leu Ala Ala Ser Lys Val Ser Ala Arg Leu Leu Thr Leu
    2510                2515                2520

Glu Glu Ala Cys Gln Leu Thr Pro Pro His Ser Ala Arg Ser Lys
    2525                2530                2535

Tyr Gly Phe Gly Ala Lys Glu Val Arg Ser Leu Ser Gly Arg Ala
    2540                2545                2550

Val Asn His Ile Lys Ser Val Trp Lys Asp Leu Leu Glu Asp Pro
    2555                2560                2565

Gln Thr Pro Ile Pro Thr Thr Ile Met Ala Lys Asn Glu Val Phe
    2570                2575                2580

Cys Val Asp Pro Ala Lys Gly Gly Lys Lys Pro Ala Arg Leu Ile
    2585                2590                2595

Val Tyr Pro Asp Leu Gly Val Arg Val Cys Glu Lys Met Ala Leu
    2600                2605                2610

Tyr Asp Ile Thr Gln Lys Leu Pro Gln Ala Val Met Gly Ala Ser
    2615                2620                2625

Tyr Gly Phe Gln Tyr Ser Pro Ala Gln Arg Val Glu Tyr Leu Leu
    2630                2635                2640

Lys Ala Trp Ala Glu Lys Lys Asp Pro Met Gly Phe Ser Tyr Asp
    2645                2650                2655

Thr Arg Cys Phe Asp Ser Thr Val Thr Glu Arg Asp Ile Arg Thr
    2660                2665                2670

Glu Glu Ser Ile Tyr Gln Ala Cys Ser Leu Pro Glu Glu Ala Arg
    2675                2680                2685

Thr Ala Ile His Ser Leu Thr Glu Arg Leu Tyr Val Gly Gly Pro
    2690                2695                2700

Met Phe Asn Ser Lys Gly Gln Thr Cys Gly Tyr Arg Arg Cys Arg
    2705                2710                2715

Ala Ser Gly Val Leu Thr Thr Ser Met Gly Asn Thr Ile Thr Cys
```

```
                    2720                2725                2730

Tyr Val Lys Ala Leu Ala Ala Cys Lys Ala Ala Gly Ile Val Ala
                    2735                2740                2745

Pro Thr Met Leu Val Cys Gly Asp Asp Leu Val Val Ile Ser Glu
                    2750                2755                2760

Ser Gln Gly Thr Glu Glu Asp Glu Arg Asn Leu Arg Ala Phe Thr
                    2765                2770                2775

Glu Ala Met Thr Arg Tyr Ser Ala Pro Pro Gly Asp Pro Pro Arg
                    2780                2785                2790

Pro Glu Tyr Asp Leu Glu Leu Ile Thr Ser Cys Ser Ser Asn Val
                    2795                2800                2805

Ser Val Ala Leu Gly Pro Arg Gly Arg Arg Tyr Tyr Leu Thr
                    2810                2815                2820

Arg Asp Pro Thr Thr Pro Leu Ala Arg Ala Ala Trp Glu Thr Val
                    2825                2830                2835

Arg His Ser Pro Ile Asn Ser Trp Leu Gly Asn Ile Ile Gln Tyr
                    2840                2845                2850

Ala Pro Thr Ile Trp Val Arg Met Val Leu Met Thr His Phe Phe
                    2855                2860                2865

Ser Ile Leu Met Val Gln Asp Thr Leu Asp Gln Asn Leu Asn Phe
                    2870                2875                2880

Glu Met Tyr Gly Ser Val Tyr Ser Val Asn Pro Leu Asp Leu Pro
                    2885                2890                2895

Ala Ile Ile Glu Arg Leu His Gly Leu Asp Ala Phe Ser Met His
                    2900                2905                2910

Thr Tyr Ser His His Glu Leu Thr Arg Val Ala Ser Ala Leu Arg
                    2915                2920                2925

Lys Leu Gly Ala Pro Pro Leu Arg Val Trp Lys Ser Arg Ala Arg
                    2930                2935                2940

Ala Val Arg Ala Ser Leu Ile Ser Arg Gly Gly Lys Ala Ala Val
                    2945                2950                2955

Cys Gly Arg Tyr Leu Phe Asn Trp Ala Val Lys Thr Lys Leu Lys
                    2960                2965                2970

Leu Thr Pro Leu Pro Glu Ala Arg Leu Leu Asp Leu Ser Ser Trp
                    2975                2980                2985

Phe Thr Val Gly Ala Gly Gly Asp Ile Phe His Ser Val Ser
                    2990                2995                3000

Arg Ala Arg Pro Arg Ser Leu Leu Phe Gly Leu Leu Leu Leu Phe
                    3005                3010                3015

Val Gly Val Gly Leu Phe Leu Leu Pro Ala Arg
                    3020                3025

<210> SEQ ID NO 20
<211> LENGTH: 3029
<212> TYPE: PRT
<213> ORGANISM: Hepatitis C virus

<400> SEQUENCE: 20

Met Ser Thr Asn Pro Lys Pro Gln Arg Lys Thr Lys Arg Asn Thr Asn
1               5                   10                  15

Arg Arg Pro Met Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
```

-continued

```
            50                  55                  60
Ile Pro Lys Ala Arg Arg Pro Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Val
130                 135                 140

Gly Gly Val Ala Arg Ala Leu Ala His Gly Val Arg Ala Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Val
            180                 185                 190

Asn Tyr Arg Asn Val Ser Gly Ile Tyr His Val Thr Asn Asp Cys Pro
            195                 200                 205

Asn Ser Ser Ile Val Tyr Glu Ala Asp His His Ile Leu His Leu Pro
210                 215                 220

Gly Cys Val Pro Cys Val Arg Glu Gly Asn Gln Ser Arg Cys Trp Val
225                 230                 235                 240

Ala Leu Thr Pro Thr Val Ala Ala Pro Tyr Ile Gly Ala Pro Leu Glu
                245                 250                 255

Ser Leu Arg Ser His Val Asp Leu Met Val Gly Ala Ala Thr Val Cys
            260                 265                 270

Ser Gly Leu Tyr Ile Gly Asp Leu Cys Gly Gly Leu Phe Leu Val Gly
            275                 280                 285

Gln Met Phe Ser Phe Arg Pro Arg Arg His Trp Thr Thr Gln Asp Cys
290                 295                 300

Asn Cys Ser Ile Tyr Thr Gly His Ile Thr Gly His Arg Met Ala Trp
305                 310                 315                 320

Asp Met Met Met Asn Trp Ser Pro Thr Thr Thr Leu Val Leu Ala Gln
                325                 330                 335

Val Met Arg Ile Pro Thr Thr Leu Val Asp Leu Leu Ser Gly Gly His
            340                 345                 350

Trp Gly Val Leu Val Gly Val Ala Tyr Phe Ser Met Gln Ala Asn Trp
            355                 360                 365

Ala Lys Val Ile Leu Val Leu Phe Leu Phe Ala Gly Val Asp Ala Glu
370                 375                 380

Thr His Val Ser Gly Ala Ala Val Gly Arg Ser Thr Ala Gly Leu Ala
385                 390                 395                 400

Asn Leu Phe Ser Ser Gly Ser Lys Gln Asn Leu Gln Leu Ile Asn Ser
                405                 410                 415

Asn Gly Ser Trp His Ile Asn Arg Thr Ala Leu Asn Cys Asn Asp Ser
            420                 425                 430

Leu Asn Thr Gly Phe Leu Ala Ser Leu Phe Tyr Thr His Lys Phe Asn
            435                 440                 445

Ser Ser Gly Cys Ser Glu Arg Leu Ala Cys Cys Lys Ser Leu Asp Ser
450                 455                 460

Tyr Gly Gln Gly Trp Gly Pro Leu Gly Val Ala Asn Ile Ser Gly Ser
465                 470                 475                 480
```

Ser Asp Asp Arg Pro Tyr Cys Trp His Tyr Ala Pro Arg Pro Cys Gly
            485                 490                 495

Ile Val Pro Ala Ser Ser Val Cys Gly Pro Val Tyr Cys Phe Thr Pro
        500                 505                 510

Ser Pro Val Val Val Gly Thr Thr Asp His Val Gly Val Pro Thr Tyr
        515                 520                 525

Thr Trp Gly Glu Asn Glu Thr Asp Val Phe Leu Leu Asn Ser Thr Arg
        530                 535                 540

Pro Pro His Gly Ala Trp Phe Gly Cys Val Trp Met Asn Ser Thr Gly
545                 550                 555                 560

Phe Thr Lys Thr Cys Gly Ala Pro Pro Cys Glu Val Asn Thr Asn Asn
            565                 570                 575

Gly Thr Trp His Cys Pro Thr Asp Cys Phe Arg Lys His Pro Glu Thr
            580                 585                 590

Thr Tyr Ala Lys Cys Gly Ser Gly Pro Trp Ile Thr Pro Arg Cys Leu
            595                 600                 605

Ile Asp Tyr Pro Tyr Arg Leu Trp His Phe Pro Cys Thr Ala Asn Phe
        610                 615                 620

Ser Val Phe Asn Ile Arg Thr Phe Val Gly Gly Ile Glu His Arg Met
625                 630                 635                 640

Gln Ala Ala Cys Asn Trp Thr Arg Gly Glu Val Cys Gly Leu Glu His
            645                 650                 655

Arg Asp Arg Val Glu Leu Ser Pro Leu Leu Leu Thr Thr Thr Ala Trp
            660                 665                 670

Gln Ile Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
        690                 695                 700

Val Gly Ser Ala Val Val Ser Trp Ala Leu Lys Trp Glu Tyr Val Val
705                 710                 715                 720

Leu Ala Phe Leu Leu Leu Ala Asp Ala Arg Val Ser Ala Cys Leu Trp
            725                 730                 735

Met Met Phe Met Val Ser Gln Val Glu Ala Ala Leu Ser Asn Leu Ile
            740                 745                 750

Asn Ile Asn Ala Ala Ser Ala Ala Gly Ala Gln Gly Phe Trp Tyr Ala
            755                 760                 765

Ile Leu Phe Ile Cys Ile Val Trp His Val Lys Gly Arg Phe Pro Ala
        770                 775                 780

Ala Ala Ala Tyr Ala Ala Cys Gly Leu Trp Pro Leu Phe Leu Leu Leu
785                 790                 795                 800

Leu Met Leu Pro Glu Arg Ala Tyr Ala Tyr Asp Gln Glu Val Ala Gly
            805                 810                 815

Ser Leu Gly Gly Ala Ile Val Val Met Leu Ala Ile Leu Thr Leu Ser
            820                 825                 830

Pro His Tyr Lys Leu Trp Leu Ala Arg Gly Leu Trp Trp Ile Gln Tyr
            835                 840                 845

Phe Ile Ala Arg Thr Glu Ala Val Leu His Val Tyr Ile Pro Ser Phe
        850                 855                 860

Asn Val Arg Gly Pro Arg Asp Ser Val Ile Val Leu Ala Val Leu Val
865                 870                 875                 880

Cys Pro His Leu Val Phe Asp Ile Thr Lys Tyr Leu Leu Ala Ile Leu
            885                 890                 895

Gly Pro Leu His Ile Leu Gln Ala Ser Leu Leu Arg Ile Pro Tyr Phe
        900                 905                 910

Val Arg Ala Gln Ala Leu Val Lys Ile Cys Ser Leu Leu Arg Gly Val
        915                 920                 925

Val Tyr Gly Lys Tyr Phe Gln Met Val Val Leu Lys Ala Gly Ala Leu
        930                 935                 940

Thr Gly Thr Tyr Ile Tyr Asp His Leu Thr Pro Met Ser Asp Trp Ala
945                 950                 955                 960

Ala Thr Gly Leu Arg Asp Leu Ala Val Ala Leu Glu Pro Val Val Phe
                965                 970                 975

Thr Pro Met Glu Lys Lys Val Ile Val Trp Gly Ala Asp Thr Ala Ala
            980                 985                 990

Cys Gly Asp Ile Ile Arg Gly Leu Pro Val Ser Ala Arg Leu Gly Asn
                995                 1000                1005

Glu Ile Leu Leu Gly Pro Ala Asp Thr Glu Thr Ser Lys Gly Trp
    1010                1015                1020

Arg Leu Leu Ala Pro Ile Thr Ala Tyr Ala Gln Gln Thr Arg Gly
    1025                1030                1035

Leu Leu Gly Ala Ile Val Val Ser Met Thr Gly Arg Asp Arg Thr
    1040                1045                1050

Glu Gln Ala Gly Glu Val Gln Ile Leu Ser Thr Val Ser Gln Ser
    1055                1060                1065

Phe Leu Gly Thr Thr Ile Ser Gly Val Leu Trp Thr Val Tyr His
    1070                1075                1080

Gly Ala Gly Asn Lys Thr Leu Ala Gly Leu Arg Gly Pro Val Thr
    1085                1090                1095

Gln Met Tyr Ser Ser Ala Glu Gly Asp Leu Val Gly Trp Pro Ser
    1100                1105                1110

Pro Pro Gly Thr Lys Ser Leu Glu Pro Cys Lys Cys Gly Ala Val
    1115                1120                1125

Asp Leu Tyr Leu Val Thr Arg Asn Ala Asp Val Ile Pro Ala Arg
    1130                1135                1140

Arg Arg Gly Asp Lys Arg Gly Ala Leu Leu Ser Pro Arg Pro Ile
    1145                1150                1155

Ser Thr Leu Lys Gly Ser Ser Gly Gly Pro Val Leu Cys Pro Arg
    1160                1165                1170

Gly His Val Val Gly Leu Phe Arg Ala Ala Val Cys Ser Arg Gly
    1175                1180                1185

Val Ala Lys Ser Ile Asp Phe Ile Pro Val Glu Thr Leu Asp Val
    1190                1195                1200

Val Thr Arg Ser Pro Thr Phe Ser Asp Asn Ser Thr Pro Pro Ala
    1205                1210                1215

Val Pro Gln Thr Tyr Gln Val Gly Tyr Leu His Ala Pro Thr Gly
    1220                1225                1230

Ser Gly Lys Ser Thr Lys Val Pro Val Ala Tyr Ala Ala Gln Gly
    1235                1240                1245

Tyr Lys Val Leu Val Leu Asn Pro Ser Val Ala Ala Thr Leu Gly
    1250                1255                1260

Phe Gly Ala Tyr Leu Ser Lys Ala His Gly Ile Asn Pro Asn Ile
    1265                1270                1275

Arg Thr Gly Val Arg Thr Val Met Thr Gly Glu Ala Ile Thr Tyr
    1280                1285                1290

Ser Thr Tyr Gly Lys Phe Leu Ala Asp Gly Gly Cys Ala Ser Gly
    1295                1300                1305

Ala Tyr Asp Ile Ile Ile Cys Asp Glu Cys His Ala Val Asp Ala

-continued

|  | 1310 |  |  |  | 1315 |  |  |  | 1320 |  |  |
|---|---|---|---|---|---|---|---|---|---|---|---|
| Thr | Ser | Ile | Leu | Gly | Ile | Gly | Thr | Val | Leu | Asp | Gln | Ala | Glu | Thr |
| 1325 |  |  |  | 1330 |  |  |  | 1335 |  |  |  |
| Ala | Gly | Val | Arg | Leu | Thr | Val | Leu | Ala | Thr | Ala | Thr | Pro | Pro | Gly |
| 1340 |  |  |  | 1345 |  |  |  | 1350 |  |  |  |
| Ser | Val | Thr | Thr | Pro | His | Pro | Asp | Ile | Glu | Glu | Val | Gly | Leu | Gly |
| 1355 |  |  |  | 1360 |  |  |  | 1365 |  |  |  |
| Arg | Glu | Gly | Glu | Ile | Pro | Phe | Tyr | Gly | Arg | Ala | Ile | Pro | Leu | Ser |
| 1370 |  |  |  | 1375 |  |  |  | 1380 |  |  |  |
| Cys | Ile | Lys | Gly | Gly | Arg | His | Leu | Ile | Phe | Cys | His | Ser | Lys | Lys |
| 1385 |  |  |  | 1390 |  |  |  | 1395 |  |  |  |
| Lys | Cys | Asp | Glu | Leu | Ala | Ala | Ala | Leu | Arg | Gly | Met | Gly | Leu | Asn |
| 1400 |  |  |  | 1405 |  |  |  | 1410 |  |  |  |
| Ala | Val | Ala | Tyr | Tyr | Arg | Gly | Leu | Asp | Val | Ser | Ile | Ile | Pro | Ala |
| 1415 |  |  |  | 1420 |  |  |  | 1425 |  |  |  |
| Gln | Gly | Asp | Val | Val | Val | Ala | Thr | Asp | Ala | Leu | Met | Thr | Gly |
| 1430 |  |  |  | 1435 |  |  |  | 1440 |  |  |  |
| Tyr | Thr | Gly | Asp | Phe | Asp | Ser | Val | Ile | Asp | Cys | Asn | Val | Ala | Val |
| 1445 |  |  |  | 1450 |  |  |  | 1455 |  |  |  |
| Thr | Gln | Ala | Val | Asp | Phe | Ser | Leu | Asp | Pro | Thr | Phe | Thr | Ile | Thr |
| 1460 |  |  |  | 1465 |  |  |  | 1470 |  |  |  |
| Thr | Gln | Thr | Val | Pro | Gln | Asp | Ala | Val | Ser | Arg | Ser | Gln | Arg | Arg |
| 1475 |  |  |  | 1480 |  |  |  | 1485 |  |  |  |
| Gly | Arg | Thr | Gly | Arg | Gly | Arg | Gln | Gly | Thr | Tyr | Arg | Tyr | Val | Ser |
| 1490 |  |  |  | 1495 |  |  |  | 1500 |  |  |  |
| Thr | Gly | Glu | Arg | Ala | Ser | Gly | Met | Phe | Asp | Ser | Val | Val | Leu | Cys |
| 1505 |  |  |  | 1510 |  |  |  | 1515 |  |  |  |
| Glu | Cys | Tyr | Asp | Ala | Gly | Ala | Ala | Trp | Tyr | Asp | Leu | Thr | Pro | Ala |
| 1520 |  |  |  | 1525 |  |  |  | 1530 |  |  |  |
| Glu | Thr | Thr | Val | Arg | Leu | Arg | Ala | Tyr | Phe | Asn | Thr | Pro | Gly | Leu |
| 1535 |  |  |  | 1540 |  |  |  | 1545 |  |  |  |
| Pro | Val | Cys | Gln | Asp | His | Leu | Glu | Phe | Trp | Glu | Ala | Val | Phe | Thr |
| 1550 |  |  |  | 1555 |  |  |  | 1560 |  |  |  |
| Gly | Leu | Thr | His | Ile | Asp | Ala | His | Phe | Leu | Ser | Gln | Thr | Lys | Gln |
| 1565 |  |  |  | 1570 |  |  |  | 1575 |  |  |  |
| Ala | Gly | Glu | Asn | Phe | Ala | Tyr | Leu | Val | Ala | Tyr | Gln | Ala | Thr | Val |
| 1580 |  |  |  | 1585 |  |  |  | 1590 |  |  |  |
| Cys | Ala | Arg | Ala | Lys | Ala | Pro | Pro | Pro | Ser | Trp | Asp | Ala | Met | Trp |
| 1595 |  |  |  | 1600 |  |  |  | 1605 |  |  |  |
| Lys | Cys | Leu | Ala | Arg | Leu | Lys | Pro | Thr | Leu | Ala | Gly | Pro | Thr | Pro |
| 1610 |  |  |  | 1615 |  |  |  | 1620 |  |  |  |
| Leu | Leu | Tyr | Arg | Leu | Gly | Pro | Ile | Thr | Asn | Glu | Val | Thr | Leu | Thr |
| 1625 |  |  |  | 1630 |  |  |  | 1635 |  |  |  |
| His | Pro | Gly | Thr | Lys | Tyr | Ile | Ala | Thr | Cys | Met | Gln | Ala | Asp | Leu |
| 1640 |  |  |  | 1645 |  |  |  | 1650 |  |  |  |
| Glu | Val | Met | Thr | Ser | Thr | Trp | Val | Leu | Ala | Gly | Gly | Val | Leu | Ala |
| 1655 |  |  |  | 1660 |  |  |  | 1665 |  |  |  |
| Ala | Val | Ala | Ala | Tyr | Cys | Leu | Ala | Thr | Gly | Cys | Val | Ser | Ile | Ile |
| 1670 |  |  |  | 1675 |  |  |  | 1680 |  |  |  |
| Gly | Arg | Leu | His | Val | Asn | Gln | Arg | Val | Val | Val | Ala | Pro | Asp | Lys |
| 1685 |  |  |  | 1690 |  |  |  | 1695 |  |  |  |
| Glu | Val | Leu | Tyr | Glu | Ala | Phe | Asp | Glu | Met | Glu | Glu | Cys | Ala | Ser |
| 1700 |  |  |  | 1705 |  |  |  | 1710 |  |  |  |

```
Arg Ala Ala Leu Ile Glu Glu Gly Gln Arg Ile Ala Glu Met Leu
    1715                1720                1725

Lys Ser Lys Ile Gln Gly Leu Leu Gln Gln Ala Ser Lys Gln Ala
    1730                1735                1740

Gln Asp Ile Gln Pro Ala Met Gln Ala Ser Trp Pro Lys Val Glu
    1745                1750                1755

Gln Phe Trp Ala Arg His Met Trp Asn Phe Ile Ser Gly Ile Gln
    1760                1765                1770

Tyr Leu Ala Gly Leu Ser Thr Leu Pro Gly Asn Pro Ala Val Ala
    1775                1780                1785

Ser Met Met Ala Phe Ser Ala Ala Leu Thr Ser Pro Leu Ser Thr
    1790                1795                1800

Ser Thr Thr Ile Leu Leu Asn Ile Met Gly Gly Trp Leu Ala Ser
    1805                1810                1815

Gln Ile Ala Pro Pro Ala Gly Ala Thr Gly Phe Val Val Ser Gly
    1820                1825                1830

Leu Val Gly Ala Ala Val Gly Ser Ile Gly Leu Gly Lys Val Leu
    1835                1840                1845

Val Asp Ile Leu Ala Gly Tyr Gly Ala Gly Ile Ser Gly Ala Leu
    1850                1855                1860

Val Ala Phe Lys Ile Met Ser Gly Glu Lys Pro Ser Met Glu Asp
    1865                1870                1875

Val Ile Asn Leu Leu Pro Gly Ile Leu Ser Pro Gly Ala Leu Val
    1880                1885                1890

Val Gly Val Ile Cys Ala Ala Ile Leu Arg Arg His Val Gly Pro
    1895                1900                1905

Gly Glu Gly Ala Val Gln Trp Met Asn Arg Leu Ile Ala Phe Ala
    1910                1915                1920

Ser Arg Gly Asn His Val Ala Pro Thr His Tyr Val Thr Glu Ser
    1925                1930                1935

Asp Ala Ser Gln Arg Val Thr Gln Leu Leu Gly Ser Leu Thr Ile
    1940                1945                1950

Thr Ser Leu Leu Arg Arg Leu His Asn Trp Ile Thr Glu Asp Cys
    1955                1960                1965

Pro Ile Pro Cys Ser Gly Ser Trp Leu Arg Asp Val Trp Asp Trp
    1970                1975                1980

Val Cys Thr Ile Leu Thr Asp Phe Lys Asn Trp Leu Thr Ser Lys
    1985                1990                1995

Leu Phe Pro Lys Leu Pro Gly Leu Pro Phe Ile Ser Cys Gln Lys
    2000                2005                2010

Gly Tyr Lys Gly Val Trp Ala Gly Thr Gly Ile Met Thr Thr Arg
    2015                2020                2025

Cys Pro Cys Gly Ala Asn Ile Ser Gly Asn Val Arg Leu Gly Ser
    2030                2035                2040

Met Arg Ile Thr Gly Pro Lys Thr Cys Met Asn Thr Trp Gln Gly
    2045                2050                2055

Thr Phe Pro Ile Asn Cys Tyr Thr Glu Gly Gln Cys Ala Pro Lys
    2060                2065                2070

Pro Pro Thr Asn Tyr Lys Thr Ala Ile Trp Arg Val Ala Ala Ser
    2075                2080                2085

Glu Tyr Ala Glu Val Thr Gln His Gly Ser Tyr Ser Tyr Val Thr
    2090                2095                2100

Gly Leu Thr Thr Asp Asn Leu Lys Ile Pro Cys Gln Leu Pro Ser
    2105                2110                2115
```

-continued

```
Pro Glu Phe Phe Ser Trp Val Asp Gly Val Gln Ile His Arg Phe
    2120                2125                2130

Ala Pro Thr Pro Lys Pro Phe Phe Arg Asp Glu Val Ser Phe Cys
    2135                2140                2145

Val Gly Leu Asn Ser Tyr Ala Val Gly Ser Gln Leu Pro Cys Glu
    2150                2155                2160

Pro Glu Pro Asp Ala Asp Val Leu Arg Ser Met Leu Thr Asp Pro
    2165                2170                2175

Pro His Ile Thr Ala Glu Thr Ala Ala Arg Arg Leu Ala Arg Gly
    2180                2185                2190

Ser Pro Pro Ser Glu Ala Ser Ser Val Ser Gln Leu Ser Ala
    2195                2200                2205

Pro Ser Leu Arg Ala Thr Cys Thr Thr His Ser Asn Thr Tyr Asp
    2210                2215                2220

Val Asp Met Val Asp Ala Asn Leu Leu Met Glu Gly Gly Val Ala
    2225                2230                2235

Gln Thr Glu Pro Glu Ser Arg Val Pro Val Leu Asp Phe Leu Glu
    2240                2245                2250

Pro Met Ala Glu Glu Glu Ser Asp Leu Glu Pro Ser Ile Pro Ser
    2255                2260                2265

Glu Cys Met Leu Pro Arg Ser Gly Phe Pro Arg Ala Leu Pro Ala
    2270                2275                2280

Trp Ala Arg Pro Asp Tyr Asn Pro Pro Leu Val Glu Ser Trp Arg
    2285                2290                2295

Arg Pro Asp Tyr Gln Pro Pro Thr Val Ala Gly Cys Ala Leu Pro
    2300                2305                2310

Pro Pro Lys Lys Ala Pro Thr Pro Pro Pro Arg Arg Arg Arg Thr
    2315                2320                2325

Val Gly Leu Ser Glu Ser Thr Ile Ser Glu Ala Leu Gln Gln Leu
    2330                2335                2340

Ala Ile Lys Thr Phe Gly Gln Pro Pro Ser Ser Gly Asp Ala Gly
    2345                2350                2355

Ser Ser Thr Gly Ala Gly Ala Ala Glu Ser Gly Gly Pro Thr Ser
    2360                2365                2370

Pro Gly Glu Pro Ala Pro Ser Glu Thr Gly Ser Ala Ser Ser Met
    2375                2380                2385

Pro Pro Leu Glu Gly Glu Pro Gly Asp Pro Asp Leu Glu Ser Asp
    2390                2395                2400

Gln Val Glu Leu Gln Pro Pro Gln Gly Gly Val Ala Pro
    2405                2410                2415

Gly Ser Gly Ser Gly Ser Trp Ser Thr Cys Ser Glu Glu Asp Asp
    2420                2425                2430

Thr Thr Val Cys Cys Ser Met Ser Tyr Ser Trp Thr Gly Ala Leu
    2435                2440                2445

Ile Thr Pro Cys Ser Pro Glu Glu Glu Lys Leu Pro Ile Asn Pro
    2450                2455                2460

Leu Ser Asn Ser Leu Leu Arg Tyr His Asn Lys Val Tyr Cys Thr
    2465                2470                2475

Thr Ser Lys Ser Ala Ser Gln Arg Ala Lys Lys Val Thr Phe Asp
    2480                2485                2490

Arg Thr Gln Val Leu Asp Ala His Tyr Asp Ser Val Leu Lys Asp
    2495                2500                2505

Ile Lys Leu Ala Ala Ser Lys Val Ser Ala Arg Leu Leu Thr Leu
```

-continued

```
                    2510                2515                2520

Glu Glu Ala Cys Gln Leu Thr Pro Pro His Ser Ala Arg Ser Lys
    2525                2530                2535

Tyr Gly Phe Gly Ala Lys Glu Val Arg Ser Leu Ser Gly Arg Ala
    2540                2545                2550

Val Asn His Ile Lys Ser Val Trp Lys Asp Leu Leu Glu Asp Pro
    2555                2560                2565

Gln Thr Pro Ile Pro Thr Thr Ile Met Ala Lys Asn Glu Val Phe
    2570                2575                2580

Cys Val Asp Pro Ala Lys Gly Gly Lys Pro Ala Arg Leu Ile
    2585                2590                2595

Val Tyr Pro Asp Leu Gly Val Arg Val Cys Glu Lys Met Ala Leu
    2600                2605                2610

Tyr Asp Ile Thr Gln Lys Leu Pro Gln Ala Val Met Gly Ala Ser
    2615                2620                2625

Tyr Gly Phe Gln Tyr Ser Pro Ala Gln Arg Val Glu Tyr Leu Leu
    2630                2635                2640

Lys Ala Trp Ala Glu Lys Lys Asp Pro Met Gly Phe Ser Tyr Asp
    2645                2650                2655

Thr Arg Cys Phe Asp Ser Thr Val Thr Glu Arg Asp Ile Arg Thr
    2660                2665                2670

Glu Glu Ser Ile Tyr Gln Ala Cys Ser Leu Pro Glu Glu Ala Arg
    2675                2680                2685

Thr Ala Ile His Ser Leu Thr Glu Arg Leu Tyr Val Gly Gly Pro
    2690                2695                2700

Met Phe Asn Ser Lys Gly Gln Thr Cys Gly Tyr Arg Arg Cys Arg
    2705                2710                2715

Ala Ser Gly Val Leu Thr Thr Ser Met Gly Asn Thr Ile Thr Cys
    2720                2725                2730

Tyr Val Lys Ala Leu Ala Ala Cys Lys Ala Ala Gly Ile Val Ala
    2735                2740                2745

Pro Thr Met Leu Val Cys Gly Asp Asp Leu Val Val Ile Ser Glu
    2750                2755                2760

Ser Gln Gly Thr Glu Glu Asp Glu Arg Asn Leu Arg Ala Phe Thr
    2765                2770                2775

Glu Ala Met Thr Arg Tyr Ser Ala Pro Pro Gly Asp Pro Pro Arg
    2780                2785                2790

Pro Glu Tyr Asp Leu Glu Leu Ile Thr Ser Cys Ser Ser Asn Val
    2795                2800                2805

Ser Val Ala Leu Gly Pro Arg Gly Arg Arg Tyr Tyr Leu Thr
    2810                2815                2820

Arg Asp Pro Thr Thr Pro Leu Ala Arg Ala Ala Trp Glu Thr Val
    2825                2830                2835

Arg His Ser Pro Ile Asn Ser Trp Leu Gly Asn Ile Ile Gln Tyr
    2840                2845                2850

Ala Pro Thr Ile Trp Val Arg Met Val Leu Met Thr His Phe Phe
    2855                2860                2865

Ser Ile Leu Met Val Gln Asp Thr Leu Asp Gln Asn Leu Asn Phe
    2870                2875                2880

Glu Met Tyr Gly Ser Val Tyr Ser Val Asn Pro Leu Asp Leu Pro
    2885                2890                2895

Ala Ile Ile Glu Arg Leu His Gly Leu Asp Ala Phe Ser Met His
    2900                2905                2910
```

-continued

| | | | | | | | | | | | |
|---|---|---|---|---|---|---|---|---|---|---|---|
|Thr|Tyr|Ser|His|His|Glu|Leu|Thr|Arg|Val|Ala|Ser|Ala|Leu|Arg|
| |2915| | | |2920| | | |2925| | |

Thr Tyr Ser His His Glu Leu Thr Arg Val Ala Ser Ala Leu Arg
    2915                2920                2925

Lys Leu Gly Ala Pro Pro Leu Arg Val Trp Lys Ser Arg Ala Arg
    2930                2935                2940

Ala Val Arg Ala Ser Leu Ile Ser Arg Gly Gly Lys Ala Ala Val
    2945                2950                2955

Cys Gly Arg Tyr Leu Phe Asn Trp Ala Val Lys Thr Lys Leu Lys
    2960                2965                2970

Leu Thr Pro Leu Pro Glu Ala Arg Leu Leu Asp Leu Ser Ser Trp
    2975                2980                2985

Phe Thr Val Gly Ala Gly Gly Asp Ile Phe His Ser Val Ser
    2990                2995                3000

Arg Ala Arg Pro Arg Ser Leu Leu Phe Gly Leu Leu Leu Leu Phe
    3005                3010                3015

Val Gly Val Gly Leu Phe Leu Leu Pro Ala Arg
    3020                3025

<210> SEQ ID NO 21
<211> LENGTH: 3029
<212> TYPE: PRT
<213> ORGANISM: Hepatitis C virus

<400> SEQUENCE: 21

Met Ser Thr Asn Pro Lys Pro Gln Arg Lys Thr Lys Arg Asn Thr Asn
1               5                   10                  15

Arg Arg Pro Met Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Val
            180                 185                 190

Asn Tyr Arg Asn Val Ser Gly Ile Tyr His Val Thr Asn Asp Cys Pro
        195                 200                 205

Asn Ser Ser Ile Val Tyr Glu Ala Asp His His Ile Leu His Leu Pro
    210                 215                 220

Gly Cys Val Pro Cys Val Arg Glu Gly Asn Gln Ser Arg Cys Trp Val
225                 230                 235                 240

Ala Leu Thr Pro Thr Val Ala Pro Tyr Ile Gly Ala Pro Leu Glu
                245                 250                 255

```
Ser Leu Arg Ser His Val Asp Leu Met Val Gly Ala Ala Thr Val Cys
            260                 265                 270

Ser Gly Leu Tyr Ile Gly Asp Leu Cys Gly Gly Leu Phe Leu Val Gly
            275                 280                 285

Gln Met Phe Ser Phe Arg Pro Arg His Trp Thr Thr Gln Asp Cys
290                 295                 300

Asn Cys Ser Ile Tyr Thr Gly His Ile Thr Gly His Arg Met Ala Trp
305                 310                 315                 320

Asp Met Met Met Asn Trp Ser Pro Thr Thr Leu Val Leu Ala Gln
                325                 330                 335

Val Met Arg Ile Pro Thr Thr Leu Val Asp Leu Leu Ser Gly Gly His
            340                 345                 350

Trp Gly Val Leu Val Gly Val Ala Tyr Phe Ser Met Gln Ala Asn Trp
            355                 360                 365

Ala Lys Val Ile Leu Val Leu Phe Leu Phe Ala Gly Val Asp Ala Glu
            370                 375                 380

Thr His Val Ser Gly Ala Ala Val Gly Arg Ser Thr Ala Gly Leu Ala
385                 390                 395                 400

Asn Leu Phe Ser Ser Gly Ser Lys Gln Asn Leu Gln Leu Ile Asn Ser
            405                 410                 415

Asn Gly Ser Trp His Ile Asn Arg Thr Ala Leu Asn Cys Asn Asp Ser
            420                 425                 430

Leu Asn Thr Gly Phe Leu Ala Ser Leu Phe Tyr Thr His Lys Phe Asn
            435                 440                 445

Ser Ser Gly Cys Ser Glu Arg Leu Ala Cys Cys Lys Ser Leu Asp Ser
            450                 455                 460

Tyr Gly Gln Gly Trp Gly Pro Leu Gly Val Ala Asn Ile Ser Gly Ser
465                 470                 475                 480

Ser Asp Asp Arg Pro Tyr Cys Trp His Tyr Ala Pro Arg Pro Cys Gly
            485                 490                 495

Ile Val Pro Ala Ser Ser Val Cys Gly Pro Val Tyr Cys Phe Thr Pro
            500                 505                 510

Ser Pro Val Val Val Gly Thr Thr Asp His Val Gly Val Pro Thr Tyr
            515                 520                 525

Thr Trp Gly Glu Asn Glu Thr Asp Val Phe Leu Leu Asn Ser Thr Arg
            530                 535                 540

Pro Pro His Gly Ala Trp Phe Gly Cys Val Trp Met Asn Ser Thr Gly
545                 550                 555                 560

Phe Thr Lys Thr Cys Gly Ala Pro Pro Cys Glu Val Asn Thr Asn Asn
                565                 570                 575

Gly Thr Trp His Cys Pro Thr Asp Cys Phe Arg Lys His Pro Glu Thr
            580                 585                 590

Thr Tyr Ala Lys Cys Gly Ser Gly Pro Trp Ile Thr Pro Arg Cys Leu
            595                 600                 605

Ile Asp Tyr Pro Tyr Arg Leu Trp His Phe Pro Cys Thr Ala Asn Phe
            610                 615                 620

Ser Val Phe Asn Ile Arg Thr Phe Val Gly Gly Ile Glu His Arg Met
625                 630                 635                 640

Gln Ala Ala Cys Asn Trp Thr Arg Gly Glu Val Cys Gly Leu Glu His
                645                 650                 655

Arg Asp Arg Val Glu Leu Ser Pro Leu Leu Leu Thr Thr Thr Ala Trp
            660                 665                 670

Gln Ile Leu Pro Cys Ser Phe Thr Thr Leu Pro Ala Leu Ser Thr Gly
            675                 680                 685
```

-continued

Leu Ile His Leu His Gln Asn Ile Val Asp Val Gln Tyr Leu Tyr Gly
690                 695                 700

Val Gly Ser Ala Val Val Ser Trp Ala Leu Lys Trp Glu Tyr Val Val
705                 710                 715                 720

Leu Ala Phe Leu Leu Leu Ala Asp Ala Arg Val Ser Ala Cys Leu Trp
            725                 730                 735

Met Met Phe Met Val Ser Gln Val Glu Ala Ala Leu Ser Asn Leu Ile
            740                 745                 750

Asn Ile Asn Ala Ala Ser Ala Ala Gly Ala Gln Gly Phe Trp Tyr Ala
            755                 760                 765

Ile Leu Phe Ile Cys Ile Val Trp His Val Lys Gly Arg Phe Pro Ala
            770                 775                 780

Ala Ala Ala Tyr Ala Ala Cys Gly Leu Trp Pro Leu Phe Leu Leu Leu
785                 790                 795                 800

Leu Met Leu Pro Glu Arg Ala Tyr Ala Tyr Asp Gln Glu Val Ala Gly
            805                 810                 815

Ser Leu Gly Gly Ala Ile Val Val Met Leu Thr Ile Leu Thr Leu Ser
            820                 825                 830

Pro His Tyr Lys Leu Trp Leu Ala Arg Gly Leu Trp Trp Ile Gln Tyr
            835                 840                 845

Phe Ile Ala Arg Thr Glu Ala Val Leu His Val Tyr Ile Pro Ser Phe
850                 855                 860

Asn Val Arg Gly Pro Arg Asp Ser Val Ile Val Leu Ala Val Leu Val
865                 870                 875                 880

Cys Pro His Leu Val Phe Asp Ile Thr Lys Tyr Leu Leu Ala Ile Leu
            885                 890                 895

Gly Pro Leu His Ile Leu Gln Ala Ser Leu Leu Arg Ile Pro Tyr Phe
            900                 905                 910

Val Arg Ala Gln Ala Leu Val Lys Ile Cys Ser Leu Leu Arg Gly Val
            915                 920                 925

Val Tyr Gly Lys Tyr Phe Gln Met Val Val Leu Lys Ala Gly Ala Leu
930                 935                 940

Thr Gly Thr Tyr Ile Tyr Asp His Leu Thr Pro Met Ser Asp Trp Ala
945                 950                 955                 960

Ala Thr Gly Leu Arg Asp Leu Ala Val Ala Leu Glu Pro Val Val Phe
            965                 970                 975

Ser Pro Met Glu Lys Lys Val Ile Val Trp Gly Ala Asp Thr Ala Ala
            980                 985                 990

Cys Gly Asp Ile Ile Arg Gly Leu Pro Val Ser Ala Arg Leu Gly Asn
            995                 1000                1005

Glu Ile Leu Leu Gly Pro Ala Asp Thr Glu Thr Ser Lys Gly Trp
    1010                1015                1020

Arg Leu Leu Ala Pro Ile Thr Ala Tyr Ala Gln Gln Thr Arg Gly
    1025                1030                1035

Leu Leu Gly Ala Ile Val Val Ser Met Thr Gly Arg Asp Arg Thr
    1040                1045                1050

Glu Gln Ala Gly Glu Val Gln Ile Leu Ser Thr Val Ser Gln Ser
    1055                1060                1065

Phe Leu Gly Thr Thr Ile Ser Gly Val Leu Trp Thr Val Tyr His
    1070                1075                1080

Gly Ala Gly Asn Lys Thr Leu Ala Gly Leu Arg Gly Pro Val Thr
    1085                1090                1095

Gln Met Tyr Ser Ser Ala Glu Gly Asp Leu Val Gly Trp Pro Ser

```
              1100            1105            1110
Pro Pro Gly Thr Lys Ser Leu Glu Pro Cys Lys Cys Gly Ala Val
    1115            1120            1125
Asp Leu Tyr Leu Val Thr Arg Asn Ala Asp Val Ile Pro Ala Arg
    1130            1135            1140
Arg Arg Gly Asp Lys Arg Gly Ala Leu Leu Ser Pro Arg Pro Ile
    1145            1150            1155
Ser Thr Leu Lys Gly Ser Ser Gly Gly Pro Val Leu Cys Pro Arg
    1160            1165            1170
Gly His Val Val Gly Leu Phe Arg Ala Ala Val Cys Ser Arg Gly
    1175            1180            1185
Val Ala Lys Ser Ile Asp Phe Ile Pro Val Glu Thr Leu Asp Val
    1190            1195            1200
Val Thr Arg Ser Pro Thr Phe Ser Asp Asn Ser Thr Pro Pro Ala
    1205            1210            1215
Val Pro Gln Thr Tyr Gln Val Gly Tyr Leu His Ala Pro Thr Gly
    1220            1225            1230
Ser Gly Lys Ser Thr Lys Val Pro Val Ala Tyr Ala Ala Gln Gly
    1235            1240            1245
Tyr Lys Val Leu Val Leu Asn Pro Ser Val Ala Ala Thr Leu Gly
    1250            1255            1260
Phe Gly Ala Tyr Leu Ser Lys Ala His Gly Ile Asn Pro Asn Ile
    1265            1270            1275
Arg Thr Gly Val Arg Thr Val Met Thr Gly Glu Ala Ile Thr Tyr
    1280            1285            1290
Ser Thr Tyr Gly Lys Phe Leu Ala Asp Gly Gly Cys Ala Ser Gly
    1295            1300            1305
Ala Tyr Asp Ile Ile Ile Cys Asp Glu Cys His Ala Val Asp Ala
    1310            1315            1320
Thr Ser Ile Leu Gly Ile Gly Thr Val Leu Asp Gln Ala Glu Thr
    1325            1330            1335
Ala Gly Val Arg Leu Thr Val Leu Ala Thr Ala Thr Pro Pro Gly
    1340            1345            1350
Ser Val Thr Thr Pro His Pro Asp Ile Glu Glu Val Gly Leu Gly
    1355            1360            1365
Arg Glu Gly Glu Ile Pro Phe Tyr Gly Arg Ala Ile Pro Leu Ser
    1370            1375            1380
Cys Ile Lys Gly Gly Arg His Leu Ile Phe Cys His Ser Lys Lys
    1385            1390            1395
Lys Cys Asp Glu Leu Ala Ala Ala Leu Arg Gly Met Gly Leu Asn
    1400            1405            1410
Ala Val Ala Tyr Tyr Arg Gly Leu Asp Val Ser Ile Ile Pro Ala
    1415            1420            1425
Gln Gly Asp Val Val Val Ala Thr Asp Ala Leu Met Thr Gly
    1430            1435            1440
Tyr Thr Gly Asp Phe Asp Ser Val Ile Asp Cys Asn Val Ala Val
    1445            1450            1455
Thr Gln Ala Val Asp Phe Ser Leu Asp Pro Thr Phe Thr Ile Thr
    1460            1465            1470
Thr Gln Thr Val Pro Gln Asp Ala Val Ser Arg Ser Gln Arg Arg
    1475            1480            1485
Gly Arg Thr Gly Arg Gly Arg Gln Gly Thr Tyr Arg Tyr Val Ser
    1490            1495            1500
```

-continued

```
Thr Gly Glu Arg Ala Ser Gly Met Phe Asp Ser Val Val Leu Cys
    1505                1510                1515

Glu Cys Tyr Asp Ala Gly Ala Ala Trp Tyr Asp Leu Thr Pro Ala
    1520                1525                1530

Glu Thr Thr Val Arg Leu Arg Ala Tyr Phe Asn Thr Pro Gly Leu
    1535                1540                1545

Pro Val Cys Gln Asp His Leu Glu Phe Trp Glu Ala Val Phe Thr
    1550                1555                1560

Gly Leu Thr His Ile Asp Ala His Phe Leu Ser Gln Thr Lys Gln
    1565                1570                1575

Ala Gly Glu Asn Phe Ala Tyr Leu Val Ala Tyr Gln Ala Thr Val
    1580                1585                1590

Cys Ala Arg Ala Lys Ala Pro Pro Pro Ser Trp Asp Ala Met Trp
    1595                1600                1605

Lys Cys Leu Ala Arg Leu Lys Pro Thr Leu Ala Gly Pro Thr Pro
    1610                1615                1620

Leu Leu Tyr Arg Leu Gly Pro Ile Thr Asn Glu Val Thr Leu Thr
    1625                1630                1635

His Pro Gly Thr Lys Tyr Ile Ala Thr Cys Met Gln Ala Asp Leu
    1640                1645                1650

Glu Val Met Thr Ser Thr Trp Val Leu Ala Gly Gly Val Leu Ala
    1655                1660                1665

Ala Val Ala Ala Tyr Cys Leu Ala Thr Gly Cys Val Ser Ile Ile
    1670                1675                1680

Gly Arg Leu His Val Asn Gln Arg Val Val Val Ala Pro Asp Lys
    1685                1690                1695

Glu Val Leu Tyr Glu Ala Phe Asp Glu Met Glu Glu Cys Ala Ser
    1700                1705                1710

Arg Ala Ala Leu Ile Glu Glu Gly Gln Arg Ile Ala Glu Met Leu
    1715                1720                1725

Lys Ser Lys Ile Gln Gly Leu Leu Gln Gln Ala Ser Lys Gln Ala
    1730                1735                1740

Gln Asp Ile Gln Pro Ala Met Gln Ala Ser Trp Pro Lys Val Glu
    1745                1750                1755

Gln Phe Trp Ala Arg His Met Trp Asn Phe Ile Ser Gly Ile Gln
    1760                1765                1770

Tyr Leu Ala Gly Leu Ser Thr Leu Pro Gly Asn Pro Ala Val Ala
    1775                1780                1785

Ser Met Met Ala Phe Ser Ala Ala Leu Thr Ser Pro Leu Ser Thr
    1790                1795                1800

Ser Thr Thr Ile Leu Leu Asn Ile Met Gly Gly Trp Leu Ala Ser
    1805                1810                1815

Gln Ile Ala Pro Pro Ala Gly Ala Thr Gly Phe Val Val Ser Gly
    1820                1825                1830

Leu Val Gly Ala Ala Val Gly Ser Ile Gly Leu Gly Lys Val Leu
    1835                1840                1845

Val Asp Ile Leu Ala Gly Tyr Gly Ala Gly Ile Ser Gly Ala Leu
    1850                1855                1860

Val Ala Phe Lys Ile Met Ser Gly Glu Lys Pro Ser Met Glu Asp
    1865                1870                1875

Val Ile Asn Leu Leu Pro Gly Ile Leu Ser Pro Gly Ala Leu Val
    1880                1885                1890

Val Gly Val Ile Cys Ala Ala Ile Leu Arg Arg His Val Gly Pro
    1895                1900                1905
```

-continued

Gly Glu Gly Ala Val Gln Trp Met Asn Arg Leu Ile Ala Phe Ala
    1910            1915                1920

Ser Arg Gly Asn His Val Ala Pro Thr His Tyr Val Thr Glu Ser
    1925            1930                1935

Asp Ala Ser Gln Arg Val Thr Gln Leu Leu Gly Ser Leu Thr Ile
    1940            1945                1950

Thr Ser Leu Leu Arg Arg Leu His Asn Trp Ile Thr Glu Asp Cys
    1955            1960                1965

Pro Ile Pro Cys Ser Gly Ser Trp Leu Arg Asp Val Trp Asp Trp
    1970            1975                1980

Val Cys Thr Ile Leu Thr Asp Phe Lys Asn Trp Leu Thr Ser Lys
    1985            1990                1995

Leu Phe Pro Lys Leu Pro Gly Leu Pro Phe Ile Ser Cys Gln Lys
    2000            2005                2010

Gly Tyr Lys Gly Val Trp Ala Gly Thr Gly Ile Met Thr Thr Arg
    2015            2020                2025

Cys Pro Cys Gly Ala Asn Ile Ser Gly Asn Val Arg Leu Gly Ser
    2030            2035                2040

Met Arg Ile Thr Gly Pro Lys Thr Cys Met Asn Thr Trp Gln Gly
    2045            2050                2055

Thr Phe Pro Ile Asn Cys Tyr Thr Glu Gly Gln Cys Ala Pro Lys
    2060            2065                2070

Pro Pro Thr Asn Tyr Lys Thr Ala Ile Trp Arg Val Ala Ala Ser
    2075            2080                2085

Glu Tyr Ala Glu Val Thr Gln His Gly Ser Tyr Ser Tyr Val Thr
    2090            2095                2100

Gly Leu Thr Thr Asp Asn Leu Lys Ile Pro Cys Gln Leu Pro Ser
    2105            2110                2115

Pro Glu Phe Phe Ser Trp Val Asp Gly Val Gln Ile His Arg Phe
    2120            2125                2130

Ala Pro Thr Pro Lys Pro Phe Phe Arg Asp Glu Val Ser Phe Cys
    2135            2140                2145

Val Gly Leu Asn Ser Tyr Ala Val Gly Ser Gln Leu Pro Cys Glu
    2150            2155                2160

Pro Glu Pro Asp Ala Asp Val Leu Arg Ser Met Leu Thr Asp Pro
    2165            2170                2175

Pro His Ile Thr Ala Glu Thr Ala Ala Arg Arg Leu Ala Arg Gly
    2180            2185                2190

Ser Pro Pro Ser Glu Ala Ser Ser Ser Val Ser Gln Leu Ser Ala
    2195            2200                2205

Pro Ser Leu Arg Ala Thr Cys Thr Thr His Ser Asn Thr Tyr Asp
    2210            2215                2220

Val Asp Met Val Asp Ala Asn Leu Leu Met Glu Gly Gly Val Ala
    2225            2230                2235

Gln Thr Glu Pro Glu Ser Arg Val Pro Val Leu Asp Phe Leu Glu
    2240            2245                2250

Pro Met Ala Glu Glu Glu Ser Asp Leu Glu Pro Ser Ile Pro Ser
    2255            2260                2265

Glu Cys Met Leu Pro Arg Ser Gly Phe Pro Arg Ala Leu Pro Ala
    2270            2275                2280

Trp Ala Arg Pro Asp Tyr Asn Pro Pro Leu Val Glu Ser Trp Arg
    2285            2290                2295

Arg Pro Asp Tyr Gln Pro Pro Thr Val Ala Gly Cys Ala Leu Pro

```
              2300                2305                2310

Pro  Pro  Lys  Lys  Ala  Pro  Thr  Pro  Pro  Arg  Arg  Arg  Arg  Thr
     2315                2320                2325

Val  Gly  Leu  Ser  Glu  Ser  Thr  Ile  Ser  Glu  Ala  Leu  Gln  Gln  Leu
     2330                2335                2340

Ala  Ile  Lys  Thr  Phe  Gly  Gln  Pro  Pro  Ser  Ser  Gly  Asp  Ala  Gly
     2345                2350                2355

Ser  Ser  Thr  Gly  Ala  Gly  Ala  Ala  Glu  Ser  Gly  Gly  Pro  Thr  Ser
     2360                2365                2370

Pro  Gly  Glu  Pro  Ala  Pro  Ser  Glu  Thr  Gly  Ser  Ala  Ser  Ser  Met
     2375                2380                2385

Pro  Pro  Leu  Glu  Gly  Glu  Pro  Gly  Asp  Pro  Asp  Leu  Glu  Ser  Asp
     2390                2395                2400

Gln  Val  Glu  Leu  Gln  Pro  Pro  Gln  Gly  Gly  Val  Ala  Pro
     2405                2410                2415

Gly  Ser  Gly  Ser  Gly  Ser  Trp  Ser  Thr  Cys  Ser  Glu  Glu  Asp  Asp
     2420                2425                2430

Thr  Thr  Val  Cys  Cys  Ser  Met  Ser  Tyr  Ser  Trp  Thr  Gly  Ala  Leu
     2435                2440                2445

Ile  Thr  Pro  Cys  Ser  Pro  Glu  Glu  Lys  Leu  Pro  Ile  Asn  Pro
     2450                2455                2460

Leu  Ser  Asn  Ser  Leu  Leu  Arg  Tyr  His  Asn  Lys  Val  Tyr  Cys  Thr
     2465                2470                2475

Thr  Ser  Lys  Ser  Ala  Ser  Gln  Arg  Ala  Lys  Lys  Val  Thr  Phe  Asp
     2480                2485                2490

Arg  Thr  Gln  Val  Leu  Asp  Ala  His  Tyr  Asp  Ser  Val  Leu  Lys  Asp
     2495                2500                2505

Ile  Lys  Leu  Ala  Ala  Ser  Lys  Val  Ser  Ala  Arg  Leu  Leu  Thr  Leu
     2510                2515                2520

Glu  Glu  Ala  Cys  Gln  Leu  Thr  Pro  Pro  His  Ser  Ala  Arg  Ser  Lys
     2525                2530                2535

Tyr  Gly  Phe  Gly  Ala  Lys  Glu  Val  Arg  Ser  Leu  Ser  Gly  Arg  Ala
     2540                2545                2550

Val  Asn  His  Ile  Lys  Ser  Val  Trp  Lys  Asp  Leu  Leu  Glu  Asp  Pro
     2555                2560                2565

Gln  Thr  Pro  Ile  Pro  Thr  Thr  Ile  Met  Ala  Lys  Asn  Glu  Val  Phe
     2570                2575                2580

Cys  Val  Asp  Pro  Ala  Lys  Gly  Gly  Lys  Lys  Pro  Ala  Arg  Leu  Ile
     2585                2590                2595

Val  Tyr  Pro  Asp  Leu  Gly  Val  Arg  Val  Cys  Glu  Lys  Met  Ala  Leu
     2600                2605                2610

Tyr  Asp  Ile  Thr  Gln  Lys  Leu  Pro  Gln  Ala  Val  Met  Gly  Ala  Ser
     2615                2620                2625

Tyr  Gly  Phe  Gln  Tyr  Ser  Pro  Ala  Gln  Arg  Val  Glu  Tyr  Leu  Leu
     2630                2635                2640

Lys  Ala  Trp  Ala  Glu  Lys  Lys  Asp  Pro  Met  Gly  Phe  Ser  Tyr  Asp
     2645                2650                2655

Thr  Arg  Cys  Phe  Asp  Ser  Thr  Val  Thr  Glu  Arg  Asp  Ile  Arg  Thr
     2660                2665                2670

Glu  Glu  Ser  Ile  Tyr  Gln  Ala  Cys  Ser  Leu  Pro  Glu  Glu  Ala  Arg
     2675                2680                2685

Thr  Ala  Ile  His  Ser  Leu  Thr  Glu  Arg  Leu  Tyr  Val  Gly  Gly  Pro
     2690                2695                2700
```

```
Met Phe Asn Ser Lys Gly Gln Thr Cys Gly Tyr Arg Arg Cys Arg
    2705                2710                2715

Ala Ser Gly Val Leu Thr Thr Ser Met Gly Asn Thr Ile Thr Cys
    2720                2725                2730

Tyr Val Lys Ala Leu Ala Ala Cys Lys Ala Ala Gly Ile Val Ala
    2735                2740                2745

Pro Thr Met Leu Val Cys Gly Asp Asp Leu Val Val Ile Ser Glu
    2750                2755                2760

Ser Gln Gly Thr Glu Glu Asp Glu Arg Asn Leu Arg Ala Phe Thr
    2765                2770                2775

Glu Ala Met Thr Arg Tyr Ser Ala Pro Pro Gly Asp Pro Pro Arg
    2780                2785                2790

Pro Glu Tyr Asp Leu Glu Leu Ile Thr Ser Cys Ser Ser Asn Val
    2795                2800                2805

Ser Val Ala Leu Gly Pro Arg Gly Arg Arg Arg Tyr Tyr Leu Thr
    2810                2815                2820

Arg Asp Pro Thr Thr Pro Leu Ala Arg Ala Ala Trp Glu Thr Val
    2825                2830                2835

Arg His Ser Pro Ile Asn Ser Trp Leu Gly Asn Ile Ile Gln Tyr
    2840                2845                2850

Ala Pro Thr Ile Trp Val Arg Met Val Leu Met Thr His Phe Phe
    2855                2860                2865

Ser Ile Leu Met Val Gln Asp Thr Leu Asp Gln Asn Leu Asn Phe
    2870                2875                2880

Glu Met Tyr Gly Ser Val Tyr Ser Val Asn Pro Leu Asp Leu Pro
    2885                2890                2895

Ala Ile Ile Glu Arg Leu His Gly Leu Asp Ala Phe Ser Met His
    2900                2905                2910

Thr Tyr Ser His His Glu Leu Thr Arg Val Ala Ser Ala Leu Arg
    2915                2920                2925

Lys Leu Gly Ala Pro Pro Leu Arg Val Trp Lys Ser Arg Ala Arg
    2930                2935                2940

Ala Val Arg Ala Ser Leu Ile Ser Arg Gly Gly Lys Ala Ala Val
    2945                2950                2955

Cys Gly Arg Tyr Leu Phe Asn Trp Ala Val Lys Thr Lys Leu Lys
    2960                2965                2970

Leu Thr Pro Leu Pro Glu Ala Arg Leu Leu Asp Leu Ser Ser Trp
    2975                2980                2985

Phe Thr Val Gly Ala Gly Gly Asp Ile Phe His Ser Val Ser
    2990                2995                3000

Arg Ala Arg Pro Arg Ser Leu Leu Phe Gly Leu Leu Leu Leu Phe
    3005                3010                3015

Val Gly Val Gly Leu Phe Leu Leu Pro Ala Arg
    3020                3025

<210> SEQ ID NO 22
<211> LENGTH: 3029
<212> TYPE: PRT
<213> ORGANISM: Hepatitis C virus

<400> SEQUENCE: 22

Met Ser Thr Asn Pro Lys Pro Gln Arg Lys Thr Lys Arg Asn Thr Asn
1               5                   10                  15

Arg Arg Pro Met Asp Val Lys Phe Pro Gly Gly Gly Gln Ile Val Gly
            20                  25                  30
```

-continued

Gly Val Tyr Leu Leu Pro Arg Gly Pro Arg Leu Gly Val Arg Ala
            35                  40                  45

Thr Arg Lys Thr Ser Glu Arg Ser Gln Pro Arg Gly Arg Gln Pro
 50                  55                  60

Ile Pro Lys Ala Arg Arg Pro Glu Gly Arg Ser Trp Ala Gln Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Asn Asp Pro
                100                 105                 110

Arg Arg Arg Ser Arg Asn Leu Gly Lys Val Ile Asp Thr Leu Thr Cys
                115                 120                 125

Gly Phe Ala Asp Leu Met Gly Tyr Ile Pro Leu Val Gly Ala Pro Val
            130                 135                 140

Gly Gly Val Ala Arg Ala Leu Ala His Gly Val Arg Ala Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Val
                180                 185                 190

Asn Tyr Arg Asn Val Ser Gly Ile Tyr His Val Thr Asn Asp Cys Pro
            195                 200                 205

Asn Ser Ser Ile Val Tyr Glu Ala Asp His His Ile Leu His Leu Pro
210                 215                 220

Gly Cys Val Pro Cys Val Arg Glu Gly Asn Gln Ser Arg Cys Trp Val
225                 230                 235                 240

Ala Leu Thr Pro Thr Val Ala Ala Pro Tyr Ile Gly Ala Pro Leu Glu
                245                 250                 255

Ser Leu Arg Ser His Val Asp Leu Met Val Gly Ala Ala Thr Val Cys
            260                 265                 270

Ser Gly Leu Tyr Ile Gly Asp Leu Cys Gly Gly Leu Phe Leu Val Gly
            275                 280                 285

Gln Met Phe Ser Phe Arg Pro Arg Arg His Trp Thr Thr Gln Asp Cys
290                 295                 300

Asn Cys Ser Ile Tyr Thr Gly His Ile Thr Gly His Arg Met Ala Trp
305                 310                 315                 320

Asp Met Met Met Asn Trp Ser Pro Ser Thr Thr Leu Val Leu Ala Gln
                325                 330                 335

Val Met Arg Ile Pro Thr Thr Leu Val Asp Leu Leu Ser Gly Gly His
            340                 345                 350

Trp Gly Val Leu Val Gly Val Ala Tyr Phe Ser Met Gln Ala Asn Trp
            355                 360                 365

Ala Lys Val Ile Leu Val Leu Phe Leu Phe Ala Gly Val Asp Ala Glu
370                 375                 380

Thr His Val Ser Gly Ala Ala Val Gly Arg Ser Thr Ala Gly Leu Ala
385                 390                 395                 400

Asn Leu Phe Ser Ser Gly Ser Lys Gln Asn Leu Gln Leu Ile Asn Ser
                405                 410                 415

Asn Gly Ser Trp His Ile Asn Arg Thr Ala Leu Asn Cys Asn Asp Ser
            420                 425                 430

Leu Asn Thr Gly Phe Leu Ala Ser Leu Phe Tyr Thr His Lys Phe Asn
            435                 440                 445

Ser Ser Gly Cys Ser Glu Arg Leu Ala Cys Cys Lys Ser Leu Asp Ser
450                 455                 460

Tyr Gly Gln Gly Trp Gly Pro Leu Gly Val Ala Asn Ile Ser Gly Ser
465                 470                 475                 480

Ser Asp Asp Arg Pro Tyr Cys Trp His Tyr Ala Pro Arg Pro Cys Gly
            485                 490                 495

Ile Val Pro Ala Ser Ser Val Cys Gly Pro Val Tyr Cys Phe Thr Pro
                500                 505                 510

Ser Pro Val Val Val Gly Thr Thr Asp His Val Gly Val Pro Thr Tyr
            515                 520                 525

Thr Trp Gly Glu Asn Glu Thr Asp Val Phe Leu Leu Asn Ser Thr Arg
        530                 535                 540

Pro Pro His Gly Ala Trp Phe Gly Cys Val Trp Met Asn Ser Thr Gly
545                 550                 555                 560

Phe Thr Lys Thr Cys Gly Ala Pro Pro Cys Glu Val Asn Thr Asn Asn
                565                 570                 575

Gly Thr Trp His Cys Pro Thr Asp Cys Phe Arg Lys His Pro Glu Thr
                580                 585                 590

Thr Tyr Ala Lys Cys Gly Ser Gly Pro Trp Ile Thr Pro Arg Cys Leu
        595                 600                 605

Ile Asp Tyr Pro Tyr Arg Leu Trp His Phe Pro Cys Thr Ala Asn Phe
610                 615                 620

Ser Val Phe Asn Ile Arg Thr Phe Val Gly Gly Ile Glu His Arg Met
625                 630                 635                 640

Gln Ala Ala Cys Asn Trp Thr Arg Gly Glu Val Cys Gly Leu Glu His
                645                 650                 655

Arg Asp Arg Val Glu Leu Ser Pro Leu Leu Leu Thr Thr Thr Ala Trp
            660                 665                 670

Gln Ile Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
        690                 695                 700

Val Gly Ser Ala Val Val Ser Trp Ala Leu Lys Trp Glu Tyr Val Val
705                 710                 715                 720

Leu Ala Phe Leu Leu Leu Ala Asp Ala Arg Val Ser Ala Cys Leu Trp
                725                 730                 735

Met Met Phe Met Val Ser Gln Val Glu Ala Ala Leu Ser Asn Leu Ile
                740                 745                 750

Asn Ile Asn Ala Ala Ser Ala Ala Gly Ala Gln Gly Phe Trp Tyr Ala
            755                 760                 765

Ile Leu Phe Ile Cys Ile Val His Val Lys Gly Arg Phe Pro Ala
770                 775                 780

Ala Ala Ala Tyr Ala Ala Cys Gly Leu Trp Pro Leu Phe Leu Leu Leu
785                 790                 795                 800

Leu Met Leu Pro Glu Arg Ala Tyr Ala Tyr Asp Gln Glu Val Ala Gly
                805                 810                 815

Ser Leu Gly Gly Ala Ile Val Val Met Leu Ala Ile Leu Thr Leu Ser
            820                 825                 830

Pro His Tyr Lys Leu Trp Leu Ala Arg Gly Leu Trp Trp Ile Gln Tyr
        835                 840                 845

Phe Ile Ala Arg Thr Glu Ala Val Leu His Val Tyr Ile Pro Ser Phe
        850                 855                 860

Asn Val Arg Gly Pro Arg Asp Ser Val Ile Val Leu Ala Val Leu Val
865                 870                 875                 880

Cys Pro His Leu Val Phe Asp Ile Thr Lys Tyr Leu Leu Ala Ile Leu

```
                885                 890                 895
Gly Pro Leu His Ile Leu Gln Ala Ser Leu Leu Arg Ile Pro Tyr Phe
        900                 905                 910
Val Arg Ala Gln Ala Leu Val Lys Ile Cys Ser Leu Leu Arg Gly Val
        915                 920                 925
Val Tyr Gly Lys Tyr Phe Gln Met Val Val Leu Lys Ala Gly Ala Leu
        930                 935                 940
Thr Gly Thr Tyr Ile Tyr Asp His Leu Thr Pro Met Ser Asp Trp Ala
945                 950                 955                 960
Ala Thr Gly Leu Arg Asp Leu Ala Val Ala Leu Glu Pro Val Val Phe
            965                 970                 975
Ser Pro Met Glu Lys Lys Val Ile Val Trp Gly Ala Asp Thr Ala Ala
            980                 985                 990
Cys Gly Asp Ile Ile Arg Gly Leu Pro Val Ser Ala Arg Leu Gly Asn
            995                 1000                1005
Glu Ile Leu Leu Gly Pro Ala Asp Thr Glu Thr Ser Lys Gly Trp
        1010                1015                1020
Arg Leu Leu Ala Pro Ile Thr Ala Tyr Ala Gln Gln Thr Arg Gly
        1025                1030                1035
Leu Leu Gly Ala Ile Val Val Ser Met Thr Gly Arg Asp Arg Thr
        1040                1045                1050
Glu Gln Ala Gly Glu Val Gln Ile Leu Ser Thr Val Ser Gln Ser
        1055                1060                1065
Phe Leu Gly Thr Thr Ile Ser Gly Val Leu Trp Thr Val Tyr His
        1070                1075                1080
Gly Ala Gly Asn Lys Thr Leu Ala Gly Leu Arg Gly Pro Val Thr
        1085                1090                1095
Gln Met Tyr Ser Ser Ala Glu Gly Asp Leu Val Gly Trp Pro Ser
        1100                1105                1110
Pro Pro Gly Thr Lys Ser Leu Glu Pro Cys Lys Cys Gly Ala Val
        1115                1120                1125
Asp Leu Tyr Leu Val Thr Arg Asn Ala Asp Val Ile Pro Ala Arg
        1130                1135                1140
Arg Arg Gly Asp Lys Arg Gly Ala Leu Leu Ser Pro Arg Pro Ile
        1145                1150                1155
Ser Thr Leu Lys Gly Ser Ser Gly Gly Pro Val Leu Cys Pro Arg
        1160                1165                1170
Gly His Val Val Gly Leu Phe Arg Ala Ala Val Cys Ser Arg Gly
        1175                1180                1185
Val Ala Lys Ser Ile Asp Phe Ile Pro Val Glu Thr Leu Asp Val
        1190                1195                1200
Val Thr Arg Ser Pro Thr Phe Ser Asp Asn Ser Thr Pro Pro Ala
        1205                1210                1215
Val Pro Gln Thr Tyr Gln Val Gly Tyr Leu His Ala Pro Thr Gly
        1220                1225                1230
Ser Gly Lys Ser Thr Lys Val Pro Val Ala Tyr Ala Ala Gln Gly
        1235                1240                1245
Tyr Lys Val Leu Val Leu Asn Pro Ser Val Ala Ala Thr Leu Gly
        1250                1255                1260
Phe Gly Ala Tyr Leu Ser Lys Ala His Gly Ile Asn Pro Asn Ile
        1265                1270                1275
Arg Thr Gly Val Arg Thr Val Met Thr Gly Glu Ala Ile Thr Tyr
        1280                1285                1290
```

-continued

```
Ser Thr Tyr Gly Lys Phe Leu Ala Asp Gly Gly Cys Ala Ser Gly
    1295                1300                1305

Ala Tyr Asp Ile Ile Ile Cys Asp Glu Cys His Ala Val Asp Ala
    1310                1315                1320

Thr Ser Ile Leu Gly Ile Gly Thr Val Leu Asp Gln Ala Glu Thr
    1325                1330                1335

Ala Gly Val Arg Leu Thr Val Leu Ala Thr Ala Thr Pro Pro Gly
    1340                1345                1350

Ser Val Thr Thr Pro His Pro Asp Ile Glu Glu Val Gly Leu Gly
    1355                1360                1365

Arg Glu Gly Glu Ile Pro Phe Tyr Gly Arg Ala Ile Pro Leu Ser
    1370                1375                1380

Cys Ile Lys Gly Gly Arg His Leu Ile Phe Cys His Ser Lys Lys
    1385                1390                1395

Lys Cys Asp Glu Leu Ala Ala Ala Leu Arg Gly Met Gly Leu Asn
    1400                1405                1410

Ala Val Ala Tyr Tyr Arg Gly Leu Asp Val Ser Ile Ile Pro Ala
    1415                1420                1425

Gln Gly Asp Val Val Val Val Ala Thr Asp Ala Leu Met Thr Gly
    1430                1435                1440

Tyr Thr Gly Asp Phe Asp Ser Val Ile Asp Cys Asn Val Ala Val
    1445                1450                1455

Thr Gln Ala Val Asp Phe Ser Leu Asp Pro Thr Phe Thr Ile Thr
    1460                1465                1470

Thr Gln Thr Val Pro Gln Asp Ala Val Ser Arg Ser Gln Arg Arg
    1475                1480                1485

Gly Arg Thr Gly Arg Gly Arg Gln Gly Thr Tyr Arg Tyr Val Ser
    1490                1495                1500

Thr Gly Glu Arg Ala Ser Gly Met Phe Asp Ser Val Val Leu Cys
    1505                1510                1515

Glu Cys Tyr Asp Ala Gly Ala Ala Trp Tyr Asp Leu Thr Pro Ala
    1520                1525                1530

Glu Thr Thr Val Arg Leu Arg Ala Tyr Phe Asn Thr Pro Gly Leu
    1535                1540                1545

Pro Val Cys Gln Asp His Leu Glu Phe Trp Glu Ala Val Phe Thr
    1550                1555                1560

Gly Leu Thr His Ile Asp Ala His Phe Leu Ser Gln Thr Lys Gln
    1565                1570                1575

Ala Gly Glu Asn Phe Ala Tyr Leu Val Ala Tyr Gln Ala Thr Val
    1580                1585                1590

Cys Ala Arg Ala Lys Ala Pro Pro Pro Ser Trp Asp Ala Met Trp
    1595                1600                1605

Lys Cys Leu Ala Arg Leu Lys Pro Thr Leu Ala Gly Pro Thr Pro
    1610                1615                1620

Leu Leu Tyr Arg Leu Gly Pro Ile Thr Asn Glu Val Thr Leu Thr
    1625                1630                1635

His Pro Gly Thr Lys Tyr Ile Ala Thr Cys Met Gln Ala Asp Leu
    1640                1645                1650

Glu Val Met Thr Ser Thr Trp Val Leu Ala Gly Gly Val Leu Ala
    1655                1660                1665

Ala Val Ala Ala Tyr Cys Leu Ala Thr Gly Cys Val Ser Ile Ile
    1670                1675                1680

Gly Arg Leu His Val Asn Gln Arg Val Val Val Ala Pro Asp Lys
    1685                1690                1695
```

```
Glu Val Leu Tyr Glu Ala Phe Asp Glu Met Glu Cys Ala Ser
    1700            1705            1710

Arg Ala Ala Leu Ile Glu Glu Gly Gln Arg Ile Ala Glu Met Leu
    1715            1720            1725

Lys Ser Lys Ile Gln Gly Leu Leu Gln Gln Ala Ser Lys Gln Ala
    1730            1735            1740

Gln Asp Ile Gln Pro Ala Met Gln Ala Ser Trp Pro Lys Val Glu
    1745            1750            1755

Gln Phe Trp Ala Arg His Met Trp Asn Phe Ile Ser Gly Ile Gln
    1760            1765            1770

Tyr Leu Ala Gly Leu Ser Thr Leu Pro Gly Asn Pro Ala Val Ala
    1775            1780            1785

Ser Met Met Ala Phe Ser Ala Ala Leu Thr Ser Pro Leu Ser Thr
    1790            1795            1800

Ser Thr Thr Ile Leu Leu Asn Ile Met Gly Gly Trp Leu Ala Ser
    1805            1810            1815

Gln Ile Ala Pro Pro Ala Gly Ala Thr Gly Phe Val Val Ser Gly
    1820            1825            1830

Leu Val Gly Ala Ala Val Gly Ser Ile Gly Leu Gly Lys Val Leu
    1835            1840            1845

Val Asp Ile Leu Ala Gly Tyr Gly Ala Gly Ile Ser Gly Ala Leu
    1850            1855            1860

Val Ala Phe Lys Ile Met Ser Gly Glu Lys Pro Ser Met Glu Asp
    1865            1870            1875

Val Ile Asn Leu Leu Pro Gly Ile Leu Ser Pro Gly Ala Leu Val
    1880            1885            1890

Val Gly Val Ile Cys Ala Ala Ile Leu Arg Arg His Val Gly Pro
    1895            1900            1905

Gly Glu Gly Ala Val Gln Trp Met Asn Arg Leu Ile Ala Phe Ala
    1910            1915            1920

Ser Arg Gly Asn His Val Ala Pro Thr His Tyr Val Thr Glu Ser
    1925            1930            1935

Asp Ala Ser Gln Arg Val Thr Gln Leu Leu Gly Ser Leu Thr Ile
    1940            1945            1950

Thr Ser Leu Leu Arg Arg Leu His Asn Trp Ile Thr Glu Asp Cys
    1955            1960            1965

Pro Ile Pro Cys Ser Gly Ser Trp Leu Arg Asp Val Trp Asp Trp
    1970            1975            1980

Val Cys Thr Ile Leu Thr Asp Phe Lys Asn Trp Leu Thr Ser Lys
    1985            1990            1995

Leu Phe Pro Lys Leu Pro Gly Leu Pro Phe Ile Ser Cys Gln Lys
    2000            2005            2010

Gly Tyr Lys Gly Val Trp Ala Gly Thr Gly Ile Met Thr Thr Arg
    2015            2020            2025

Cys Pro Cys Gly Ala Asn Ile Ser Gly Asn Val Arg Leu Gly Ser
    2030            2035            2040

Met Arg Ile Thr Gly Pro Lys Thr Cys Met Asn Thr Trp Gln Gly
    2045            2050            2055

Thr Phe Pro Ile Asn Cys Tyr Thr Glu Gly Gln Cys Ala Pro Lys
    2060            2065            2070

Pro Pro Thr Asn Tyr Lys Thr Ala Ile Trp Arg Val Ala Ala Ser
    2075            2080            2085

Glu Tyr Ala Glu Val Thr Gln His Gly Ser Tyr Ser Tyr Val Thr
```

```
                    2090                    2095                    2100

Gly Leu Thr Thr Asp Asn Leu Lys Ile Pro Cys Gln Leu Pro Ser
    2105                    2110                    2115

Pro Glu Phe Phe Ser Trp Val Asp Gly Val Gln Ile His Arg Phe
    2120                    2125                    2130

Ala Pro Thr Pro Lys Pro Phe Phe Arg Asp Glu Val Ser Phe Cys
    2135                    2140                    2145

Val Gly Leu Asn Ser Tyr Ala Val Gly Ser Gln Leu Pro Cys Glu
    2150                    2155                    2160

Pro Glu Pro Asp Ala Asp Val Leu Arg Ser Met Leu Thr Asp Pro
    2165                    2170                    2175

Pro His Ile Thr Ala Glu Thr Ala Ala Arg Arg Leu Ala Arg Gly
    2180                    2185                    2190

Ser Pro Pro Ser Glu Ala Ser Ser Val Ser Gln Leu Ser Ala
    2195                    2200                    2205

Pro Ser Leu Arg Ala Thr Cys Thr Thr His Ser Asn Thr Tyr Asp
    2210                    2215                    2220

Val Asp Met Val Asp Ala Asn Leu Leu Met Glu Gly Gly Val Ala
    2225                    2230                    2235

Gln Thr Glu Pro Glu Ser Arg Val Pro Val Leu Asp Phe Leu Glu
    2240                    2245                    2250

Pro Met Ala Glu Glu Ser Asp Leu Glu Pro Ser Ile Pro Ser
    2255                    2260                    2265

Glu Cys Met Leu Pro Arg Ser Gly Phe Pro Arg Ala Leu Pro Ala
    2270                    2275                    2280

Trp Ala Arg Pro Asp Tyr Asn Pro Pro Leu Val Glu Ser Trp Arg
    2285                    2290                    2295

Arg Pro Asp Tyr Gln Pro Pro Thr Val Ala Gly Cys Ala Leu Pro
    2300                    2305                    2310

Pro Pro Lys Lys Ala Pro Thr Pro Pro Pro Arg Arg Arg Arg Thr
    2315                    2320                    2325

Val Gly Leu Ser Glu Ser Thr Ile Ser Glu Ala Leu Gln Gln Leu
    2330                    2335                    2340

Ala Ile Lys Thr Phe Gly Gln Pro Pro Ser Ser Gly Asp Ala Gly
    2345                    2350                    2355

Ser Ser Thr Gly Ala Gly Ala Ala Glu Ser Gly Gly Pro Thr Ser
    2360                    2365                    2370

Pro Gly Glu Pro Ala Pro Ser Glu Thr Gly Ser Ala Ser Ser Met
    2375                    2380                    2385

Pro Pro Leu Glu Gly Glu Pro Gly Asp Pro Asp Leu Glu Ser Asp
    2390                    2395                    2400

Gln Val Glu Leu Gln Pro Pro Gln Gly Gly Val Ala Pro
    2405                    2410                    2415

Gly Ser Gly Ser Gly Ser Trp Ser Thr Cys Ser Glu Glu Asp Asp
    2420                    2425                    2430

Thr Thr Val Cys Cys Ser Met Ser Tyr Ser Trp Thr Gly Ala Leu
    2435                    2440                    2445

Ile Thr Pro Cys Ser Pro Glu Glu Glu Lys Leu Pro Ile Asn Pro
    2450                    2455                    2460

Leu Ser Asn Ser Leu Leu Arg Tyr His Asn Lys Val Tyr Cys Thr
    2465                    2470                    2475

Thr Ser Lys Ser Ala Ser Gln Arg Ala Lys Lys Val Thr Phe Asp
    2480                    2485                    2490
```

-continued

Arg Thr Gln Val Leu Asp Ala His Tyr Asp Ser Val Leu Lys Asp
2495                2500                2505

Ile Lys Leu Ala Ala Ser Lys Val Ser Ala Arg Leu Leu Thr Leu
2510                2515                2520

Glu Glu Ala Cys Gln Leu Thr Pro Pro His Ser Ala Arg Ser Lys
2525                2530                2535

Tyr Gly Phe Gly Ala Lys Glu Val Arg Ser Leu Ser Gly Arg Ala
2540                2545                2550

Val Asn His Ile Lys Ser Val Trp Lys Asp Leu Leu Glu Asp Pro
2555                2560                2565

Gln Thr Pro Ile Pro Thr Thr Ile Met Ala Lys Asn Glu Val Phe
2570                2575                2580

Cys Val Asp Pro Ala Lys Gly Gly Lys Lys Pro Ala Arg Leu Ile
2585                2590                2595

Val Tyr Pro Asp Leu Gly Val Arg Val Cys Glu Lys Met Ala Leu
2600                2605                2610

Tyr Asp Ile Thr Gln Lys Leu Pro Gln Ala Val Met Gly Ala Ser
2615                2620                2625

Tyr Gly Phe Gln Tyr Ser Pro Ala Gln Arg Val Glu Tyr Leu Leu
2630                2635                2640

Lys Ala Trp Ala Glu Lys Lys Asp Pro Met Gly Phe Ser Tyr Asp
2645                2650                2655

Thr Arg Cys Phe Asp Ser Thr Val Thr Glu Arg Asp Ile Arg Thr
2660                2665                2670

Glu Glu Ser Ile Tyr Gln Ala Cys Ser Leu Pro Glu Glu Ala Arg
2675                2680                2685

Thr Ala Ile His Ser Leu Thr Glu Arg Leu Tyr Val Gly Gly Pro
2690                2695                2700

Met Phe Asn Ser Lys Gly Gln Thr Cys Gly Tyr Arg Arg Cys Arg
2705                2710                2715

Ala Ser Gly Val Leu Thr Thr Ser Met Gly Asn Thr Ile Thr Cys
2720                2725                2730

Tyr Val Lys Ala Leu Ala Ala Cys Lys Ala Ala Gly Ile Val Ala
2735                2740                2745

Pro Thr Met Leu Val Cys Gly Asp Asp Leu Val Val Ile Ser Glu
2750                2755                2760

Ser Gln Gly Thr Glu Glu Asp Glu Arg Asn Leu Arg Ala Phe Thr
2765                2770                2775

Glu Ala Met Thr Arg Tyr Ser Ala Pro Pro Gly Asp Pro Pro Arg
2780                2785                2790

Pro Glu Tyr Asp Leu Glu Leu Ile Thr Ser Cys Ser Ser Asn Val
2795                2800                2805

Ser Val Ala Leu Gly Pro Arg Gly Arg Arg Tyr Tyr Leu Thr
2810                2815                2820

Arg Asp Pro Thr Thr Pro Leu Ala Arg Ala Ala Trp Glu Thr Val
2825                2830                2835

Arg His Ser Pro Ile Asn Ser Trp Leu Gly Asn Ile Ile Gln Tyr
2840                2845                2850

Ala Pro Thr Ile Trp Val Arg Met Val Leu Met Thr His Phe Phe
2855                2860                2865

Ser Ile Leu Met Val Gln Asp Thr Leu Asp Gln Asn Leu Asn Phe
2870                2875                2880

Glu Met Tyr Gly Ser Val Tyr Ser Val Asn Pro Leu Asp Leu Pro
2885                2890                2895

Ala Ile Ile Glu Arg Leu His Gly Leu Asp Ala Phe Ser Met His
        2900                2905                2910

Thr Tyr Ser His His Glu Leu Thr Arg Val Ala Ser Ala Leu Arg
        2915                2920                2925

Lys Leu Gly Ala Pro Pro Leu Arg Val Trp Lys Ser Arg Ala Arg
        2930                2935                2940

Ala Val Arg Ala Ser Leu Ile Ser Arg Gly Gly Lys Ala Ala Val
        2945                2950                2955

Cys Gly Arg Tyr Leu Phe Asn Trp Ala Val Lys Thr Lys Leu Lys
        2960                2965                2970

Leu Thr Pro Leu Pro Glu Ala Arg Leu Leu Asp Leu Ser Ser Trp
        2975                2980                2985

Phe Thr Val Gly Ala Gly Gly Asp Ile Phe His Ser Val Ser
        2990                2995                3000

Arg Ala Arg Pro Arg Ser Leu Leu Phe Gly Leu Leu Leu Leu Phe
        3005                3010                3015

Val Gly Val Gly Leu Phe Leu Leu Pro Ala Arg
        3020                3025

<210> SEQ ID NO 23
<211> LENGTH: 3029
<212> TYPE: PRT
<213> ORGANISM: Hepatitis C virus

<400> SEQUENCE: 23

Met Ser Thr Asn Pro Lys Pro Gln Arg Lys Thr Lys Arg Asn Thr Asn
1               5                   10                  15

Arg Arg Pro Met Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Val
        130                 135                 140

Gly Gly Val Ala Arg Ala Leu Ala His Gly Val Arg Ala Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Val
                180                 185                 190

Asn Tyr Arg Asn Val Ser Gly Ile Tyr His Val Thr Asn Asp Cys Pro
            195                 200                 205

Asn Ser Ser Ile Val Tyr Glu Ala Asp His His Ile Leu His Leu Pro
        210                 215                 220

Gly Cys Val Pro Cys Val Arg Glu Gly Asn Gln Ser Arg Cys Trp Val
225                 230                 235                 240

```
Ala Leu Thr Pro Thr Val Ala Ala Pro Tyr Ile Gly Ala Pro Leu Glu
            245                 250                 255

Ser Leu Arg Ser His Val Asp Leu Met Val Gly Ala Ala Thr Val Cys
        260                 265                 270

Ser Gly Leu Tyr Ile Gly Asp Leu Cys Gly Gly Leu Phe Leu Val Gly
            275                 280                 285

Gln Met Phe Ser Phe Arg Pro Arg His Trp Thr Thr Gln Asp Cys
290                 295                 300

Asn Cys Ser Ile Tyr Thr Gly His Ile Thr Gly His Arg Met Ala Trp
305                 310                 315                 320

Asp Met Met Met Asn Trp Ser Pro Thr Thr Leu Val Leu Ala Gln
                325                 330                 335

Val Met Arg Ile Pro Thr Thr Leu Val Asp Leu Leu Ser Gly Gly His
            340                 345                 350

Trp Gly Val Leu Val Gly Val Ala Tyr Phe Ser Met Gln Ala Asn Trp
        355                 360                 365

Ala Lys Val Ile Leu Val Leu Phe Leu Phe Ala Gly Val Asp Ala Glu
    370                 375                 380

Thr His Val Ser Gly Ala Ala Val Gly Arg Ser Thr Ala Gly Leu Ala
385                 390                 395                 400

Asn Leu Phe Ser Ser Gly Ser Lys Gln Asn Leu Gln Leu Ile Asn Ser
                405                 410                 415

Asn Gly Ser Trp His Ile Asn Arg Thr Ala Leu Asn Cys Asn Asp Ser
            420                 425                 430

Leu Asn Thr Gly Phe Leu Ala Ser Leu Phe Tyr Thr His Lys Phe Asn
        435                 440                 445

Ser Ser Gly Cys Ser Glu Arg Leu Ala Cys Cys Lys Ser Leu Asp Ser
    450                 455                 460

Tyr Gly Gln Gly Trp Gly Pro Leu Gly Val Ala Asn Ile Ser Gly Ser
465                 470                 475                 480

Ser Asp Asp Arg Pro Tyr Cys Trp His Tyr Ala Pro Arg Pro Cys Gly
                485                 490                 495

Ile Val Pro Ala Ser Ser Val Cys Gly Pro Val Tyr Cys Phe Thr Pro
            500                 505                 510

Ser Pro Val Val Val Gly Thr Thr Asp His Val Gly Val Pro Thr Tyr
        515                 520                 525

Thr Trp Gly Glu Asn Glu Thr Asp Val Phe Leu Leu Asn Ser Thr Arg
    530                 535                 540

Pro Pro His Gly Ala Trp Phe Gly Cys Val Trp Met Asn Ser Thr Gly
545                 550                 555                 560

Phe Thr Lys Thr Cys Gly Ala Pro Pro Cys Glu Val Asn Thr Asn Asn
                565                 570                 575

Gly Thr Trp His Cys Pro Thr Asp Cys Phe Arg Lys His Pro Glu Thr
            580                 585                 590

Thr Tyr Ala Lys Cys Gly Ser Gly Pro Trp Ile Thr Pro Arg Cys Leu
        595                 600                 605

Ile Asp Tyr Pro Tyr Arg Leu Trp His Phe Pro Cys Thr Ala Asn Phe
    610                 615                 620

Ser Val Phe Asn Ile Arg Thr Phe Val Gly Gly Ile Glu His Arg Met
625                 630                 635                 640

Gln Ala Ala Cys Asn Trp Thr Arg Gly Glu Val Cys Gly Leu Glu His
                645                 650                 655

Arg Asp Arg Val Glu Leu Ser Pro Leu Leu Leu Thr Thr Thr Ala Trp
```

-continued

```
                660                 665                 670
Gln Ile Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
            690                 695                 700

Val Gly Ser Ala Val Val Ser Trp Ala Leu Lys Trp Glu Tyr Val Val
705                 710                 715                 720

Leu Ala Phe Leu Leu Leu Ala Asp Ala Arg Val Ser Ala Cys Leu Trp
            725                 730                 735

Met Met Phe Met Val Ser Gln Val Glu Ala Ala Leu Ser Asn Leu Ile
                740                 745                 750

Asn Ile Asn Ala Ala Ser Ala Ala Gly Ala Gln Gly Phe Trp Tyr Ala
            755                 760                 765

Ile Leu Phe Ile Cys Ile Val Trp His Val Lys Gly Arg Phe Pro Ala
            770                 775                 780

Ala Ala Ala Tyr Ala Ala Cys Gly Leu Trp Pro Leu Phe Leu Leu Leu
785                 790                 795                 800

Leu Met Leu Pro Glu Arg Ala Tyr Ala Tyr Asp Gln Glu Val Ala Gly
                805                 810                 815

Ser Leu Gly Gly Ala Ile Val Val Met Leu Ala Ile Leu Thr Leu Ser
                820                 825                 830

Pro His Tyr Lys Leu Trp Leu Ala Arg Gly Leu Trp Trp Ile Gln Tyr
            835                 840                 845

Phe Ile Ala Arg Thr Glu Ala Val Leu His Val Tyr Ile Pro Ser Phe
            850                 855                 860

Asn Val Arg Gly Pro Arg Asp Ser Val Ile Val Leu Ala Val Leu Val
865                 870                 875                 880

Cys Pro His Leu Val Phe Asp Ile Thr Lys Tyr Leu Leu Ala Ile Leu
                885                 890                 895

Gly Pro Leu His Ile Leu Gln Ala Ser Leu Leu Arg Ile Pro Tyr Phe
            900                 905                 910

Val Arg Ala Gln Ala Leu Val Lys Ile Cys Ser Leu Leu Arg Gly Val
            915                 920                 925

Val Tyr Gly Lys Tyr Phe Gln Met Val Val Leu Lys Ala Gly Ala Leu
930                 935                 940

Thr Gly Thr Tyr Ile Tyr Asp His Leu Thr Pro Met Ser Asp Trp Ala
945                 950                 955                 960

Ala Ser Gly Leu Arg Asp Leu Ala Val Ala Val Glu Pro Ile Ile Phe
                965                 970                 975

Ser Pro Met Glu Lys Lys Val Ile Val Trp Gly Ala Lys Thr Ala Ala
                980                 985                 990

Cys Gly Asp Ile Leu His Gly Leu Pro Val Ser Ala Arg Leu Gly Gln
            995                 1000                1005

Glu Ile Leu Leu Gly Pro Ala Asp Gly Tyr Thr Ser Lys Gly Trp
            1010                1015                1020

Lys Leu Leu Ala Pro Ile Thr Ala Tyr Ala Gln Gln Thr Arg Gly
            1025                1030                1035

Leu Leu Gly Ala Ile Val Val Ser Met Thr Gly Arg Asp Arg Thr
            1040                1045                1050

Glu Gln Ala Gly Glu Val Gln Ile Leu Ser Thr Val Ser Gln Ser
            1055                1060                1065

Phe Leu Gly Thr Thr Ile Ser Gly Val Leu Trp Thr Val Tyr His
            1070                1075                1080
```

-continued

```
Gly Ala Gly Asn Lys Thr Leu Ala Gly Leu Arg Gly Pro Val Thr
        1085                1090                1095

Gln Met Tyr Ser Ser Ala Glu Gly Asp Leu Val Gly Trp Pro Ser
    1100                1105                1110

Pro Pro Gly Thr Lys Ser Leu Glu Pro Cys Lys Cys Gly Ala Val
    1115                1120                1125

Asp Leu Tyr Leu Val Thr Arg Asn Ala Asp Val Ile Pro Ala Arg
    1130                1135                1140

Arg Arg Gly Asp Lys Arg Gly Ala Leu Leu Ser Pro Arg Pro Ile
    1145                1150                1155

Ser Thr Leu Lys Gly Ser Ser Gly Gly Pro Val Leu Cys Pro Arg
    1160                1165                1170

Gly His Val Val Gly Leu Phe Arg Ala Ala Val Cys Ser Arg Gly
    1175                1180                1185

Val Ala Lys Ser Ile Asp Phe Ile Pro Val Glu Thr Leu Asp Val
    1190                1195                1200

Val Thr Arg Ser Pro Thr Phe Ser Asp Asn Ser Thr Pro Pro Ala
    1205                1210                1215

Val Pro Gln Thr Tyr Gln Val Gly Tyr Leu His Ala Pro Thr Gly
    1220                1225                1230

Ser Gly Lys Ser Thr Lys Val Pro Val Ala Tyr Ala Ala Gln Gly
    1235                1240                1245

Tyr Lys Val Leu Val Leu Asn Pro Ser Val Ala Ala Thr Leu Gly
    1250                1255                1260

Phe Gly Ala Tyr Leu Ser Lys Ala His Gly Ile Asn Pro Asn Ile
    1265                1270                1275

Arg Thr Gly Val Arg Thr Val Met Thr Gly Glu Ala Ile Thr Tyr
    1280                1285                1290

Ser Thr Tyr Gly Lys Phe Leu Ala Asp Gly Gly Cys Ala Ser Gly
    1295                1300                1305

Ala Tyr Asp Ile Ile Ile Cys Asp Glu Cys His Ala Val Asp Ala
    1310                1315                1320

Thr Ser Ile Leu Gly Ile Gly Thr Val Leu Asp Gln Ala Glu Thr
    1325                1330                1335

Ala Gly Val Arg Leu Thr Val Leu Ala Thr Ala Thr Pro Pro Gly
    1340                1345                1350

Ser Val Thr Thr Pro His Pro Asp Ile Glu Glu Val Gly Leu Gly
    1355                1360                1365

Arg Glu Gly Glu Ile Pro Phe Tyr Gly Arg Ala Ile Pro Leu Ser
    1370                1375                1380

Cys Ile Lys Gly Gly Arg His Leu Ile Phe Cys His Ser Lys Lys
    1385                1390                1395

Lys Cys Asp Glu Leu Ala Ala Ala Leu Arg Gly Met Gly Leu Asn
    1400                1405                1410

Ala Val Ala Tyr Tyr Arg Gly Leu Asp Val Ser Ile Ile Pro Ala
    1415                1420                1425

Gln Gly Asp Val Val Val Ala Thr Asp Ala Leu Met Thr Gly
    1430                1435                1440

Tyr Thr Gly Asp Phe Asp Ser Val Ile Asp Cys Asn Val Ala Val
    1445                1450                1455

Thr Gln Ala Val Asp Phe Ser Leu Asp Pro Thr Phe Thr Ile Thr
    1460                1465                1470

Thr Gln Thr Val Pro Gln Asp Ala Val Ser Arg Ser Gln Arg Arg
    1475                1480                1485
```

-continued

```
Gly Arg Thr Gly Arg Gly Gln Gly Thr Tyr Arg Tyr Val Ser
    1490            1495                1500

Thr Gly Glu Arg Ala Ser Gly Met Phe Asp Ser Val Val Leu Cys
    1505            1510                1515

Glu Cys Tyr Asp Ala Gly Ala Ala Trp Tyr Asp Leu Thr Pro Ala
    1520            1525                1530

Glu Thr Thr Val Arg Leu Arg Ala Tyr Phe Asn Thr Pro Gly Leu
    1535            1540                1545

Pro Val Cys Gln Asp His Leu Glu Phe Trp Glu Ala Val Phe Thr
    1550            1555                1560

Gly Leu Thr His Ile Asp Ala His Phe Leu Ser Gln Thr Lys Gln
    1565            1570                1575

Ala Gly Glu Asn Phe Ala Tyr Leu Val Ala Tyr Gln Ala Thr Val
    1580            1585                1590

Cys Ala Arg Ala Lys Ala Pro Pro Pro Ser Trp Asp Ala Met Trp
    1595            1600                1605

Lys Cys Leu Ala Arg Leu Lys Pro Thr Leu Ala Gly Pro Thr Pro
    1610            1615                1620

Leu Leu Tyr Arg Leu Gly Pro Ile Thr Asn Glu Val Thr Leu Thr
    1625            1630                1635

His Pro Gly Thr Lys Tyr Ile Ala Thr Cys Met Gln Ala Asp Leu
    1640            1645                1650

Glu Val Met Thr Ser Thr Trp Val Leu Ala Gly Gly Val Leu Ala
    1655            1660                1665

Ala Val Ala Ala Tyr Cys Leu Ala Thr Gly Cys Val Ser Ile Ile
    1670            1675                1680

Gly Arg Leu His Val Asn Gln Arg Val Val Ala Pro Asp Lys
    1685            1690                1695

Glu Val Leu Tyr Glu Ala Phe Asp Glu Met Glu Glu Cys Ala Ser
    1700            1705                1710

Arg Ala Ala Leu Ile Glu Glu Gly Gln Arg Ile Ala Glu Met Leu
    1715            1720                1725

Lys Ser Lys Ile Gln Gly Leu Leu Gln Gln Ala Ser Lys Gln Ala
    1730            1735                1740

Gln Asp Ile Gln Pro Ala Met Gln Ala Ser Trp Pro Lys Val Glu
    1745            1750                1755

Gln Phe Trp Ala Arg His Met Trp Asn Phe Ile Ser Gly Ile Gln
    1760            1765                1770

Tyr Leu Ala Gly Leu Ser Thr Leu Pro Gly Asn Pro Ala Val Ala
    1775            1780                1785

Ser Met Met Ala Phe Ser Ala Ala Leu Thr Ser Pro Leu Ser Thr
    1790            1795                1800

Ser Thr Thr Ile Leu Leu Asn Ile Met Gly Gly Trp Leu Ala Ser
    1805            1810                1815

Gln Ile Ala Pro Pro Ala Gly Ala Thr Gly Phe Val Val Ser Gly
    1820            1825                1830

Leu Val Gly Ala Ala Val Gly Ser Ile Gly Leu Gly Lys Val Leu
    1835            1840                1845

Val Asp Ile Leu Ala Gly Tyr Gly Ala Gly Ile Ser Gly Ala Leu
    1850            1855                1860

Val Ala Phe Lys Ile Met Ser Gly Glu Lys Pro Ser Met Glu Asp
    1865            1870                1875

Val Ile Asn Leu Leu Pro Gly Ile Leu Ser Pro Gly Ala Leu Val
```

```
                1880                1885                1890

Val Gly Val Ile Cys Ala Ala Ile Leu Arg Arg His Val Gly Pro
    1895                1900                1905

Gly Glu Gly Ala Val Gln Trp Met Asn Arg Leu Ile Ala Phe Ala
    1910                1915                1920

Ser Arg Gly Asn His Val Ala Pro Thr His Tyr Val Thr Glu Ser
    1925                1930                1935

Asp Ala Ser Gln Arg Val Thr Gln Leu Leu Gly Ser Leu Thr Ile
    1940                1945                1950

Thr Ser Leu Leu Arg Arg Leu His Asn Trp Ile Thr Glu Asp Cys
    1955                1960                1965

Pro Ile Pro Cys Ser Gly Ser Trp Leu Arg Asp Val Trp Asp Trp
    1970                1975                1980

Val Cys Thr Ile Leu Thr Asp Phe Lys Asn Trp Leu Thr Ser Lys
    1985                1990                1995

Leu Phe Pro Lys Leu Pro Gly Leu Pro Phe Ile Ser Cys Gln Lys
    2000                2005                2010

Gly Tyr Lys Gly Val Trp Ala Gly Thr Gly Ile Met Thr Thr Arg
    2015                2020                2025

Cys Pro Cys Gly Ala Asn Ile Ser Gly Asn Val Arg Leu Gly Ser
    2030                2035                2040

Met Arg Ile Thr Gly Pro Lys Thr Cys Met Asn Thr Trp Gln Gly
    2045                2050                2055

Thr Phe Pro Ile Asn Cys Tyr Thr Glu Gly Gln Cys Ala Pro Lys
    2060                2065                2070

Pro Pro Thr Asn Tyr Lys Thr Ala Ile Trp Arg Val Ala Ala Ser
    2075                2080                2085

Glu Tyr Ala Glu Val Thr Gln His Gly Ser Tyr Ser Tyr Val Thr
    2090                2095                2100

Gly Leu Thr Thr Asp Asn Leu Lys Ile Pro Cys Gln Leu Pro Ser
    2105                2110                2115

Pro Glu Phe Phe Ser Trp Val Asp Gly Val Gln Ile His Arg Phe
    2120                2125                2130

Ala Pro Thr Pro Lys Pro Phe Phe Arg Asp Glu Val Ser Phe Cys
    2135                2140                2145

Val Gly Leu Asn Ser Tyr Ala Val Gly Ser Gln Leu Pro Cys Glu
    2150                2155                2160

Pro Glu Pro Asp Ala Asp Val Leu Arg Ser Met Leu Thr Asp Pro
    2165                2170                2175

Pro His Ile Thr Ala Glu Thr Ala Ala Arg Arg Leu Ala Arg Gly
    2180                2185                2190

Ser Pro Pro Ser Glu Ala Ser Ser Ser Val Ser Gln Leu Ser Ala
    2195                2200                2205

Pro Ser Leu Arg Ala Thr Cys Thr Thr His Ser Asn Thr Tyr Asp
    2210                2215                2220

Val Asp Met Val Asp Ala Asn Leu Leu Met Glu Gly Gly Val Ala
    2225                2230                2235

Gln Thr Glu Pro Glu Ser Arg Val Pro Val Leu Asp Phe Leu Glu
    2240                2245                2250

Pro Met Ala Glu Glu Glu Ser Asp Leu Glu Pro Ser Ile Pro Ser
    2255                2260                2265

Glu Cys Met Leu Pro Arg Ser Gly Phe Pro Arg Ala Leu Pro Ala
    2270                2275                2280
```

-continued

```
Trp Ala Arg Pro Asp Tyr Asn Pro Pro Leu Val Glu Ser Trp Arg
2285                2290                2295

Arg Pro Asp Tyr Gln Pro Pro Thr Val Ala Gly Cys Ala Leu Pro
2300                2305                2310

Pro Pro Lys Lys Ala Pro Thr Pro Pro Pro Arg Arg Arg Arg Thr
2315                2320                2325

Val Gly Leu Ser Glu Ser Thr Ile Ser Glu Ala Leu Gln Gln Leu
2330                2335                2340

Ala Ile Lys Thr Phe Gly Gln Pro Pro Ser Ser Gly Asp Ala Gly
2345                2350                2355

Ser Ser Thr Gly Ala Gly Ala Ala Glu Ser Gly Gly Pro Thr Ser
2360                2365                2370

Pro Gly Glu Pro Ala Pro Ser Glu Thr Gly Ser Ala Ser Ser Met
2375                2380                2385

Pro Pro Leu Glu Gly Glu Pro Gly Asp Pro Asp Leu Glu Ser Asp
2390                2395                2400

Gln Val Glu Leu Gln Pro Pro Gln Gly Gly Gly Val Ala Pro
2405                2410                2415

Gly Ser Gly Ser Gly Ser Trp Ser Thr Cys Ser Glu Glu Asp Asp
2420                2425                2430

Thr Thr Val Cys Cys Ser Met Ser Tyr Ser Trp Thr Gly Ala Leu
2435                2440                2445

Ile Thr Pro Cys Ser Pro Glu Glu Lys Leu Pro Ile Asn Pro
2450                2455                2460

Leu Ser Asn Ser Leu Leu Arg Tyr His Asn Lys Val Tyr Cys Thr
2465                2470                2475

Thr Ser Lys Ser Ala Ser Gln Arg Ala Lys Lys Val Thr Phe Asp
2480                2485                2490

Arg Thr Gln Val Leu Asp Ala His Tyr Asp Ser Val Leu Lys Asp
2495                2500                2505

Ile Lys Leu Ala Ala Ser Lys Val Ser Ala Arg Leu Leu Thr Leu
2510                2515                2520

Glu Glu Ala Cys Gln Leu Thr Pro Pro His Ser Ala Arg Ser Lys
2525                2530                2535

Tyr Gly Phe Gly Ala Lys Glu Val Arg Ser Leu Ser Gly Arg Ala
2540                2545                2550

Val Asn His Ile Lys Ser Val Trp Lys Asp Leu Leu Glu Asp Pro
2555                2560                2565

Gln Thr Pro Ile Pro Thr Thr Ile Met Ala Lys Asn Glu Val Phe
2570                2575                2580

Cys Val Asp Pro Ala Lys Gly Gly Lys Lys Pro Ala Arg Leu Ile
2585                2590                2595

Val Tyr Pro Asp Leu Gly Val Arg Val Cys Glu Lys Met Ala Leu
2600                2605                2610

Tyr Asp Ile Thr Gln Lys Leu Pro Gln Ala Val Met Gly Ala Ser
2615                2620                2625

Tyr Gly Phe Gln Tyr Ser Pro Ala Gln Arg Val Glu Tyr Leu Leu
2630                2635                2640

Lys Ala Trp Ala Glu Lys Lys Asp Pro Met Gly Phe Ser Tyr Asp
2645                2650                2655

Thr Arg Cys Phe Asp Ser Thr Val Thr Glu Arg Asp Ile Arg Thr
2660                2665                2670

Glu Glu Ser Ile Tyr Gln Ala Cys Ser Leu Pro Glu Glu Ala Arg
2675                2680                2685
```

```
Thr Ala Ile His Ser Leu Thr Glu Arg Leu Tyr Val Gly Gly Pro
    2690            2695                2700

Met Phe Asn Ser Lys Gly Gln Thr Cys Gly Tyr Arg Arg Cys Arg
    2705            2710                2715

Ala Ser Gly Val Leu Thr Thr Ser Met Gly Asn Thr Ile Thr Cys
    2720            2725                2730

Tyr Val Lys Ala Leu Ala Ala Cys Lys Ala Ala Gly Ile Val Ala
    2735            2740                2745

Pro Thr Met Leu Val Cys Gly Asp Asp Leu Val Val Ile Ser Glu
    2750            2755                2760

Ser Gln Gly Thr Glu Glu Asp Glu Arg Asn Leu Arg Ala Phe Thr
    2765            2770                2775

Glu Ala Met Thr Arg Tyr Ser Ala Pro Pro Gly Asp Pro Pro Arg
    2780            2785                2790

Pro Glu Tyr Asp Leu Glu Leu Ile Thr Ser Cys Ser Ser Asn Val
    2795            2800                2805

Ser Val Ala Leu Gly Pro Arg Gly Arg Arg Tyr Tyr Leu Thr
    2810            2815                2820

Arg Asp Pro Thr Thr Pro Leu Ala Arg Ala Ala Trp Glu Thr Val
    2825            2830                2835

Arg His Ser Pro Ile Asn Ser Trp Leu Gly Asn Ile Ile Gln Tyr
    2840            2845                2850

Ala Pro Thr Ile Trp Val Arg Met Val Leu Met Thr His Phe Phe
    2855            2860                2865

Ser Ile Leu Met Val Gln Asp Thr Leu Asp Gln Asn Leu Asn Phe
    2870            2875                2880

Glu Met Tyr Gly Ser Val Tyr Ser Val Asn Pro Leu Asp Leu Pro
    2885            2890                2895

Ala Ile Ile Glu Arg Leu His Gly Leu Asp Ala Phe Ser Met His
    2900            2905                2910

Thr Tyr Ser His His Glu Leu Thr Arg Val Ala Ser Ala Leu Arg
    2915            2920                2925

Lys Leu Gly Ala Pro Pro Leu Arg Val Trp Lys Ser Arg Ala Arg
    2930            2935                2940

Ala Val Arg Ala Ser Leu Ile Ser Arg Gly Gly Lys Ala Ala Val
    2945            2950                2955

Cys Gly Arg Tyr Leu Phe Asn Trp Ala Val Lys Thr Lys Leu Lys
    2960            2965                2970

Leu Thr Pro Leu Pro Glu Ala Arg Leu Leu Asp Leu Ser Ser Trp
    2975            2980                2985

Phe Thr Val Gly Ala Gly Gly Asp Ile Phe His Ser Val Ser
    2990            2995                3000

Arg Ala Arg Pro Arg Ser Leu Leu Phe Gly Leu Leu Leu Leu Phe
    3005            3010                3015

Val Gly Val Gly Leu Phe Leu Leu Pro Ala Arg
    3020            3025
```

<210> SEQ ID NO 24
<211> LENGTH: 3029
<212> TYPE: PRT
<213> ORGANISM: Hepatitis C virus

<400> SEQUENCE: 24

```
Met Ser Thr Asn Pro Lys Pro Gln Arg Lys Thr Lys Arg Asn Thr Asn
1               5                   10                  15
```

```
Arg Arg Pro Met Asp Val Lys Phe Pro Gly Gly Gln Ile Val Gly
         20                  25                  30

Gly Val Tyr Leu Leu Pro Arg Arg Gly Pro Arg Leu Gly Val Arg Ala
             35                  40                  45

Thr Arg Lys Thr Ser Glu Arg Ser Gln Pro Arg Gly Arg Gln Pro
 50                  55                  60

Ile Pro Lys Ala Arg Arg Pro Glu Gly Arg Ser Trp Ala Gln Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Asn Asp Pro
                100                 105                 110

Arg Arg Arg Ser Arg Asn Leu Gly Lys Val Ile Asp Thr Leu Thr Cys
                115                 120                 125

Gly Phe Ala Asp Leu Met Gly Tyr Ile Pro Leu Val Gly Ala Pro Val
 130                 135                 140

Gly Gly Val Ala Arg Ala Leu Ala His Gly Val Arg Ala Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Val
                180                 185                 190

Asn Tyr Arg Asn Val Ser Gly Ile Tyr His Val Thr Asn Asp Cys Pro
                195                 200                 205

Asn Ser Ser Ile Val Tyr Glu Ala Asp His His Ile Leu His Leu Pro
210                 215                 220

Gly Cys Val Pro Cys Val Arg Glu Gly Asn Gln Ser Arg Cys Trp Val
225                 230                 235                 240

Ala Leu Thr Pro Thr Val Ala Ala Pro Tyr Ile Gly Ala Pro Leu Glu
                245                 250                 255

Ser Leu Arg Ser His Val Asp Leu Met Val Gly Ala Ala Thr Val Cys
                260                 265                 270

Ser Gly Leu Tyr Ile Gly Asp Leu Cys Gly Gly Leu Phe Leu Val Gly
                275                 280                 285

Gln Met Phe Ser Phe Arg Pro Arg Arg His Trp Thr Thr Gln Asp Cys
290                 295                 300

Asn Cys Ser Ile Tyr Thr Gly His Ile Thr Gly His Arg Met Ala Trp
305                 310                 315                 320

Asp Met Met Met Asn Trp Ser Pro Thr Thr Thr Leu Val Leu Ala Gln
                325                 330                 335

Val Met Arg Ile Pro Thr Thr Leu Val Asp Leu Leu Ser Gly Gly His
                340                 345                 350

Trp Gly Val Leu Val Gly Val Ala Tyr Phe Ser Met Gln Ala Asn Trp
                355                 360                 365

Ala Lys Val Ile Leu Val Leu Phe Leu Phe Ala Gly Val Asp Ala Glu
370                 375                 380

Thr His Val Ser Gly Ala Ala Val Gly Arg Ser Thr Ala Gly Leu Ala
385                 390                 395                 400

Asn Leu Phe Ser Ser Gly Ser Lys Gln Asn Leu Gln Leu Ile Asn Ser
                405                 410                 415

Asn Gly Ser Trp His Ile Asn Arg Thr Ala Leu Asn Cys Asn Asp Ser
                420                 425                 430

Leu Asn Thr Gly Phe Leu Ala Ser Leu Phe Tyr Thr His Lys Phe Asn
```

```
                435                 440                 445
Ser Ser Gly Cys Ser Glu Arg Leu Ala Cys Cys Lys Ser Leu Asp Ser
450                 455                 460

Tyr Gly Gln Gly Trp Gly Pro Leu Gly Val Ala Asn Ile Ser Gly Ser
465                 470                 475                 480

Ser Asp Asp Arg Pro Tyr Cys Trp His Tyr Ala Pro Arg Pro Cys Gly
                485                 490                 495

Ile Val Pro Ala Ser Ser Val Cys Gly Pro Val Tyr Cys Phe Thr Pro
                500                 505                 510

Ser Pro Val Val Val Gly Thr Thr Asp His Val Gly Val Pro Thr Tyr
                515                 520                 525

Thr Trp Gly Glu Asn Glu Thr Asp Val Phe Leu Leu Asn Ser Thr Arg
530                 535                 540

Pro Pro His Gly Ala Trp Phe Gly Cys Val Trp Met Asn Ser Thr Gly
545                 550                 555                 560

Phe Thr Lys Thr Cys Gly Ala Pro Pro Cys Glu Val Asn Thr Asn Asn
                565                 570                 575

Gly Thr Trp His Cys Pro Thr Asp Cys Phe Arg Lys His Pro Glu Thr
                580                 585                 590

Thr Tyr Ala Lys Cys Gly Ser Gly Pro Trp Ile Thr Pro Arg Cys Leu
                595                 600                 605

Ile Asp Tyr Pro Tyr Arg Leu Trp His Phe Pro Cys Thr Ala Asn Phe
610                 615                 620

Ser Val Phe Asn Ile Arg Thr Phe Val Gly Gly Ile Glu His Arg Met
625                 630                 635                 640

Gln Ala Ala Cys Asn Trp Thr Arg Gly Glu Val Cys Gly Leu Glu His
                645                 650                 655

Arg Asp Arg Val Glu Leu Ser Pro Leu Leu Leu Thr Thr Thr Ala Trp
                660                 665                 670

Gln Ile Leu Pro Cys Ser Phe Thr Thr Leu Pro Ala Leu Ser Thr Gly
                675                 680                 685

Leu Ile His Leu His Gln Asn Ile Val Asp Val Gln Tyr Leu Tyr Gly
690                 695                 700

Val Gly Ser Ala Val Val Ser Trp Ala Leu Lys Trp Glu Tyr Val Val
705                 710                 715                 720

Leu Ala Phe Leu Leu Leu Ala Asp Ala Arg Val Ser Ala Cys Leu Trp
                725                 730                 735

Met Met Phe Met Val Ser Gln Val Glu Ala Ala Leu Ser Asn Leu Ile
                740                 745                 750

Asn Ile Asn Ala Ala Ser Ala Ala Gly Ala Gln Gly Phe Trp Tyr Ala
                755                 760                 765

Ile Leu Phe Ile Cys Ile Val His Val Lys Gly Arg Phe Pro Ala
                770                 775                 780

Ala Ala Ala Tyr Ala Ala Cys Gly Leu Trp Pro Leu Phe Leu Leu Leu
785                 790                 795                 800

Leu Met Leu Pro Glu Arg Ala Tyr Ala Tyr Asp Gln Glu Val Ala Gly
                805                 810                 815

Ser Leu Gly Gly Ala Ile Val Val Met Leu Ala Ile Leu Thr Leu Ser
                820                 825                 830

Pro His Tyr Lys Leu Trp Leu Ala Arg Gly Leu Trp Trp Ile Gln Tyr
                835                 840                 845

Phe Ile Ala Arg Thr Glu Ala Val Leu His Val Tyr Ile Pro Ser Phe
850                 855                 860
```

-continued

Asn Val Arg Gly Pro Arg Asp Ser Val Ile Val Leu Ala Val Leu Val
865                 870                 875                 880

Cys Pro His Leu Val Phe Asp Ile Thr Lys Tyr Leu Leu Ala Ile Leu
                885                 890                 895

Gly Pro Leu His Ile Leu Gln Ala Ser Leu Leu Arg Ile Pro Tyr Phe
        900                 905                 910

Val Arg Ala Gln Ala Leu Val Lys Ile Cys Ser Leu Arg Gly Val
            915                 920                 925

Val Tyr Gly Lys Tyr Phe Gln Met Val Val Leu Lys Ala Gly Ala Leu
        930                 935                 940

Thr Gly Thr Tyr Ile Tyr Asp His Leu Thr Pro Met Ser Asp Trp Ala
945                 950                 955                 960

Ala Ser Gly Leu Arg Asp Leu Ala Val Ala Val Glu Pro Ile Ile Phe
                965                 970                 975

Ser Pro Met Glu Lys Lys Val Ile Val Trp Gly Ala Glu Thr Ala Ala
                980                 985                 990

Cys Gly Asp Ile Leu His Gly Leu Pro Val Ser Ala Arg Leu Gly Gln
            995                 1000                1005

Glu Ile Leu Leu Gly Pro Ala Asp Gly Tyr Thr Ser Lys Gly Trp
    1010                1015                1020

Lys Leu Leu Ala Pro Ile Thr Ala Tyr Ala Gln Gln Thr Arg Gly
    1025                1030                1035

Leu Leu Gly Ala Ile Val Val Ser Met Thr Gly Arg Asp Arg Thr
    1040                1045                1050

Glu Gln Ala Gly Glu Val Gln Ile Leu Ser Thr Val Ser Gln Ser
    1055                1060                1065

Phe Leu Gly Thr Thr Ile Ser Gly Val Leu Trp Thr Val Tyr His
    1070                1075                1080

Gly Ala Gly Asn Lys Thr Leu Ala Gly Leu Arg Gly Pro Val Thr
    1085                1090                1095

Gln Met Tyr Ser Ser Ala Glu Gly Asp Leu Val Gly Trp Pro Ser
    1100                1105                1110

Pro Pro Gly Thr Lys Ser Leu Glu Pro Cys Lys Cys Gly Ala Val
    1115                1120                1125

Asp Leu Tyr Leu Val Thr Arg Asn Ala Asp Val Ile Pro Ala Arg
    1130                1135                1140

Arg Arg Gly Asp Lys Arg Gly Ala Leu Leu Ser Pro Arg Pro Ile
    1145                1150                1155

Ser Thr Leu Lys Gly Ser Ser Gly Gly Pro Val Leu Cys Pro Arg
    1160                1165                1170

Gly His Val Val Gly Leu Phe Arg Ala Ala Val Cys Ser Arg Gly
    1175                1180                1185

Val Ala Lys Ser Ile Asp Phe Ile Pro Val Glu Thr Leu Asp Val
    1190                1195                1200

Val Thr Arg Ser Pro Thr Phe Ser Asp Asn Ser Thr Pro Pro Ala
    1205                1210                1215

Val Pro Gln Thr Tyr Gln Val Gly Tyr Leu His Ala Pro Thr Gly
    1220                1225                1230

Ser Gly Lys Ser Thr Lys Val Pro Val Ala Tyr Ala Ala Gln Gly
    1235                1240                1245

Tyr Lys Val Leu Val Leu Asn Pro Ser Val Ala Ala Thr Leu Gly
    1250                1255                1260

Phe Gly Ala Tyr Leu Ser Lys Ala His Gly Ile Asn Pro Asn Ile
    1265                1270                1275

```
Arg Thr Gly Val Arg Thr Val Met Thr Gly Glu Ala Ile Thr Tyr
    1280                1285                1290

Ser Thr Tyr Gly Lys Phe Leu Ala Asp Gly Gly Cys Ala Ser Gly
    1295                1300                1305

Ala Tyr Asp Ile Ile Ile Cys Asp Glu Cys His Ala Val Asp Ala
    1310                1315                1320

Thr Ser Ile Leu Gly Ile Gly Thr Val Leu Asp Gln Ala Glu Thr
    1325                1330                1335

Ala Gly Val Arg Leu Thr Val Leu Ala Thr Ala Thr Pro Pro Gly
    1340                1345                1350

Ser Val Thr Thr Pro His Pro Asp Ile Glu Glu Val Gly Leu Gly
    1355                1360                1365

Arg Glu Gly Glu Ile Pro Phe Tyr Gly Arg Ala Ile Pro Leu Ser
    1370                1375                1380

Cys Ile Lys Gly Gly Arg His Leu Ile Phe Cys His Ser Lys Lys
    1385                1390                1395

Lys Cys Asp Glu Leu Ala Ala Ala Leu Arg Gly Met Gly Leu Asn
    1400                1405                1410

Ala Val Ala Tyr Tyr Arg Gly Leu Asp Val Ser Ile Ile Pro Ala
    1415                1420                1425

Gln Gly Asp Val Val Val Ala Thr Asp Ala Leu Met Thr Gly
    1430                1435                1440

Tyr Thr Gly Asp Phe Asp Ser Val Ile Asp Cys Asn Val Ala Val
    1445                1450                1455

Thr Gln Ala Val Asp Phe Ser Leu Asp Pro Thr Phe Thr Ile Thr
    1460                1465                1470

Thr Gln Thr Val Pro Gln Asp Ala Val Ser Arg Ser Gln Arg Arg
    1475                1480                1485

Gly Arg Thr Gly Arg Gly Arg Gln Gly Thr Tyr Arg Tyr Val Ser
    1490                1495                1500

Thr Gly Glu Arg Ala Ser Gly Met Phe Asp Ser Val Val Leu Cys
    1505                1510                1515

Glu Cys Tyr Asp Ala Gly Ala Ala Trp Tyr Asp Leu Thr Pro Ala
    1520                1525                1530

Glu Thr Thr Val Arg Leu Arg Ala Tyr Phe Asn Thr Pro Gly Leu
    1535                1540                1545

Pro Val Cys Gln Asp His Leu Glu Phe Trp Glu Ala Val Phe Thr
    1550                1555                1560

Gly Leu Thr His Ile Asp Ala His Phe Leu Ser Gln Thr Lys Gln
    1565                1570                1575

Ala Gly Glu Asn Phe Ala Tyr Leu Val Ala Tyr Gln Ala Thr Val
    1580                1585                1590

Cys Ala Arg Ala Lys Ala Pro Pro Pro Ser Trp Asp Ala Met Trp
    1595                1600                1605

Lys Cys Leu Ala Arg Leu Lys Pro Thr Leu Ala Gly Pro Thr Pro
    1610                1615                1620

Leu Leu Tyr Arg Leu Gly Pro Ile Thr Asn Glu Val Thr Leu Thr
    1625                1630                1635

His Pro Gly Thr Lys Tyr Ile Ala Thr Cys Met Gln Ala Asp Leu
    1640                1645                1650

Glu Val Met Thr Ser Thr Trp Val Leu Ala Gly Gly Val Leu Ala
    1655                1660                1665

Ala Val Ala Ala Tyr Cys Leu Ala Thr Gly Cys Val Ser Ile Ile
```

-continued

```
              1670                1675                1680

Gly  Arg  Leu  His  Val  Asn  Gln  Arg  Val  Val  Ala  Pro  Asp  Lys
         1685                1690                1695

Glu  Val  Leu  Tyr  Glu  Ala  Phe  Asp  Glu  Met  Glu  Cys  Ala  Ser
         1700                1705                1710

Arg  Ala  Ala  Leu  Ile  Glu  Glu  Gly  Gln  Arg  Ile  Ala  Glu  Met  Leu
         1715                1720                1725

Lys  Ser  Lys  Ile  Gln  Gly  Leu  Leu  Gln  Ala  Ser  Lys  Gln  Ala
         1730                1735                1740

Gln  Asp  Ile  Gln  Pro  Ala  Met  Gln  Ala  Ser  Trp  Pro  Lys  Val  Glu
         1745                1750                1755

Gln  Phe  Trp  Ala  Arg  His  Met  Trp  Asn  Phe  Ile  Ser  Gly  Ile  Gln
         1760                1765                1770

Tyr  Leu  Ala  Gly  Leu  Ser  Thr  Leu  Pro  Gly  Asn  Pro  Ala  Val  Ala
         1775                1780                1785

Ser  Met  Met  Ala  Phe  Ser  Ala  Ala  Leu  Thr  Ser  Pro  Leu  Ser  Thr
         1790                1795                1800

Ser  Thr  Thr  Ile  Leu  Leu  Asn  Ile  Met  Gly  Gly  Trp  Leu  Ala  Ser
         1805                1810                1815

Gln  Ile  Ala  Pro  Pro  Ala  Gly  Ala  Thr  Gly  Phe  Val  Val  Ser  Gly
         1820                1825                1830

Leu  Val  Gly  Ala  Ala  Val  Gly  Ser  Ile  Gly  Leu  Gly  Lys  Val  Leu
         1835                1840                1845

Val  Asp  Ile  Leu  Ala  Gly  Tyr  Gly  Ala  Gly  Ile  Ser  Gly  Ala  Leu
         1850                1855                1860

Val  Ala  Phe  Lys  Ile  Met  Ser  Gly  Glu  Lys  Pro  Ser  Met  Glu  Asp
         1865                1870                1875

Val  Ile  Asn  Leu  Leu  Pro  Gly  Ile  Leu  Ser  Pro  Gly  Ala  Leu  Val
         1880                1885                1890

Val  Gly  Val  Ile  Cys  Ala  Ala  Ile  Leu  Arg  Arg  His  Val  Gly  Pro
         1895                1900                1905

Gly  Glu  Gly  Ala  Val  Gln  Trp  Met  Asn  Arg  Leu  Ile  Ala  Phe  Ala
         1910                1915                1920

Ser  Arg  Gly  Asn  His  Val  Ala  Pro  Thr  His  Tyr  Val  Thr  Glu  Ser
         1925                1930                1935

Asp  Ala  Ser  Gln  Arg  Val  Thr  Gln  Leu  Leu  Gly  Ser  Leu  Thr  Ile
         1940                1945                1950

Thr  Ser  Leu  Leu  Arg  Arg  Leu  His  Asn  Trp  Ile  Thr  Glu  Asp  Cys
         1955                1960                1965

Pro  Ile  Pro  Cys  Ser  Gly  Ser  Trp  Leu  Arg  Asp  Val  Trp  Asp  Trp
         1970                1975                1980

Val  Cys  Thr  Ile  Leu  Thr  Asp  Phe  Lys  Asn  Trp  Leu  Thr  Ser  Lys
         1985                1990                1995

Leu  Phe  Pro  Lys  Leu  Pro  Gly  Leu  Pro  Phe  Ile  Ser  Cys  Gln  Lys
         2000                2005                2010

Gly  Tyr  Lys  Gly  Val  Trp  Ala  Gly  Thr  Gly  Ile  Met  Thr  Thr  Arg
         2015                2020                2025

Cys  Pro  Cys  Gly  Ala  Asn  Ile  Ser  Gly  Asn  Val  Arg  Leu  Gly  Ser
         2030                2035                2040

Met  Arg  Ile  Thr  Gly  Pro  Lys  Thr  Cys  Met  Asn  Thr  Trp  Gln  Gly
         2045                2050                2055

Thr  Phe  Pro  Ile  Asn  Cys  Tyr  Thr  Glu  Gly  Gln  Cys  Ala  Pro  Lys
         2060                2065                2070
```

-continued

Pro Pro Thr Asn Tyr Lys Thr Ala Ile Trp Arg Val Ala Ala Ser
2075                    2080                    2085

Glu Tyr Ala Glu Val Thr Gln His Gly Ser Tyr Ser Tyr Val Thr
2090                    2095                    2100

Gly Leu Thr Thr Asp Asn Leu Lys Ile Pro Cys Gln Leu Pro Ser
2105                    2110                    2115

Pro Glu Phe Phe Ser Trp Val Asp Gly Val Gln Ile His Arg Phe
2120                    2125                    2130

Ala Pro Thr Pro Lys Pro Phe Phe Arg Asp Glu Val Ser Phe Cys
2135                    2140                    2145

Val Gly Leu Asn Ser Tyr Ala Val Gly Ser Gln Leu Pro Cys Glu
2150                    2155                    2160

Pro Glu Pro Asp Ala Asp Val Leu Arg Ser Met Leu Thr Asp Pro
2165                    2170                    2175

Pro His Ile Thr Ala Glu Thr Ala Ala Arg Arg Leu Ala Arg Gly
2180                    2185                    2190

Ser Pro Pro Ser Glu Ala Ser Ser Val Ser Gln Leu Ser Ala
2195                    2200                    2205

Pro Ser Leu Arg Ala Thr Cys Thr Thr His Ser Asn Thr Tyr Asp
2210                    2215                    2220

Val Asp Met Val Asp Ala Asn Leu Leu Met Glu Gly Gly Val Ala
2225                    2230                    2235

Gln Thr Glu Pro Glu Ser Arg Val Pro Val Leu Asp Phe Leu Glu
2240                    2245                    2250

Pro Met Ala Glu Glu Ser Asp Leu Glu Pro Ser Ile Pro Ser
2255                    2260                    2265

Glu Cys Met Leu Pro Arg Ser Gly Phe Pro Arg Ala Leu Pro Ala
2270                    2275                    2280

Trp Ala Arg Pro Asp Tyr Asn Pro Pro Leu Val Glu Ser Trp Arg
2285                    2290                    2295

Arg Pro Asp Tyr Gln Pro Pro Thr Val Ala Gly Cys Ala Leu Pro
2300                    2305                    2310

Pro Pro Lys Lys Ala Pro Thr Pro Pro Pro Arg Arg Arg Arg Thr
2315                    2320                    2325

Val Gly Leu Ser Glu Ser Thr Ile Ser Glu Ala Leu Gln Gln Leu
2330                    2335                    2340

Ala Ile Lys Thr Phe Gly Gln Pro Pro Ser Ser Gly Asp Ala Gly
2345                    2350                    2355

Ser Ser Thr Gly Ala Gly Ala Glu Ser Gly Gly Pro Thr Ser
2360                    2365                    2370

Pro Gly Glu Pro Ala Pro Ser Glu Thr Gly Ser Ala Ser Ser Met
2375                    2380                    2385

Pro Pro Leu Glu Gly Glu Pro Gly Asp Pro Asp Leu Glu Ser Asp
2390                    2395                    2400

Gln Val Glu Leu Gln Pro Pro Gln Gly Gly Val Ala Pro
2405                    2410                    2415

Gly Ser Gly Ser Gly Ser Trp Ser Thr Cys Ser Glu Glu Asp Asp
2420                    2425                    2430

Thr Thr Leu Cys Cys Ser Met Ser Tyr Ser Trp Thr Gly Ala Leu
2435                    2440                    2445

Ile Thr Pro Cys Ser Pro Glu Glu Lys Leu Pro Ile Asn Pro
2450                    2455                    2460

Leu Ser Asn Ser Leu Leu Arg Tyr His Asn Lys Val Tyr Cys Thr
2465                    2470                    2475

```
Thr Ser Lys Ser Ala Ser Gln Arg Ala Lys Lys Val Thr Phe Asp
    2480            2485                2490

Arg Thr Gln Val Leu Asp Ala His Tyr Asp Ser Val Leu Lys Asp
    2495            2500                2505

Ile Lys Leu Ala Ala Ser Lys Val Ser Ala Arg Leu Leu Thr Leu
    2510            2515                2520

Glu Glu Ala Cys Gln Leu Thr Pro Pro His Ser Ala Arg Ser Lys
    2525            2530                2535

Tyr Gly Phe Gly Ala Lys Glu Val Arg Ser Leu Ser Gly Arg Ala
    2540            2545                2550

Val Asn His Ile Lys Ser Val Trp Lys Asp Leu Leu Glu Asp Pro
    2555            2560                2565

Gln Thr Pro Ile Pro Thr Thr Ile Met Ala Lys Asn Glu Val Phe
    2570            2575                2580

Cys Val Asp Pro Ala Lys Gly Gly Lys Lys Pro Ala Arg Leu Ile
    2585            2590                2595

Val Tyr Pro Asp Leu Gly Val Arg Val Cys Glu Lys Met Ala Leu
    2600            2605                2610

Tyr Asp Ile Thr Gln Lys Leu Pro Gln Ala Val Met Gly Ala Ser
    2615            2620                2625

Tyr Gly Phe Gln Tyr Ser Pro Ala Gln Arg Val Glu Tyr Leu Leu
    2630            2635                2640

Lys Ala Trp Ala Glu Lys Lys Asp Pro Met Gly Phe Ser Tyr Asp
    2645            2650                2655

Thr Arg Cys Phe Asp Ser Thr Val Thr Glu Arg Asp Ile Arg Thr
    2660            2665                2670

Glu Glu Ser Ile Tyr Gln Ala Cys Ser Leu Pro Glu Glu Ala Arg
    2675            2680                2685

Thr Ala Ile His Ser Leu Thr Glu Arg Leu Tyr Val Gly Gly Pro
    2690            2695                2700

Met Phe Asn Ser Lys Gly Gln Thr Cys Gly Tyr Arg Arg Cys Arg
    2705            2710                2715

Ala Ser Gly Val Leu Thr Thr Ser Met Gly Asn Thr Ile Thr Cys
    2720            2725                2730

Tyr Val Lys Ala Leu Ala Ala Cys Lys Ala Ala Gly Ile Val Ala
    2735            2740                2745

Pro Thr Met Leu Val Cys Gly Asp Asp Leu Val Val Ile Ser Glu
    2750            2755                2760

Ser Gln Gly Thr Glu Glu Asp Glu Arg Asn Leu Arg Ala Phe Thr
    2765            2770                2775

Glu Ala Met Thr Arg Tyr Ser Ala Pro Pro Gly Asp Pro Pro Arg
    2780            2785                2790

Pro Glu Tyr Asp Leu Glu Leu Ile Thr Ser Cys Ser Ser Asn Val
    2795            2800                2805

Ser Val Ala Leu Gly Pro Arg Gly Arg Arg Tyr Tyr Leu Thr
    2810            2815                2820

Arg Asp Pro Thr Thr Pro Leu Ala Arg Ala Ala Trp Glu Thr Val
    2825            2830                2835

Arg His Ser Pro Ile Asn Ser Trp Leu Gly Asn Ile Ile Gln Tyr
    2840            2845                2850

Ala Pro Thr Ile Trp Val Arg Met Val Leu Met Thr His Phe Phe
    2855            2860                2865

Ser Ile Leu Met Val Gln Asp Thr Leu Asp Gln Asn Leu Asn Phe
```

-continued

```
                2870                2875                2880

Glu Met Tyr Gly Ser Val Tyr Ser Val Asn Pro Leu Asp Leu Pro
        2885                2890                2895

Ala Ile Ile Glu Arg Leu His Gly Leu Asp Ala Phe Ser Met His
    2900                2905                2910

Thr Tyr Ser His His Glu Leu Thr Arg Val Ala Ser Ala Leu Arg
    2915                2920                2925

Lys Leu Gly Ala Pro Pro Leu Arg Val Trp Lys Ser Arg Ala Arg
    2930                2935                2940

Ala Val Arg Ala Ser Leu Ile Ser Arg Gly Gly Lys Ala Ala Val
    2945                2950                2955

Cys Gly Arg Tyr Leu Phe Asn Trp Ala Val Lys Thr Lys Leu Lys
    2960                2965                2970

Leu Thr Pro Leu Pro Glu Ala Arg Leu Leu Asp Leu Ser Ser Trp
    2975                2980                2985

Phe Thr Val Gly Ala Gly Gly Asp Ile Phe His Ser Val Ser
    2990                2995                3000

Arg Ala Arg Pro Arg Ser Leu Leu Phe Gly Leu Leu Leu Leu Phe
    3005                3010                3015

Val Gly Val Gly Leu Phe Leu Leu Pro Ala Arg
    3020                3025

<210> SEQ ID NO 25
<211> LENGTH: 3029
<212> TYPE: PRT
<213> ORGANISM: Hepatitis C virus

<400> SEQUENCE: 25

Met Ser Thr Asn Pro Lys Pro Gln Arg Lys Thr Lys Arg Asn Thr Asn
1               5                   10                  15

Arg Arg Pro Met Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Val
            180                 185                 190

Asn Tyr Arg Asn Val Ser Gly Ile Tyr His Val Thr Asn Asp Cys Pro
        195                 200                 205

Asn Ser Ser Ile Val Tyr Glu Ala Asp His His Ile Leu His Leu Pro
```

-continued

```
            210                 215                 220
Gly Cys Val Pro Cys Val Arg Glu Gly Asn Gln Ser Arg Cys Trp Val
225                 230                 235                 240

Ala Leu Thr Pro Thr Val Ala Ala Pro Tyr Ile Gly Ala Pro Leu Glu
                245                 250                 255

Ser Leu Arg Ser His Val Asp Leu Met Val Gly Ala Ala Thr Val Cys
                260                 265                 270

Ser Gly Leu Tyr Ile Gly Asp Leu Cys Gly Leu Phe Leu Val Gly
                275                 280                 285

Gln Met Phe Ser Phe Arg Pro Arg His Trp Thr Thr Gln Asp Cys
    290                 295                 300

Asn Cys Ser Ile Tyr Thr Gly His Ile Thr Gly His Arg Met Ala Trp
305                 310                 315                 320

Asp Met Met Met Asn Trp Ser Pro Thr Thr Leu Val Leu Ala Gln
                325                 330                 335

Val Met Arg Ile Pro Thr Thr Leu Val Asp Leu Leu Ser Gly Gly His
                340                 345                 350

Trp Gly Val Leu Val Gly Val Ala Tyr Phe Ser Met Gln Ala Asn Trp
    355                 360                 365

Ala Lys Val Ile Leu Val Leu Phe Leu Phe Ala Gly Val Asp Ala Glu
370                 375                 380

Thr His Val Ser Gly Ala Ala Val Gly Arg Ser Thr Ala Gly Leu Ala
385                 390                 395                 400

Asn Leu Phe Ser Ser Gly Ser Lys Gln Asn Leu Gln Leu Ile Asn Ser
                405                 410                 415

Asn Gly Ser Trp His Ile Asn Arg Thr Ala Leu Asn Cys Asn Asp Ser
                420                 425                 430

Leu Asn Thr Gly Phe Leu Ala Ser Leu Phe Tyr Thr His Lys Phe Asn
                435                 440                 445

Ser Ser Gly Cys Ser Glu Arg Leu Ala Cys Cys Lys Ser Leu Asp Ser
                450                 455                 460

Tyr Gly Gln Gly Trp Gly Pro Leu Gly Val Ala Asn Ile Ser Gly Ser
465                 470                 475                 480

Ser Asp Asp Arg Pro Tyr Cys Trp His Tyr Ala Pro Arg Pro Cys Gly
                485                 490                 495

Ile Val Pro Ala Ser Ser Val Cys Gly Pro Val Tyr Cys Phe Thr Pro
                500                 505                 510

Ser Pro Val Val Val Gly Thr Thr Asp His Val Gly Val Pro Thr Tyr
                515                 520                 525

Thr Trp Gly Glu Asn Glu Thr Asp Val Phe Leu Leu Asn Ser Thr Arg
530                 535                 540

Pro Pro His Gly Ala Trp Phe Gly Cys Val Trp Met Asn Ser Thr Gly
545                 550                 555                 560

Phe Thr Lys Thr Cys Gly Ala Pro Pro Cys Glu Val Asn Thr Asn Asn
                565                 570                 575

Gly Thr Trp His Cys Pro Thr Asp Cys Phe Arg Lys His Pro Glu Thr
                580                 585                 590

Thr Tyr Ala Lys Cys Gly Ser Gly Pro Trp Ile Thr Pro Arg Cys Leu
                595                 600                 605

Ile Asp Tyr Pro Tyr Arg Leu Trp His Phe Pro Cys Thr Ala Asn Phe
                610                 615                 620

Ser Val Phe Asn Ile Arg Thr Phe Val Gly Gly Ile Glu His Arg Met
625                 630                 635                 640
```

-continued

```
Gln Ala Ala Cys Asn Trp Thr Arg Gly Glu Val Cys Gly Leu Glu His
            645                 650                 655

Arg Asp Arg Val Glu Leu Ser Pro Leu Leu Leu Thr Thr Thr Ala Trp
            660                 665                 670

Gln Ile Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
            690                 695                 700

Val Gly Ser Ala Val Val Ser Trp Ala Leu Lys Trp Glu Tyr Val Val
705                 710                 715                 720

Leu Ala Phe Leu Leu Leu Ala Asp Ala Arg Val Ser Ala Cys Leu Trp
            725                 730                 735

Met Met Phe Met Val Ser Gln Val Glu Ala Ala Leu Ser Asn Leu Ile
            740                 745                 750

Asn Ile Asn Ala Ala Ser Ala Ala Gly Ala Gln Gly Phe Trp Tyr Ala
            755                 760                 765

Ile Leu Phe Ile Cys Ile Val Trp His Val Lys Gly Arg Phe Pro Ala
            770                 775                 780

Ala Ala Ala Tyr Ala Ala Cys Gly Leu Trp Pro Leu Phe Leu Leu Leu
785                 790                 795                 800

Leu Met Leu Pro Glu Arg Ala Tyr Ala Tyr Asp Gln Glu Val Ala Gly
            805                 810                 815

Ser Leu Gly Gly Ala Ile Val Val Met Leu Ala Ile Leu Thr Leu Ser
            820                 825                 830

Pro His Tyr Lys Leu Trp Leu Ala Arg Gly Leu Trp Trp Ile Gln Tyr
            835                 840                 845

Phe Ile Ala Arg Thr Glu Ala Val Leu His Val Tyr Ile Pro Ser Phe
            850                 855                 860

Asn Val Arg Gly Pro Arg Asp Ser Val Ile Val Leu Ala Val Leu Val
865                 870                 875                 880

Cys Pro His Leu Val Phe Asp Ile Thr Lys Tyr Leu Leu Ala Ile Leu
            885                 890                 895

Gly Pro Leu His Ile Leu Gln Ala Ser Leu Leu Arg Ile Pro Tyr Phe
            900                 905                 910

Val Arg Ala Gln Ala Leu Val Lys Ile Cys Ser Leu Leu Arg Gly Val
            915                 920                 925

Val Tyr Gly Lys Tyr Phe Gln Met Val Val Leu Lys Ala Gly Ala Leu
            930                 935                 940

Thr Gly Thr Tyr Ile Tyr Asp His Leu Thr Pro Met Ser Asp Trp Ala
945                 950                 955                 960

Ala Ser Gly Leu Arg Asp Leu Ala Val Ala Val Glu Pro Ile Ile Phe
            965                 970                 975

Ser Pro Met Glu Lys Lys Val Ile Val Trp Gly Ala Lys Thr Ala Ala
            980                 985                 990

Cys Gly Asp Ile Leu His Gly Leu  Pro Val Ser Ala Arg  Leu Gly Gln
            995                 1000                1005

Glu Ile Leu Leu Gly Pro Ala  Asp Gly Tyr Thr Ser  Lys Gly Trp
            1010                1015                1020

Lys Leu Leu Ala Pro Ile Thr  Ala Tyr Ala Gln Gln  Thr Arg Gly
            1025                1030                1035

Leu Leu  Gly Ala Ile Val Val  Ser Met Thr Gly Arg  Asp Arg Thr
            1040                1045                1050

Glu Gln  Ala Gly Glu Val Gln  Ile Leu Ser Thr Val  Ser Gln Ser
            1055                1060                1065
```

-continued

```
Phe Leu Gly Thr Thr Ile Ser Gly Val Leu Trp Thr Val Tyr His
    1070                1075                1080

Gly Ala Gly Asn Lys Thr Leu Ala Gly Leu Arg Gly Pro Val Thr
    1085                1090                1095

Gln Met Tyr Ser Ser Ala Glu Gly Asp Leu Val Gly Trp Pro Ser
    1100                1105                1110

Pro Pro Gly Thr Lys Ser Leu Glu Pro Cys Lys Cys Gly Ala Val
    1115                1120                1125

Asp Leu Tyr Leu Val Thr Arg Asn Ala Asp Val Ile Pro Ala Arg
    1130                1135                1140

Arg Arg Gly Asp Lys Arg Gly Ala Leu Leu Ser Pro Arg Pro Ile
    1145                1150                1155

Ser Thr Leu Lys Gly Ser Ser Gly Gly Pro Val Leu Cys Pro Arg
    1160                1165                1170

Gly His Val Val Gly Leu Phe Arg Ala Ala Val Cys Ser Arg Gly
    1175                1180                1185

Val Ala Lys Ser Ile Asp Phe Ile Pro Val Glu Thr Leu Asp Val
    1190                1195                1200

Val Thr Arg Ser Pro Thr Phe Ser Asp Asn Ser Thr Pro Pro Ala
    1205                1210                1215

Val Pro Gln Thr Tyr Gln Val Gly Tyr Leu His Ala Pro Thr Gly
    1220                1225                1230

Ser Gly Lys Ser Thr Lys Val Pro Val Ala Tyr Ala Ala Gln Gly
    1235                1240                1245

Tyr Lys Val Leu Val Leu Asn Pro Ser Val Ala Ala Thr Leu Gly
    1250                1255                1260

Phe Gly Ala Tyr Leu Ser Lys Ala His Gly Ile Asn Pro Asn Ile
    1265                1270                1275

Arg Thr Gly Val Arg Thr Val Met Thr Gly Glu Ala Ile Thr Tyr
    1280                1285                1290

Ser Thr Tyr Gly Lys Phe Leu Ala Asp Gly Gly Cys Ala Ser Gly
    1295                1300                1305

Ala Tyr Asp Ile Ile Ile Cys Asp Glu Cys His Ala Val Asp Ala
    1310                1315                1320

Thr Ser Ile Leu Gly Ile Gly Thr Val Leu Asp Gln Ala Glu Thr
    1325                1330                1335

Ala Gly Val Arg Leu Thr Val Leu Ala Thr Ala Thr Pro Pro Gly
    1340                1345                1350

Ser Val Thr Thr Pro His Pro Asp Ile Glu Glu Val Gly Leu Gly
    1355                1360                1365

Arg Glu Gly Glu Ile Pro Phe Tyr Gly Arg Ala Ile Pro Leu Ser
    1370                1375                1380

Cys Ile Lys Gly Gly Arg His Leu Ile Phe Cys His Ser Lys Lys
    1385                1390                1395

Lys Cys Asp Glu Leu Ala Ala Ala Leu Arg Gly Met Gly Leu Asn
    1400                1405                1410

Ala Val Ala Tyr Tyr Arg Gly Leu Asp Val Ser Ile Ile Pro Ala
    1415                1420                1425

Gln Gly Asp Val Val Val Ala Thr Asp Ala Leu Met Thr Gly
    1430                1435                1440

Tyr Thr Gly Asp Phe Asp Ser Val Ile Asp Cys Asn Val Ala Val
    1445                1450                1455

Thr Gln Ala Val Asp Phe Ser Leu Asp Pro Thr Phe Thr Ile Thr
```

-continued

```
              1460                1465                1470

Thr Gln Thr Val Pro Gln Asp Ala Val Ser Arg Ser Gln Arg Arg
    1475                1480                1485

Gly Arg Thr Gly Arg Gly Arg Gln Gly Thr Tyr Arg Tyr Val Ser
    1490                1495                1500

Thr Gly Glu Arg Ala Ser Gly Met Phe Asp Ser Val Val Leu Cys
    1505                1510                1515

Glu Cys Tyr Asp Ala Gly Ala Ala Trp Tyr Asp Leu Thr Pro Ala
    1520                1525                1530

Glu Thr Thr Val Arg Leu Arg Ala Tyr Phe Asn Thr Pro Gly Leu
    1535                1540                1545

Pro Val Cys Gln Asp His Leu Glu Phe Trp Glu Ala Val Phe Thr
    1550                1555                1560

Gly Leu Thr His Ile Asp Ala His Phe Leu Ser Gln Thr Lys Gln
    1565                1570                1575

Ala Gly Glu Asn Phe Ala Tyr Leu Val Ala Tyr Gln Ala Thr Val
    1580                1585                1590

Cys Ala Arg Ala Lys Ala Pro Pro Pro Ser Trp Asp Ala Met Trp
    1595                1600                1605

Lys Cys Leu Ala Arg Leu Lys Pro Thr Leu Ala Gly Pro Thr Pro
    1610                1615                1620

Leu Leu Tyr Arg Leu Gly Pro Ile Thr Asn Glu Val Thr Leu Thr
    1625                1630                1635

His Pro Gly Thr Lys Tyr Ile Ala Thr Cys Met Gln Ala Asp Leu
    1640                1645                1650

Glu Val Met Thr Ser Thr Trp Val Leu Ala Gly Gly Val Leu Ala
    1655                1660                1665

Ala Val Ala Ala Tyr Cys Leu Ala Thr Gly Cys Val Ser Ile Ile
    1670                1675                1680

Gly Arg Leu His Val Asn Gln Arg Val Val Val Ala Pro Asp Lys
    1685                1690                1695

Glu Val Leu Tyr Glu Ala Phe Asp Glu Met Glu Glu Cys Ala Ser
    1700                1705                1710

Arg Ala Ala Leu Ile Glu Glu Gly Gln Arg Ile Ala Glu Met Leu
    1715                1720                1725

Lys Ser Lys Ile Gln Gly Leu Leu Gln Gln Ala Ser Lys Gln Ala
    1730                1735                1740

Gln Asp Ile Gln Pro Ala Met Gln Ala Ser Trp Pro Lys Val Glu
    1745                1750                1755

Gln Phe Trp Ala Arg His Met Trp Asn Phe Ile Ser Gly Ile Gln
    1760                1765                1770

Tyr Leu Ala Gly Leu Ser Thr Leu Pro Gly Asn Pro Ala Val Ala
    1775                1780                1785

Ser Met Met Ala Phe Ser Ala Ala Leu Thr Ser Pro Leu Ser Thr
    1790                1795                1800

Ser Thr Thr Ile Leu Leu Asn Ile Met Gly Gly Trp Leu Ala Ser
    1805                1810                1815

Gln Ile Ala Pro Pro Ala Gly Ala Thr Gly Phe Val Val Ser Gly
    1820                1825                1830

Leu Val Gly Ala Ala Val Gly Ser Ile Gly Leu Gly Lys Val Leu
    1835                1840                1845

Val Asp Ile Leu Ala Gly Tyr Gly Ala Gly Ile Ser Gly Ala Leu
    1850                1855                1860
```

-continued

```
Val Ala Phe Lys Ile Met Ser Gly Glu Lys Pro Ser Met Glu Asp
        1865                1870                1875

Val Ile Asn Leu Leu Pro Gly Ile Leu Ser Pro Gly Ala Leu Val
        1880                1885                1890

Val Gly Val Ile Cys Ala Ala Ile Leu Arg Arg His Val Gly Pro
        1895                1900                1905

Gly Glu Gly Ala Val Gln Trp Met Asn Arg Leu Ile Ala Phe Ala
        1910                1915                1920

Ser Arg Gly Asn His Val Ala Pro Thr His Tyr Val Thr Glu Ser
        1925                1930                1935

Asp Ala Ser Gln Arg Val Thr Gln Leu Leu Gly Ser Leu Thr Ile
        1940                1945                1950

Thr Ser Leu Leu Arg Arg Leu His Asn Trp Ile Thr Glu Asp Cys
        1955                1960                1965

Pro Ile Pro Cys Ser Gly Ser Trp Leu Arg Asp Val Trp Asp Trp
        1970                1975                1980

Val Cys Thr Ile Leu Ile Asp Phe Lys Asn Trp Leu Thr Ser Lys
        1985                1990                1995

Leu Phe Pro Lys Leu Pro Gly Leu Pro Phe Ile Ser Cys Gln Lys
        2000                2005                2010

Gly Tyr Lys Gly Val Trp Ala Gly Thr Gly Ile Met Thr Thr Arg
        2015                2020                2025

Cys Pro Cys Gly Ala Asn Ile Ser Gly Asn Val Arg Leu Gly Ser
        2030                2035                2040

Met Arg Ile Thr Gly Pro Lys Thr Cys Met Asn Thr Trp Gln Gly
        2045                2050                2055

Thr Phe Pro Ile Asn Cys Tyr Thr Glu Gly Gln Cys Ala Pro Lys
        2060                2065                2070

Pro Pro Thr Asn Tyr Lys Thr Ala Ile Trp Arg Val Ala Ala Ser
        2075                2080                2085

Glu Tyr Ala Glu Val Thr Gln His Gly Ser Tyr Ser Tyr Val Thr
        2090                2095                2100

Gly Leu Thr Thr Asp Asn Leu Lys Ile Pro Cys Gln Leu Pro Ser
        2105                2110                2115

Pro Glu Phe Phe Ser Trp Val Asp Gly Val Gln Ile His Arg Phe
        2120                2125                2130

Ala Pro Thr Pro Lys Pro Phe Phe Arg Asp Glu Val Ser Phe Cys
        2135                2140                2145

Val Gly Leu Asn Ser Tyr Ala Val Gly Ser Gln Leu Pro Cys Glu
        2150                2155                2160

Pro Glu Pro Asp Ala Asp Val Leu Arg Ser Met Leu Thr Asp Pro
        2165                2170                2175

Pro His Ile Thr Ala Glu Thr Ala Ala Arg Arg Leu Ala Arg Gly
        2180                2185                2190

Ser Pro Pro Ser Glu Ala Ser Ser Ser Val Ser Gln Leu Ser Ala
        2195                2200                2205

Pro Ser Leu Arg Ala Thr Cys Thr Thr His Ser Asn Thr Tyr Asp
        2210                2215                2220

Val Asp Met Val Asp Ala Asn Leu Leu Met Glu Gly Gly Val Ala
        2225                2230                2235

Gln Thr Glu Pro Glu Ser Arg Val Pro Val Leu Asp Phe Leu Glu
        2240                2245                2250

Pro Met Ala Glu Glu Glu Ser Asp Leu Glu Pro Ser Ile Pro Ser
        2255                2260                2265
```

```
Glu Cys Met Leu Pro Arg Ser Gly Phe Pro Arg Ala Leu Pro Ala
    2270                2275                2280

Trp Ala Arg Pro Asp Tyr Asn Pro Pro Leu Val Glu Ser Trp Arg
    2285                2290                2295

Arg Pro Asp Tyr Gln Pro Pro Thr Val Ala Gly Cys Ala Leu Pro
    2300                2305                2310

Pro Pro Lys Lys Ala Pro Thr Pro Pro Arg Arg Arg Arg Thr
    2315                2320                2325

Val Gly Leu Ser Glu Ser Thr Ile Ser Glu Ala Leu Gln Gln Leu
    2330                2335                2340

Ala Ile Lys Thr Phe Gly Gln Pro Pro Ser Ser Gly Asp Ala Gly
    2345                2350                2355

Ser Ser Thr Gly Ala Gly Ala Ala Glu Ser Gly Gly Pro Thr Ser
    2360                2365                2370

Pro Gly Glu Pro Ala Pro Ser Glu Thr Gly Ser Ala Ser Ser Met
    2375                2380                2385

Pro Pro Leu Glu Gly Glu Pro Gly Asp Pro Asp Leu Glu Ser Asp
    2390                2395                2400

Gln Val Glu Leu Gln Pro Pro Gln Gly Gly Val Ala Pro
    2405                2410                2415

Gly Ser Gly Ser Gly Ser Trp Ser Thr Cys Ser Glu Glu Asp Asp
    2420                2425                2430

Thr Thr Leu Cys Cys Ser Met Ser Tyr Ser Trp Thr Gly Ala Leu
    2435                2440                2445

Ile Thr Pro Cys Ser Pro Glu Glu Lys Leu Pro Ile Asn Pro
    2450                2455                2460

Leu Ser Asn Ser Leu Leu Arg Tyr His Asn Lys Val Tyr Cys Thr
    2465                2470                2475

Thr Ser Lys Ser Ala Ser Gln Arg Ala Lys Lys Val Thr Phe Asp
    2480                2485                2490

Arg Thr Gln Val Leu Asp Ala His Tyr Asp Ser Val Leu Lys Asp
    2495                2500                2505

Ile Lys Leu Ala Ala Ser Lys Val Ser Ala Arg Leu Leu Thr Leu
    2510                2515                2520

Glu Glu Ala Cys Gln Leu Thr Pro Pro His Ser Ala Arg Ser Lys
    2525                2530                2535

Tyr Gly Phe Gly Ala Lys Glu Val Arg Ser Leu Ser Gly Arg Ala
    2540                2545                2550

Val Asn His Ile Lys Ser Val Trp Lys Asp Leu Leu Glu Asp Pro
    2555                2560                2565

Gln Thr Pro Ile Pro Thr Thr Ile Met Ala Lys Asn Glu Val Phe
    2570                2575                2580

Cys Val Asp Pro Ala Lys Gly Gly Lys Lys Pro Ala Arg Leu Ile
    2585                2590                2595

Val Tyr Pro Asp Leu Gly Val Arg Val Cys Glu Lys Met Ala Leu
    2600                2605                2610

Tyr Asp Ile Thr Gln Lys Leu Pro Gln Ala Val Met Gly Ala Ser
    2615                2620                2625

Tyr Gly Phe Gln Tyr Ser Pro Ala Gln Arg Val Glu Tyr Leu Leu
    2630                2635                2640

Lys Ala Trp Ala Glu Lys Lys Asp Pro Met Gly Phe Ser Tyr Asp
    2645                2650                2655

Thr Arg Cys Phe Asp Ser Thr Val Thr Glu Arg Asp Ile Arg Thr
```

```
                        2660                2665                2670
Glu Glu Ser Ile Tyr Gln Ala Cys Ser Leu Pro Glu Glu Ala Arg
    2675                2680                2685
Thr Ala Ile His Ser Leu Thr Glu Arg Leu Tyr Val Gly Gly Pro
    2690                2695                2700
Met Phe Asn Ser Lys Gly Gln Thr Cys Gly Tyr Arg Arg Cys Arg
    2705                2710                2715
Ala Ser Gly Val Leu Thr Thr Ser Met Gly Asn Thr Ile Thr Cys
    2720                2725                2730
Tyr Val Lys Ala Leu Ala Ala Cys Lys Ala Ala Gly Ile Val Ala
    2735                2740                2745
Pro Thr Met Leu Val Cys Gly Asp Asp Leu Val Val Ile Ser Glu
    2750                2755                2760
Ser Gln Gly Thr Glu Glu Asp Glu Arg Asn Leu Arg Ala Phe Thr
    2765                2770                2775
Glu Ala Met Thr Arg Tyr Ser Ala Pro Pro Gly Asp Pro Pro Arg
    2780                2785                2790
Pro Glu Tyr Asp Leu Glu Leu Ile Thr Ser Cys Ser Ser Asn Val
    2795                2800                2805
Ser Val Ala Leu Gly Pro Arg Gly Arg Arg Tyr Tyr Leu Thr
    2810                2815                2820
Arg Asp Pro Thr Thr Pro Leu Ala Arg Ala Ala Trp Glu Thr Val
    2825                2830                2835
Arg His Ser Pro Ile Asn Ser Trp Leu Gly Asn Ile Ile Gln Tyr
    2840                2845                2850
Ala Pro Thr Ile Trp Val Arg Met Val Leu Met Thr His Phe Phe
    2855                2860                2865
Ser Ile Leu Met Val Gln Asp Thr Leu Asp Gln Asn Leu Asn Phe
    2870                2875                2880
Glu Met Tyr Gly Ser Val Tyr Ser Val Asn Pro Leu Asp Leu Pro
    2885                2890                2895
Ala Ile Ile Glu Arg Leu His Gly Leu Asp Ala Phe Ser Met His
    2900                2905                2910
Thr Tyr Ser His His Glu Leu Thr Arg Val Ala Ser Ala Leu Arg
    2915                2920                2925
Lys Leu Gly Ala Pro Pro Leu Arg Val Trp Lys Ser Arg Ala Arg
    2930                2935                2940
Ala Val Arg Ala Ser Leu Ile Ser Arg Gly Gly Lys Ala Ala Val
    2945                2950                2955
Cys Gly Arg Tyr Leu Phe Asn Trp Ala Val Lys Thr Lys Leu Lys
    2960                2965                2970
Leu Thr Pro Leu Pro Glu Ala Arg Leu Leu Asp Leu Ser Ser Trp
    2975                2980                2985
Phe Thr Val Gly Ala Gly Gly Asp Ile Phe His Ser Val Ser
    2990                2995                3000
Arg Ala Arg Pro Arg Ser Leu Leu Phe Gly Leu Leu Leu Leu Phe
    3005                3010                3015
Val Gly Val Gly Leu Phe Leu Leu Pro Ala Arg
    3020                3025

<210> SEQ ID NO 26
<211> LENGTH: 3029
<212> TYPE: PRT
<213> ORGANISM: Hepatitis C virus
```

<400> SEQUENCE: 26

```
Met Ser Thr Asn Pro Lys Pro Gln Arg Lys Thr Lys Arg Asn Thr Asn
1               5                   10                  15

Arg Arg Pro Met Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
50                  55                  60

Ile Pro Lys Ala Arg Arg Pro Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Val
        130                 135                 140

Gly Gly Val Ala Arg Ala Leu Ala His Gly Val Arg Ala Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Val
            180                 185                 190

Asn Tyr Arg Asn Val Ser Gly Ile Tyr His Val Thr Asn Asp Cys Pro
            195                 200                 205

Asn Ser Ser Ile Val Tyr Glu Thr Asp His His Ile Leu His Leu Pro
210                 215                 220

Gly Cys Val Pro Cys Val Arg Glu Gly Asn Gln Ser Arg Cys Trp Val
225                 230                 235                 240

Ala Leu Thr Pro Thr Val Ala Ala Pro Tyr Ile Gly Ala Pro Leu Glu
                245                 250                 255

Ser Leu Arg Ser His Val Asp Leu Met Val Gly Ala Ala Thr Val Cys
            260                 265                 270

Ser Gly Leu Tyr Ile Gly Asp Leu Cys Gly Gly Leu Phe Leu Val Gly
        275                 280                 285

Gln Met Phe Ser Phe Arg Pro Arg Arg His Trp Thr Thr Gln Asp Cys
290                 295                 300

Asn Cys Ser Ile Tyr Thr Gly His Ile Thr Gly His Arg Met Ala Trp
305                 310                 315                 320

Asp Met Met Met Asn Trp Ser Pro Thr Thr Thr Leu Val Leu Ala Gln
                325                 330                 335

Val Met Arg Ile Pro Thr Thr Leu Val Asp Leu Leu Ser Gly Gly His
            340                 345                 350

Trp Gly Val Leu Val Gly Val Ala Tyr Phe Ser Met Gln Ala Asn Trp
        355                 360                 365

Ala Lys Val Ile Leu Val Leu Phe Leu Phe Ala Gly Val Asp Ala Glu
    370                 375                 380

Thr His Val Ser Gly Ala Ala Val Gly Arg Ser Thr Ala Gly Leu Ala
385                 390                 395                 400

Asn Leu Phe Ser Ser Gly Ser Lys Gln Asn Leu Gln Leu Ile Asn Ser
                405                 410                 415
```

-continued

```
Asn Gly Ser Trp His Ile Asn Arg Thr Ala Leu Asn Cys Asn Asp Ser
            420                 425                 430

Leu Asn Thr Gly Phe Leu Ala Ser Leu Phe Tyr Thr His Lys Phe Asn
            435                 440                 445

Ser Ser Gly Cys Ser Glu Arg Leu Ala Cys Cys Lys Ser Leu Asp Ser
450                 455                 460

Tyr Gly Gln Gly Trp Gly Pro Leu Gly Val Ala Asn Ile Ser Gly Ser
465                 470                 475                 480

Ser Asp Asp Arg Pro Tyr Cys Trp His Tyr Ala Pro Arg Pro Cys Gly
                485                 490                 495

Ile Val Pro Ala Ser Ser Val Cys Gly Pro Val Tyr Cys Phe Thr Pro
            500                 505                 510

Ser Pro Val Val Val Gly Thr Thr Asp His Val Gly Val Pro Thr Tyr
            515                 520                 525

Thr Trp Gly Glu Asn Glu Thr Asp Val Phe Leu Leu Asn Ser Thr Arg
        530                 535                 540

Pro Pro His Gly Ala Trp Phe Gly Cys Val Trp Met Asn Ser Thr Gly
545                 550                 555                 560

Phe Thr Lys Thr Cys Gly Ala Pro Pro Cys Glu Val Asn Thr Asn Asn
                565                 570                 575

Gly Thr Trp His Cys Pro Thr Asp Cys Phe Arg Lys His Pro Glu Thr
            580                 585                 590

Thr Tyr Ala Lys Cys Gly Ser Gly Pro Trp Ile Thr Pro Arg Cys Leu
        595                 600                 605

Ile Asp Tyr Pro Tyr Arg Leu Trp His Phe Pro Cys Thr Ala Asn Phe
610                 615                 620

Ser Val Phe Asn Ile Arg Thr Phe Val Gly Gly Ile Glu His Arg Met
625                 630                 635                 640

Gln Ala Ala Cys Asn Trp Thr Arg Gly Glu Val Cys Gly Leu Glu His
                645                 650                 655

Arg Asp Arg Val Glu Leu Ser Pro Leu Leu Leu Thr Thr Thr Ala Trp
            660                 665                 670

Gln Ile Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
690                 695                 700

Val Gly Ser Ala Val Val Ser Trp Ala Leu Lys Trp Glu Tyr Val Val
705                 710                 715                 720

Leu Ala Phe Leu Leu Leu Ala Asp Ala Arg Val Ser Ala Cys Leu Trp
                725                 730                 735

Met Met Phe Met Val Ser Gln Val Glu Ala Ala Leu Ser Asn Leu Ile
            740                 745                 750

Asn Ile Asn Ala Ala Ser Ala Ala Gly Ala Gln Gly Phe Trp Tyr Ala
        755                 760                 765

Ile Leu Phe Ile Cys Ile Val Trp His Val Lys Gly Arg Phe Pro Ala
770                 775                 780

Ala Ala Ala Tyr Ala Ala Cys Gly Leu Trp Pro Leu Phe Leu Leu Leu
785                 790                 795                 800

Leu Met Leu Pro Glu Arg Ala Tyr Ala Tyr Asp Gln Glu Val Ala Gly
                805                 810                 815

Ser Leu Gly Gly Ala Ile Val Val Met Leu Ala Ile Leu Thr Leu Ser
            820                 825                 830

Pro His Tyr Lys Leu Trp Leu Ala Arg Gly Leu Trp Trp Ile Gln Tyr
        835                 840                 845
```

```
Phe Ile Ala Arg Thr Glu Ala Val Leu His Val Tyr Ile Pro Ser Phe
    850                 855                 860

Asn Val Arg Gly Pro Arg Asp Ser Val Ile Val Leu Ala Val Leu Val
865                 870                 875                 880

Cys Pro His Leu Val Phe Asp Ile Thr Lys Tyr Leu Leu Ala Ile Leu
                885                 890                 895

Gly Pro Leu His Ile Leu Gln Ala Ser Leu Leu Arg Ile Pro Tyr Phe
            900                 905                 910

Val Arg Ala Gln Ala Leu Val Lys Ile Cys Ser Leu Leu Arg Gly Val
        915                 920                 925

Val Tyr Gly Lys Tyr Phe Gln Met Val Val Leu Lys Ala Gly Ala Leu
    930                 935                 940

Thr Gly Thr Tyr Ile Tyr Asp His Leu Thr Pro Met Ser Asp Trp Ala
945                 950                 955                 960

Ala Thr Gly Leu Arg Asp Leu Ala Val Ala Leu Glu Pro Val Val Phe
                965                 970                 975

Ser Pro Met Glu Lys Lys Val Ile Val Trp Gly Ala Asp Thr Ala Ala
            980                 985                 990

Cys Gly Asp Ile Ile Arg Gly Leu  Pro Val Ser Ala Arg  Leu Gly Asn
                995                 1000                1005

Glu Ile  Leu Leu Gly Pro Ala  Asp Thr Glu Thr Ser  Lys Gly Trp
    1010                1015                1020

Arg Leu  Leu Ala Pro Ile Thr  Ala Tyr Ala Gln Gln  Thr Arg Gly
    1025                1030                1035

Leu Leu  Gly Ala Ile Val Val  Ser Met Thr Gly Arg  Asp Arg Thr
    1040                1045                1050

Glu Gln  Ala Gly Glu Val Gln  Ile Leu Ser Thr Val  Ser Gln Ser
    1055                1060                1065

Phe Leu  Gly Thr Thr Ile Ser  Gly Val Leu Trp Thr  Val Tyr His
    1070                1075                1080

Gly Ala  Gly Asn Lys Thr Leu  Ala Gly Leu Arg Gly  Pro Val Thr
    1085                1090                1095

Gln Met  Tyr Ser Ser Ala Glu  Gly Asp Leu Val Gly  Trp Pro Ser
    1100                1105                1110

Pro Pro  Gly Thr Lys Ser Leu  Glu Pro Cys Lys Cys  Gly Ala Val
    1115                1120                1125

Asp Leu  Tyr Leu Val Thr Arg  Asn Ala Asp Val Ile  Pro Ala Arg
    1130                1135                1140

Arg Arg  Gly Asp Lys Arg Gly  Ala Leu Leu Ser Pro  Arg Pro Ile
    1145                1150                1155

Ser Thr  Leu Lys Gly Ser Ser  Gly Gly Pro Val Leu  Cys Pro Arg
    1160                1165                1170

Gly His  Val Val Gly Leu Phe  Arg Ala Ala Val Cys  Ser Arg Gly
    1175                1180                1185

Val Ala  Lys Ser Ile Asp Phe  Ile Pro Val Glu Thr  Leu Asp Val
    1190                1195                1200

Val Thr  Arg Ser Pro Thr Phe  Ser Asp Asn Ser Thr  Pro Pro Ala
    1205                1210                1215

Val Pro  Gln Thr Tyr Gln Val  Gly Tyr Leu His Ala  Pro Thr Gly
    1220                1225                1230

Ser Gly  Lys Ser Thr Lys Val  Pro Val Ala Tyr Ala  Ala Gln Gly
    1235                1240                1245

Tyr Lys  Val Leu Val Leu Asn  Pro Ser Val Ala Ala  Thr Leu Gly
```

-continued

```
            1250                1255                1260
Phe Gly Ala Tyr Leu Ser Lys Ala His Gly Ile Asn Pro Asn Ile
        1265                1270                1275
Arg Thr Gly Val Arg Thr Val Met Thr Gly Glu Ala Ile Thr Tyr
        1280                1285                1290
Ser Thr Tyr Gly Lys Phe Leu Ala Asp Gly Gly Cys Ala Ser Gly
        1295                1300                1305
Ala Tyr Asp Ile Ile Ile Cys Asp Glu Cys His Ala Val Asp Ala
        1310                1315                1320
Thr Ser Ile Leu Gly Ile Gly Thr Val Leu Asp Gln Ala Glu Thr
        1325                1330                1335
Ala Gly Val Arg Leu Thr Val Leu Ala Thr Ala Thr Pro Pro Gly
        1340                1345                1350
Ser Val Thr Thr Pro His Pro Asp Ile Glu Glu Val Gly Leu Gly
        1355                1360                1365
Arg Glu Gly Glu Ile Pro Phe Tyr Gly Arg Ala Ile Pro Leu Ser
        1370                1375                1380
Cys Ile Lys Gly Gly Arg His Leu Ile Phe Cys His Ser Lys Lys
        1385                1390                1395
Lys Cys Asp Glu Leu Ala Ala Ala Leu Arg Gly Met Gly Leu Asn
        1400                1405                1410
Ala Val Ala Tyr Tyr Arg Gly Leu Asp Val Ser Ile Ile Pro Ala
        1415                1420                1425
Gln Gly Asp Val Val Val Ala Thr Asp Ala Leu Met Thr Gly
        1430                1435                1440
Tyr Thr Gly Asp Phe Asp Ser Val Ile Asp Cys Asn Val Ala Val
        1445                1450                1455
Thr Gln Ala Val Asp Phe Ser Leu Asp Pro Thr Phe Thr Ile Thr
        1460                1465                1470
Thr Gln Thr Val Pro Gln Asp Ala Val Ser Arg Ser Gln Arg Arg
        1475                1480                1485
Gly Arg Thr Gly Arg Gly Arg Gln Gly Thr Tyr Arg Tyr Val Ser
        1490                1495                1500
Thr Gly Glu Arg Ala Ser Gly Met Phe Asp Ser Val Val Leu Cys
        1505                1510                1515
Glu Cys Tyr Asp Ala Gly Ala Ala Trp Tyr Asp Leu Thr Pro Ala
        1520                1525                1530
Glu Thr Thr Val Arg Leu Arg Ala Tyr Phe Asn Thr Pro Gly Leu
        1535                1540                1545
Pro Val Cys Gln Asp His Leu Glu Phe Trp Glu Ala Val Phe Thr
        1550                1555                1560
Gly Leu Thr His Ile Asp Ala His Phe Leu Ser Gln Thr Lys Gln
        1565                1570                1575
Ala Gly Glu Asn Phe Ala Tyr Leu Val Ala Tyr Gln Ala Thr Val
        1580                1585                1590
Cys Ala Arg Ala Lys Ala Pro Pro Pro Ser Trp Asp Ala Met Trp
        1595                1600                1605
Lys Cys Leu Ala Arg Leu Lys Pro Thr Leu Ala Gly Pro Thr Pro
        1610                1615                1620
Leu Leu Tyr Arg Leu Gly Pro Ile Thr Asn Glu Val Thr Leu Thr
        1625                1630                1635
His Pro Gly Thr Lys Tyr Ile Ala Thr Cys Met Gln Ala Asp Leu
        1640                1645                1650
```

```
Glu Val Met Thr Ser Thr Trp Val Leu Ala Gly Gly Val Leu Ala
1655                1660                1665

Ala Val Ala Ala Tyr Cys Leu Ala Thr Gly Cys Val Ser Ile Ile
1670                1675                1680

Gly Arg Leu His Val Asn Gln Arg Val Val Ala Pro Asp Lys
1685                1690                1695

Glu Val Leu Tyr Glu Ala Phe Asp Glu Met Glu Cys Ala Ser
1700                1705                1710

Arg Ala Ala Leu Ile Glu Glu Gly Gln Arg Ile Ala Glu Met Leu
1715                1720                1725

Lys Ser Lys Ile Gln Gly Leu Leu Gln Gln Ala Ser Lys Gln Ala
1730                1735                1740

Gln Asp Ile Gln Pro Ala Met Gln Ala Ser Trp Pro Lys Val Glu
1745                1750                1755

Gln Phe Trp Ala Arg His Met Trp Asn Phe Ile Ser Gly Ile Gln
1760                1765                1770

Tyr Leu Ala Gly Leu Ser Thr Leu Pro Gly Asn Pro Ala Val Ala
1775                1780                1785

Ser Met Met Ala Phe Ser Ala Ala Leu Thr Ser Pro Leu Ser Thr
1790                1795                1800

Ser Thr Thr Ile Leu Leu Asn Ile Met Gly Gly Trp Leu Ala Ser
1805                1810                1815

Gln Ile Ala Pro Pro Ala Gly Ala Thr Gly Phe Val Val Ser Gly
1820                1825                1830

Leu Val Gly Ala Ala Val Gly Ser Ile Gly Leu Gly Lys Val Leu
1835                1840                1845

Val Asp Ile Leu Ala Gly Tyr Gly Ala Gly Ile Ser Gly Ala Leu
1850                1855                1860

Val Ala Phe Lys Ile Met Ser Gly Glu Lys Pro Ser Met Glu Asp
1865                1870                1875

Val Ile Asn Leu Leu Pro Gly Ile Leu Ser Pro Gly Ala Leu Val
1880                1885                1890

Val Gly Val Ile Cys Ala Ala Ile Leu Arg Arg His Val Gly Pro
1895                1900                1905

Gly Glu Gly Ala Val Gln Trp Met Asn Arg Leu Ile Ala Phe Ala
1910                1915                1920

Ser Arg Gly Asn His Val Ala Pro Thr His Tyr Val Thr Glu Ser
1925                1930                1935

Asp Ala Ser Gln Arg Val Thr Gln Leu Leu Gly Ser Leu Thr Ile
1940                1945                1950

Thr Ser Leu Leu Arg Arg Leu His Asn Trp Ile Thr Glu Asp Cys
1955                1960                1965

Pro Ile Pro Cys Ser Gly Ser Trp Leu Arg Asp Val Trp Asp Trp
1970                1975                1980

Val Cys Thr Ile Leu Thr Asp Phe Lys Asn Trp Leu Thr Ser Lys
1985                1990                1995

Leu Phe Pro Lys Leu Pro Gly Leu Pro Phe Ile Ser Cys Gln Lys
2000                2005                2010

Gly Tyr Lys Gly Val Trp Ala Gly Thr Gly Ile Met Thr Thr Arg
2015                2020                2025

Cys Pro Cys Gly Ala Asn Ile Ser Gly Asn Val Arg Leu Gly Ser
2030                2035                2040

Met Arg Ile Thr Gly Pro Lys Thr Cys Met Asn Thr Trp Gln Gly
2045                2050                2055
```

-continued

```
Thr Phe Pro Ile Asn Cys Tyr Thr Glu Gly Gln Cys Ala Pro Lys
    2060              2065              2070
Pro Pro Thr Asn Tyr Lys Thr Ala Ile Trp Arg Val Ala Ala Ser
    2075              2080              2085
Glu Tyr Ala Glu Val Thr Gln His Gly Ser Tyr Ser Tyr Val Thr
    2090              2095              2100
Gly Leu Thr Thr Asp Asn Leu Lys Ile Pro Cys Gln Leu Pro Ser
    2105              2110              2115
Pro Glu Phe Phe Ser Trp Val Asp Gly Val Gln Ile His Arg Phe
    2120              2125              2130
Ala Pro Thr Pro Lys Pro Phe Phe Arg Asp Glu Val Ser Phe Cys
    2135              2140              2145
Val Gly Leu Asn Ser Tyr Ala Val Gly Ser Gln Leu Pro Cys Glu
    2150              2155              2160
Pro Glu Pro Asp Ala Asp Val Leu Arg Ser Met Leu Thr Asp Pro
    2165              2170              2175
Pro His Ile Thr Ala Glu Thr Ala Ala Arg Arg Leu Ala Arg Gly
    2180              2185              2190
Ser Pro Pro Ser Glu Ala Ser Ser Ser Val Ser Gln Leu Ser Ala
    2195              2200              2205
Pro Ser Leu Arg Ala Thr Cys Thr Thr His Ser Asn Thr Tyr Asp
    2210              2215              2220
Val Asp Met Val Asp Ala Asn Leu Leu Met Glu Gly Gly Val Ala
    2225              2230              2235
Gln Thr Glu Pro Glu Ser Arg Val Pro Val Leu Asp Phe Leu Glu
    2240              2245              2250
Pro Met Ala Glu Glu Ser Asp Leu Glu Pro Ser Ile Pro Ser
    2255              2260              2265
Glu Cys Met Leu Pro Arg Ser Gly Phe Pro Arg Ala Leu Pro Ala
    2270              2275              2280
Trp Ala Arg Pro Asp Tyr Asn Pro Pro Leu Val Glu Ser Trp Arg
    2285              2290              2295
Arg Pro Asp Tyr Gln Pro Pro Thr Val Ala Gly Cys Ala Leu Pro
    2300              2305              2310
Pro Pro Lys Lys Ala Pro Thr Pro Pro Pro Arg Arg Arg Arg Thr
    2315              2320              2325
Val Gly Leu Ser Glu Ser Thr Ile Ser Glu Ala Leu Gln Gln Leu
    2330              2335              2340
Ala Ile Lys Thr Phe Gly Gln Pro Pro Ser Ser Gly Asp Ala Gly
    2345              2350              2355
Ser Ser Thr Gly Ala Gly Ala Ala Glu Ser Gly Gly Pro Thr Ser
    2360              2365              2370
Pro Gly Glu Pro Ala Pro Ser Glu Thr Gly Ser Ala Ser Ser Met
    2375              2380              2385
Pro Pro Leu Glu Gly Glu Pro Gly Asp Pro Asp Leu Glu Ser Asp
    2390              2395              2400
Gln Val Glu Leu Gln Pro Pro Gln Gly Gly Gly Val Ala Pro
    2405              2410              2415
Gly Ser Gly Ser Gly Ser Trp Ser Thr Cys Ser Glu Glu Asp Asp
    2420              2425              2430
Thr Thr Val Cys Cys Ser Met Ser Tyr Ser Trp Thr Gly Ala Leu
    2435              2440              2445
Ile Thr Pro Cys Ser Pro Glu Glu Glu Lys Leu Pro Ile Asn Pro
```

-continued

```
              2450                2455                2460

Leu Ser Asn Ser Leu Leu Arg Tyr His Asn Lys Val Tyr Cys Thr
    2465                2470                2475

Thr Ser Lys Ser Ala Ser Gln Arg Ala Lys Lys Val Thr Phe Asp
    2480                2485                2490

Arg Thr Gln Val Leu Asp Ala His Tyr Asp Ser Val Leu Lys Asp
    2495                2500                2505

Ile Lys Leu Ala Ala Ser Lys Val Ser Ala Arg Leu Leu Thr Leu
    2510                2515                2520

Glu Glu Ala Cys Gln Leu Thr Pro Pro His Ser Ala Arg Ser Lys
    2525                2530                2535

Tyr Gly Phe Gly Ala Lys Glu Val Arg Ser Leu Ser Gly Arg Ala
    2540                2545                2550

Val Asn His Ile Lys Ser Val Trp Lys Asp Leu Leu Glu Asp Pro
    2555                2560                2565

Gln Thr Pro Ile Pro Thr Thr Ile Met Ala Lys Asn Glu Val Phe
    2570                2575                2580

Cys Val Asp Pro Ala Lys Gly Gly Lys Lys Pro Ala Arg Leu Ile
    2585                2590                2595

Val Tyr Pro Asp Leu Gly Val Arg Val Cys Glu Lys Met Ala Leu
    2600                2605                2610

Tyr Asp Ile Thr Gln Lys Leu Pro Gln Ala Val Met Gly Ala Ser
    2615                2620                2625

Tyr Gly Phe Gln Tyr Ser Pro Ala Gln Arg Val Glu Tyr Leu Leu
    2630                2635                2640

Lys Ala Trp Ala Glu Lys Lys Asp Pro Met Gly Phe Ser Tyr Asp
    2645                2650                2655

Thr Arg Cys Phe Asp Ser Thr Val Thr Glu Arg Asp Ile Arg Thr
    2660                2665                2670

Glu Glu Ser Ile Tyr Gln Ala Cys Ser Leu Pro Glu Glu Ala Arg
    2675                2680                2685

Thr Ala Ile His Ser Leu Thr Glu Arg Leu Tyr Val Gly Gly Pro
    2690                2695                2700

Met Phe Asn Ser Lys Gly Gln Thr Cys Gly Tyr Arg Arg Cys Arg
    2705                2710                2715

Ala Ser Gly Val Leu Thr Thr Ser Met Gly Asn Thr Ile Thr Cys
    2720                2725                2730

Tyr Val Lys Ala Leu Ala Ala Cys Lys Ala Ala Gly Ile Val Ala
    2735                2740                2745

Pro Thr Met Leu Val Cys Gly Asp Asp Leu Val Val Ile Ser Glu
    2750                2755                2760

Ser Gln Gly Thr Glu Glu Asp Glu Arg Asn Leu Arg Ala Phe Thr
    2765                2770                2775

Glu Ala Met Thr Arg Tyr Ser Ala Pro Pro Gly Asp Pro Pro Arg
    2780                2785                2790

Pro Glu Tyr Asp Leu Glu Leu Ile Thr Ser Cys Ser Ser Asn Val
    2795                2800                2805

Ser Val Ala Leu Gly Pro Arg Gly Arg Arg Tyr Tyr Leu Thr
    2810                2815                2820

Arg Asp Pro Thr Thr Pro Leu Ala Arg Ala Ala Trp Glu Thr Val
    2825                2830                2835

Arg His Ser Pro Ile Asn Ser Trp Leu Gly Asn Ile Ile Gln Tyr
    2840                2845                2850
```

```
Ala Pro Thr Ile Trp Val Arg Met Val Leu Met Thr His Phe Phe
    2855            2860                2865

Ser Ile Leu Met Val Gln Asp Thr Leu Asp Gln Asn Leu Asn Phe
    2870            2875                2880

Glu Met Tyr Gly Ser Val Tyr Ser Val Asn Pro Leu Asp Leu Pro
    2885            2890                2895

Ala Ile Ile Glu Arg Leu His Gly Leu Asp Ala Phe Ser Met His
    2900            2905                2910

Thr Tyr Ser His His Glu Leu Thr Arg Val Ala Ser Ala Leu Arg
    2915            2920                2925

Lys Leu Gly Ala Pro Pro Leu Arg Val Trp Lys Ser Arg Ala Arg
    2930            2935                2940

Ala Val Arg Ala Ser Leu Ile Ser Arg Gly Gly Lys Ala Ala Val
    2945            2950                2955

Cys Gly Arg Tyr Leu Phe Asn Trp Ala Val Lys Thr Lys Leu Lys
    2960            2965                2970

Leu Thr Pro Leu Pro Glu Ala Arg Leu Leu Asp Leu Ser Ser Trp
    2975            2980                2985

Phe Thr Val Gly Ala Gly Gly Gly Asp Ile Phe His Ser Val Ser
    2990            2995                3000

Arg Ala Arg Pro Arg Ser Leu Leu Phe Gly Leu Leu Leu Leu Phe
    3005            3010                3015

Val Gly Val Gly Leu Phe Leu Leu Pro Ala Arg
    3020            3025

<210> SEQ ID NO 27
<211> LENGTH: 3029
<212> TYPE: PRT
<213> ORGANISM: Hepatitis C virus

<400> SEQUENCE: 27

Met Ser Thr Asn Pro Lys Pro Gln Arg Lys Thr Lys Arg Asn Thr Asn
1               5                   10                  15

Arg Arg Pro Met Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Val
            180                 185                 190
```

-continued

```
Asn Tyr Arg Asn Val Ser Gly Ile Tyr His Val Thr Asn Asp Cys Pro
            195                 200                 205

Asn Ser Ser Ile Val Tyr Glu Ala Asp His His Ile Leu His Leu Pro
        210                 215                 220

Gly Cys Val Pro Cys Val Arg Glu Gly Asn Gln Ser Arg Cys Trp Val
225                 230                 235                 240

Ala Leu Thr Pro Thr Val Ala Ala Pro Tyr Ile Gly Ala Pro Leu Glu
                245                 250                 255

Ser Leu Arg Ser His Val Asp Leu Met Val Gly Ala Ala Thr Val Cys
            260                 265                 270

Ser Gly Leu Tyr Ile Gly Asp Leu Cys Gly Leu Phe Leu Val Gly
        275                 280                 285

Gln Met Phe Ser Phe Arg Pro Arg His Trp Thr Thr Gln Asp Cys
290                 295                 300

Asn Cys Ser Ile Tyr Thr Gly His Ile Thr Gly His Arg Met Ala Trp
305                 310                 315                 320

Asp Met Met Met Asn Trp Ser Pro Thr Thr Leu Val Leu Ala Gln
                325                 330                 335

Val Met Arg Ile Pro Thr Thr Leu Val Asp Leu Leu Ser Gly Gly His
            340                 345                 350

Trp Gly Val Leu Val Gly Val Ala Tyr Phe Ser Met Gln Ala Asn Trp
        355                 360                 365

Ala Lys Val Ile Leu Val Leu Phe Leu Phe Ala Gly Val Asp Ala Glu
370                 375                 380

Thr His Val Ser Gly Ala Ala Val Gly Arg Ser Thr Ala Gly Leu Ala
385                 390                 395                 400

Asn Leu Phe Ser Ser Gly Ser Lys Gln Asn Leu Gln Leu Ile Asn Ser
                405                 410                 415

Asn Gly Ser Trp His Ile Asn Arg Thr Ala Leu Asn Cys Asn Asp Ser
            420                 425                 430

Leu Asn Thr Gly Phe Leu Ala Ser Leu Phe Tyr Thr His Lys Phe Asn
        435                 440                 445

Ser Ser Gly Cys Ser Glu Arg Leu Ala Cys Cys Lys Ser Leu Asp Ser
450                 455                 460

Tyr Gly Gln Gly Trp Gly Pro Leu Gly Val Ala Asn Ile Ser Gly Ser
465                 470                 475                 480

Ser Asp Asp Arg Pro Tyr Cys Trp His Tyr Ala Pro Arg Pro Cys Gly
                485                 490                 495

Ile Val Pro Ala Ser Ser Val Cys Gly Pro Val Tyr Cys Phe Thr Pro
            500                 505                 510

Ser Pro Val Val Gly Thr Thr Asp His Val Gly Val Pro Thr Tyr
        515                 520                 525

Thr Trp Gly Glu Asn Glu Thr Asp Val Phe Leu Leu Asn Ser Thr Arg
530                 535                 540

Pro Pro His Gly Ala Trp Phe Gly Cys Val Trp Met Asn Ser Thr Gly
545                 550                 555                 560

Phe Thr Lys Thr Cys Gly Ala Pro Pro Cys Glu Val Asn Thr Asn
                565                 570                 575

Gly Thr Trp His Cys Pro Thr Asp Cys Phe Arg Lys His Pro Glu Thr
            580                 585                 590

Thr Tyr Ala Lys Cys Gly Ser Gly Pro Trp Ile Thr Pro Arg Cys Leu
        595                 600                 605

Ile Asp Tyr Pro Tyr Arg Leu Trp His Phe Pro Cys Thr Ala Asn Phe
610                 615                 620
```

```
Ser Val Phe Asn Ile Arg Thr Phe Val Gly Gly Ile Glu His Arg Met
625                 630                 635                 640

Gln Ala Ala Cys Asn Trp Thr Arg Gly Glu Val Cys Gly Leu Glu His
            645                 650                 655

Arg Asp Arg Val Glu Leu Ser Pro Leu Leu Thr Thr Ala Trp
                660                 665                 670

Gln Ile Leu Pro Cys Ser Phe Thr Thr Leu Pro Ala Leu Ser Thr Gly
    675                 680                 685

Leu Ile His Leu His Gln Asn Ile Val Asp Val Gln Tyr Leu Tyr Gly
    690                 695                 700

Val Gly Ser Ala Val Val Ser Trp Ala Leu Lys Trp Glu Tyr Val Val
705                 710                 715                 720

Leu Ala Phe Leu Leu Leu Ala Asp Ala Arg Val Ser Ala Cys Leu Trp
                725                 730                 735

Met Met Phe Met Val Ser Gln Val Glu Ala Ala Leu Ser Asn Leu Ile
                740                 745                 750

Asn Ile Asn Ala Ala Ser Ala Ala Gly Ala Gln Gly Phe Trp Tyr Ala
            755                 760                 765

Ile Leu Phe Ile Cys Ile Val Trp His Val Lys Gly Arg Phe Pro Ala
770                 775                 780

Ala Ala Ala Tyr Ala Ala Cys Gly Leu Trp Pro Leu Phe Leu Leu Leu
785                 790                 795                 800

Leu Met Leu Pro Glu Arg Ala Tyr Ala Tyr Asp Gln Glu Val Ala Gly
                805                 810                 815

Ser Leu Gly Gly Ala Ile Val Val Met Leu Ala Ile Leu Thr Leu Ser
                820                 825                 830

Pro His Tyr Lys Leu Trp Leu Ala Arg Gly Leu Trp Trp Ile Gln Tyr
        835                 840                 845

Phe Ile Ala Arg Thr Glu Ala Val Leu His Val Tyr Ile Pro Ser Phe
850                 855                 860

Asn Val Arg Gly Pro Arg Asp Ser Val Ile Val Leu Ala Val Leu Val
865                 870                 875                 880

Cys Pro His Leu Val Phe Asp Ile Thr Lys Tyr Leu Leu Ala Ile Leu
                885                 890                 895

Gly Pro Leu His Ile Leu Gln Ala Ser Leu Leu Arg Ile Pro Tyr Phe
        900                 905                 910

Val Arg Ala Gln Ala Leu Val Lys Ile Cys Ser Leu Leu Arg Gly Val
        915                 920                 925

Val Tyr Gly Lys Tyr Phe Gln Met Val Val Leu Lys Ala Gly Ala Leu
930                 935                 940

Thr Gly Thr Tyr Ile Tyr Asp His Leu Thr Pro Met Ser Asp Trp Ala
945                 950                 955                 960

Ala Thr Gly Leu Arg Asp Leu Ala Val Ala Leu Glu Pro Val Val Phe
                965                 970                 975

Ser Pro Met Glu Lys Lys Val Ile Val Trp Gly Ala Asp Thr Ala Ala
            980                 985                 990

Cys Gly Asp Ile Ile Arg Gly Leu Pro Val Ser Ala Arg Leu Gly Asn
        995                 1000                1005

Glu Ile Leu Leu Gly Pro Ala Asp Thr Glu Thr Ser Lys Gly Trp
    1010                1015                1020

Arg Leu Leu Ala Pro Ile Ala Tyr Ala Gln Gln Thr Arg Gly
    1025                1030                1035

Leu Leu Gly Ala Ile Val Val Ser Met Thr Gly Arg Asp Arg Thr
```

-continued

```
              1040                1045                1050
Glu Gln Ala Gly Glu Val Gln Ile Leu Ser Thr Val Ser Gln Ser
    1055                1060                1065
Phe Leu Gly Thr Thr Ile Ser Gly Val Leu Trp Thr Val Tyr His
    1070                1075                1080
Gly Ala Gly Asn Lys Thr Leu Ala Gly Leu Arg Gly Pro Val Thr
    1085                1090                1095
Gln Met Tyr Ser Ser Ala Glu Gly Asp Leu Val Gly Trp Pro Ser
    1100                1105                1110
Pro Pro Gly Thr Lys Ser Leu Glu Pro Cys Lys Cys Gly Ala Val
    1115                1120                1125
Asp Leu Tyr Leu Val Thr Arg Asn Ala Asp Val Ile Pro Ala Arg
    1130                1135                1140
Arg Arg Gly Asp Lys Arg Gly Ala Leu Leu Ser Pro Arg Pro Ile
    1145                1150                1155
Ser Thr Leu Lys Gly Ser Ser Gly Gly Pro Val Leu Cys Pro Arg
    1160                1165                1170
Gly His Val Val Gly Leu Phe Arg Ala Ala Val Cys Ser Arg Gly
    1175                1180                1185
Val Ala Lys Ser Ile Asp Phe Ile Pro Val Glu Thr Leu Asp Val
    1190                1195                1200
Val Thr Arg Ser Pro Thr Phe Ser Asp Asn Ser Thr Pro Pro Ala
    1205                1210                1215
Val Pro Gln Thr Tyr Gln Val Gly Tyr Leu His Ala Pro Thr Gly
    1220                1225                1230
Ser Gly Lys Ser Thr Lys Val Pro Val Ala Tyr Ala Ala Gln Gly
    1235                1240                1245
Tyr Lys Val Leu Val Leu Asn Pro Ser Val Ala Ala Thr Leu Gly
    1250                1255                1260
Phe Gly Ala Tyr Leu Ser Lys Ala His Gly Ile Asn Pro Asn Ile
    1265                1270                1275
Arg Thr Gly Val Arg Thr Val Met Thr Gly Glu Ala Ile Thr Tyr
    1280                1285                1290
Ser Thr Tyr Gly Lys Phe Leu Ala Asp Gly Gly Cys Ala Ser Gly
    1295                1300                1305
Ala Tyr Asp Ile Ile Ile Cys Asp Glu Cys His Ala Val Asp Ala
    1310                1315                1320
Thr Ser Ile Leu Gly Ile Gly Thr Val Leu Asp Gln Ala Glu Thr
    1325                1330                1335
Ala Gly Val Arg Leu Thr Val Leu Ala Thr Ala Thr Pro Pro Gly
    1340                1345                1350
Ser Val Thr Thr Pro His Pro Asp Ile Glu Glu Val Gly Leu Gly
    1355                1360                1365
Arg Glu Gly Glu Ile Pro Phe Tyr Gly Arg Ala Ile Pro Leu Ser
    1370                1375                1380
Cys Ile Lys Gly Gly Arg His Leu Ile Phe Cys His Ser Lys Lys
    1385                1390                1395
Lys Cys Asp Glu Leu Ala Ala Ala Leu Arg Gly Met Gly Leu Asn
    1400                1405                1410
Ala Val Ala Tyr Tyr Arg Gly Leu Asp Val Ser Ile Ile Pro Ala
    1415                1420                1425
Gln Gly Asp Val Val Val Val Ala Thr Asp Ala Leu Met Thr Gly
    1430                1435                1440
```

```
Tyr Thr Gly Asp Phe Asp Ser Val Ile Asp Cys Asn Val Ala Val
1445                1450                1455

Thr Gln Ala Val Asp Phe Ser Leu Asp Pro Thr Phe Thr Ile Thr
1460                1465                1470

Thr Gln Thr Val Pro Gln Asp Ala Val Ser Arg Ser Gln Arg Arg
1475                1480                1485

Gly Arg Thr Gly Arg Gly Arg Gln Gly Thr Tyr Arg Tyr Val Ser
1490                1495                1500

Thr Gly Glu Arg Ala Ser Gly Met Phe Asp Ser Val Val Leu Cys
1505                1510                1515

Glu Cys Tyr Asp Ala Gly Ala Ala Trp Tyr Asp Leu Thr Pro Ala
1520                1525                1530

Glu Thr Thr Val Arg Leu Arg Ala Tyr Phe Asn Thr Pro Gly Leu
1535                1540                1545

Pro Val Cys Gln Asp His Leu Glu Phe Trp Glu Ala Val Phe Thr
1550                1555                1560

Gly Leu Thr His Ile Asp Ala His Phe Leu Ser Gln Thr Lys Gln
1565                1570                1575

Ala Gly Glu Asn Phe Ala Tyr Leu Val Ala Tyr Gln Ala Thr Val
1580                1585                1590

Cys Ala Arg Ala Lys Ala Pro Pro Pro Ser Trp Asp Ala Met Trp
1595                1600                1605

Lys Cys Leu Ala Arg Leu Lys Pro Thr Leu Ala Gly Pro Thr Pro
1610                1615                1620

Leu Leu Tyr Arg Leu Gly Pro Ile Thr Asn Glu Val Thr Leu Thr
1625                1630                1635

His Pro Gly Thr Lys Tyr Ile Ala Thr Cys Met Gln Ala Asp Leu
1640                1645                1650

Glu Val Met Thr Ser Thr Trp Val Leu Ala Gly Gly Val Leu Ala
1655                1660                1665

Ala Val Ala Ala Tyr Cys Leu Ala Thr Gly Cys Val Ser Ile Ile
1670                1675                1680

Gly Arg Leu His Val Asn Gln Arg Val Val Ala Pro Asp Lys
1685                1690                1695

Glu Val Leu Tyr Glu Ala Phe Asp Glu Met Glu Glu Cys Ala Ser
1700                1705                1710

Arg Ala Ala Leu Ile Glu Glu Gly Gln Arg Ile Ala Glu Met Leu
1715                1720                1725

Lys Ser Lys Ile Gln Gly Leu Leu Gln Gln Ala Ser Lys Gln Ala
1730                1735                1740

Gln Asp Ile Gln Pro Ala Met Gln Ala Ser Trp Pro Lys Val Glu
1745                1750                1755

Gln Phe Trp Ala Arg His Met Trp Asn Phe Ile Ser Gly Ile Gln
1760                1765                1770

Tyr Leu Ala Gly Leu Ser Thr Leu Pro Gly Asn Pro Ala Val Ala
1775                1780                1785

Ser Met Met Ala Phe Ser Ala Ala Leu Thr Ser Pro Leu Ser Thr
1790                1795                1800

Ser Thr Thr Ile Leu Leu Asn Ile Met Gly Gly Trp Leu Ala Ser
1805                1810                1815

Gln Ile Ala Pro Pro Ala Gly Ala Thr Gly Phe Val Val Ser Gly
1820                1825                1830

Leu Val Gly Ala Ala Val Gly Ser Ile Gly Leu Gly Lys Val Leu
1835                1840                1845
```

-continued

Val Asp Ile Leu Ala Gly Tyr Gly Ala Gly Ile Ser Gly Ala Leu
    1850            1855            1860

Val Ala Phe Lys Ile Met Ser Gly Glu Lys Pro Ser Met Glu Asp
    1865            1870            1875

Val Ile Asn Leu Leu Pro Gly Ile Leu Ser Pro Gly Ala Leu Val
    1880            1885            1890

Val Gly Val Ile Cys Ala Ala Ile Leu Arg Arg His Val Gly Pro
    1895            1900            1905

Gly Glu Gly Ala Val Gln Trp Met Asn Arg Leu Ile Ala Phe Ala
    1910            1915            1920

Ser Arg Gly Asn His Val Ala Pro Thr His Tyr Val Thr Glu Ser
    1925            1930            1935

Asp Ala Ser Gln Arg Val Thr Gln Leu Leu Gly Ser Leu Thr Ile
    1940            1945            1950

Thr Ser Leu Leu Arg Arg Leu His Asn Trp Ile Thr Glu Asp Cys
    1955            1960            1965

Pro Ile Pro Cys Ser Gly Ser Trp Leu Arg Asp Val Trp Asp Trp
    1970            1975            1980

Val Cys Thr Ile Leu Thr Asp Phe Lys Asn Trp Leu Thr Ser Lys
    1985            1990            1995

Leu Phe Pro Lys Leu Pro Gly Leu Pro Phe Ile Ser Cys Gln Lys
    2000            2005            2010

Gly Tyr Lys Gly Val Trp Ala Gly Thr Gly Ile Met Thr Thr Arg
    2015            2020            2025

Cys Pro Cys Gly Ala Asn Ile Ser Gly Asn Val Arg Leu Gly Ser
    2030            2035            2040

Met Arg Ile Thr Gly Pro Lys Thr Cys Met Asn Thr Trp Gln Gly
    2045            2050            2055

Thr Phe Pro Ile Asn Cys Tyr Thr Glu Gly Gln Cys Ala Pro Lys
    2060            2065            2070

Pro Pro Thr Asn Tyr Lys Thr Ala Ile Trp Arg Val Ala Ala Ser
    2075            2080            2085

Glu Tyr Ala Glu Val Thr Gln His Gly Ser Tyr Ser Tyr Val Thr
    2090            2095            2100

Gly Leu Thr Thr Asp Asn Leu Lys Ile Pro Cys Gln Leu Pro Ser
    2105            2110            2115

Pro Glu Phe Phe Ser Trp Val Asp Gly Val Gln Ile His Arg Phe
    2120            2125            2130

Ala Pro Thr Pro Lys Pro Phe Phe Arg Asp Glu Val Ser Phe Cys
    2135            2140            2145

Val Gly Leu Asn Ser Tyr Ala Val Gly Ser Gln Leu Pro Cys Glu
    2150            2155            2160

Pro Glu Pro Asp Ala Asp Val Leu Arg Ser Met Leu Thr Asp Pro
    2165            2170            2175

Pro His Ile Thr Ala Glu Thr Ala Ala Arg Arg Leu Ala Arg Gly
    2180            2185            2190

Ser Pro Pro Ser Glu Ala Ser Ser Ser Val Ser Gln Leu Ser Ala
    2195            2200            2205

Pro Ser Leu Arg Ala Thr Cys Thr Thr His Ser Asn Thr Tyr Asp
    2210            2215            2220

Val Asp Met Val Asp Ala Asn Leu Leu Met Glu Gly Gly Val Ala
    2225            2230            2235

Gln Thr Glu Pro Glu Ser Arg Val Pro Val Leu Asp Phe Leu Glu

-continued

```
                2240                2245                2250

Pro Met Ala Glu Glu Ser Asp Leu Glu Pro Ser Ile Pro Ser
    2255                2260                2265

Glu Arg Met Leu Pro Arg Ser Gly Phe Pro Arg Ala Leu Pro Ala
    2270                2275                2280

Trp Ala Arg Pro Asp Tyr Asn Pro Pro Leu Val Glu Ser Trp Arg
    2285                2290                2295

Arg Pro Asp Tyr Gln Pro Pro Thr Val Ala Gly Cys Ala Leu Pro
    2300                2305                2310

Pro Pro Lys Lys Ala Pro Thr Pro Pro Arg Arg Arg Arg Thr
    2315                2320                2325

Val Gly Leu Ser Glu Ser Thr Ile Ser Glu Ala Leu Gln Gln Leu
    2330                2335                2340

Ala Ile Lys Thr Phe Gly Gln Pro Pro Ser Ser Gly Asp Ala Gly
    2345                2350                2355

Ser Ser Thr Gly Ala Gly Ala Ala Glu Ser Gly Gly Pro Thr Ser
    2360                2365                2370

Pro Gly Glu Pro Ala Pro Ser Glu Thr Gly Ser Ala Ser Ser Met
    2375                2380                2385

Pro Pro Leu Glu Gly Glu Pro Gly Asp Pro Asp Leu Glu Ser Asp
    2390                2395                2400

Gln Val Glu Leu Gln Pro Pro Pro Gln Gly Gly Gly Val Ala Pro
    2405                2410                2415

Gly Ser Gly Ser Gly Ser Trp Ser Thr Cys Ser Glu Glu Asp Asp
    2420                2425                2430

Thr Thr Val Cys Cys Ser Met Ser Tyr Ser Trp Thr Gly Ala Leu
    2435                2440                2445

Ile Thr Pro Cys Ser Pro Glu Glu Lys Leu Pro Ile Asn Pro
    2450                2455                2460

Leu Ser Asn Ser Leu Leu Arg Tyr His Asn Lys Val Tyr Cys Thr
    2465                2470                2475

Thr Ser Lys Ser Ala Ser Gln Arg Ala Lys Lys Val Thr Phe Asp
    2480                2485                2490

Arg Thr Gln Val Leu Asp Ala His Tyr Asp Ser Val Leu Lys Asp
    2495                2500                2505

Ile Lys Leu Ala Ala Ser Lys Val Ser Ala Arg Leu Leu Thr Leu
    2510                2515                2520

Glu Glu Ala Cys Gln Leu Thr Pro Pro His Ser Ala Arg Ser Lys
    2525                2530                2535

Tyr Gly Phe Gly Ala Lys Glu Val Arg Ser Leu Ser Gly Arg Ala
    2540                2545                2550

Val Asn His Ile Lys Ser Val Trp Lys Asp Leu Leu Glu Asp Pro
    2555                2560                2565

Gln Thr Pro Ile Pro Thr Thr Ile Met Ala Lys Asn Glu Val Phe
    2570                2575                2580

Cys Val Asp Pro Ala Lys Gly Gly Lys Lys Pro Ala Arg Leu Ile
    2585                2590                2595

Val Tyr Pro Asp Leu Gly Val Arg Val Cys Glu Lys Met Ala Leu
    2600                2605                2610

Tyr Asp Ile Thr Gln Lys Leu Pro Gln Ala Val Met Gly Ala Ser
    2615                2620                2625

Tyr Gly Phe Gln Tyr Ser Pro Ala Gln Arg Val Glu Tyr Leu Leu
    2630                2635                2640
```

Lys Ala Trp Ala Glu Lys Lys Asp Pro Met Gly Phe Ser Tyr Asp
2645                2650                2655

Thr Arg Cys Phe Asp Ser Thr Val Thr Glu Arg Asp Ile Arg Thr
2660                2665                2670

Glu Glu Ser Ile Tyr Gln Ala Cys Ser Leu Pro Glu Glu Ala Arg
2675                2680                2685

Thr Ala Ile His Ser Leu Thr Glu Arg Leu Tyr Val Gly Gly Pro
2690                2695                2700

Met Phe Asn Ser Lys Gly Gln Thr Cys Gly Tyr Arg Arg Cys Arg
2705                2710                2715

Ala Ser Gly Val Leu Thr Thr Ser Met Gly Asn Thr Ile Thr Cys
2720                2725                2730

Tyr Val Lys Ala Leu Ala Ala Cys Lys Ala Ala Gly Ile Val Ala
2735                2740                2745

Pro Thr Met Leu Val Cys Gly Asp Asp Leu Val Val Ile Ser Glu
2750                2755                2760

Ser Gln Gly Thr Glu Glu Asp Glu Arg Asn Leu Arg Ala Phe Thr
2765                2770                2775

Glu Ala Met Thr Arg Tyr Ser Ala Pro Pro Gly Asp Pro Pro Arg
2780                2785                2790

Pro Glu Tyr Asp Leu Glu Leu Ile Thr Ser Cys Ser Ser Asn Val
2795                2800                2805

Ser Val Ala Leu Gly Pro Arg Gly Arg Arg Arg Tyr Tyr Leu Thr
2810                2815                2820

Arg Asp Pro Thr Thr Pro Leu Ala Arg Ala Ala Trp Glu Thr Val
2825                2830                2835

Arg His Ser Pro Ile Asn Ser Trp Leu Gly Asn Ile Ile Gln Tyr
2840                2845                2850

Ala Pro Thr Ile Trp Val Arg Met Val Leu Met Thr His Phe Phe
2855                2860                2865

Ser Ile Leu Met Val Gln Asp Thr Leu Asp Gln Asn Leu Asn Phe
2870                2875                2880

Glu Met Tyr Gly Ser Val Tyr Ser Val Asn Pro Leu Asp Leu Pro
2885                2890                2895

Ala Ile Ile Glu Arg Leu His Gly Leu Asp Ala Phe Ser Met His
2900                2905                2910

Thr Tyr Ser His His Glu Leu Thr Arg Val Ala Ser Ala Leu Arg
2915                2920                2925

Lys Leu Gly Ala Pro Pro Leu Arg Val Trp Lys Ser Arg Ala Arg
2930                2935                2940

Ala Val Arg Ala Ser Leu Ile Ser Arg Gly Gly Lys Ala Ala Val
2945                2950                2955

Cys Gly Arg Tyr Leu Phe Asn Trp Ala Val Lys Thr Lys Leu Lys
2960                2965                2970

Leu Thr Pro Leu Pro Glu Ala Arg Leu Leu Asp Leu Ser Ser Trp
2975                2980                2985

Phe Thr Val Gly Ala Gly Gly Asp Ile Phe His Ser Val Ser
2990                2995                3000

Arg Ala Arg Pro Arg Ser Leu Leu Phe Gly Leu Leu Leu Leu Phe
3005                3010                3015

Val Gly Val Gly Leu Phe Leu Leu Pro Ala Arg
3020                3025

<210> SEQ ID NO 28

```
<211> LENGTH: 3029
<212> TYPE: PRT
<213> ORGANISM: Hepatitis C virus

<400> SEQUENCE: 28
```

| | | | | | | | | | | | | | | |
|---|---|---|---|---|---|---|---|---|---|---|---|---|---|---|
| Met | Ser | Thr | Asn | Pro | Lys | Pro | Gln | Arg | Lys | Thr | Lys | Arg | Asn | Thr | Asn |
| 1 | | | | 5 | | | | | 10 | | | | | 15 | |

Met Ser Thr Asn Pro Lys Pro Gln Arg Lys Thr Lys Arg Asn Thr Asn
1               5                   10                  15

Arg Arg Pro Met Asp Val Lys Phe Pro Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
50                  55                  60

Ile Pro Lys Ala Arg Arg Pro Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Val
130                 135                 140

Gly Gly Val Ala Arg Ala Leu Ala His Gly Val Arg Ala Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Val
            180                 185                 190

Asn Tyr Arg Asn Val Ser Gly Ile Tyr His Val Thr Asn Asp Cys Pro
        195                 200                 205

Asn Ser Ser Ile Val Tyr Glu Thr Asp His His Ile Leu His Leu Pro
210                 215                 220

Gly Cys Val Pro Cys Val Arg Glu Gly Asn Gln Ser Arg Cys Trp Val
225                 230                 235                 240

Ala Leu Thr Pro Thr Val Ala Ala Pro Tyr Ile Gly Ala Pro Leu Glu
                245                 250                 255

Ser Leu Arg Ser His Val Asp Leu Met Val Gly Ala Ala Thr Val Cys
            260                 265                 270

Ser Gly Leu Tyr Ile Gly Asp Leu Cys Gly Gly Leu Phe Leu Val Gly
        275                 280                 285

Gln Met Phe Ser Phe Arg Pro Arg Arg His Trp Thr Thr Gln Asp Cys
290                 295                 300

Asn Cys Ser Ile Tyr Thr Gly His Ile Thr Gly His Arg Met Ala Trp
305                 310                 315                 320

Asp Met Met Met Asn Trp Ser Pro Thr Thr Thr Leu Val Leu Ala Gln
                325                 330                 335

Val Met Arg Ile Pro Thr Thr Leu Val Asp Leu Leu Ser Gly Gly His
            340                 345                 350

Trp Gly Val Leu Val Gly Val Ala Tyr Phe Ser Met Gln Ala Asn Trp
        355                 360                 365

Ala Lys Val Ile Leu Val Leu Phe Leu Phe Ala Gly Val Asp Ala Glu
370                 375                 380

Thr His Val Ser Gly Ala Ala Val Gly Arg Ser Thr Ala Gly Leu Ala
385                 390                 395                 400

```
Asn Leu Phe Ser Ser Gly Ser Lys Gln Asn Leu Gln Leu Ile Asn Ser
                405                 410                 415

Asn Gly Ser Trp His Ile Asn Arg Thr Ala Leu Asn Cys Asn Asp Ser
            420                 425                 430

Leu Asn Thr Gly Phe Leu Ala Ser Leu Phe Tyr Thr His Lys Phe Asn
        435                 440                 445

Ser Ser Gly Cys Ser Glu Arg Leu Ala Cys Cys Lys Ser Leu Asp Ser
    450                 455                 460

Tyr Gly Gln Gly Trp Gly Pro Leu Gly Val Ala Asn Ile Ser Gly Ser
465                 470                 475                 480

Ser Asp Asp Arg Pro Tyr Cys Trp His Tyr Ala Pro Arg Pro Cys Gly
                485                 490                 495

Ile Val Pro Ala Ser Ser Val Cys Gly Pro Val Tyr Cys Phe Thr Pro
            500                 505                 510

Ser Pro Val Val Val Gly Thr Thr Asp His Val Gly Val Pro Thr Tyr
        515                 520                 525

Thr Trp Gly Glu Asn Glu Thr Asp Val Phe Leu Leu Asn Ser Thr Arg
    530                 535                 540

Pro Pro His Gly Ala Trp Phe Gly Cys Val Trp Met Asn Ser Thr Gly
545                 550                 555                 560

Phe Thr Lys Thr Cys Gly Ala Pro Pro Cys Glu Val Asn Thr Asn Asn
                565                 570                 575

Gly Thr Trp His Cys Pro Thr Asp Cys Phe Arg Lys His Pro Glu Thr
            580                 585                 590

Thr Tyr Ala Lys Cys Gly Ser Gly Pro Trp Ile Thr Pro Arg Cys Leu
        595                 600                 605

Ile Asp Tyr Pro Tyr Arg Leu Trp His Phe Pro Cys Thr Ala Asn Phe
    610                 615                 620

Ser Val Phe Asn Ile Arg Thr Phe Val Gly Gly Ile Glu His Arg Met
625                 630                 635                 640

Gln Ala Ala Cys Asn Trp Thr Arg Gly Glu Val Cys Gly Leu Glu His
                645                 650                 655

Arg Asp Arg Val Glu Leu Ser Pro Leu Leu Thr Thr Thr Ala Trp
            660                 665                 670

Gln Ile Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
    690                 695                 700

Val Gly Ser Ala Val Val Ser Trp Ala Leu Lys Trp Glu Tyr Val Val
705                 710                 715                 720

Leu Ala Phe Leu Leu Leu Ala Asp Ala Arg Val Ser Ala Cys Leu Trp
                725                 730                 735

Met Met Phe Met Val Ser Gln Val Glu Ala Ala Leu Ser Asn Leu Ile
            740                 745                 750

Asn Ile Asn Ala Ala Ser Ala Ala Gly Ala Gln Gly Phe Trp Tyr Ala
        755                 760                 765

Ile Leu Phe Ile Cys Ile Val Trp His Val Lys Gly Arg Phe Pro Ala
    770                 775                 780

Ala Ala Ala Tyr Ala Ala Cys Gly Leu Trp Pro Leu Phe Leu Leu Leu
785                 790                 795                 800

Leu Met Leu Pro Glu Arg Ala Tyr Ala Tyr Asp Gln Glu Val Ala Gly
                805                 810                 815

Ser Leu Gly Gly Ala Ile Val Val Met Leu Ala Ile Leu Thr Leu Ser
```

-continued

```
                820                 825                 830
Pro His Tyr Lys Leu Trp Leu Ala Arg Gly Leu Trp Trp Ile Gln Tyr
                    835                 840                 845
Phe Ile Ala Arg Thr Glu Ala Val Leu His Val Tyr Ile Pro Ser Phe
850                 855                 860
Asn Val Arg Gly Pro Arg Asp Ser Val Ile Val Leu Ala Val Leu Val
865                 870                 875                 880
Cys Pro His Leu Val Phe Asp Ile Thr Lys Tyr Leu Leu Ala Ile Leu
                    885                 890                 895
Gly Pro Leu His Ile Leu Gln Ala Ser Leu Leu Arg Ile Pro Tyr Phe
                900                 905                 910
Val Arg Ala Gln Ala Leu Val Lys Ile Cys Ser Leu Leu Arg Gly Val
                915                 920                 925
Val Tyr Gly Lys Tyr Phe Gln Met Val Val Leu Lys Ala Gly Ala Leu
                930                 935                 940
Thr Gly Thr Tyr Ile Tyr Asp His Leu Thr Pro Met Ser Asp Trp Ala
945                 950                 955                 960
Ala Thr Gly Leu Arg Asp Leu Ala Val Ala Leu Glu Pro Val Val Phe
                    965                 970                 975
Ser Pro Met Glu Lys Lys Val Ile Val Trp Gly Ala Asp Thr Ala Ala
                980                 985                 990
Cys Gly Asp Ile Ile Arg Gly Leu  Pro Val Ser Ala Arg  Leu Gly Asn
                    995                1000                1005
Glu Ile  Leu Leu Gly Pro Ala  Asp Thr Glu Thr Ser  Lys Gly Trp
1010                1015                1020
Arg Leu  Leu Ala Pro Ile  Thr Ala Tyr Ala Gln Gln  Thr Arg Gly
1025                1030                1035
Leu Leu  Gly Ala Ile Val Val  Ser Met Thr Gly Arg  Asp Arg Thr
1040                1045                1050
Glu Gln  Ala Gly Glu Val Gln  Ile Leu Ser Thr Val  Ser Gln Ser
1055                1060                1065
Phe Leu  Gly Thr Thr Ile Ser  Gly Val Leu Trp Thr  Val Tyr His
1070                1075                1080
Gly Ala  Gly Asn Lys Thr Leu  Ala Gly Leu Arg Gly  Pro Val Thr
1085                1090                1095
Gln Met  Tyr Ser Ser Ala Glu  Gly Asp Leu Val Gly  Trp Pro Ser
1100                1105                1110
Pro Pro  Gly Thr Lys Ser Leu  Glu Pro Cys Lys Cys  Gly Ala Val
1115                1120                1125
Asp Leu  Tyr Leu Val Thr Arg  Asn Ala Asp Val Ile  Pro Ala Arg
1130                1135                1140
Arg Arg  Gly Asp Lys Arg Gly  Ala Leu Leu Ser Pro  Arg Pro Ile
1145                1150                1155
Ser Thr  Leu Lys Gly Ser Ser  Gly Gly Pro Val Leu  Cys Pro Arg
1160                1165                1170
Gly His  Val Val Gly Leu Phe  Arg Ala Ala Val Cys  Ser Arg Gly
1175                1180                1185
Val Ala  Lys Ser Ile Asp Phe  Ile Pro Val Glu Thr  Leu Asp Val
1190                1195                1200
Val Thr  Arg Ser Pro Thr Phe  Ser Asp Asn Ser Thr  Pro Pro Ala
1205                1210                1215
Val Pro  Gln Thr Tyr Gln Val  Gly Tyr Leu His Ala  Pro Thr Gly
1220                1225                1230
```

-continued

```
Ser Gly Lys Ser Thr Lys Val Pro Val Ala Tyr Ala Ala Gln Gly
1235                1240                1245

Tyr Lys Val Leu Val Leu Asn Pro Ser Val Ala Ala Thr Leu Gly
1250                1255                1260

Phe Gly Ala Tyr Leu Ser Lys Ala His Gly Ile Asn Pro Asn Ile
1265                1270                1275

Arg Thr Gly Val Arg Thr Val Met Thr Gly Glu Ala Ile Thr Tyr
1280                1285                1290

Ser Thr Tyr Gly Lys Phe Leu Ala Asp Gly Gly Cys Ala Ser Gly
1295                1300                1305

Ala Tyr Asp Ile Ile Ile Cys Asp Glu Cys His Ala Val Asp Ala
1310                1315                1320

Thr Ser Ile Leu Gly Ile Gly Thr Val Leu Asp Gln Ala Glu Thr
1325                1330                1335

Ala Gly Val Arg Leu Thr Val Leu Ala Thr Ala Thr Pro Pro Gly
1340                1345                1350

Ser Val Thr Thr Pro His Pro Asp Ile Glu Glu Val Gly Leu Gly
1355                1360                1365

Arg Glu Gly Glu Ile Pro Phe Tyr Gly Arg Ala Ile Pro Leu Ser
1370                1375                1380

Cys Ile Lys Gly Gly Arg His Leu Ile Phe Cys His Ser Lys Lys
1385                1390                1395

Lys Cys Asp Glu Leu Ala Ala Ala Leu Arg Gly Met Gly Leu Asn
1400                1405                1410

Ala Val Ala Tyr Tyr Arg Gly Leu Asp Val Ser Ile Ile Pro Ala
1415                1420                1425

Gln Gly Asp Val Val Val Ala Thr Asp Ala Leu Met Thr Gly
1430                1435                1440

Tyr Thr Gly Asp Phe Asp Ser Val Ile Asp Cys Asn Val Ala Val
1445                1450                1455

Thr Gln Ala Val Asp Phe Ser Leu Asp Pro Thr Phe Thr Ile Thr
1460                1465                1470

Thr Gln Thr Val Pro Gln Asp Ala Val Ser Arg Ser Gln Arg Arg
1475                1480                1485

Gly Arg Thr Gly Arg Gly Arg Gln Gly Thr Tyr Arg Tyr Val Ser
1490                1495                1500

Thr Gly Glu Arg Ala Ser Gly Met Phe Asp Ser Val Val Leu Cys
1505                1510                1515

Glu Cys Tyr Asp Ala Gly Ala Ala Trp Tyr Asp Leu Thr Pro Ala
1520                1525                1530

Glu Thr Thr Val Arg Leu Arg Ala Tyr Phe Asn Thr Pro Gly Leu
1535                1540                1545

Pro Val Cys Gln Asp His Leu Glu Phe Trp Glu Ala Val Phe Thr
1550                1555                1560

Gly Leu Thr His Ile Asp Ala His Phe Leu Ser Gln Thr Lys Gln
1565                1570                1575

Ala Gly Glu Asn Phe Ala Tyr Leu Val Ala Tyr Gln Ala Thr Val
1580                1585                1590

Cys Ala Arg Ala Lys Ala Pro Pro Pro Ser Trp Asp Ala Met Trp
1595                1600                1605

Lys Cys Leu Ala Arg Leu Lys Pro Thr Leu Ala Gly Pro Thr Pro
1610                1615                1620

Leu Leu Tyr Arg Leu Gly Pro Ile Thr Asn Glu Val Thr Leu Thr
1625                1630                1635
```

-continued

His Pro Gly Thr Lys Tyr Ile Ala Thr Cys Met Gln Ala Asp Leu
1640                1645                1650

Glu Val Met Thr Ser Thr Trp Val Leu Ala Gly Gly Val Leu Ala
1655                1660                1665

Ala Val Ala Ala Tyr Cys Leu Ala Thr Gly Cys Val Ser Ile Ile
1670                1675                1680

Gly Arg Leu His Val Asn Gln Arg Val Val Ala Pro Asp Lys
1685                1690                1695

Glu Val Leu Tyr Glu Ala Phe Asp Glu Met Glu Glu Cys Ala Ser
1700                1705                1710

Arg Ala Ala Leu Ile Glu Glu Gly Gln Arg Ile Ala Glu Met Leu
1715                1720                1725

Lys Ser Lys Ile Gln Gly Leu Leu Gln Gln Ala Ser Lys Gln Ala
1730                1735                1740

Gln Asp Ile Gln Pro Ala Met Gln Ala Ser Trp Pro Lys Val Glu
1745                1750                1755

Gln Phe Trp Ala Arg His Met Trp Asn Phe Ile Ser Gly Ile Gln
1760                1765                1770

Tyr Leu Ala Gly Leu Ser Thr Leu Pro Gly Asn Pro Ala Val Ala
1775                1780                1785

Ser Met Met Ala Phe Ser Ala Ala Leu Thr Ser Pro Leu Ser Thr
1790                1795                1800

Ser Thr Thr Ile Leu Leu Asn Ile Met Gly Gly Trp Leu Ala Ser
1805                1810                1815

Gln Ile Ala Pro Pro Ala Gly Ala Thr Gly Phe Val Val Ser Gly
1820                1825                1830

Leu Val Gly Ala Ala Val Gly Ser Ile Gly Leu Gly Lys Val Leu
1835                1840                1845

Val Asp Ile Leu Ala Gly Tyr Gly Ala Gly Ile Ser Gly Ala Leu
1850                1855                1860

Val Ala Phe Lys Ile Met Ser Gly Glu Lys Pro Ser Met Glu Asp
1865                1870                1875

Val Ile Asn Leu Leu Pro Gly Ile Leu Ser Pro Gly Ala Leu Val
1880                1885                1890

Val Gly Val Ile Cys Ala Ala Ile Leu Arg Arg His Val Gly Pro
1895                1900                1905

Gly Glu Gly Ala Val Gln Trp Met Asn Arg Leu Ile Ala Phe Ala
1910                1915                1920

Ser Arg Gly Asn His Val Ala Pro Thr His Tyr Val Thr Glu Ser
1925                1930                1935

Asp Ala Ser Gln Arg Val Thr Gln Leu Leu Gly Ser Leu Thr Ile
1940                1945                1950

Thr Ser Leu Leu Arg Arg Leu His Asn Trp Ile Thr Glu Asp Cys
1955                1960                1965

Pro Ile Pro Cys Ser Gly Ser Trp Leu Arg Asp Val Trp Asp Trp
1970                1975                1980

Val Cys Thr Ile Leu Thr Asp Phe Lys Asn Trp Leu Thr Ser Lys
1985                1990                1995

Leu Phe Pro Lys Leu Pro Gly Leu Pro Phe Ile Ser Cys Gln Lys
2000                2005                2010

Gly Tyr Lys Gly Val Trp Ala Gly Thr Gly Ile Met Thr Thr Arg
2015                2020                2025

Cys Pro Cys Gly Ala Asn Ile Ser Gly Asn Val Arg Leu Gly Ser

-continued

```
              2030                2035                2040

Met Arg Ile Thr Gly Pro Lys Thr Cys Met Asn Thr Trp Gln Gly
       2045                2050                2055

Thr Phe Pro Ile Asn Cys Tyr Thr Glu Gly Gln Cys Ala Pro Lys
       2060                2065                2070

Pro Pro Thr Asn Tyr Lys Thr Ala Ile Trp Arg Val Ala Ala Ser
       2075                2080                2085

Glu Tyr Ala Glu Val Thr Gln His Gly Ser Tyr Ser Tyr Val Thr
       2090                2095                2100

Gly Leu Thr Thr Asp Asn Leu Lys Ile Pro Cys Gln Leu Pro Ser
       2105                2110                2115

Pro Glu Phe Phe Ser Trp Val Asp Gly Val Gln Ile His Arg Phe
       2120                2125                2130

Ala Pro Thr Pro Lys Pro Phe Phe Arg Asp Glu Val Ser Phe Cys
       2135                2140                2145

Val Gly Leu Asn Ser Tyr Ala Val Gly Ser Gln Leu Pro Cys Glu
       2150                2155                2160

Pro Glu Pro Asp Ala Asp Val Leu Arg Ser Met Leu Thr Asp Pro
       2165                2170                2175

Pro His Ile Thr Ala Glu Thr Ala Ala Arg Arg Leu Ala Arg Gly
       2180                2185                2190

Ser Pro Pro Ser Glu Ala Ser Ser Ser Val Ser Gln Leu Ser Ala
       2195                2200                2205

Pro Ser Leu Arg Ala Thr Cys Thr Thr His Ser Asn Thr Tyr Asp
       2210                2215                2220

Val Asp Met Val Asp Ala Asn Leu Leu Met Glu Gly Gly Val Ala
       2225                2230                2235

Gln Thr Glu Pro Glu Ser Arg Val Pro Val Leu Asp Phe Leu Glu
       2240                2245                2250

Pro Met Ala Glu Glu Ser Asp Leu Glu Pro Ser Ile Pro Ser
       2255                2260                2265

Glu Arg Met Leu Pro Arg Ser Gly Phe Pro Arg Ala Leu Pro Ala
       2270                2275                2280

Trp Ala Arg Pro Asp Tyr Asn Pro Pro Leu Val Glu Ser Trp Arg
       2285                2290                2295

Arg Pro Asp Tyr Gln Pro Pro Thr Val Ala Gly Cys Ala Leu Pro
       2300                2305                2310

Pro Pro Lys Lys Ala Pro Thr Pro Pro Pro Arg Arg Arg Arg Thr
       2315                2320                2325

Val Gly Leu Ser Glu Ser Thr Ile Ser Glu Ala Leu Gln Gln Leu
       2330                2335                2340

Ala Ile Lys Thr Phe Gly Gln Pro Pro Ser Ser Gly Asp Ala Gly
       2345                2350                2355

Ser Ser Thr Gly Ala Gly Ala Ala Glu Ser Gly Gly Pro Thr Ser
       2360                2365                2370

Pro Gly Glu Pro Ala Pro Ser Glu Thr Gly Ser Ala Ser Ser Met
       2375                2380                2385

Pro Pro Leu Glu Gly Glu Pro Gly Asp Pro Asp Leu Glu Ser Asp
       2390                2395                2400

Gln Val Glu Leu Gln Pro Pro Gln Gly Gly Gly Val Ala Pro
       2405                2410                2415

Gly Ser Gly Ser Gly Ser Trp Ser Thr Cys Ser Glu Glu Asp Asp
       2420                2425                2430
```

```
Thr Thr Val Cys Cys Ser Met Ser Tyr Ser Trp Thr Gly Ala Leu
2435                    2440                2445

Ile Thr Pro Cys Ser Pro Glu Glu Lys Leu Pro Ile Asn Pro
    2450                2455                2460

Leu Ser Asn Ser Leu Leu Arg Tyr His Asn Lys Val Tyr Cys Thr
2465                    2470                2475

Thr Ser Lys Ser Ala Ser Gln Arg Ala Lys Lys Val Thr Phe Asp
    2480                2485                2490

Arg Thr Gln Val Leu Asp Ala His Tyr Asp Ser Val Leu Lys Asp
    2495                2500                2505

Ile Lys Leu Ala Ala Ser Lys Val Ser Ala Arg Leu Leu Thr Leu
    2510                2515                2520

Glu Glu Ala Cys Gln Leu Thr Pro Pro His Ser Ala Arg Ser Lys
2525                    2530                2535

Tyr Gly Phe Gly Ala Lys Glu Val Arg Ser Leu Ser Gly Arg Ala
    2540                2545                2550

Val Asn His Ile Lys Ser Val Trp Lys Asp Leu Leu Glu Asp Pro
2555                    2560                2565

Gln Thr Pro Ile Pro Thr Thr Ile Met Ala Lys Asn Glu Val Phe
    2570                2575                2580

Cys Val Asp Pro Ala Lys Gly Gly Lys Lys Pro Ala Arg Leu Ile
2585                    2590                2595

Val Tyr Pro Asp Leu Gly Val Arg Val Cys Glu Lys Met Ala Leu
2600                    2605                2610

Tyr Asp Ile Thr Gln Lys Leu Pro Gln Ala Val Met Gly Ala Ser
    2615                2620                2625

Tyr Gly Phe Gln Tyr Ser Pro Ala Gln Arg Val Glu Tyr Leu Leu
    2630                2635                2640

Lys Ala Trp Ala Glu Lys Lys Asp Pro Met Gly Phe Ser Tyr Asp
2645                    2650                2655

Thr Arg Cys Phe Asp Ser Thr Val Thr Glu Arg Asp Ile Arg Thr
2660                    2665                2670

Glu Glu Ser Ile Tyr Gln Ala Cys Ser Leu Pro Glu Glu Ala Arg
2675                    2680                2685

Thr Ala Ile His Ser Leu Thr Glu Arg Leu Tyr Val Gly Gly Pro
2690                    2695                2700

Met Phe Asn Ser Lys Gly Gln Thr Cys Gly Tyr Arg Arg Cys Arg
2705                    2710                2715

Ala Ser Gly Val Leu Thr Thr Ser Met Gly Asn Thr Ile Thr Cys
2720                    2725                2730

Tyr Val Lys Ala Leu Ala Ala Cys Lys Ala Ala Gly Ile Val Ala
2735                    2740                2745

Pro Thr Met Leu Val Cys Gly Asp Asp Leu Val Val Ile Ser Glu
2750                    2755                2760

Ser Gln Gly Thr Glu Glu Asp Glu Arg Asn Leu Arg Ala Phe Thr
2765                    2770                2775

Glu Ala Met Thr Arg Tyr Ser Ala Pro Pro Gly Asp Pro Pro Arg
2780                    2785                2790

Pro Glu Tyr Asp Leu Glu Leu Ile Thr Ser Cys Ser Ser Asn Val
2795                    2800                2805

Ser Val Ala Leu Gly Pro Arg Gly Arg Arg Tyr Tyr Leu Thr
2810                    2815                2820

Arg Asp Pro Thr Thr Pro Leu Ala Arg Ala Ala Trp Glu Thr Val
2825                    2830                2835
```

```
Arg His Ser Pro Ile Asn Ser Trp Leu Gly Asn Ile Ile Gln Tyr
    2840            2845                2850

Ala Pro Thr Ile Trp Val Arg Met Val Leu Met Thr His Phe Phe
    2855            2860                2865

Ser Ile Leu Met Val Gln Asp Thr Leu Asp Gln Asn Leu Asn Phe
    2870            2875                2880

Glu Met Tyr Gly Ser Val Tyr Ser Val Asn Pro Leu Asp Leu Pro
    2885            2890                2895

Ala Ile Ile Glu Arg Leu His Gly Leu Asp Ala Phe Ser Met His
    2900            2905                2910

Thr Tyr Ser His His Glu Leu Thr Arg Val Ala Ser Ala Leu Arg
    2915            2920                2925

Lys Leu Gly Ala Pro Pro Leu Arg Val Trp Lys Ser Arg Ala Arg
    2930            2935                2940

Ala Val Arg Ala Ser Leu Ile Ser Arg Gly Gly Lys Ala Ala Val
    2945            2950                2955

Cys Gly Arg Tyr Leu Phe Asn Trp Ala Val Lys Thr Lys Leu Lys
    2960            2965                2970

Leu Thr Pro Leu Pro Glu Ala Arg Leu Leu Asp Leu Ser Ser Trp
    2975            2980                2985

Phe Thr Val Gly Ala Gly Gly Gly Asp Ile Phe His Ser Val Ser
    2990            2995                3000

Arg Ala Arg Pro Arg Ser Leu Leu Phe Gly Leu Leu Leu Leu Phe
    3005            3010                3015

Val Gly Val Gly Leu Phe Leu Leu Pro Ala Arg
    3020            3025

<210> SEQ ID NO 29
<211> LENGTH: 24
<212> TYPE: DNA
<213> ORGANISM: Artificial
<220> FEATURE:
<223> OTHER INFORMATION: oligoDNA primer

<400> SEQUENCE: 29
tttcttggat taacccgctc aatg                                          24

<210> SEQ ID NO 30
<211> LENGTH: 61
<212> TYPE: DNA
<213> ORGANISM: Artificial
<220> FEATURE:
<223> OTHER INFORMATION: oligoDNA primer

<400> SEQUENCE: 30 tttttttgc ggccgctaat acgactcact atagacctgc tctctatgag agcaacactc    60
c                                                                   61

<210> SEQ ID NO 31
<211> LENGTH: 20
<212> TYPE: DNA
<213> ORGANISM: Artificial
<220> FEATURE:
<223> OTHER INFORMATION: oligoDNA primer

<400> SEQUENCE: 31
agggccggtt cccagctgct                                               20

<210> SEQ ID NO 32
```

```
<211> LENGTH: 23
<212> TYPE: DNA
<213> ORGANISM: Artificial
<220> FEATURE:
<223> OTHER INFORMATION: oligoDNA primer

<400> SEQUENCE: 32
gtggccctgt tttctcctgc ttc                                          23

<210> SEQ ID NO 33
<211> LENGTH: 22
<212> TYPE: DNA
<213> ORGANISM: Artificial
<220> FEATURE:
<223> OTHER INFORMATION: oligoDNA primer

<400> SEQUENCE: 33
agtgccccgg gaggtctcgt ag                                           22

<210> SEQ ID NO 34
<211> LENGTH: 30
<212> TYPE: DNA
<213> ORGANISM: Artificial
<220> FEATURE:
<223> OTHER INFORMATION: oligoDNA primer

<400> SEQUENCE: 34
ccaacagttc gacgaaatgg aggagtgttc                                   30

<210> SEQ ID NO 35
<211> LENGTH: 22
<212> TYPE: DNA
<213> ORGANISM: Artificial
<220> FEATURE:
<223> OTHER INFORMATION: oligoDNA primer

<400> SEQUENCE: 35
tgggatacat cccgctcgta gg                                           22

<210> SEQ ID NO 36
<211> LENGTH: 30
<212> TYPE: DNA
<213> ORGANISM: Artificial
<220> FEATURE:
<223> OTHER INFORMATION: oligoDNA primer

<400> SEQUENCE: 36
ggcgccggcg ggggagacat ttatcacagc                                   30

<210> SEQ ID NO 37
<211> LENGTH: 38
<212> TYPE: DNA
<213> ORGANISM: Artificial
<220> FEATURE:
<223> OTHER INFORMATION: oligoDNA primer

<400> SEQUENCE: 37
gtccaagctt atcacagcat gtctcatgcc cgaccccg                          38

<210> SEQ ID NO 38
<211> LENGTH: 24
<212> TYPE: DNA
<213> ORGANISM: Artificial
<220> FEATURE:
<223> OTHER INFORMATION: oligoDNA primer

<400> SEQUENCE: 38
```
acactactcg gctagcagtc ttgc                                          24

<210> SEQ ID NO 39
<211> LENGTH: 22
<212> TYPE: DNA
<213> ORGANISM: Artificial
<220> FEATURE:
<223> OTHER INFORMATION: oligoDNA primer

<400> SEQUENCE: 39
cgagtcgcgc gcacacccaa tc                                            22

<210> SEQ ID NO 40
<211> LENGTH: 33
<212> TYPE: DNA
<213> ORGANISM: Artificial
<220> FEATURE:
<223> OTHER INFORMATION: oligoDNA primer

<400> SEQUENCE: 40
agatattgaa tgccgctgat gaaattccac atg                                33

<210> SEQ ID NO 41
<211> LENGTH: 22
<212> TYPE: DNA
<213> ORGANISM: Artificial
<220> FEATURE:
<223> OTHER INFORMATION: oligoDNA primer

<400> SEQUENCE: 41
aaaggagcaa ccggggagat tc                                            22

<210> SEQ ID NO 42
<211> LENGTH: 30
<212> TYPE: DNA
<213> ORGANISM: Artificial
<220> FEATURE:
<223> OTHER INFORMATION: oligoDNA primer

<400> SEQUENCE: 42
aaaaaacaag gggaccctaa ggtcggagtg                                    30

<210> SEQ ID NO 43
<211> LENGTH: 39
<212> TYPE: DNA
<213> ORGANISM: Artificial
<220> FEATURE:
<223> OTHER INFORMATION: oligoDNA primer

<400> SEQUENCE: 43
cgtctctaga ggacctttca cagctagccg tgactaggg                          39

<210> SEQ ID NO 44
<211> LENGTH: 30
<212> TYPE: DNA
<213> ORGANISM: Artificial
<220> FEATURE:
<223> OTHER INFORMATION: oligoDNA primer

<400> SEQUENCE: 44
tcatgcggct cacggacctt tcacagctag                                    30

<210> SEQ ID NO 45
<211> LENGTH: 22
<212> TYPE: DNA
<213> ORGANISM: Artificial
<220> FEATURE:

<223> OTHER INFORMATION: oligoDNA primer

<400> SEQUENCE: 45
ctgtggtggt tgtgctatct cc          22

<210> SEQ ID NO 46
<211> LENGTH: 22
<212> TYPE: DNA
<213> ORGANISM: Artificial
<220> FEATURE:
<223> OTHER INFORMATION: oligoDNA primer

<400> SEQUENCE: 46
tgatggcatc atatgggccg tc          22

<210> SEQ ID NO 47
<211> LENGTH: 23
<212> TYPE: DNA
<213> ORGANISM: Artificial
<220> FEATURE:
<223> OTHER INFORMATION: oligoDNA primer

<400> SEQUENCE: 47
tctatgacca cctcacacct atg         23

<210> SEQ ID NO 48
<211> LENGTH: 23
<212> TYPE: DNA
<213> ORGANISM: Artificial
<220> FEATURE:
<223> OTHER INFORMATION: oligoDNA primer

<400> SEQUENCE: 48
ctcatggtgc acggtctacg aga         23

<210> SEQ ID NO 49
<211> LENGTH: 20
<212> TYPE: DNA
<213> ORGANISM: Artificial
<220> FEATURE:
<223> OTHER INFORMATION: oligoDNA primer

<400> SEQUENCE: 49
ttgccagctc cgtggtaaac             20

<210> SEQ ID NO 50
<211> LENGTH: 21
<212> TYPE: DNA
<213> ORGANISM: Artificial
<220> FEATURE:
<223> OTHER INFORMATION: oligoDNA primer

<400> SEQUENCE: 50
cctgatgtct ctctcagtga c           21

<210> SEQ ID NO 51
<211> LENGTH: 21
<212> TYPE: DNA
<213> ORGANISM: Artificial
<220> FEATURE:
<223> OTHER INFORMATION: oligoDNA primer

<400> SEQUENCE: 51
tccgtgaagg ctctcaggtt c           21

<210> SEQ ID NO 52

<211> LENGTH: 21
<212> TYPE: DNA
<213> ORGANISM: Artificial
<220> FEATURE:
<223> OTHER INFORMATION: oligoDNA primer

<400> SEQUENCE: 52
gctcccatca ctgcttatgc c                                             21

<210> SEQ ID NO 53
<211> LENGTH: 21
<212> TYPE: DNA
<213> ORGANISM: Artificial
<220> FEATURE:
<223> OTHER INFORMATION: oligoDNA primer

<400> SEQUENCE: 53
gctaccgagg ggttaagcac t                                             21

<210> SEQ ID NO 54
<211> LENGTH: 23
<212> TYPE: DNA
<213> ORGANISM: Artificial
<220> FEATURE:
<223> OTHER INFORMATION: oligoDNA primer

<400> SEQUENCE: 54
cgttgtaaaa cgacggccag tga                                           23

<210> SEQ ID NO 55
<211> LENGTH: 44
<212> TYPE: DNA
<213> ORGANISM: Artificial
<220> FEATURE:
<223> OTHER INFORMATION: oligoDNA primer

<400> SEQUENCE: 55
ggagatagca caaccaccac agtcccctag ccagccataa cttg                    44

<210> SEQ ID NO 56
<211> LENGTH: 45
<212> TYPE: DNA
<213> ORGANISM: Artificial
<220> FEATURE:
<223> OTHER INFORMATION: oligoDNA primer

<400> SEQUENCE: 56
cataggtgtg aggtggtcat agatgtaagt accagtcagg gcccc                   45

<210> SEQ ID NO 57
<211> LENGTH: 41
<212> TYPE: DNA
<213> ORGANISM: Artificial
<220> FEATURE:
<223> OTHER INFORMATION: oligoDNA primer

<400> SEQUENCE: 57
ggcataagca gtgatgggag caaggagtct ccacccettt g                       41

<210> SEQ ID NO 58
<211> LENGTH: 30
<212> TYPE: DNA
<213> ORGANISM: Artificial
<220> FEATURE:
<223> OTHER INFORMATION: oligoDNA primer

<400> SEQUENCE: 58
actgtcttca cgcagaaagc gcctagccat                                    30

<210> SEQ ID NO 59
<211> LENGTH: 24
<212> TYPE: DNA
<213> ORGANISM: Artificial
<220> FEATURE:
<223> OTHER INFORMATION: oligoDNA primer

<400> SEQUENCE: 59
ctatggagtg tacctagtgt gtgc                                          24

<210> SEQ ID NO 60
<211> LENGTH: 19
<212> TYPE: DNA
<213> ORGANISM: Artificial
<220> FEATURE:
<223> OTHER INFORMATION: oligoDNA primer

<400> SEQUENCE: 60
acccaacgct actcggcta                                                19

<210> SEQ ID NO 61
<211> LENGTH: 25
<212> TYPE: DNA
<213> ORGANISM: Artificial
<220> FEATURE:
<223> OTHER INFORMATION: oligoDNA primer

<400> SEQUENCE: 61
cgcaagcrcc ctatcaggca gtacc                                         25

<210> SEQ ID NO 62
<211> LENGTH: 24
<212> TYPE: DNA
<213> ORGANISM: Artificial
<220> FEATURE:
<223> OTHER INFORMATION: oligoDNA primer

<400> SEQUENCE: 62
ggtctacgag rcctcccggg gcac                                          24

<210> SEQ ID NO 63
<211> LENGTH: 40
<212> TYPE: DNA
<213> ORGANISM: Artificial
<220> FEATURE:
<223> OTHER INFORMATION: oligoDNA primer

<400> SEQUENCE: 63
gtagcgttgg gttgcgaaag gccttgtggt actgcctgat                         40

<210> SEQ ID NO 64
<211> LENGTH: 27
<212> TYPE: DNA
<213> ORGANISM: Artificial
<220> FEATURE:
<223> OTHER INFORMATION: oligoDNA primer

<400> SEQUENCE: 64
aattcaagca tagtgtatga ggccgac                                       27

<210> SEQ ID NO 65
<211> LENGTH: 23
<212> TYPE: DNA
<213> ORGANISM: Artificial
<220> FEATURE:

```
<223> OTHER INFORMATION: oligoDNA primer

<400> SEQUENCE: 65
ggggtcccta cttacacctg ggg                                              23

<210> SEQ ID NO 66
<211> LENGTH: 23
<212> TYPE: DNA
<213> ORGANISM: Artificial
<220> FEATURE:
<223> OTHER INFORMATION: oligoDNA primer

<400> SEQUENCE: 66
gtggccctgt tttctcctgc ttc                                              23

<210> SEQ ID NO 67
<211> LENGTH: 24
<212> TYPE: DNA
<213> ORGANISM: Artificial
<220> FEATURE:
<223> OTHER INFORMATION: oligoDNA primer

<400> SEQUENCE: 67
accttaccca aattgcggga cctc                                             24

<210> SEQ ID NO 68
<211> LENGTH: 25
<212> TYPE: DNA
<213> ORGANISM: Artificial
<220> FEATURE:
<223> OTHER INFORMATION: oligoDNA primer

<400> SEQUENCE: 68
gcgacggtag gagtaagggc caccc                                            25

<210> SEQ ID NO 69
<211> LENGTH: 22
<212> TYPE: DNA
<213> ORGANISM: Artificial
<220> FEATURE:
<223> OTHER INFORMATION: oligoDNA primer

<400> SEQUENCE: 69
ttcatccaca cgcatccaaa cc                                               22

<210> SEQ ID NO 70
<211> LENGTH: 24
<212> TYPE: DNA
<213> ORGANISM: Artificial
<220> FEATURE:
<223> OTHER INFORMATION: oligoDNA primer

<400> SEQUENCE: 70
cacaatcccc tagccagcca taac                                             24

<210> SEQ ID NO 71
<211> LENGTH: 23
<212> TYPE: DNA
<213> ORGANISM: Artificial
<220> FEATURE:
<223> OTHER INFORMATION: oligoDNA primer

<400> SEQUENCE: 71
ccctcagcac tcgagtacat ctg                                              23

<210> SEQ ID NO 72
```

```
<211> LENGTH: 24
<212> TYPE: DNA
<213> ORGANISM: Artificial
<220> FEATURE:
<223> OTHER INFORMATION: oligoDNA primer

<400> SEQUENCE: 72
caccgcatgg cgtgggacat gatg                                       24

<210> SEQ ID NO 73
<211> LENGTH: 26
<212> TYPE: DNA
<213> ORGANISM: Artificial
<220> FEATURE:
<223> OTHER INFORMATION: oligoDNA primer

<400> SEQUENCE: 73
tacaggctct ggcattaccc ctgcac                                     26

<210> SEQ ID NO 74
<211> LENGTH: 33
<212> TYPE: DNA
<213> ORGANISM: Artificial
<220> FEATURE:
<223> OTHER INFORMATION: oligoDNA primer

<400> SEQUENCE: 74
tagcattgcc ccaacaggct tatgcttatg acg                             33

<210> SEQ ID NO 75
<211> LENGTH: 18
<212> TYPE: DNA
<213> ORGANISM: Artificial
<220> FEATURE:
<223> OTHER INFORMATION: oligoDNA primer

<400> SEQUENCE: 75
gctgggaccg ctccgaag                                              18

<210> SEQ ID NO 76
<211> LENGTH: 26
<212> TYPE: DNA
<213> ORGANISM: Artificial
<220> FEATURE:
<223> OTHER INFORMATION: oligoDNA primer

<400> SEQUENCE: 76
tttgcccacg ctccctgcat agagaa                                     26

<210> SEQ ID NO 77
<211> LENGTH: 23
<212> TYPE: DNA
<213> ORGANISM: Artificial
<220> FEATURE:
<223> OTHER INFORMATION: oligoDNA primer

<400> SEQUENCE: 77
tgcacgtcca cgatgttttg gtg                                        23

<210> SEQ ID NO 78
<211> LENGTH: 24
<212> TYPE: DNA
<213> ORGANISM: Artificial
<220> FEATURE:
<223> OTHER INFORMATION: oligoDNA primer

<400> SEQUENCE: 78
```

-continued

```
agcgtgagcc ctgacgaagt acgg                                          24

<210> SEQ ID NO 79
<211> LENGTH: 29
<212> TYPE: DNA
<213> ORGANISM: Artificial
<220> FEATURE:
<223> OTHER INFORMATION: oligoDNA primer

<400> SEQUENCE: 79
gggatgacat cagcgttccg cgtgaccag                                     29

<210> SEQ ID NO 80
<211> LENGTH: 25
<212> TYPE: DNA
<213> ORGANISM: Artificial
<220> FEATURE:
<223> OTHER INFORMATION: oligoDNA primer

<400> SEQUENCE: 80
ggagtcttct cgctcccatc actgc                                         25

<210> SEQ ID NO 81
<211> LENGTH: 24
<212> TYPE: DNA
<213> ORGANISM: Artificial
<220> FEATURE:
<223> OTHER INFORMATION: oligoDNA primer

<400> SEQUENCE: 81
cccatcacgt actccacata tggc                                          24

<210> SEQ ID NO 82
<211> LENGTH: 25
<212> TYPE: DNA
<213> ORGANISM: Artificial
<220> FEATURE:
<223> OTHER INFORMATION: oligoDNA primer

<400> SEQUENCE: 82
gagcgagcct caggaatgtt tgaca                                         25

<210> SEQ ID NO 83
<211> LENGTH: 24
<212> TYPE: DNA
<213> ORGANISM: Artificial
<220> FEATURE:
<223> OTHER INFORMATION: oligoDNA primer

<400> SEQUENCE: 83
tggcccaaag tggaacaatt ttgg                                          24

<210> SEQ ID NO 84
<211> LENGTH: 24
<212> TYPE: DNA
<213> ORGANISM: Artificial
<220> FEATURE:
<223> OTHER INFORMATION: oligoDNA primer

<400> SEQUENCE: 84
gacctttcct atcaattgct acac                                          24

<210> SEQ ID NO 85
<211> LENGTH: 20
<212> TYPE: DNA
<213> ORGANISM: Artificial
<220> FEATURE:
```

<223> OTHER INFORMATION: oligoDNA primer

<400> SEQUENCE: 85
tgggcacggc ctgactacaa                                           20

<210> SEQ ID NO 86
<211> LENGTH: 24
<212> TYPE: DNA
<213> ORGANISM: Artificial
<220> FEATURE:
<223> OTHER INFORMATION: oligoDNA primer

<400> SEQUENCE: 86
atggccaaaa atgaggtgtt ctgc                                      24

<210> SEQ ID NO 87
<211> LENGTH: 26
<212> TYPE: DNA
<213> ORGANISM: Artificial
<220> FEATURE:
<223> OTHER INFORMATION: oligoDNA primer

<400> SEQUENCE: 87
ggtcaaacct gcggttacag acgttg                                    26

<210> SEQ ID NO 88
<211> LENGTH: 26
<212> TYPE: DNA
<213> ORGANISM: Artificial
<220> FEATURE:
<223> OTHER INFORMATION: oligoDNA primer

<400> SEQUENCE: 88
cgcccgaggc ctacctcttc tatatc                                    26

<210> SEQ ID NO 89
<211> LENGTH: 22
<212> TYPE: DNA
<213> ORGANISM: Artificial
<220> FEATURE:
<223> OTHER INFORMATION: oligoDNA primer

<400> SEQUENCE: 89
gcgcacaccg tagcttggta gg                                        22

<210> SEQ ID NO 90
<211> LENGTH: 24
<212> TYPE: DNA
<213> ORGANISM: Artificial
<220> FEATURE:
<223> OTHER INFORMATION: oligoDNA primer

<400> SEQUENCE: 90
tgatgttgag aaggatggtg gtac                                      24

<210> SEQ ID NO 91
<211> LENGTH: 24
<212> TYPE: DNA
<213> ORGANISM: Artificial
<220> FEATURE:
<223> OTHER INFORMATION: oligoDNA primer

<400> SEQUENCE: 91
caacgcagaa cgagacctca tccc                                      24

<210> SEQ ID NO 92

```
<211> LENGTH: 24
<212> TYPE: DNA
<213> ORGANISM: Artificial
<220> FEATURE:
<223> OTHER INFORMATION: oligoDNA primer

<400> SEQUENCE: 92
gaagctctac ctgatcagac tcca                                              24

<210> SEQ ID NO 93
<211> LENGTH: 24
<212> TYPE: DNA
<213> ORGANISM: Artificial
<220> FEATURE:
<223> OTHER INFORMATION: oligoDNA primer

<400> SEQUENCE: 93
ggccattttc tcgcagaccc ggac                                              24

<210> SEQ ID NO 94
<211> LENGTH: 24
<212> TYPE: DNA
<213> ORGANISM: Artificial
<220> FEATURE:
<223> OTHER INFORMATION: oligoDNA primer

<400> SEQUENCE: 94
aaggtccaaa ggattcacgg agta                                              24

<210> SEQ ID NO 95
<211> LENGTH: 24
<212> TYPE: DNA
<213> ORGANISM: Artificial
<220> FEATURE:
<223> OTHER INFORMATION: oligoDNA primer

<400> SEQUENCE: 95
gtgtacctag tgtgtgccgc tcta                                              24

<210> SEQ ID NO 96
<211> LENGTH: 20
<212> TYPE: DNA
<213> ORGANISM: Artificial
<220> FEATURE:
<223> OTHER INFORMATION: oligoDNA primer

<400> SEQUENCE: 96
caagcggcat gcaactggac                                                   20
```